(12) United States Patent
Ren et al.

(10) Patent No.: US 12,780,842 B2
(45) Date of Patent: Nov. 3, 2026

US012780842B2

(54) SUBSTITUTED PYRIDO[4,3-D]PYRIMIDINES AND QUINAZOLINES AS INHIBITORS OF RAS PATHWAY SIGNALING

(71) Applicant: Kumquat Biosciences Inc., San Diego, CA (US)

(72) Inventors: Pingda Ren, San Diego, CA (US); Xiaohui He, San Diego, CA (US); Xiaoming Li, San Diego, CA (US); Siling Zhao, San Diego, CA (US); Baogen Wu, San Diego, CA (US)

(73) Assignee: Kumquat Biosciences Inc., San Diego, CA (US)

( * ) Notice: Subject to any disclaimer, the term of this patent is extended or adjusted under 35 U.S.C. 154(b) by 0 days.

(21) Appl. No.: 19/644,459

(22) Filed: Apr. 10, 2026

(65) Prior Publication Data

US 2026/0217735 A1 Jul. 30, 2026

Related U.S. Application Data

(63) Continuation of application No. PCT/US2024/054958, filed on Nov. 7, 2024.

(60) Provisional application No. 63/597,325, filed on Nov. 8, 2023.

(51) Int. Cl.

| | |
|---|---|
| ***C07D 519/00*** | (2006.01) |
| ***A61K 31/517*** | (2006.01) |
| ***A61K 31/519*** | (2006.01) |
| ***A61P 35/00*** | (2006.01) |
| ***C07D 487/04*** | (2006.01) |

(52) U.S. Cl.

CPC .......... *C07D 519/00* (2013.01); *A61K 31/517* (2013.01); *A61K 31/519* (2013.01); *A61P 35/00* (2018.01); *C07D 487/04* (2013.01)

(58) Field of Classification Search

CPC .................................................... C07D 519/00

See application file for complete search history.

(56) References Cited

U.S. PATENT DOCUMENTS

| | | | |
|---|---|---|---|
| 12,286,427 | B2 | 4/2025 | Liu et al. |
| 12,365,676 | B2 | 7/2025 | Liu et al. |
| 2024/0109918 | A1 | 4/2024 | Li et al. |
| 2024/0116951 | A1 | 4/2024 | Li et al. |
| 2024/0368191 | A1 | 11/2024 | Li et al. |
| 2025/0381243 | A1 | 12/2025 | Ren et al. |

FOREIGN PATENT DOCUMENTS

| | | | |
|---|---|---|---|
| CN | 116143806 | A | 5/2023 |
| WO | WO-2013155223 | A1 | 10/2013 |
| WO | WO-2015054572 | A1 | 4/2015 |
| WO | WO-2016014975 | A2 | 1/2016 |
| WO | WO-2016164675 | A1 | 10/2016 |
| WO | WO-2017172979 | A1 | 10/2017 |
| WO | WO-2018217651 | A1 | 11/2018 |
| WO | WO-2018218070 | A2 | 11/2018 |
| WO | WO-2019099524 | A1 | 5/2019 |
| WO | WO-2019215203 | A1 | 11/2019 |
| WO | WO-2020081282 | A1 | 4/2020 |
| WO | WO-2020097537 | A2 | 5/2020 |
| WO | WO-2020113071 | A1 | 6/2020 |
| WO | WO-2020177629 | A1 | 9/2020 |
| WO | WO-2021041671 | A1 | 3/2021 |
| WO | WO-2021108683 | A1 | 6/2021 |
| WO | WO-2021118877 | A1 | 6/2021 |
| WO | WO-2021129820 | A1 | 7/2021 |
| WO | WO-2021216770 | A1 | 10/2021 |
| WO | WO-2022105855 | A1 | 5/2022 |
| WO | WO-2022106897 | A2 | 5/2022 |
| WO | WO-2022132200 | A1 | 6/2022 |
| WO | WO-2022152233 | A1 | 7/2022 |
| WO | WO-2022177917 | A2 | 8/2022 |

(Continued)

OTHER PUBLICATIONS

Aaltonen, Niina. et al. Piperazine and Piperidine Triazole Ureas as Ultrapotent and Highly Selective Inhibitors of Monoacylglycerol Lipase. Chemistry & Biology 20(3):379-390 (2013).

Adibekian, Alexander. et al. Click-generated triazole ureas as ultrapotent in vivo-active serine hydrolase inhibitors. Nature chemical biology 7(7):469-478 (2011).

Bertrand, T. et al. Structural Basis for Human Monoglyceride Lipase Inhibition. Journal of Molecular Biology 396(3):663-673 (2010). Published Online Dec. 3, 2009.

Cisar, Justin S. et al. Identification of ABX-1431, A Selective Inhibitor of Monoacylglycerol Lipase and Clinical Candidate for Treatment of Neurological Disorders. Journal of Medicinal Chemistry 61(20):9062-9084 (2018).

(Continued)

*Primary Examiner* — John S Kenyon
*Assistant Examiner* — Sara Elizabeth Bell
(74) *Attorney, Agent, or Firm* — Wilson Sonsini Goodrich & Rosati

(57) ABSTRACT

The present disclosure provides compounds represented by Formula (II):

(II)

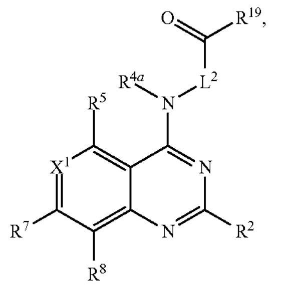

and pharmaceutically acceptable salts thereof, and methods of using the same. The compounds and methods have a range of utilities as therapeutics, diagnostics, and research tools. In particular, the subject compositions and methods are useful for reducing signaling output of oncogenic proteins.

20 Claims, 1 Drawing Sheet

Specification includes a Sequence Listing.

(56) References Cited

FOREIGN PATENT DOCUMENTS

| | | | |
|---|---|---|---|
| WO | WO-2023004102 | A2 | 1/2023 |
| WO | WO-2023018810 | A1 | 2/2023 |
| WO | WO-2023081840 | A1 | 5/2023 |
| WO | WO-2023141300 | A1 | 7/2023 |
| WO | WO-2023150284 | A2 | 8/2023 |
| WO | WO-2023159086 | A1 | 8/2023 |
| WO | WO-2023213269 | A1 | 11/2023 |
| WO | WO-2023215801 | A1 | 11/2023 |
| WO | WO-2023240188 | A1 | 12/2023 |
| WO | WO-2023244615 | A1 | 12/2023 |
| WO | WO-2024002373 | A1 | 1/2024 |
| WO | WO-2024030633 | A1 | 2/2024 |
| WO | WO-2024030647 | A1 | 2/2024 |
| WO | WO-2024031088 | A1 | 2/2024 |
| WO | WO-2024036270 | A1 | 2/2024 |
| WO | WO-2024158778 | A1 | 8/2024 |
| WO | WO-2024227091 | A1 | 10/2024 |
| WO | WO-2024238633 | A2 | 11/2024 |
| WO | WO-2024254334 | A1 | 12/2024 |
| WO | WO-2025059366 | A1 | 3/2025 |
| WO | WO-2025101776 | A1 | 5/2025 |

OTHER PUBLICATIONS

Co-pending U.S. Appl. No. 19/306,039, filed Aug. 21, 2025.

Co-pending U.S. Appl. No. 19/564,596, inventor Pingda; Ren, filed on Mar. 12, 2026.

Deng, Hui, and Weimin Li. Monoacylglycerol Lipase Inhibitors: Modulators for Lipid Metabolism in Cancer Malignancy, Neurological and Metabolic Disorders. Acta Pharmaceutica Sinica B 10(4):582-602 (2020).

Gorgulla, Christoph. et al. A Multi-pronged Approach Targeting SARS-CoV-2 Proteins using Ultra-large Virtual Screening. iScience 24(2):102021, 1-156 (2021).

Hyun, Soonsil, and Dongyun Shin. Small-molecule Inhibitors and Degraders Targeting KRAS-driven Cancers. International Journal of Molecular Sciences 22(22):12142, 1-16 (2021).

Li, Bingke. et al. Machine Learning Models Combined With Virtual Screening and Molecular Docking to Predict Human Topoisomerase I Inhibitors. Molecules 24(11):2107, 1-16 (2019).

Mcaulay, K. et al. Reactivity of Covalent Fragments and Their Role in Fragment Based Drug Discovery. Pharmaceuticals (Basel) 15(11):1366: pp. 1-22 (2022).

McGregor, Lynn M. et al. Expanding the Scope of Electrophiles Capable of Targeting K-Ras Oncogenes. Biochemistry 56(25):3178-3183 (2017).

Morera, Ludovica. et al. Development and Characterization of Endocannabinoid Hydrolases FAAH and MAGL Inhibitors Bearing a Benzotriazol-1-yl Carboxamide Scaffold. Bioorganic & Medicinal Chemistry 20(21):6260-6275 (2012).

Niphakis et al. Ace-ylation in the Hole. Nature Chemical Biology 18(11): 1166-1167 ( 2022).

Patel, Jayendra Z. et al. Loratadine Analogues as MAGL Inhibitors. Bioorganic & Medicinal Chemistry Letters 25(7):1436-1442 (2015).

PCT/US2024/054958 International Search Report and Written Opinion dated Jan. 24, 2025.

Reed, Carson W. et al. Discovery of VU6027459: A First-in-class Selective and CNS Penetrant mGlu7 Positive Allosteric Modulator Tool Compound. ACS Medicinal Chemistry Letters 11(9):1773-1779 (2020).

Remsberg, Jarrett R. et al. ABHD17 Regulation of Plasma Membrane Palmitoylation and N-ras-dependent Cancer Growth. Nature Chemical Biology 17(8):856-864 (2021).

Shannon et al. Covalent Protein Modification: The Current Landscape of Residue-Specific Electrophiles. Current Opinion in Chemical Biology vol. 24: 18-26 (2015).

Shi, Bao-Bao. et al. Alkaloids Isolated From Tabernaemontana Bufalina Display Xanthine Oxidase Inhibitory Activity. Phytochemistry 166:112060, 1-8 (2019).

Wright, Shawn E, and Jeffrey S. Bandar. A Base-promoted Reductive Coupling Platform for the Divergent Defluorofunctionalization of Trifluoromethylarenes. Journal of the American Chemical Society 144(29):13032-13038 (2022).

Zhang, Z. et al. Chemical Acylation of an Acquired Serine Suppresses Oncogenic Signaling of K-Ras(G12S). Nature Chemical Biology 18(11): 1177-1183 (2022).

Zhang, Ziyang. et al. Chemoselective Covalent Modification of K-ras (G12r) With a Small Molecule Electrophile. Journal of the American Chemical Society 144(35):15916-15921 (2022).

| | 1 | | 20 | | 40 | |
|---|---|---|---|---|---|---|
| **K-Ras** (SEQ ID No. 10) | mte------- ----ykl vvv | gaggvgksal | tiqliqnhfv | deydptieds | yrkqvvidge | **49** |
| **H-Ras** (SEQ ID No. 11) | mte------- ----ykl vvv | gaggvgksal | tiqliqnhfv | deydptieds | yrkqvvidge | **49** |
| **N-Ras** (SEQ ID No. 12) | mte------- ----ykl vvv | gaggvgksal | tiqliqnhfv | deydptieds | yrkqvvidge | **49** |
| **RalA** (SEQ ID No. 13) | maankpkgqn slalhkvimv | gsggvgksal | tlqfmydefv | edyeptkads | yrkkvvldge | **60** |
| **RalB** (SEQ ID No. 14) | maankskgqs slalhkvimv | gsggvgksal | tlqfmydefv | edyeptkads | yrkkvvldge | **60** |

| | 60 | | 80 | | 100 | |
|---|---|---|---|---|---|---|
| **K-Ras** | tclldildta | gqeeysamrd | qymrtgegfl | cvfainntks | fedihhyreq | ikrvkdsed- **108** |
| **H-Ras** | tclldildta | gqeeysamrd | qymrtgegfl | cvfainntks | fedihqyreq | ikrvkdsdd- **108** |
| **N-Ras** | tclldildta | gqeeysamrd | qymrtgegfl | cvfainnsks | fadinlyreq | ikrvkdsdd- **108** |
| **RalA** | evqidildta | gqedyaaird | nyfrsgegfl | cvfsitemes | faatadfreq | ilrvk-eden **119** |
| **RalB** | evqidildta | gqedyaaird | nyfrsgegfl | lvfsitehes | ftataefreq | ilrvkaeedk **120** |

SUBSTITUTED PYRIDO[4,3-D]PYRIMIDINES AND QUINAZOLINES AS INHIBITORS OF RAS PATHWAY SIGNALING

CROSS-REFERENCE

This application is a continuation of International Application No. PCT/US2024/054958, filed Nov. 7, 2024, which claims the benefit of U.S. Provisional Application No. 63/597,325, filed Nov. 8, 2023, each incorporated herein by reference in its entirety.

SEQUENCE LISTING

The instant application contains a Sequence Listing which has been submitted electronically in XML format and is hereby incorporated by reference in its entirety. Said XML copy, created on Apr. 8, 2026, is named 56690_782_301_SL.xml and is 15,022 bytes in size.

BACKGROUND

Cancer (e.g., tumor, neoplasm, metastases) is the second leading cause of death worldwide estimated to be responsible for about 10 million deaths each year. Many types of cancers are marked with mutations in one or more proteins involved in various signaling pathways leading to unregulated growth of cancerous cells. In some cases, about 25 to 30 percent (%) of tumors are known to harbor Rat sarcoma (Ras) mutations. In particular, mutations in the Kirsten Ras oncogene (K-Ras) are one of the most frequent Ras mutations detected in human cancers, including lung adenocarcinomas (LUADs) and pancreatic ductal adenocarcinoma (PDAC).

Ras proteins have long been considered "undruggable," due to, in part, high affinity to their substrate guanosine-5'-triphosphate (GTP) and/or their smooth surfaces without any obvious targeting region. The specific G12C Ras gene mutation has been identified as a druggable target to which a number of G12C specific inhibitors have been developed. However, such therapeutics are still of limited application, as the G12C mutation in Ras exhibits a much lower prevalence rate as compared to other known Ras mutations, such as G12D and G12V. Drug resistance and lack of durability impose further limitations to such therapeutics.

SUMMARY

In view of the foregoing, there remains a considerable need for a new design of therapeutics and diagnostics that can specifically target Ras, including wildtype Ras, mutants and/or associated proteins of Ras to reduce Ras signaling output. Of particular interest are Ras inhibitors, including pan Ras inhibitors capable of inhibiting two or more Ras mutants and/or wildtype Ras, as well as mutant-selective inhibitors targeting mutant Ras proteins such as Ras G12D, G12C, G12S, G13D, and/or G12V, for the treatment of Ras-associated diseases (e.g., cancer). Such compositions and methods can be particularly useful for treating a variety of diseases including, but not limited to, cancers and neoplasia conditions. The present disclosure addresses these needs, and provides additional advantages applicable for diagnosis, prognosis, and/or treatment for a wide diversity of diseases.

In certain aspects, the present disclosure provides a compound of Formula (I):

(I)

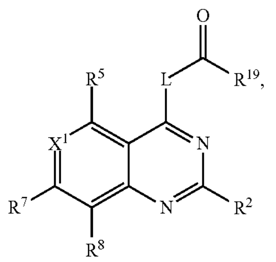

or a pharmaceutically acceptable salt or solvate thereof, wherein:

$X^1$ is selected from $CR^6$ and N;

L is $-L^1-L^2-L^3-$, wherein $L^1$, $L^2$, or $L^3$ is bound to $—C(O)R^{19}$ via a nitrogen atom, thereby forming a urea;

$L^1$ is selected from a bond, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —O—, $—N(R^{12})—$, —C(O)—, —S—, —S(O)—, $—S(O)_2—$, $—P(O)R^{12}—$, $—P(O)R^{12}O—$, $—N(R^{12})C(O)—$, $—N(R^{12})S(O)—$, $—N(R^{12})S(O)_2—$, $—N(R^{12})P(O)R^{12}—$, $—OP(O)R^{12}—$, $—C(O)N(R^{12})—$, $—S(O)N(R^{12})—$, $—S(O)_2N(R^{12})—$, and $—P(O)R^{12}N(R^{12})—$, wherein each of $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl is optionally substituted;

$L^2$ is selected from a bond, $C_{3-12}$ carbocycle and 3- to 12-membered heterocycle, wherein each of $C_{3-12}$ carbocycle and 3- to 12-membered heterocycle is optionally substituted;

$L^3$ is selected from a bond, 2- to 6-membered heteroalkyl, 3- to 6-membered heteroalkenyl, 3- to 6-membered heteroalkynyl, nitrene, $—C_{0-6}$ alkyl-(3- to 12-membered heterocycle), and -(2- to 6-membered heteroalkyl)-(3- to 12-membered heterocycle), wherein each of 2- to 6-membered heteroalkyl, 3- to 6-membered heteroalkenyl, 3- to 6-membered heteroalkynyl, nitrene, $—C_{0-6}$ alkyl-(3- to 12-membered heterocycle), and -(2- to 6-membered heteroalkyl)-(3- to 12-membered heterocycle) is optionally substituted;

$R^{19}$ is imidazol-1-yl, wherein the imidazol-1-yl is:

(a) substituted with one substituent selected from —Br, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), -(2- to 6-membered heteroalkyl)-(3- to 12-membered heterocycle), $—OR^{12}$, $—SR^{12}$, $—N(R^{12})(R^{13})$, $—C(O)OR^{12}$, $—OC(O)N(R^{12})(R^{13})$, $—N(R^{12})C(O)N(R^{12})(R^{13})$, $—N(R^{12})C(O)OR^{12}$, $—N(R^{12})S(O)_2R^{12}$, $—C(O)R^{12}$, $—S(O)R^{12}$, $—OC(O)R^{12}$, $—C(O)N(R^{12})(R^{13})$, $—C(O)C(O)N(R^{12})(R^{13})$, $—N(R^{12})C(O)R^{12}$, $—S(O)_2R^{12}$, $—S(O)(NR^{12})R^{12}$, $—S(O)_2N(R^{12})(R^{13})$, $—S(O)(NR^{12})N(R^{12})(R^{13})$, and $—OCH_2C(O)OR^{12}$, wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), and -(2- to 6-membered heteroalkyl)-(3- to 12-membered heterocycle) is optionally substituted; or (b) substituted with two or three substituents independently selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, optionally wherein two adjacent substituents are taken together with the carbon atoms to which they are attached to form $C_{3-12}$ carbocycle or 3- to 12-membered heterocycle, and wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $C_{3-12}$ carbocycle, 3- to 12-membered heterocycle, —$C_{0-6}$ alkyl-($C_{3-12}$ carbocycle), -(2- to 6-membered heteroalkyl)-($C_{3-12}$ carbocycle), —$C_{0-6}$ alkyl- (3- to 12-membered heterocycle), and -(2- to 6-membered heteroalkyl)-(3- to 12-membered heterocycle) is optionally substituted;

$R^2$, $R^5$, $R^6$, and $R^8$ are each independently selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted;

$R^7$ is selected from $C_{6-12}$ aryl and 5- to 12-membered heteroaryl, each of which is optionally substituted;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein each of $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) is optionally substituted; and $R^{13}$ is independently selected at each occurrence from hydrogen, $C_{1-6}$ alkyl, and $C_{1-6}$ haloalkyl; or $R^{12}$ and $R^{13}$ attached to the same nitrogen atom form optionally substituted 3- to 10-membered heterocycle.

In some embodiments, for a compound of Formula (I), $L^1$ is selected from a bond, $C_{1-6}$ alkyl, 2- to 6-membered heteroalkyl, —$N(R^{12})$—, —C(O)—, —$N(R^{12})C(O)$—, and —$C(O)N(R^{12})$—, wherein each of $C_{1-6}$ alkyl and 2- to 6-membered heteroalkyl is optionally substituted; $L^2$ is selected from a bond, $C_{3-12}$ carbocycle and 3- to 12-membered heterocycle, wherein each of $C_{3-12}$ carbocycle and 3- to 12-membered heterocycle is optionally substituted; and $L^3$ is selected from a bond, 2- to 6-membered heteroalkyl, and nitrene, wherein each of 2- to 6-membered heteroalkyl and nitrene is optionally substituted. In some embodiments, $L^2$ is optionally substituted 3- to 12-membered heterocycle; and $L^3$ is a bond. In some embodiments, $L^2$ is selected from $C_{3-12}$ carbocycle and 3- to 12-membered heterocycle, each of which is optionally substituted; and $L^3$ is optionally substituted nitrene. In some embodiments, $L^1$ is selected from a bond and optionally substituted 2- to 6-membered heteroalkyl. In some embodiments, $L^2$ is optionally substituted 6- to 12-membered spirocyclic heterocycle.

In some embodiments, for a compound of Formula (I), $-L^2-L^3-C(O)R^{19}$ is selected from:

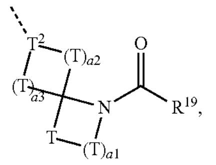
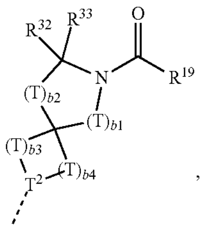
,
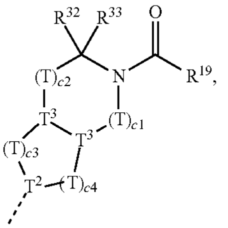
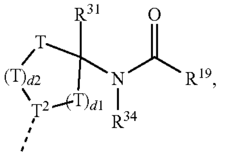
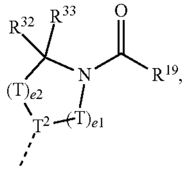
and
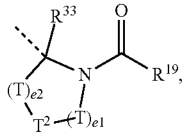

wherein:

a1, b1, b3, and b4 are independently 1, 2, 3, 4, or 5;

a2, a3, and b2 are independently 0, 1, 2, 3, 4, or 5;

c1, c2, c3, c4, d1, d2, e1, and e2 are independently 0, 1, 2, 3, or 4;

wherein the sum of a1, a2, and a3 is less than 9; the sum of b1, b2, b3, and b4 is less than 9; the sum of c1, c2, c3, and c4 is less than 8; the sum of d1 and d2 is less than 6; and the sum of e1 and e2 is less than 6;

T is independently selected at each occurrence from $N(R^{35})$, $C(R^{36})_2$, C(O), O, S(O), and $S(O)_2$;

$T^2$ and $T^3$ are independently selected at each occurrence from N and $C(R^{36})$;

$R^{31}$, $R^{32}$, $R^{33}$, and $R^{36}$ are independently selected at each occurrence from hydrogen and $R^{40}$;

$R^{34}$ and $R^{35}$ are independently selected at each occurrence from hydrogen and $R^{41}$;

$R^{40}$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(=O)(=NR^{12})N(R^{12})(R^{13})$, and —$OCH_2C(O)OR^{12}$; wherein two $R^{40}$ attached to the same carbon atom optionally join to form $=NR^{12}$, $=C(R^{14})_2$, or $=O$; wherein two $R^{40}$ and the atom(s) to which they are attached optionally form $C_{3-12}$ carbocycle or 3- to 12-membered heterocycle; wherein $R^{40}$ and $R^{41}$ and the atoms to which they are attached optionally form 3- to 12-membered heterocycle; and wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted;

$R^{41}$ is independently selected at each occurrence from —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted; and $R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein each of $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle is optionally substituted.

In some embodiments, $R^{40}$ is independently selected at each occurrence from halogen, —CN, $C_{1-6}$ alkyl, and $C_{3-6}$ cycloalkyl, or two $R^{40}$ attached to the same carbon atom form $C_{3-6}$ cycloalkyl, wherein each of $C_{1-6}$ alkyl and $C_{3-6}$ cycloalkyl is optionally substituted with one, two, or three substituents selected from halogen, —CN, $C_{1-6}$ alkyl, $C_{1-6}$ haloalkyl, $C_{3-6}$ cycloalkyl, —O($C_{1-6}$ alkyl), and —O($C_{1-6}$ haloalkyl). In some embodiments, $R^{41}$ is independently selected at each occurrence from $C_{1-6}$ alkyl and $C_{3-6}$ cycloalkyl, each of which is optionally substituted with one, two, or three substituents selected from halogen, —CN, $C_{1-6}$ alkyl, $C_{1-6}$ haloalkyl, —O($C_{1-6}$ alkyl), and —O($C_{1-6}$ haloalkyl).

In certain aspects, the present disclosure provides a compound of Formula (II):

(II)

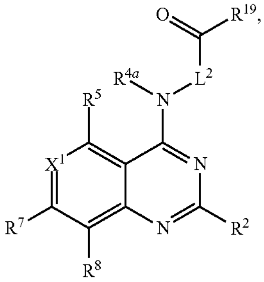

or a pharmaceutically acceptable salt or solvate thereof, wherein:

$X^1$ is selected from $CR^6$ and N;

$R^{4a}$ is selected from $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein each of $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) is optionally substituted;

$L^2$ is saturated, monocyclic 4- to 7-membered heterocycle, wherein the heterocycle is optionally substituted, and wherein —$C(O)R^{19}$ is bound to $L^2$ via a nitrogen atom, thereby forming a urea;

$R^{19}$ is selected from pyrrol-1-yl, pyrazol-1-yl, imidazol-1-yl, 1,2,3-triazol-1-yl, 1,2,3-triazol-2-yl, 1,2,4-triazol-1-yl, and 1,2,4-triazol-4-yl, each of which is optionally substituted, optionally wherein two adjacent substituents are taken together with the carbon atoms to which they are attached to form $C_{3-12}$ carbocycle or 3- to 12-membered heterocycle;

$R^2$, $R^5$, $R^6$, and $R^8$ are each independently selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted;

$R^7$ is selected from $C_{6-12}$ aryl and 5- to 12-membered heteroaryl, each of which is optionally substituted;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein each of $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) is optionally substituted; and $R^{13}$ is independently selected at each occurrence from hydrogen, $C_{1-6}$ alkyl, and $C_{1-6}$ haloalkyl; or $R^{12}$ and $R^{13}$ attached to the same nitrogen atom form optionally substituted 3- to 10-membered heterocycle.

In some embodiments, for a compound of Formula (I) or (II), $L^2$ is selected from azetidin-1,3-diyl, pyrrolidin-1,3-diyl, piperidin-1,3-diyl, piperidin-1,4-diyl, azepan-1,3-diyl, and azepan-1,4-diyl, each of which is optionally substituted. In some embodiments, $L^2$ is substituted with $C_{1-6}$ alkyl, such as —$CH_3$, —$CH_2CH_3$, or —$CH(CH_3)_2$. In some embodiments, $L^2$ is selected from pyrrolidin-1,3-diyl, 4-fluoropyrrolidin-1,3-diyl, 2-methylpyrrolidin-1,3-diyl, 2-ethylpyrrolidin-1,3-diyl, 2-isopropylpyrrolidin-1,3-diyl, 5-fluoropyrrolidin-1,3-diyl, 5-methylpyrrolidin-1,3-diyl, and 5-isopropylpyrrolidin-1,3-diyl. In some embodiments, $L^2$ is pyrrolidin-1,3-diyl, optionally substituted with halogen or $C_{1-3}$ alkyl.

In some embodiments, for a compound of Formula (II), $R^{19}$ is selected from $C_{1-6}$ alkyl and $C_{2-6}$ alkenyl. In some embodiments, $R^{4a}$ is selected from —$CH_3$, —$CH_2CH_3$, and —$CH(CH_3)_2$.

In some embodiments, for a compound of Formula (II), $R^{19}$ is selected from imidazol-1-yl and 1,2,4-triazol-1-yl, each of which is optionally substituted. In some embodiments, $R^{19}$ is optionally substituted with one or two substituents independently selected from halogen, —CN, $C_{1-6}$ alkyl, —O($C_{1-6}$ alkyl), and $C_{3-6}$ cycloalkyl, wherein each of $C_{1-6}$ alkyl —O($C_{1-6}$ alkyl), and $C_{3-6}$ cycloalkyl is optionally substituted with one, two, or three substituents independently selected from halogen, —CN, $C_{1-6}$ alkyl, —O($C_{1-6}$ alkyl), and —O($C_{1-6}$ haloalkyl). In some embodiments, $R^{19}$ is selected from

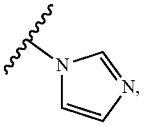 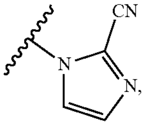 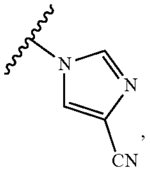

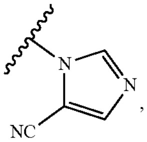 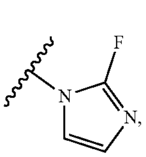 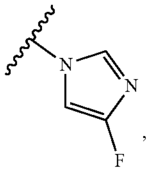

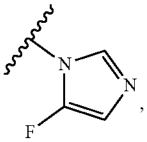 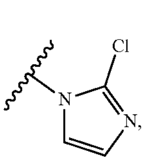 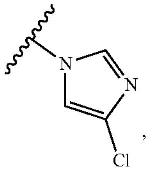

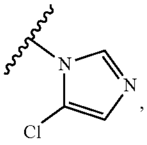 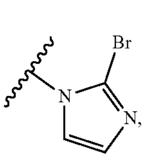 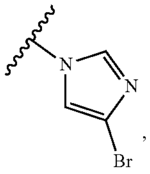

-continued

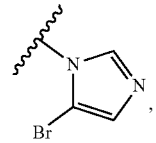 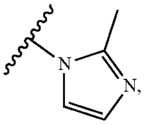 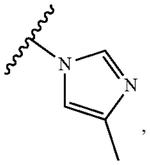

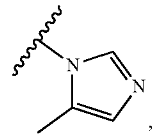 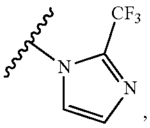 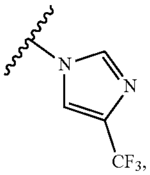

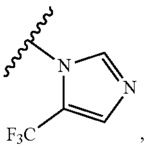 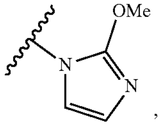 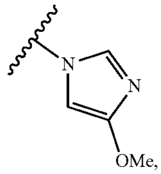

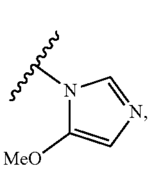 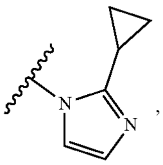 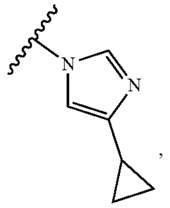

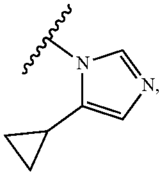 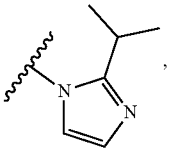 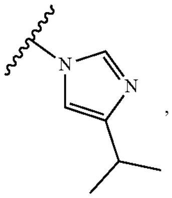

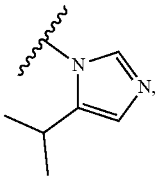 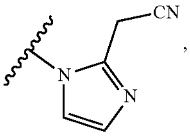 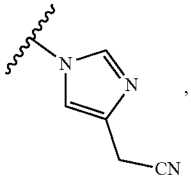

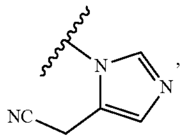 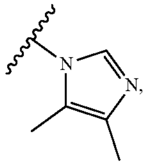 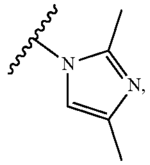

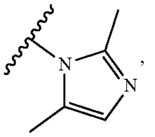 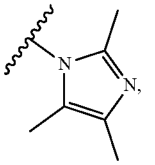 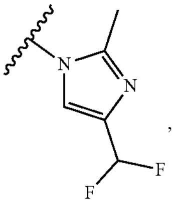

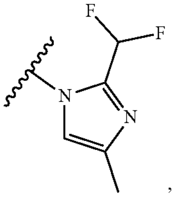 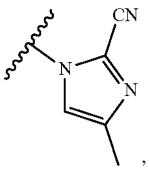 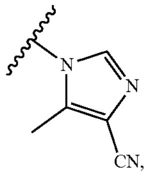

-continued
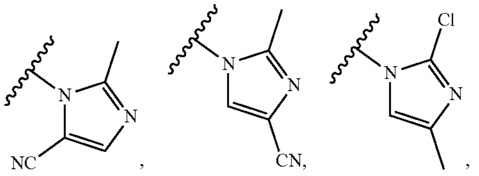
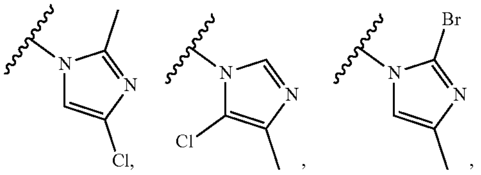
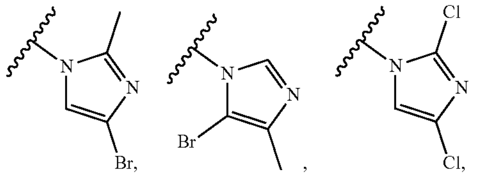
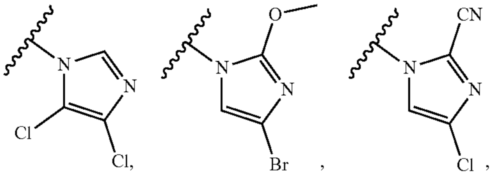
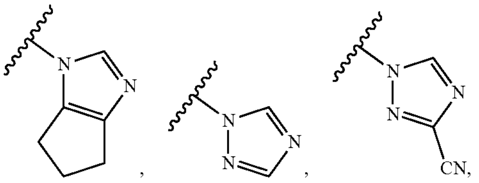
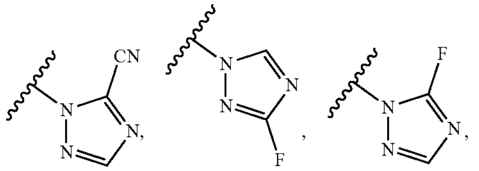
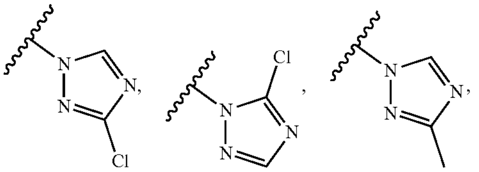
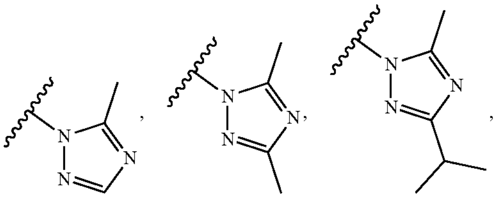
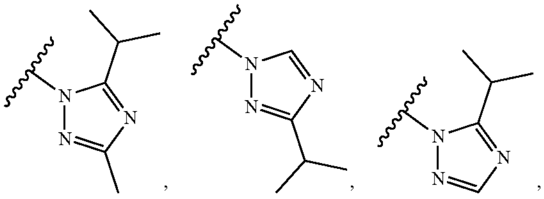
-continued
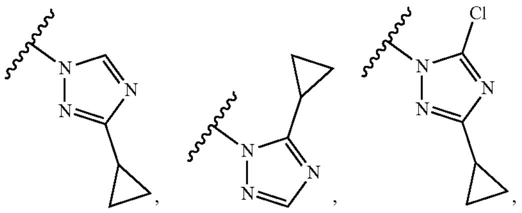
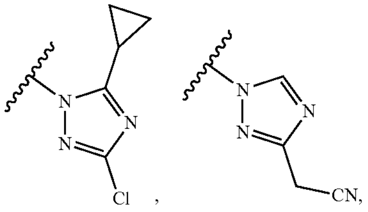
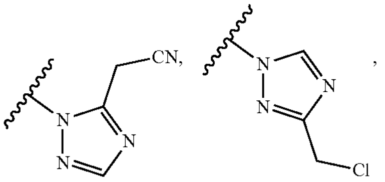
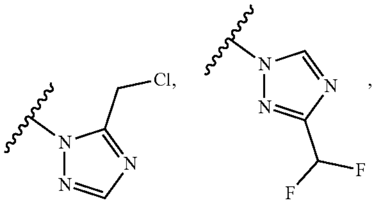
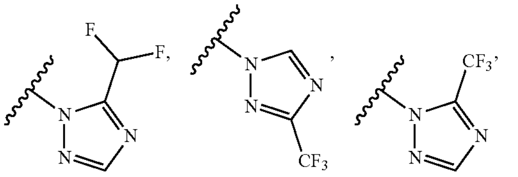
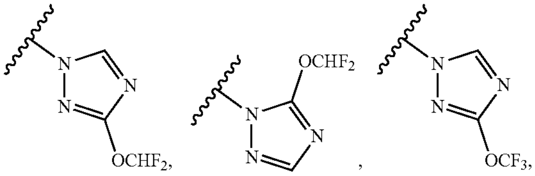
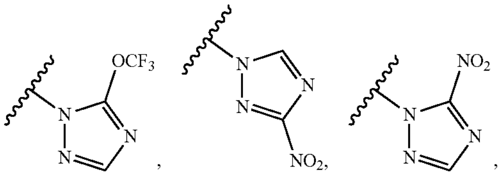
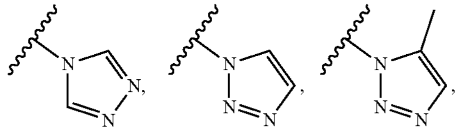
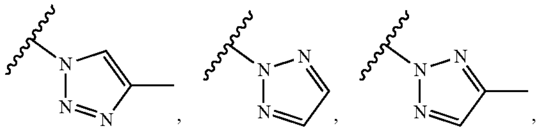

-continued

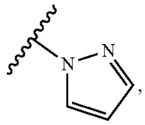, 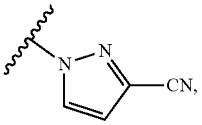 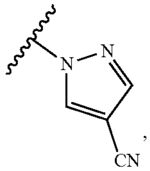,

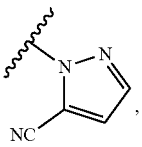, 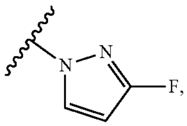 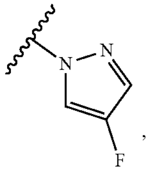,

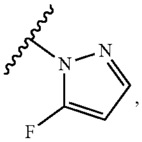, 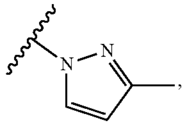, 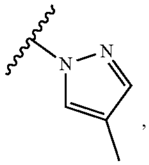,

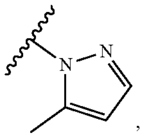, 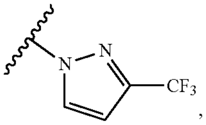, 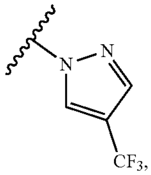

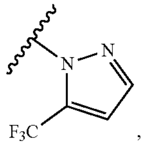, 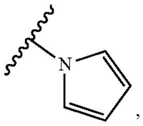,

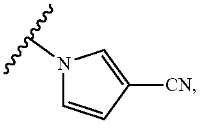 and 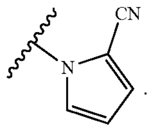.

In some embodiments, for a compound of Formula (I) or (II), $R^2$ is selected from hydrogen, $C_{1-3}$ alkyl, —$OR^{12}$, and 3- to 10-membered heterocycle, wherein each of $C_{1-3}$ alkyl and 3- to 10-membered heterocycle is optionally substituted. In some embodiments, $R^2$ is —$OR^{12}$. In some embodiments, $R^2$ is —$O(C_{1-3}$ alkyl)(4- to 10-membered heterocycle) optionally substituted with one, two, or three substituents independently selected from halogen, $C_{1-3}$ alkyl, $C_{1-3}$ haloalkyl, and =$C(R^{21})_2$, wherein $R^{21}$ is independently selected at each occurrence from hydrogen, halogen, and $C_{1-3}$ alkyl. In some embodiments, $R^2$ is selected from

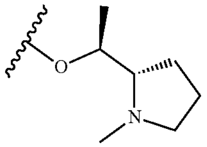, 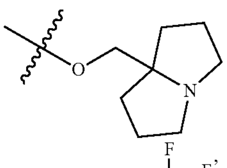,

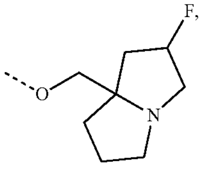 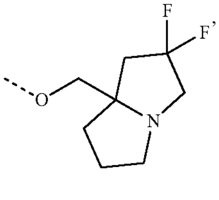

-continued

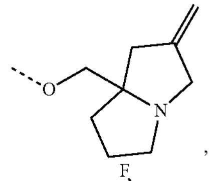, 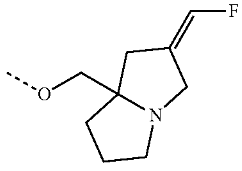,

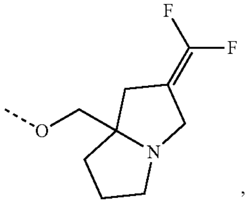, and 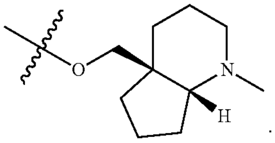.

In some embodiments, $R^2$ is

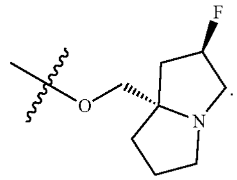 [SMILES: *OC[C@@]12CCCN1C[C@H](F)C2]

In some embodiments, $R^2$ is —$O(C_{1-3}$ alkyl)(4- to 10-membered heterocycle) optionally substituted with one, two, or three substituents independently selected from halogen and -(2- to 6-membered heteroalkyl)-(3- to 12-membered heterocycle), wherein -(2- to 6-membered heteroalkyl)-(3- to 12-membered heterocycle) is optionally substituted with $C_{1-6}$ haloalkyl. In some embodiments, $R^2$ is

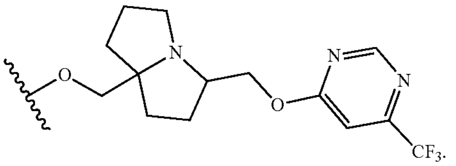 [SMILES: *OCC12CCCN1C(COc1cc(C(F)(F)F)ncn1)CC2]

In some embodiments, for a compound of Formula (I) or (II), $X^1$ is $CR^6$. In some embodiments, $X^1$ is N. In some embodiments, $R^6$ is selected from hydrogen, halogen, and $C_{1-3}$ haloalkyl. In some embodiments, $R^6$ is selected from chlorine and $CF_3$. In some embodiments, $R^5$ and $R^8$ are independently selected from hydrogen, halogen, and $C_{1-3}$ haloalkyl. In some embodiments, $R^5$ is hydrogen. In some embodiments, $R^8$ is fluorine.

In some embodiments, for a compound of Formula (I) or (II), $R^7$ is selected from $C_{6-12}$ aryl and 5- to 12-membered heteroaryl, each of which is optionally substituted. In some embodiments, $R^7$ is selected from naphthyl, isoquinolinyl, indazolyl, benzothiazolyl, benzothiophenyl, phenyl, and pyridinyl, each of which is optionally substituted. In some embodiments, $R^7$ is substituted with one, two, three, or four substituents independently selected from halogen, —CN, $C_{1-3}$ alkyl, $C_{1-3}$ haloalkyl, $C_{2-3}$ alkenyl, $C_{2-3}$ alkynyl, —$OR^{12}$, —$N(R^{12})(R^{13})$, and $C_{3-6}$ cycloalkyl. In some embodiments, $R^2$ is substituted with one, two, three, or four substituents independently selected from halogen, —CN, —$CH_3$, —$CH_2CH_3$, —CH=$CH_2$, —$CF_3$, —C≡CH, —OH, —$NH_2$, and -cyclopropyl. In some embodiments, $R^7$ is selected from

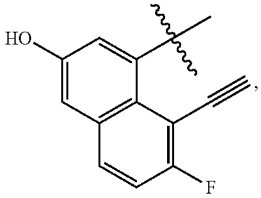,
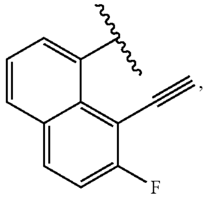,
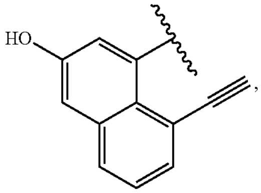,
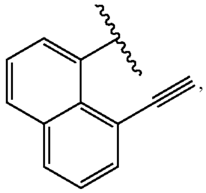,
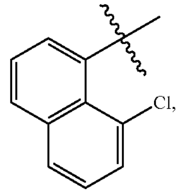,
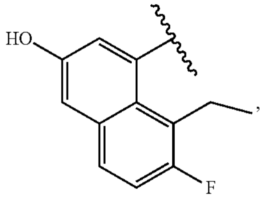,
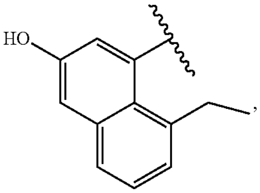,
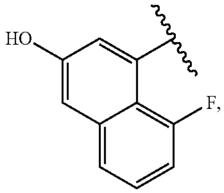,
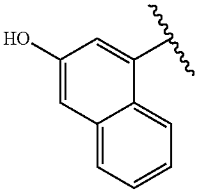,
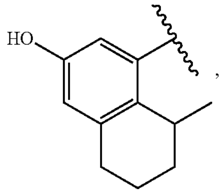,
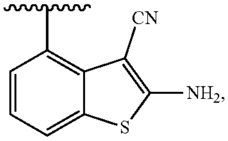,
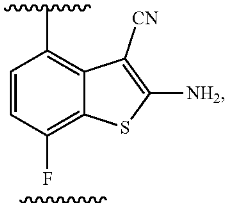,
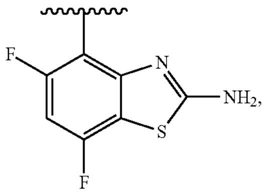,
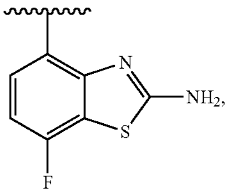,
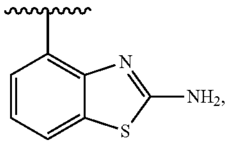,
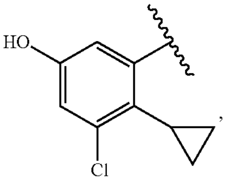, -continued

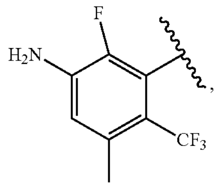, and 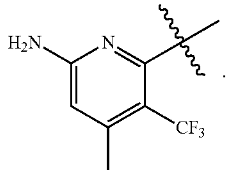.

In some embodiments, $R^7$ is

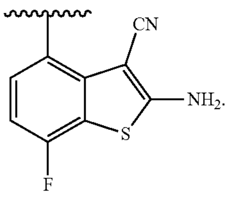 [SMILES: *c1ccc(F)c2sc(N)c(C#N)c12]

In some embodiments, for a compound of Formula (I) or (II), $R^5$ is hydrogen; $R^6$ is selected from halogen and $C_{1-3}$ haloalkyl; $R^7$ is selected from naphthyl, isoquinolinyl, indazolyl, benzothiazolyl, benzothiophenyl, phenyl, and pyridinyl, each of which is optionally substituted; and $R^8$ is halogen. In some embodiments, $R^2$ is selected from

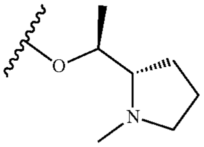,
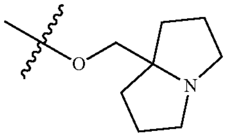,
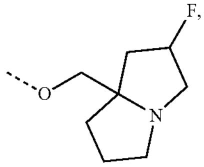
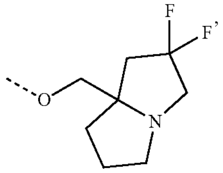
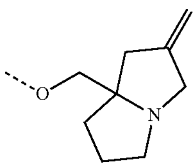,
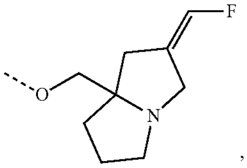,
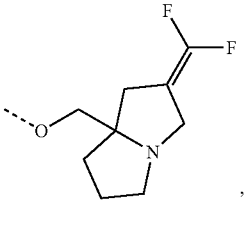, and
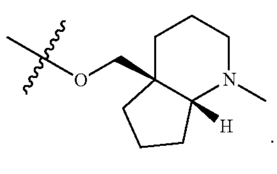.

$R^5$ is hydrogen; $R^6$ is selected from halogen and $C_{1-3}$ haloalkyl; $R^7$ is

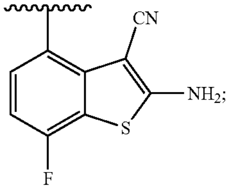 [SMILES: *c1ccc(F)c2sc(N)c(C#N)c12]

and $R^8$ is halogen.

In some embodiments, for a compound of Formula (I) or (II), $R^{19}$ is Br-substituted imidazol-1-yl. In some embodiments, $R^{19}$ is imidazol-1-yl substituted with $C_{1-3}$ alkyl and optionally further substituted with one or two substituents independently selected from halogen, —CN, $C_{1-3}$ alkyl, and $C_{3-6}$ cycloalkyl, wherein each of $C_{1-3}$ alkyl and $C_{3-6}$ cycloalkyl is optionally substituted with one, two, or three substituents independently selected from halogen, —CN, $C_{1-6}$ alkyl, —O($C_{1-6}$ alkyl), and —O($C_{1-6}$ haloalkyl). In some embodiments, $R^{19}$ is imidazol-1-yl substituted with —$CH_3$ and optionally further substituted with —F, —Cl, —Br, —CN, or —$CH_3$. In some embodiments, $R^{19}$ is selected from

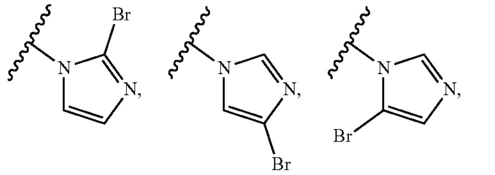

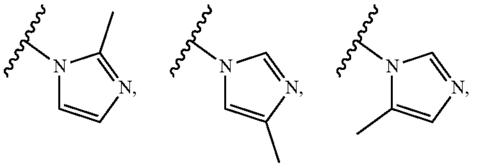

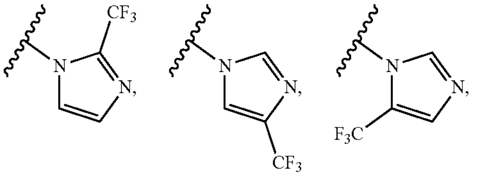

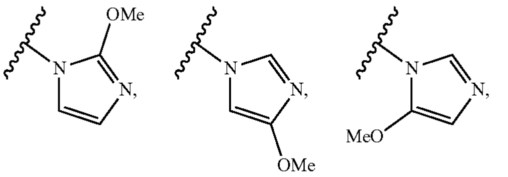

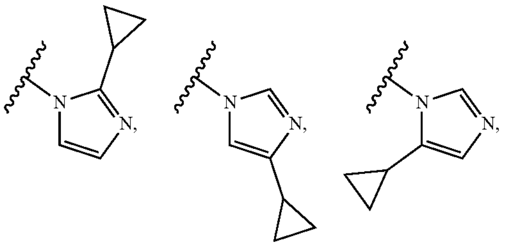

-continued

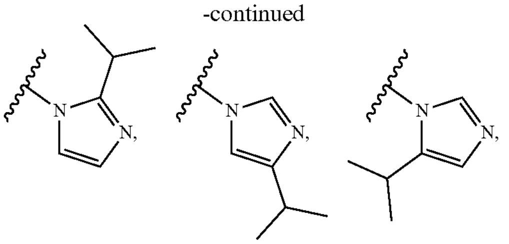

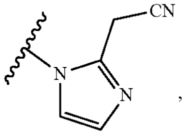
,
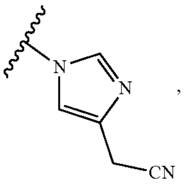
,
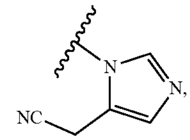

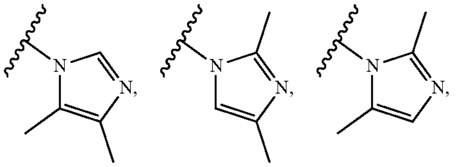

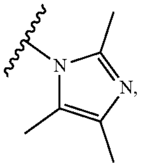

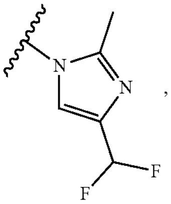
,
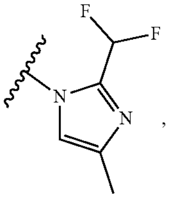
,

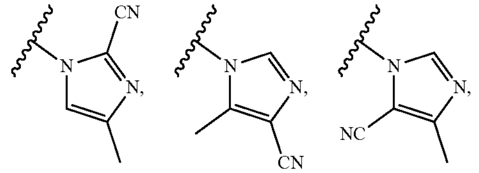

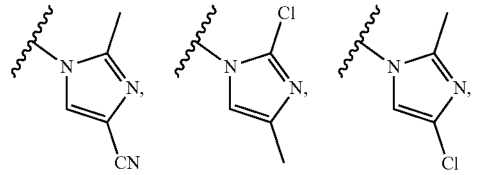

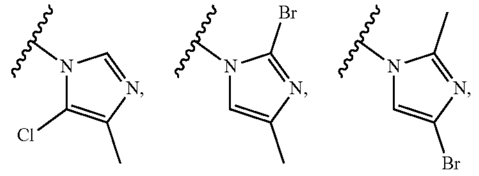

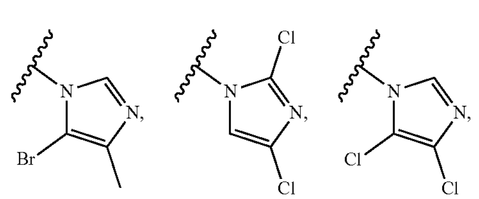

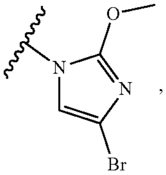
,
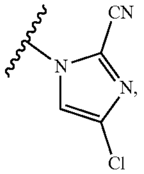
and
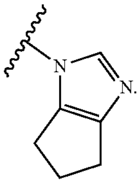

In certain aspects, the present disclosure provides a compound selected from Table 1, or a pharmaceutically acceptable salt or solvate thereof. In certain aspects, the present disclosure provides a compound of the formula

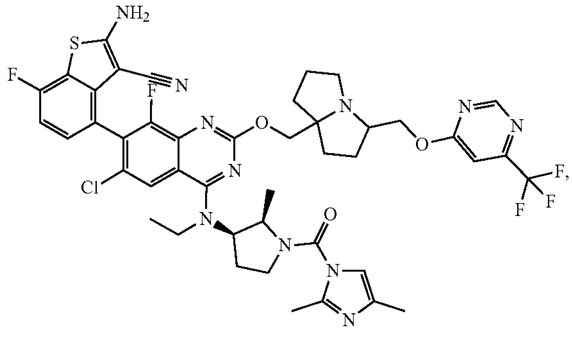 [SMILES: CCN(c1nc(OCC23CCCN2C(COc2cc(C(F)(F)F)ncn2)CC3)nc2c(F)c(-c3ccc(F)c4sc(N)c(C#N)c34)c(Cl)cc12)[C@@H]1CCN(C(=O)n2cc(C)nc2C)[C@@H]1C]

or a pharmaceutically acceptable salt or solvate thereof.

In certain aspects, the present disclosure provides a pharmaceutical composition comprising a compound disclosed herein, such as a compound of Table 1, or a pharmaceutically acceptable salt or solvate thereof, and a pharmaceutically acceptable excipient.

In certain aspects, the present disclosure provides a method of modifying a Ras mutant protein, comprising contacting the Ras mutant protein with an effective amount of a compound disclosed herein, or a salt or solvate thereof. In some embodiments, the modified Ras mutant protein exhibits a reduced Ras signaling output. In some embodiments, the reduced Ras signaling output is evidenced by one or more output selected from (i) an increase in steady state level of GDP-bound modified protein; (ii) a reduction in steady state level of GTP-bound modified protein; (iii) a reduction of phosphorylated AKTs473; (iv) a reduction of phosphorylated ERK T202/Y204; (v) a reduction of phosphorylated S6 5235/236; (vi) a reduction of cell growth of a tumor cell expressing a Ras G12S mutant protein; and (vii) a reduction in Ras interaction with a Ras-pathway signaling protein. In some embodiments, the Ras mutant protein comprises an amino acid sequence in SEQ ID No. 4 or SEQ ID No. 9 having a serine or cysteine residue corresponding to position 12 of SEQ ID No. 1. In some embodiments, the Ras mutant protein comprises an amino acid sequence of SEQ ID No. 4 or SEQ ID No. 9. In some embodiments, the modified Ras mutant protein comprises an amino acid sequence of SEQ ID No. 1, or a fragment thereof that comprises the serine or cysteine residue corresponding to position 12 of SEQ ID No. 1, and wherein the compound selectively labels the serine or cysteine residue as compared to (i) an aspartate residue of a K-Ras G12D mutant protein, said aspartate corresponding to position 12 of SEQ ID No. 2; (ii) a valine residue of a K-Ras G12V mutant protein, said valine corresponding to position 12 of SEQ ID No. 3; and/or (iii) a glycine residue of a K-Ras wildtype protein, said glycine corresponding to position 12 of SEQ ID No. 1. In some embodiments, the compound selectively labels the serine or cysteine residue by at least 2-fold when assayed under comparable conditions. In some embodiments, the compound selectively labels the serine or cysteine residue by at least 5-fold when assayed under comparable conditions. In some embodiments, the contacting occurs in vivo.

In certain aspects, the present disclosure provides a method of treating cancer in a subject in need thereof, comprising administering to the subject a therapeutically effective amount of a compound disclosed herein, or a pharmaceutically acceptable salt or solvate thereof. In certain aspects, the present disclosure provides a method of treating cancer in a subject comprising a Ras mutant protein, the method comprising: inhibiting the Ras mutant protein of said subject by administering to said subject a compound disclosed herein, or a pharmaceutically acceptable salt or solvate thereof, wherein the compound is characterized in that upon contacting the Ras mutant protein, said Ras mutant protein exhibits reduced Ras signaling output. In some embodiments, the cancer is a solid tumor or a hematological cancer. In some embodiments, the cancer comprises a K-Ras G12S or K-Ras G12C mutant protein.

In certain aspects, the present disclosure provides a method of modulating signaling output of a Ras protein, comprising contacting a Ras protein with an effective amount of a compound disclosed herein, or a pharmaceutically acceptable salt or solvate thereof, thereby modulating the signaling output of the Ras protein. In certain aspects, the present disclosure provides a method of inhibiting cell growth, comprising administering an effective amount of a compound disclosed herein, or a pharmaceutically acceptable salt or solvate thereof, to a cell expressing a Ras protein, thereby inhibiting growth of said cells. A method described herein may further comprise administering an additional agent.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts a sequence alignment of various wild type Ras proteins including K-Ras, H-Ras, N-Ras, RalA, and RalB, from top to bottom.

DETAILED DESCRIPTION

Unless defined otherwise, all technical and scientific terms used herein have the same meaning as is commonly understood by one of skill in the art to which this disclosure belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Chemical structures are named herein according to IUPAC conventions as implemented in ChemDraw® software (Perkin Elmer, Inc., Cambridge, MA). The section headings used herein are for organizational purposes only and are not to be construed as limiting the subject matter described. As used in the specification and claims, the singular forms "a", "an" and "the" include plural references unless the context clearly dictates otherwise. Furthermore, use of the term "including" as well as other forms, such as "include", "includes", and "included", is not limiting. The section headings used herein are for organizational purposes only and are not to be construed as limiting the subject matter described.

The term "$C_{x-y}$" or "$C_x$-$C_y$" when used in conjunction with a chemical moiety, such as alkyl, alkenyl, or alkynyl, is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups, that contain from x to y carbons in the chain.

"Alkyl" refers to substituted or unsubstituted saturated hydrocarbon groups, including linear and branched alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including linear and branched alkenyl groups, containing at least one double bond. An alkenyl group may contain from two to twelve carbon atoms (e.g., $C_{2-12}$ alkenyl), such as two to eight carbon atoms ($C_{2-8}$ alkenyl) or two to six carbon atoms ($C_{2-6}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including linear and branched alkynyl groups, containing at least one triple bond. An alkynyl group may contain from two to twelve carbon atoms (e.g., $C_{2-12}$ alkynyl), such as two to eight carbon atoms ($C_{2-8}$ alkynyl) or two to six carbon atoms ($C_{2-6}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to substituted or unsubstituted divalent saturated hydrocarbon groups, including linear alkylene and branched alkylene groups, that contain from one to twelve carbon atoms (e.g., $C_{1-12}$ alkylene), such as one to eight carbon atoms ($C_{1-8}$ alkylene) or one to six carbon atoms ($C_{1-6}$ alkylene). Exemplary alkylene groups include methylene, ethylene, propylene, and n-butylene. Similarly, "alkenylene" and "alkynylene" refer to alkylene groups, as defined above, which comprise one or more carbon-carbon double or triple bonds, respectively. The points of attachment of the alkylene, alkenylene or alkynylene chain to the rest of the molecule can be through one carbon or any two carbons of the chain. Unless stated otherwise specifically in the specification, an alkylene, alkenylene, or alkynylene group is optionally substituted by one or more substituents such as those substituents described herein.

"Heteroalkyl", "heteroalkenyl" and "heteroalkynyl" refer to substituted or unsubstituted alkyl, alkenyl and alkynyl groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkyl group has a chain length of 3 to 8 atoms. Connection to the rest of the molecule may be through either a heteroatom or a carbon in the heteroalkyl, heteroalkenyl, or heteroalkynyl chain. Unless stated otherwise specifically in the specification, a heteroalkyl, heteroalkenyl, or heteroalkynyl group is optionally substituted by one or more substituents such as those substituents described herein.

"Heteroalkylene", "heteroalkenylene" and "heteroalkynylene" refer to substituted or unsubstituted alkylene, alkenylene and alkynylene groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkylene group has a chain length of 3 to 8 atoms. The points of attachment of the heteroalkylene, heteroalkenylene or heteroalkynylene chain to the rest of the molecule can be through either one heteroatom or one carbon, or any two heteroatoms, any two carbons, or any one heteroatom and any one carbon in the heteroalkylene, heteroalkenylene or heteroalkynylene chain. Unless stated otherwise specifically in the specification, a heteroalkylene, heteroalkenylene, or heteroalkynylene group is optionally substituted by one or more substituents such as those substituents described herein.

"Nitrene" refers to an unsubstituted divalent group of the general formula —NH— and its R-substituted derivatives of the general formula —N(R)—. Unless stated otherwise specifically in the specification, a nitrene group is optionally substituted, such as by a substituent described herein. Exemplary nitrene groups include —NH—, —$N(CH_3)$—, —$N(CH_2CH_3)$—, —$N(CH_2CH_2CH_3)$, —$N(CH(CH_3)_2)$—, —$N(CH_2CH(CH_3)_2)$—, —$N(C(CH_3)_3)$, —$N(CH_2F)$—, —$N(CHF_2)$—, —$N(CF_3)$—, —N(cyclopropyl)-, —N(cyclobutyl)-, and —N(cyclopentyl)-.

"Carbocycle" refers to a saturated, unsaturated or aromatic ring in which each atom of the ring is a carbon atom. Carbocycle may include $C_{3-10}$ monocyclic rings, $C_{5-12}$ bicyclic rings, $C_{5-18}$ polycyclic rings, $C_{5-12}$ spirocyclic rings, and $C_{5-12}$ bridged rings. Each ring of a bicyclic or polycyclic carbocycle may be selected from saturated, unsaturated, and aromatic rings. A polycyclic carbocycle contains a number or rings equal to the minimum number of scissions required to convert the carbocycle into an acyclic skeleton (e.g., bicyclic, tricyclic, tetracyclic, etc.). In some embodiments, the carbocycle is a $C_{6-12}$ aryl group, such as $C_{6-10}$ aryl. In some embodiments, the carbocycle is a $C_{3-12}$ cycloalkyl group. In some embodiments, the carbocycle is a $C_{5-12}$ cycloalkenyl group. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic rings, as valence permits, are included in the definition of carbocycle. A carbocycle may comprise a fused ring, a bridged ring, a spirocyclic ring, a saturated ring, an unsaturated ring, an aromatic ring, or any combination thereof. Exemplary carbocycles include cyclopentyl, cyclohexyl, cyclohexenyl, adamantly, phenyl, indanyl, and naphthyl. Unless state otherwise specifically in the specification, a carbocycle is optionally substituted by one or more substituents such as those substituents described herein.

“Heterocycle” refers to a saturated, unsaturated or aromatic ring comprising one or more heteroatoms, for example 1, 2, 3, or 4 heteroatoms selected from O, S, P, and N. Heterocycle may include 3- to 10-membered monocyclic rings, 5- to 12-membered bicyclic rings, 5- to 18-membered polycyclic rings, 5- to 12-membered spirocyclic rings, and 5- to 12-membered bridged rings. Each ring of a bicyclic or polycyclic heterocycle may be selected from saturated, unsaturated, and aromatic rings. A polycyclic heterocycle contains a number or rings equal to the minimum number of scissions required to convert the heterocycle into an acyclic skeleton (e.g., bicyclic, tricyclic, tetracyclic, etc.). The heterocycle may be attached to the rest of the molecule through any atom of the heterocycle, valence permitting, such as a carbon or nitrogen atom of the heterocycle. In some embodiments, the heterocycle is a 5- to 10-membered heteroaryl group, such as 5- or 6-membered heteroaryl. In some embodiments, the heterocycle is a 3- to 12-membered heterocycloalkyl group. A heterocycle may comprise a fused ring, a bridged ring, a spirocyclic ring, a saturated ring, an unsaturated ring, an aromatic ring, or any combination thereof. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, benzothienyl, benzoxazolyl, and quinolinyl. Unless stated otherwise specifically in the specification, a heterocycle is optionally substituted by one or more substituents such as those substituents described herein.

“Heteroaryl” refers to an aromatic ring that comprises at least one heteroatom, for example 1, 2, 3, or 4 heteroatoms selected from O, S and N. Heteroaryl may include 5- to 10-membered monocyclic rings, 6- to 12-membered bicyclic rings, 6- to 18-membered polycyclic rings, 5- to 12-membered spirocyclic rings, and 6- to 12-membered bridged rings. As used herein, the heteroaryl ring may be selected from monocyclic, bicyclic, or polycyclic-including fused, spirocyclic and bridged ring systems—wherein at least one of the rings in the ring system is aromatic and comprises at least one heteroatom. A polycyclic heteroaryl contains a number or rings equal to the minimum number of scissions required to convert the heteroaryl into an acyclic skeleton (e.g., bicyclic, tricyclic, tetracyclic, etc.). The heteroatom(s) in the heteroaryl may optionally be oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryl groups include, but are not limited to, azepinyl, benzimidazolyl, benzisothiazolyl, benzisoxazolyl, benzofuranyl, benzothiazolyl, benzothiophenyl, benzoxazolyl, furanyl, imidazolyl, indazolyl, indolyl, isoquinolinyl, isothiazolyl, isoxazolyl, oxadiazolyl, oxazolyl, purinyl, pyrazinyl, pyrazolidinyl, pyrazolyl, pyridazinyl, pyridazolyl, pyridyl, pyrimidinyl, pyrrolyl, quinazolinyl, quinolinyl, quinoxalinyl, tetrahydroquinolinyl, thiadiazolyl, thiazolyl, and thienyl groups. Unless stated otherwise specifically in the specification, a heteroaryl is optionally substituted by one or more substituents such as those substituents described herein.

Unless stated otherwise, hydrogen atoms are implied in structures depicted herein as necessary to satisfy the valence requirement.

A waved line “~” drawn across or at the end of a bond or a dashed bond “---” are used interchangeably herein to denote where a bond disconnection or attachment occurs. For example, in the structure

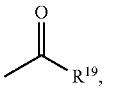

if $R^{19}$ is 1,2,4-triazol-1-yl as in

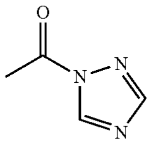

then $R^{19}$ may be depicted as

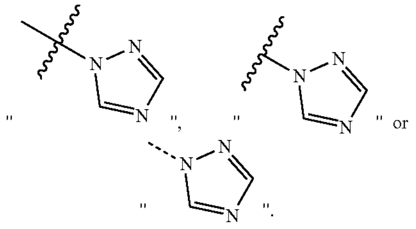

The term “substituted” refers to moieties having substituents replacing a hydrogen on one or more carbons or heteroatoms of the structure. It will be understood that “substitution” or “substituted with” includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term “substituted” is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, heteroatoms such as nitrogen may have any permissible substituents of organic compounds described herein which satisfy the valences of the heteroatoms.

A compound disclosed herein, such as a compound of Formula (I) or (II), is optionally substituted by one or more-such as 1, 2 or 3-substituents selected from:

halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, and —S(=O)(=$NR^{22}$)$N(R^{22})(R^{23})$; wherein two substituents attached to the same or adjacent atoms optionally join to form $C_{3-12}$ carbocycle or 3- to 12-membered heterocycle; wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle is optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —S(=O)(=$NR^{22}$)$N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein each of —$C_{0-6}$ alkyl-($C_{3-12}$ carbocycle) and —$C_{0-6}$ alkyl-(3- to 12-membered heterocycle) is optionally substituted with one, two, or three groups independently selected from halogen and $C_{1-6}$ alkyl; and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, a compound disclosed herein, such as a compound of Formula (I) or (II), is optionally substituted by one or more—such as 1, 2 or 3-substituents selected from:

halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, and —$S(O)_2N(R^{22})(R^{23})$—, wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle is optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, and =$C(R^{21})_2$;

$R^{21}$ is independently selected at each occurrence from hydrogen, halogen, $C_{1-6}$ alkyl, and $C_{1-6}$ haloalkyl;

$R^{22}$ is independently selected at each occurrence from hydrogen, $C_{1-6}$ alkyl, $C_{1-6}$ haloalkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein each of —$C_{0-6}$ alkyl-($C_{3-12}$ carbocycle) and —$C_{0-6}$ alkyl-(3- to 12-membered heterocycle) is optionally substituted with one, two, or three groups independently selected from halogen and $C_{1-6}$ alkyl;

$R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, a compound disclosed herein, such as a compound of Formula (I) or (II), is optionally substituted by one or more-such as 1, 2 or 3-substituents selected from halogen, oxo, =NH, —CN, —$NO_2$, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, —$CH_2$-(3- to 10-membered heterocycle), —OH, —$OCH_3$, —$OCH_2CH_3$, —$NH_2$, —$NHCH_3$, and —$NHCH_2CH_3$, wherein each of $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle) is optionally substituted with one, two, or three groups independently selected from halogen, oxo, =NH, —CN, —$NO_2$, —$CH_3$, —$CH_2CH_3$, —$CH(CH_3)_2$, —$C(CH_3)_3$, —OH, —$OCH_3$, —$OCH_2CH_3$, —$NH_2$, —$NHCH_3$, and —$NHCH_2CH_3$.

It will be understood by those skilled in the art that substituents can themselves be substituted, if appropriate. Unless specifically stated as "unsubstituted", references to chemical moieties herein are understood to include substituted variants. For example, reference to a "heteroaryl" group or moiety implicitly includes both substituted and unsubstituted variants.

Where bivalent substituent groups are specified herein by their conventional chemical formulae, written from left to right, they are intended to encompass the isomer that would result from writing the structure from right to left, e.g., —$CH_2O$— is also intended to encompass —$OCH_2$—.

"Optional" or "optionally" means that the subsequently described event or circumstances may or may not occur, and that the description includes instances where the event or circumstance occurs and instances in which it does not. For example, an "optionally substituted" group may be either unsubstituted or substituted.

Compounds of the present disclosure also include crystalline and amorphous forms of those compounds, pharmaceutically acceptable salts, and active metabolites having the same type of activity, including, for example, polymorphs, pseudopolymorphs, solvates, hydrates, unsolvated polymorphs (including anhydrates), conformational polymorphs, amorphous forms of the compounds, and mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^{1}H$ (protium), $^{2}H$ (deuterium), and $^{3}H$ (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Examples of isotopes that may be incorporated into compounds of the present disclosure include, but are not limited to, $^{2}H$, $^{3}H$, $^{13}C$, $^{14}C$, $^{15}N$, $^{18}O$, $^{17}O$, $^{35}S$, $^{36}C_1$, and $^{18}F$. Of particular interest are compounds of Formula (I) or (II) enriched in tritium or carbon-14, which can be used, for example, in tissue distribution studies; compounds of the disclosure enriched in deuterium-especially at a site of metabolism-resulting, for example, in compounds having greater metabolic stability; and compounds of Formula (I) or (II) enriched in a positron emitting isotope, such as $^{11}C$, $^{18}F$, $^{15}O$ and $^{13}N$, which can be used, for example, in Positron Emission Topography (PET) studies. Isotopically-enriched compounds may be prepared by conventional techniques well known to those skilled in the art.

As used herein, the phrase "of the formula", "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. In some embodiments, in order to optimize the therapeutic activity of the compounds of the disclosure, e.g., to treat cancer, it may be desirable that the carbon atoms have a particular configuration (e.g., (R,R), (S,S), (S,R), or (R,S)) or are enriched in a stereoisomeric form having such configuration. The compounds of the disclosure may be provided as racemic mixtures. Accordingly, the disclosure relates to racemic mixtures, pure stereoisomers (e.g., enantiomers and diastereomers), stereoisomer-enriched mixtures, and the like, unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the disclosure unless otherwise indicated, provided that the utility of the composition as a whole is not eliminated by the presence of such other isomers. Individual stereoisomers may be obtained by numerous methods that are known in the art, including preparation using chiral synthons or chiral reagents, resolution using chiral chromatography using a suitable chiral stationary phase or support, or by chemically converting them into diastereomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds described herein are included with the scope of the disclosure unless otherwise specified.

The term "pharmaceutically acceptable" refers to a material that is not biologically or otherwise unacceptable when used in the subject compositions and methods. For example, the term "pharmaceutically acceptable carrier" refers to a material-such as an adjuvant, excipient, glidant, sweetening agent, diluent, preservative, dye, colorant, flavor enhancer, surfactant, wetting agent, dispersing agent, suspending agent, stabilizer, isotonic agent, solvent or emulsifier—that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The terms "salt" and "pharmaceutically acceptable salt" refer to a salt prepared from a base or an acid. Pharmaceutically acceptable salts are suitable for administration to a patient, such as a mammal (for example, salts having acceptable mammalian safety for a given dosage regime). Salts can be formed from inorganic bases, organic bases, inorganic acids and organic acids. In addition, when a compound contains both a basic moiety, such as an amine, pyridine or imidazole, and an acidic moiety, such as a carboxylic acid or tetrazole, zwitterions may be formed and are included within the term "salt" as used herein. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc., and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein. The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, "treating" or "treatment" refers to an approach for obtaining beneficial or desired results with respect to a disease, disorder, or medical condition (such as cancer) in a subject, including but not limited to the following: (a) ameliorating the disease or medical condition, e.g., eliminating or causing regression of the disease or medical condition in a subject; (b) suppressing the disease or medical condition, e.g., slowing or arresting the development of the disease or medical condition in a subject; or (c) alleviating symptoms of the disease or medical condition in a subject. For example, "treating cancer" would include preventing cancer from reoccurring, ameliorating cancer, suppressing cancer, and alleviating the symptoms of cancer. Also, a therapeutic benefit is achieved with the eradication or amelioration of one or more of the physiological symptoms associated with the underlying disorder such that an improvement is observed in the subject, notwithstanding that the subject may still be afflicted with the underlying disorder.

A "therapeutic effect", as that term is used herein, encompasses a therapeutic benefit and/or prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "antagonist" and "inhibitor" are used interchangeably, and they refer to a compound having the ability to inhibit a biological function (e.g., activity, expression, binding, protein-protein interaction) of a target protein (e.g., K-Ras). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition.

The term "selective inhibition" or "selectively inhibit" refers to the ability of a biologically active agent to preferentially reduce the target signaling activity as compared to off-target signaling activity, via direct or indirect interaction with the target.

The terms "subject" and "patient" refer to an animal, such as a mammal, for example a human. The methods described herein can be useful in both human therapeutics and veterinary applications. In some embodiments, the subject is a mammal, such as a human. "Mammal" includes humans and both domestic animals such as laboratory animals and household pets (e.g., cats, dogs, swine, cattle, sheep, goats, horses, rabbits), and non-domestic animals such as wildlife and the like.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), morpholino and locked nucleic acid (LNA), glycol nucleic acid (GNA), threose nucleic acid (TNA), 2'-fluoro, 2'-OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

An "antigen" is a moiety or molecule that contains an epitope, and, as such, also specifically binds to an antibody. An "antigen binding unit" may be whole or a fragment (or fragments) of a full-length antibody, a structural variant thereof, a functional variant thereof, or a combination thereof. A full-length antibody may be, for example, a monoclonal, recombinant, chimeric, deimmunized, humanized and human antibody. Examples of a fragment of a full-length antibody may include, but are not limited to, variable heavy (VH), variable light (VL), a heavy chain found in camelids, such as camels, llamas, and alpacas (VHH or $V_HH$), a heavy chain found in sharks (V-NAR domain), a single domain antibody (sdAb, e.g., "nanobody") that comprises a single antigen-binding domain, Fv, Fd, Fab, Fab', $F(ab')_2$, and "r IgG" (or half antibody). Examples of modified fragments of antibodies may include, but are not limited to scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, minibodies (e.g., (VH-VL-CH3)2, (scFv-CH3)2, ((scFv)2-CH3+CH3), ((scFv)2-CH3) or (scFv-CH3-scFv)2), and multibodies (e.g., triabodies or tetrabodies).

The term "antibody" and "antibodies" encompass any antigen binding units, including without limitation: monoclonal antibodies, human antibodies, humanized antibodies, camelised antibodies, chimeric antibodies, and any other epitope-binding fragments.

"Prodrug" is meant to indicate a compound that may be converted under physiological conditions or by solvolysis to a biologically active compound described herein (e.g., a compound of Formula (I) or (II)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press each of which is incorporated in full by reference herein). The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound, and the like.

The term "in vivo" refers to an event that takes place in a subject's body. The term "ex vivo" refers to an event that first takes place outside of the subject's body for a subsequent in vivo application into a subject's body. For example, an ex vivo preparation may involve preparation of cells outside of a subject's body for the purpose of introduction of the prepared cells into the same or a different subject's body. The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound disclosed herein to a mammal for a period of time sufficient to yield a metabolic product thereof. Such products are typically identified by administering a radiolabeled compound of the disclosure in a detectable dose to an animal, such as rat, mouse, guinea pig, monkey, or to a human, allowing sufficient time for metabolism to occur, and isolating its conversion products from the urine, blood or other biological samples.

The term "Ras" or "RAS" refers to a protein in the Rat sarcoma (Ras) superfamily of small GTPases, such as in the Ras subfamily. The Ras superfamily includes, but is not limited to, the Ras subfamily, Rho subfamily, Rab subfamily, Rap subfamily, Arf subfamily, Ran subfamily, Rheb subfamily, RGK subfamily, Rit subfamily, Miro subfamily, and Unclassified subfamily. In some embodiments, a Ras protein is selected from the group consisting of KRAS (also used interchangeably herein as K-Ras, K-ras, or Kras), HRAS (or H-Ras), NRAS (or N-Ras), MRAS (or M-Ras), ERAS (or E-Ras), RRAS2 (or R-Ras2), RALA (or RalA), RALB (or RalB), RIT1, and any combination thereof, such as from KRAS, HRAS, NRAS, RALA, RALB, and any combination thereof.

The terms "mutant Ras" and "Ras mutant", as used interchangeably herein, refer to a Ras protein with one or more amino acid mutations, such as with respect to a common reference sequence such as a wild-type (WT) sequence. In some embodiments, a mutant Ras is selected from a mutant KRAS, mutant HRAS, mutant NRAS, mutant MRAS, mutant ERAS, mutant RRAS2, mutant RALA, mutant RALB, mutant RIT1, and any combination thereof, such as from a mutant KRAS, mutant HRAS, mutant NRAS, mutant RALA, mutant RALB, and any combination thereof. In some embodiments, a mutation can be an introduced mutation, a naturally occurring mutation, or a non-naturally occurring mutation. In some embodiments, a mutation can be a substitution (e.g., a substituted amino acid), insertion (e.g., addition of one or more amino acids), or deletion (e.g., removal of one or more amino acids). In some embodiments, two or more mutations can be consecutive, non-consecutive, or a combination thereof. In some embodiments, a mutation can be present at any position of Ras. In some embodiments, a mutation can be present at position 12, 13, 62, 92, 95, 96 (e.g., Y96D), or any combination thereof of Ras relative to SEQ ID No. 1 when optimally aligned. In some embodiments, a mutant Ras may comprise about or at least about 1, 2, 3, 4, 5, 6, 7, 8, 9, 10, 11, 12, 13, 14, 15, 16, 17, 18, 19, 20, 25, 30, 35, 40, 45, 50, or more than 50 mutations. In some embodiments, a mutant Ras may comprise up to about 1, 2, 3, 4, 5, 6, 7, 8, 9, 10, 11, 12, 13, 14, 15, 16, 17, 18, 19, 20, 25, 30, 35, 40, 45, or 50 mutations. In some embodiments, the mutant Ras is about or up to about 500, 400, 300, 250, 240, 233, 230, 220, 219, 210, 208, 206, 204, 200, 195, 190, 189, 188, 187, 186, 185, 180, 175, 174, 173, 172, 171, 170, 169,168, 167, 166, 165, 160, 155, 150, 125, 100, 90, 80, 70, 60, 50, or fewer than 50 amino acids in length. In some embodiments, an amino acid of a mutation is a proteinogenic, natural, standard, non-standard, non-canonical, essential, non-essential, or non-natural amino acid. In some embodiments, an amino acid of a mutation has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, a mutation comprises a reactive moiety. In some embodiments, a substituted amino acid comprises a reactive moiety. In some embodiments, a mutant Ras can be further modified, such as by conjugation with a detectable label. In some embodiments, a mutant Ras is a full-length or truncated polypeptide. For example, a mutant Ras can be a truncated polypeptide comprising residues 1-169 or residues 11-183 (e.g., residues 11-183 of a mutant RALA or mutant RALB).

As used herein, the term "corresponding to" or "corresponds to" as applied to an amino acid residue in a polypeptide sequence refers to the correspondence of such amino acid relative to a reference sequence when optimally aligned (e.g., taking into consideration of gaps, insertions and mismatches; wherein alignment may be primary sequence alignment or three-dimensional structural alignment of the folded proteins). For instance, the serine residue in a K-Ras G12S mutant refers to the serine corresponding to residue 12 of SEQ ID No. 4, which can serve as a reference sequence. For instance, the aspartate residue in a K-Ras G12D mutant refers to the aspartate corresponding to residue 12 of SEQ ID No. 2, which can serve as a reference sequence. When an amino acid of a mutant Ras protein corresponds to an amino acid position in the WT Ras protein, it will be understood that although the mutant Ras protein amino acid may be a different amino acid (e.g., G12D, wherein the wildtype G at position 12 is replaced by an aspartate at position 12 of SEQ ID. No. 1), the mutant amino acid is at the position corresponding to the wildtype amino acid (e.g., of SEQ ID No. 1). In embodiments, a modified Ras mutant protein disclosed herein may comprise truncations at the C-terminus, or truncations at the N-terminal end preceding the serine residue. The serine residue in such N-terminal truncated modified mutant is still considered corresponding to position 12 of SEQ ID No. 1. In addition, an aspartate residue at position 12 of SEQ ID No. 2 finds a corresponding residue in SEQ ID Nos. 6 and 8.

As used herein, the term "leaving group" refers to an atom or group that becomes detached from an atom in the residual or main part of the substrate in a specified reaction. The residual or main part of the substrate is also referred to herein as the "staying group".

Compounds

In certain aspects, the present disclosure provides a compound of Formula (I):

(I)

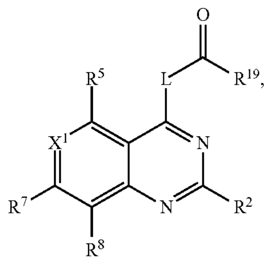

or a pharmaceutically acceptable salt or solvate thereof, wherein:

$X^1$ is selected from $CR^6$ and N;

L is $-L^1-L^2-L^3-$, wherein $L^1$, $L^2$, or $L^3$ is bound to $-C(O)R^{19}$ via a nitrogen atom, thereby forming a urea;

$L^1$ is selected from a bond, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —O—, —$N(R^{12})$—, —C(O)—, —S—, —S(O)—, —$S(O)_2$—, —$P(O)R^{12}$—, —$P(O)R^{12}O$—, —$N(R^{12})C(O)$—, —$N(R^{12})S(O)$—, —$N(R^{12})S(O)_2$—, —$N(R^{12})P(O)R^{12}$—, —$OP(O)R^{12}$—, —$C(O)N(R^{12})$—, —$S(O)N(R^{12})$—, —$S(O)_2N(R^{12})$—, and —$P(O)R^{12}N(R^{12})$—, wherein each of $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl is optionally substituted;

$L^2$ is selected from a bond, $C_{3-12}$ carbocycle and 3- to 12-membered heterocycle, wherein each of $C_{3-12}$ carbocycle and 3- to 12-membered heterocycle is optionally substituted;

$L^3$ is selected from a bond, 2- to 6-membered heteroalkyl, 3- to 6-membered heteroalkenyl, 3- to 6-membered heteroalkynyl, nitrene, —$C_{0-6}$ alkyl-(3- to 12-membered heterocycle), and -(2- to 6-membered heteroalkyl)-(3- to 12-membered heterocycle), wherein each of 2- to 6-membered heteroalkyl, 3- to 6-membered heteroalkenyl, 3- to 6-membered heteroalkynyl, nitrene, —$C_{0-6}$ alkyl-(3- to 12-membered heterocycle), and -(2- to 6-membered heteroalkyl)-(3- to 12-membered heterocycle) is optionally substituted;

$R^{19}$ is imidazol-1-yl, wherein the imidazol-1-yl is:

(a) substituted with one substituent selected from —Br, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted; or (b) substituted with two or three substituents independently selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, optionally wherein two adjacent substituents are taken together with the carbon atoms to which they are attached to form $C_{3-12}$ carbocycle or 3- to 12-membered heterocycle, and wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $C_{3-12}$ carbocycle, 3- to 12-membered heterocycle, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted;

$R^2$, $R^5$, $R^6$, and $R^8$ are each independently selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted;

$R^7$ is selected from $C_{6-12}$ aryl and 5- to 12-membered heteroaryl, each of which is optionally substituted;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein each of $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) is optionally substituted; and $R^{13}$ is independently selected at each occurrence from hydrogen, $C_{1-6}$ alkyl, and $C_{1-6}$ haloalkyl; or $R^{12}$ and $R^{13}$ attached to the same nitrogen atom form optionally substituted 3- to 10-membered heterocycle.

In certain aspects, the present disclosure provides a compound of Formula (II):

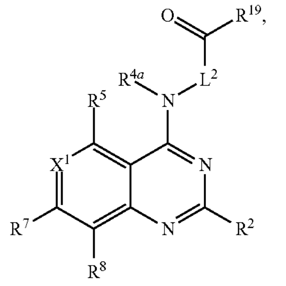

(II)

or a pharmaceutically acceptable salt or solvate thereof, wherein:

$X^1$ is selected from $CR^6$ and N;

$R^{4a}$ is selected from $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein each of $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) is optionally substituted;

$L^2$ is saturated, monocyclic 4- to 7-membered heterocycle, wherein the heterocycle is optionally substituted, and wherein —$C(O)R^{19}$ is bound to $L^2$ via a nitrogen atom, thereby forming a urea;

$R^{19}$ is selected from pyrrol-1-yl, pyrazol-1-yl, imidazol-1-yl, 1,2,3-triazol-1-yl, 1,2,3-triazol-2-yl, 1,2,4-triazol-1-yl, and 1,2,4-triazol-4-yl, each of which is optionally substituted, optionally wherein two adjacent substituents are taken together with the carbon atoms to which they are attached to form $C_{3-12}$ carbocycle or 3- to 12-membered heterocycle;

$R^2$, $R^6$, and $R^8$ are each independently selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted;

$R^7$ is selected from $C_{6-12}$ aryl and 5- to 12-membered heteroaryl, each of which is optionally substituted;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein each of $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) is optionally substituted; and $R^{13}$ is independently selected at each occurrence from hydrogen, $C_{1-6}$ alkyl, and $C_{1-6}$ haloalkyl; or $R^{12}$ and $R^{13}$ attached to the same nitrogen atom form optionally substituted 3- to 10-membered heterocycle.

In some embodiments, for a compound of Formula (II), $R^2$, $R^5$, $R^6$, and $R^8$ are each independently selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted.

In some embodiments, the compound of Formula (I) is selected from:

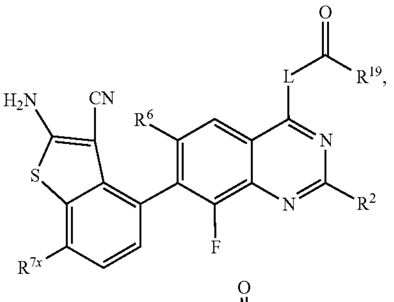

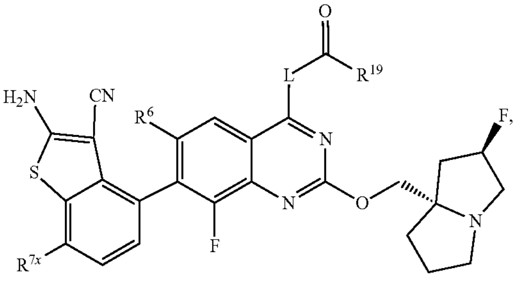

and

-continued

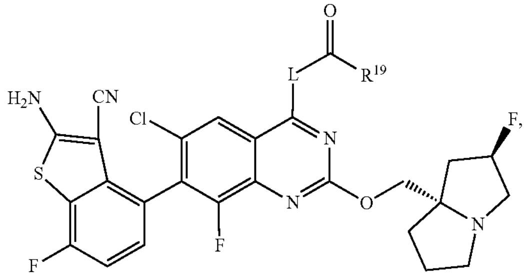

or a pharmaceutically acceptable salt or solvate thereof, wherein $R^{7x}$ is selected from hydrogen and —F. In some embodiments, the compound of Formula (I)

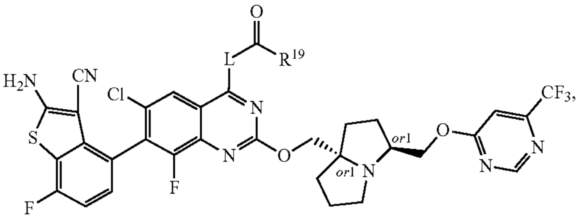

or a pharmaceutically acceptable salt or solvate thereof.

In some embodiments, the compound of Formula (II) is selected from:

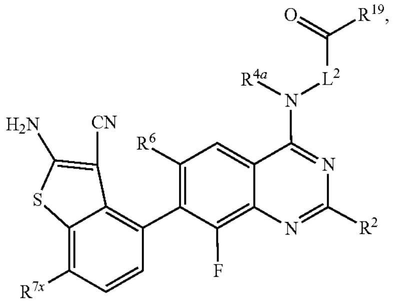

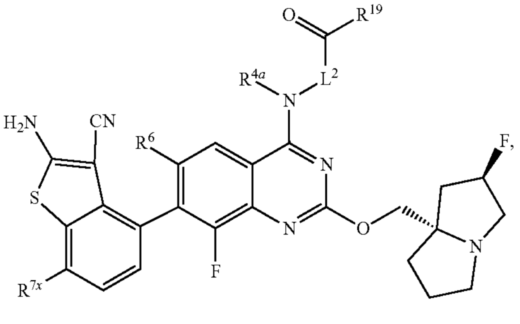

and

-continued

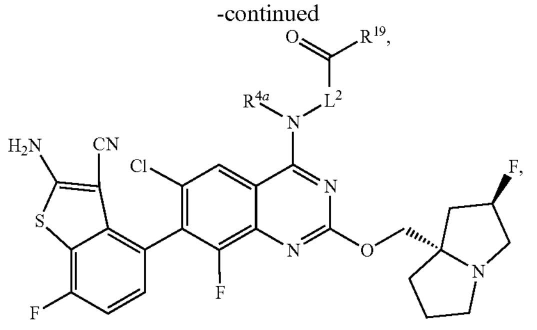

or a pharmaceutically acceptable salt or solvate thereof, wherein $R^{7x}$ is selected from hydrogen and —F. In some embodiments, the compound of Formula (II)

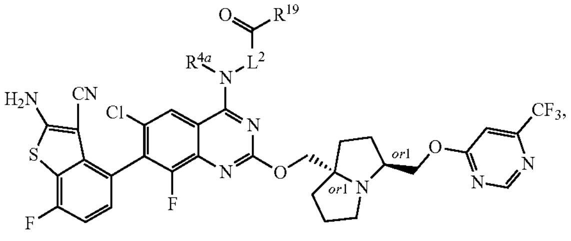

or a pharmaceutically acceptable salt or solvate thereof.

In some embodiments, for a compound of Formula (I), L is $-L^1-L^2-L^3-$, wherein $L^3$ is bound to —C(O)$R^{19}$ via a nitrogen atom, thereby forming a urea. In some embodiments, L is $-L^1-L^2-$, wherein $L^2$ is bound to —C(O)$R^{19}$ via a nitrogen atom, thereby forming a urea. In some embodiments, L is $-L^2-L^3-$, wherein $L^3$ is bound to —C(O)$R^{19}$ via a nitrogen atom, thereby forming a urea. In some embodiments, L is $-L^1-L^3-$, wherein $L^3$ is bound to —C(O)$R^{19}$ via a nitrogen atom, thereby forming a urea. In some embodiments, L is $-L^1-$, wherein $L^1$ is bound to —C(O)$R^{19}$ via a nitrogen atom, thereby forming a urea. In some embodiments, L is $-L^2-$, wherein $L^2$ is bound to —C(O)$R^{19}$ via a nitrogen atom, thereby forming a urea. In some embodiments, L is $-L^3-$, wherein $L^3$ is bound to —C(O)$R^{19}$ via a nitrogen atom, thereby forming a urea.

In some embodiments, for a compound of Formula (I), $L^1$ is selected from a bond, $C_{1-6}$ alkyl, 2- to 6-membered heteroalkyl, —O—, —N($R^{12}$)—, —C(O)—, —N($R^{12}$)C(O)—, —N($R^{12}$)S(O)—, —N($R^{12}$)S(O)$_2$—, —C(O)N($R^{12}$)—, —S(O)N($R^{12}$)—, and —S(O)$_2$N($R^{12}$)—, wherein each of $C_{1-6}$ alkyl and 2- to 6-membered heteroalkyl is optionally substituted. In some embodiments, $L^1$ is selected from a bond, $C_{1-6}$ alkyl, 2- to 6-membered heteroalkyl, —O—, —N($R^{12}$)—, —C(O)—, —N($R^{12}$)C(O)—, —N($R^{12}$)S(O)—, —N($R^{12}$)S(O)$_2$—, —C(O)N($R^{12}$)—, —S(O)N($R^{12}$)—, and —S(O)$_2$N($R^{12}$)—. In some embodiments, $L^1$ is selected from a bond, $C_{1-6}$ alkyl, 2- to 6-membered heteroalkyl, —N($R^{12}$)—, —C(O)—, —N($R^{12}$)C(O)—, and —C(O)N($R^{12}$)—, wherein each of $C_{1-6}$ alkyl and 2- to 6-membered heteroalkyl is optionally substituted. In some embodiments, $L^1$ is a bond. In some embodiments, $L^1$ is 2- to 6-membered heteroalkyl, such as —$CH_2$NH—, —$CH_2N(CH_3)$—, —NH$CH_2$—, or —$N(CH_3)CH_2$—. In some embodiments, $L^1$ is —N($R^{12}$)—, such as —$N(CH_3)$—, —$N(CH_2CH_3)$—, or —$N(CH(CH_3)_2)$—. In some embodiments, $L^1$ is selected from a bond, 2- to 6-membered heteroalkyl, and —N($R^{12}$)—.

In some embodiments, for a compound of Formula (I), $L^2$ is selected from $C_{3-12}$ carbocycle and 3- to 12-membered heterocycle, each of which is optionally substituted. In some embodiments, $L^2$ is a bond. In some embodiments, $L^2$ is optionally substituted 3- to 7-membered monocyclic heterocycle, such as optionally substituted 3- to 7-membered monocyclic heterocycloalkyl. In some embodiments, $L^2$ is optionally substituted 6- to 12-membered spirocyclic heterocycle, such as optionally substituted 6- to 12-membered spirocyclic heterocycloalkyl. In some embodiments, $L^2$ is optionally substituted 7- to 12-membered fused bicyclic heterocycle, such as optionally substituted 7- to 12-membered fused bicyclic heterocycloalkyl.

In some embodiments, for a compound of Formula (I) or (II), $L^2$ is saturated, monocyclic 4- to 7-membered heterocycle, wherein the heterocycle is optionally substituted, and wherein —C(O)$R^{19}$ is bound to $L^2$ via a nitrogen atom, thereby forming a urea. In some embodiments, $L^2$ is saturated 5- to 6-membered monocyclic heterocycle, wherein the heterocycle is optionally substituted. In some embodiments, $L^2$ is saturated 5-membered monocyclic heterocycle, wherein the heterocycle is optionally substituted. In some embodiments, $L^2$ is saturated 6-membered monocyclic heterocycle, wherein the heterocycle is optionally substituted. In some embodiments, $L^2$ is selected from azetidin-1,3-diyl, pyrrolidin-1,3-diyl, piperidin-1,3-diyl, piperidin-1,4-diyl, azepan-1,3-diyl, and azepan-1,4-diyl, each of which is optionally substituted. In some embodiments, $L^2$ is pyrrolidin-1,3-diyl. In some embodiments, $L^2$ is piperidin-1,3-diyl. In some embodiments, $L^2$ is piperidin-1,4-diyl. In some embodiments, $L^2$ is substituted with $C_{1-6}$ alkyl. In some embodiments, $L^2$ is substituted with —$CH_3$, —$CH_2CH_3$, or —$CH(CH_3)_2$. In some embodiments, $L^2$ is substituted with —$CH_3$. In some embodiments, $L^2$ is substituted with —$CH_2CH_3$. In some embodiments, $L^2$ is substituted with —$CH(CH_3)_2$. In some embodiments, $L^2$ is selected from pyrrolidin-1,3-diyl, 4-fluoropyrrolidin-1,3-diyl, 2-methylpyrrolidin-1,3-diyl, 2-ethylpyrrolidin-1,3-diyl, 2-isopropylpyrrolidin-1,3-diyl, 5-fluoropyrrolidin-1,3-diyl, 5-methylpyrrolidin-1,3-diyl, and 5-isopropylpyrrolidin-1,3-diyl. In some embodiments, $L^2$ is pyrrolidin-1,3-diyl. In some embodiments, $L^2$ is 4-fluoropyrrolidin-1,3-diyl. In some embodiments, $L^2$ is 2-methylpyrrolidin-1,3-diyl. In some embodiments, $L^2$ is 2-ethylpyrrolidin-1,3-diyl. In some embodiments, $L^2$ is 2-isopropylpyrrolidin-1,3-diyl. In some embodiments, $L^2$ is 5-fluoropyrrolidin-1,3-diyl. In some embodiments, $L^2$ is 5-methylpyrrolidin-1,3-diyl. In some embodiments, $L^2$ is 5-isopropylpyrrolidin-1,3-diyl. In some embodiments, $L^2$ is pyrrolidin-1,3-diyl, optionally substituted with halogen or $C_{1-3}$ alkyl.

In some embodiments, for a compound of Formula (I), $L^3$ is selected from a bond, 2- to 6-membered heteroalkyl, nitrene, —$C_{0-6}$ alkyl-(3- to 12-membered heterocycle), and -(2- to 6-membered heteroalkyl)-(3- to 12-membered heterocycle), wherein each of 2- to 6-membered heteroalkyl, nitrene, —$C_{0-6}$ alkyl-(3- to 12-membered heterocycle), and -(2- to 6-membered heteroalkyl)-(3- to 12-membered heterocycle) is optionally substituted. In some embodiments, $L^3$ is selected from a bond, 2- to 6-membered heteroalkyl, and nitrene, wherein each of 2- to 6-membered heteroalkyl and nitrene is optionally substituted. In some embodiments, $L^3$ is optionally substituted nitrene, such as —NH—, —$N(CH_3)$—, —$N(CH_2CH_3)$—, or —$N(CH(CH_3)_2)$—. In some embodiments, $L^3$ is 2- to 6-membered heteroalkyl, such as —$CH_2$NH—, —$CH_2N(CH_3)$—, —NH$CH_2$—, or —$N(CH_3)CH_2$—. In some embodiments, $L^3$ is a bond.

In some embodiments, for a compound of Formula (I), $L^1$ is selected from a bond, $C_{1-6}$ alkyl, 2- to 6-membered heteroalkyl, —N($R^{12}$)—, —C(O)—, —N($R^{12}$)C(O)—, and —C(O)N($R^{12}$)—, wherein each of $C_{1-6}$ alkyl and 2- to 6-membered heteroalkyl is optionally substituted; $L^2$ is selected from a bond, $C_{3-12}$ carbocycle and 3- to 12-membered heterocycle, wherein each of $C_{3-12}$ carbocycle and 3- to 12-membered heterocycle is optionally substituted; and $L^3$ is selected from a bond, 2- to 6-membered heteroalkyl, and nitrene, wherein each of 2- to 6-membered heteroalkyl and nitrene is optionally substituted. In some embodiments, $L^1$ is a bond; $L^2$ is selected from a bond, $C_{3-12}$ carbocycle and 3- to 12-membered heterocycle, wherein each of $C_{3-12}$ carbocycle and 3- to 12-membered heterocycle is optionally substituted; and $L^3$ is selected from a bond, 2- to 6-membered heteroalkyl, and nitrene, wherein each of 2- to 6-membered heteroalkyl and nitrene is optionally substituted. In some embodiments, $L^1$ is a bond; $L^2$ is selected from a bond and optionally substituted 3- to 12-membered heterocycle; and $L^3$ is selected from a bond, 2- to 6-membered heteroalkyl, and nitrene, wherein each of 2- to 6-membered heteroalkyl and nitrene is optionally substituted. In some embodiments, $L^1$ is a bond; $L^2$ is optionally substituted 3- to 12-membered heterocycle; and $L^3$ is a bond. In some embodiments, $L^1$ is a bond; $L^2$ is optionally substituted 6- to 12-membered spirocyclic heterocycle; and $L^3$ is a bond. In some embodiments, $L^1$ is —N($R^{12}$)—; $L^2$ is optionally substituted 4- to 7-membered heterocycle; and $L^3$ is a bond. In some embodiments, $L^1$ is —N($R^{12}$)—; $L^2$ is saturated, monocyclic 4- to 7-membered heterocycle, wherein the heterocycle is optionally substituted; and $L^3$ is a bond. In some embodiments, $L^1$ is a bond; $L^2$ is selected from $C_{3-12}$ carbocycle and 3- to 12-membered heterocycle, each of which is optionally substituted; and $L^3$ is optionally substituted 2- to 6-membered heteroalkyl. In some embodiments, $L^2$ is optionally substituted 3- to 12-membered heterocycle; and $L^3$ is a bond. In some embodiments, $L^1$ is a bond; $L^2$ is selected from $C_{3-12}$ carbocycle and 3- to 12-membered heterocycle, each of which is optionally substituted; and $L^3$ is optionally substituted nitrene. In some embodiments, $L^2$ is selected from $C_{3-12}$ carbocycle and 3- to 12-membered heterocycle, each of which is optionally substituted; and $L^3$ is optionally substituted nitrene. In some embodiments, $L^2$ is optionally substituted 6- to 12-membered spirocyclic heterocycle.

In some embodiments, for a compound of Formula (I), -$L^2$-$L^3$-C(O)$R^{19}$ is selected from:

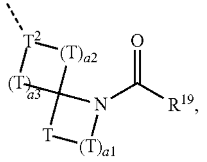

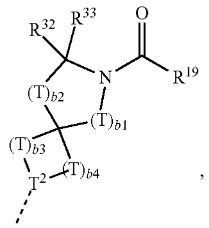
,

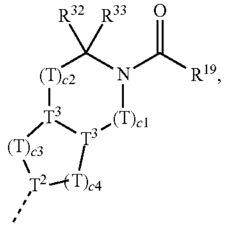

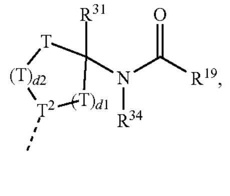

-continued

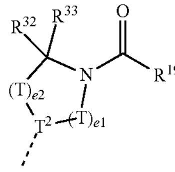
and
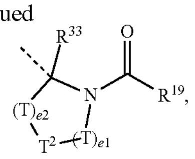

wherein:

a1, b1, b3, and b4 are independently 1, 2, 3, 4, or 5;

a2, a3, and b2 are independently 0, 1, 2, 3, 4, or 5;

c1, c2, c3, c4, d1, d2, e1, and e2 are independently 0, 1, 2, 3, or 4;

wherein the sum of a1, a2, and a3 is less than 9; the sum of b1, b2, b3, and b4 is less than 9; the sum of c1, c2, c3, and c4 is less than 8; the sum of d1 and d2 is less than 6; and the sum of e1 and e2 is less than 6;

T is independently selected at each occurrence from N($R^{35}$), C($R^{36}$)$_2$, C(O), O, S(O), and S(O)$_2$;

$T^2$ and $T^3$ are independently selected at each occurrence from N and C($R^{36}$);

$R^{31}$, $R^{32}$, $R^{33}$, and $R^{36}$ are independently selected at each occurrence from hydrogen and $R^{40}$;

$R^{34}$ and $R^{35}$ are independently selected at each occurrence from hydrogen and $R^{41}$;

$R^{40}$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —O$R^{12}$, —S$R^{12}$, —N($R^{12}$)($R^{13}$), —C(O)O$R^{12}$, —OC(O)N($R^{12}$)($R^{13}$), —N($R^{12}$)C(O)N($R^{12}$)($R^{13}$), —N($R^{12}$)C(O)O$R^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)(N$R^{12}$)$R^{12}$, —S(O)$_2$N($R^{12}$)($R^{13}$), —S(═O)(═N$R^{12}$)N($R^{12}$)($R^{13}$), and —OCH$_2$C(O)O$R^{12}$; wherein two $R^{40}$ attached to the same carbon atom optionally join to form ═N$R^{12}$, ═C($R^{14}$)$_2$, or ═O; wherein two $R^{40}$ and the atom(s) to which they are attached optionally form $C_{3-12}$ carbocycle or 3- to 12-membered heterocycle; wherein $R^{40}$ and $R^{41}$ and the atoms to which they are attached optionally form 3- to 12-membered heterocycle; and wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted;

$R^{41}$ is independently selected at each occurrence from —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —C(O)O$R^{12}$, —C(O)$R^{12}$, —C(O)N($R^{12}$)($R^{13}$), —C(O)C(O)N($R^{12}$)($R^{13}$), —S(O)$_2R^{12}$, —S(O)(N$R^{12}$)$R^{12}$, —S(O)$_2$N($R^{12}$)($R^{13}$), and —S(═O)(═N$R^{12}$)N($R^{12}$)($R^{13}$), wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted; and $R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein each of $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle is optionally substituted.

In some embodiments, for a compound of Formula (II), -$L^2$-C(O)$R^{19}$ is selected from:

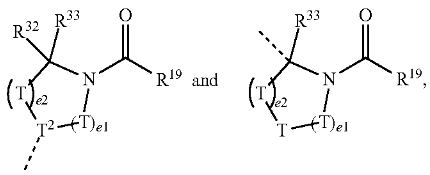

wherein:

e1 and e2 are independently 0, 1, 2, 3, or 4;

wherein the sum of e1 and e2 is less than 5;

T is independently selected at each occurrence from N($R^{31}$), C($R^{36}$)$_2$, C(O), O, S(O), and S(O)$_2$;

$T^2$ is selected from N and C($R^{36}$);

$R^{32}$, $R^{33}$, and $R^{36}$ are independently selected at each occurrence from hydrogen and $R^{40}$;

$R^{35}$ is independently selected at each occurrence from hydrogen and $R^{41}$;

$R^{40}$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(═O)(═$NR^{12}$)N($R^{12}$)($R^{13}$), and —$OCH_2$C(O)$OR^{12}$; wherein two $R^{40}$ attached to the same carbon atom optionally join to form ═$NR^{12}$, ═C($R^{14}$)$_2$, or ═O; wherein two $R^{40}$ and the atom(s) to which they are attached optionally form $C_{3-12}$ carbocycle or 3- to 12-membered heterocycle; wherein $R^{40}$ and $R^{41}$ and the atoms to which they are attached optionally form 3- to 12-membered heterocycle; and wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted;

$R^{41}$ is independently selected at each occurrence from —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —C(O)$OR^{12}$, —C(O)$R^{12}$, —C(O)N($R^{12}$)($R^{13}$), —C(O)C(O)N($R^{12}$)($R^{13}$), —S(O)$_2R^{12}$, —S(O)($NR^{12}$)$R^{12}$, —S(O)$_2$N($R^{12}$)($R^{13}$), and —S(═O)(═$NR^{12}$)N($R^{12}$)($R^{13}$), wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) is optionally substituted; and $R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein each of $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle is optionally substituted.

In some embodiments, $R^{40}$ is independently selected at each occurrence from halogen, —CN, $C_{1-6}$ alkyl, and $C_{3-6}$ cycloalkyl, or two $R^{40}$ attached to the same carbon atom form $C_{3-6}$ cycloalkyl, wherein each of $C_{1-6}$ alkyl and $C_{3-6}$ cycloalkyl is optionally substituted with one, two, or three substituents selected from halogen, —CN, $C_{1-6}$ alkyl, $C_{1-6}$ haloalkyl, $C_{3-6}$ cycloalkyl, —O($C_{1-6}$ alkyl), and —O($C_{1-6}$ haloalkyl). In some embodiments, $R^{41}$ is independently selected at each occurrence from $C_{1-6}$ alkyl and $C_{3-6}$ cycloalkyl, each of which is optionally substituted with one, two, or three substituents selected from halogen, —CN, $C_{1-6}$ alkyl, $C_{1-6}$ haloalkyl, —O($C_{1-6}$ alkyl), and —O($C_{1-6}$ haloalkyl).

In some embodiments, $R^{31}$ is selected from hydrogen, halogen, —CN, $C_{1-6}$ alkyl, and $C_{3-6}$ cycloalkyl, wherein each of $C_{1-6}$ alkyl and $C_{3-6}$ cycloalkyl is optionally substituted with one, two, or three substituents selected from halogen, —CN, $C_{1-6}$ alkyl, $C_{1-6}$ haloalkyl, $C_{3-6}$ cycloalkyl, —O($C_{1-6}$ alkyl), and —O($C_{1-6}$ haloalkyl). In some embodiments, $R^{31}$ is selected from hydrogen and $C_{1-6}$ alkyl. In some embodiments, $R^{31}$ is hydrogen.

In some embodiments, $R^{32}$ is selected from hydrogen, halogen, —CN, $C_{1-6}$ alkyl, and $C_{3-6}$ cycloalkyl, wherein each of $C_{1-6}$ alkyl and $C_{3-6}$ cycloalkyl is optionally substituted with one, two, or three substituents selected from halogen, —CN, $C_{1-6}$ alkyl, $C_{1-6}$ haloalkyl, $C_{3-6}$ cycloalkyl, —O($C_{1-6}$ alkyl), and —O($C_{1-6}$ haloalkyl). In some embodiments, $R^{32}$ is selected from hydrogen and $C_{1-6}$ alkyl. In some embodiments, $R^{32}$ is hydrogen.

In some embodiments, $R^{33}$ is selected from hydrogen, halogen, —CN, $C_{1-6}$ alkyl, and $C_{3-6}$ cycloalkyl, wherein each of $C_{1-6}$ alkyl and $C_{3-6}$ cycloalkyl is optionally substituted with one, two, or three substituents selected from halogen, —CN, $C_{1-6}$ alkyl, $C_{1-6}$ haloalkyl, $C_{3-6}$ cycloalkyl, —O($C_{1-6}$ alkyl), and —O($C_{1-6}$ haloalkyl). In some embodimentsments, $R^{33}$ is selected from hydrogen and $C_{1-6}$ alkyl. In some embodiments, $R^{33}$ is hydrogen.

In some embodiments, $R^{36}$ is independently selected at each occurrence from hydrogen, halogen, —CN, $C_{1-6}$ alkyl, and $C_{3-6}$ cycloalkyl, wherein each of $C_{1-6}$ alkyl and $C_{3-6}$ cycloalkyl is optionally substituted with one, two, or three substituents selected from halogen, —CN, $C_{1-6}$ alkyl, $C_{1-6}$ haloalkyl, $C_{3-6}$ cycloalkyl, —O($C_{1-6}$ alkyl), and —O($C_{1-6}$ haloalkyl). In some embodiments, $R^{36}$ is independently selected at each occurrence from hydrogen and $C_{1-6}$ alkyl. In some embodiments, $R^{36}$ is hydrogen.

In some embodiments, $R^{34}$ is selected from hydrogen, $C_{1-6}$ alkyl and $C_{3-6}$ cycloalkyl, each of which is optionally substituted with one, two, or three substituents selected from halogen, —CN, $C_{1-6}$ alkyl, $C_{1-6}$ haloalkyl, —O($C_{1-6}$ alkyl), and —O($C_{1-6}$ haloalkyl). In some embodiments, $R^{34}$ is selected from hydrogen and $C_{1-6}$ alkyl. In some embodiments, $R^{34}$ is hydrogen. In some embodiments, $R^{34}$ is $C_{1-6}$ alkyl.

In some embodiments, $R^{35}$ is independently selected at each occurrence from hydrogen, $C_{1-6}$ alkyl and $C_{3-6}$ cycloalkyl, each of which is optionally substituted with one, two, or three substituents selected from halogen, —CN, $C_{1-6}$ alkyl, $C_{1-6}$ haloalkyl, —O($C_{1-6}$ alkyl), and —O($C_{1-6}$ haloalkyl). In some embodiments, $R^{35}$ is independently selected at each occurrence from hydrogen and $C_{1-6}$ alkyl. In some embodiments, $R^{35}$ is hydrogen.

In some embodiments, for a compound of Formula (I) or (II), $R^{19}$ is substituted with —Br. In some embodiments, $R^{19}$ is substituted with $C_{1-3}$ alkyl and optionally further substituted with one or two substituents independently selected from halogen, —CN, $C_{1-3}$ alkyl, and $C_{3-6}$ cycloalkyl, wherein each of $C_{1-3}$ alkyl and $C_{3-6}$ cycloalkyl is optionally substituted with one, two, or three substituents independently selected from halogen, —CN, $C_{1-6}$ alkyl, —O($C_{1-6}$ alkyl), and —O($C_{1-6}$ haloalkyl). In some embodiments, $R^{19}$ is substituted with —$CH_3$ and optionally further substituted with —F, —Cl, —Br, —CN, or —$CH_3$. In some embodiments, $R^{19}$ is substituted with two —$CH_3$ groups. In some embodiments, $R^{19}$ is substituted with —$CH_3$ and —F. In some embodiments, $R^{19}$ is substituted with —$CH_3$ and —Cl. In some embodiments, $R^{19}$ is substituted with —$CH_3$ and —Br. In some embodiments, $R^{19}$ is substituted with —$CH_3$ and —CN. In some embodiments, $R^{19}$ is unsubstituted. In some embodiments, $R^{19}$ is substituted with —$CH_3$. In some embodiments, $R^{19}$ is substituted with —F. In some embodiments, $R^{19}$ is substituted with —Cl. In some embodiments, $R^{19}$ is substituted with —Br. In some embodiments, $R^{19}$ is substituted with —CN.

In some embodiments, for a compound of Formula (II), $R^{19}$ is selected from 1,2,3-triazol-1-yl, 1,2,3-triazol-2-yl, 1,2,4-triazol-1-yl, and 1,2,4-triazol-4-yl, each of which is optionally substituted. In some embodiments, $R^{19}$ is 1,2,3-triazol-1-yl. In some embodiments, $R^{19}$ is 1,2,3-triazol-2-yl. In some embodiments, $R^{19}$ is 1,2,4-triazol-1-yl. In some embodiments, $R^{19}$ is 1,2,4-triazol-4-yl. In some embodiments, $R^{19}$ is optionally substituted imidazol-1-yl. In some embodiments, $R^{19}$ is selected from imidazol-1-yl and 1,2,4-triazol-1-yl, each of which is optionally substituted.

In some embodiments, for a compound of Formula (II), $R^{19}$ is optionally substituted with one or two substituents independently selected from halogen, —CN, $C_{1-6}$ alkyl, and $C_{3-6}$ cycloalkyl, wherein each of $C_{1-6}$ alkyl and $C_{3-6}$ cycloalkyl is optionally substituted with one, two, or three substituents independently selected from halogen, —CN, $C_{1-6}$ alkyl, —O($C_{1-6}$ alkyl), and —O($C_{1-6}$ haloalkyl). In some embodiments, $R^{19}$ is optionally substituted with one or two substituents independently selected from halogen, —CN, $C_{1-6}$ alkyl, $C_{1-6}$ haloalkyl, and $C_{3-6}$ cycloalkyl. In some embodiments, $R^{19}$ is substituted with one or two substituents independently selected from halogen, —CN, $C_{1-6}$ alkyl, and $C_{1-6}$ haloalkyl. In some embodiments, $R^{19}$ is substituted with halogen, such as —F or —Cl. In some embodiments, $R^{19}$ is substituted with —CN. In some embodiments, $R^{19}$ is unsubstituted. In some embodiments, $R^{19}$ is optionally substituted with one or two substituents independently selected from halogen, —CN, $C_{1-6}$ alkyl, —O($C_{1-6}$ alkyl), and $C_{3-6}$ cycloalkyl, wherein each of $C_{1-6}$ alkyl —O($C_{1-6}$ alkyl), and $C_{3-6}$ cycloalkyl is optionally substituted with one, two, or three substituents independently selected from halogen, —CN, $C_{1-6}$ alkyl, —O($C_{1-6}$ alkyl), and —O($C_{1-6}$ haloalkyl).

In some embodiments, for a compound of Formula (II), $R^{19}$ is selected from

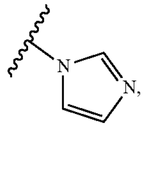 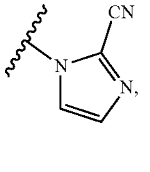 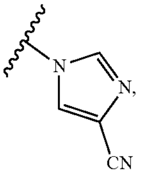

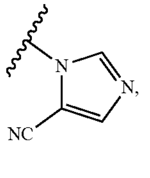 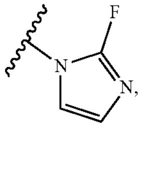 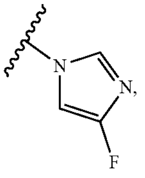

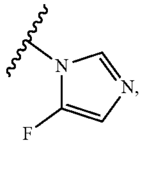 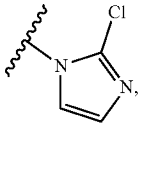 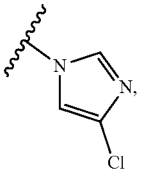

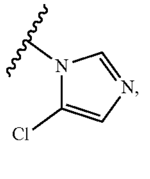 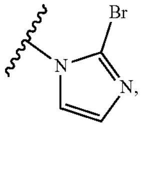 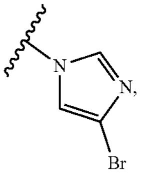

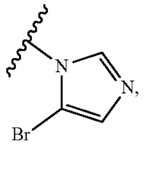 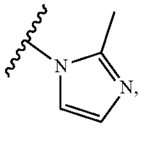 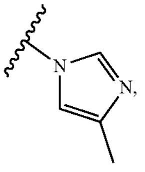

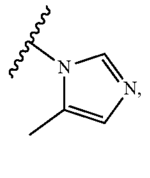 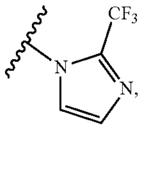 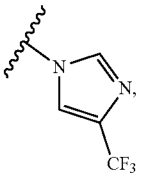

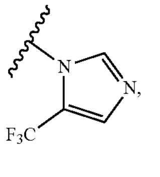 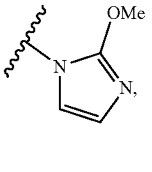 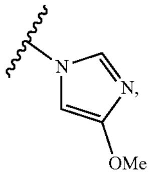

-continued
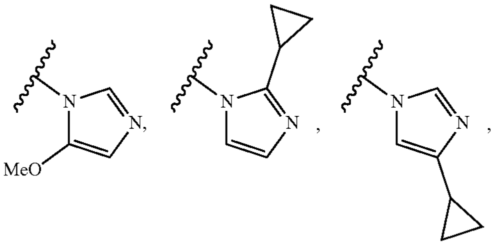
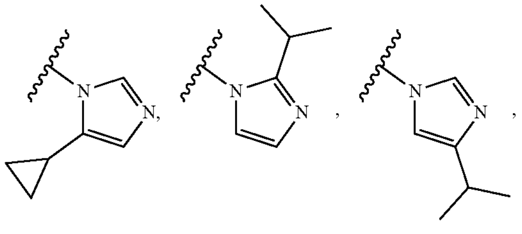
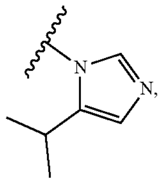
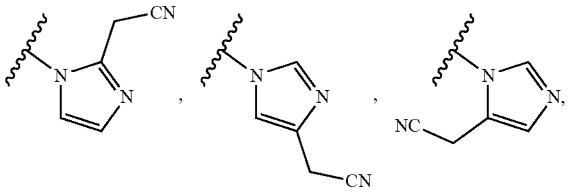
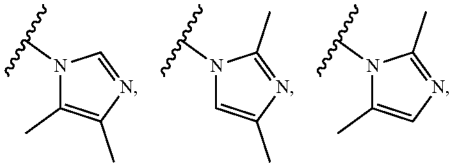
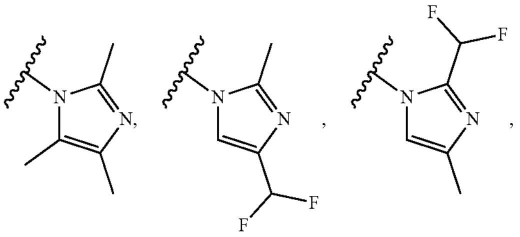
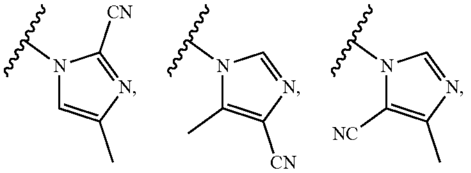
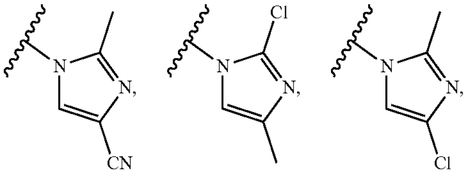
-continued
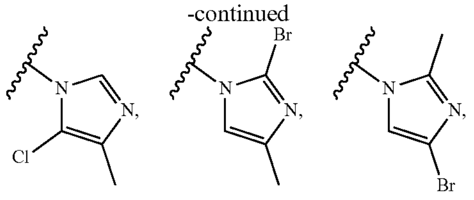
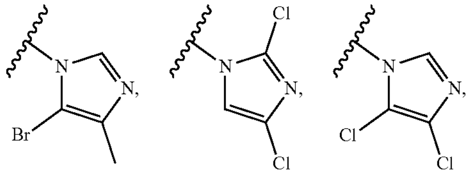
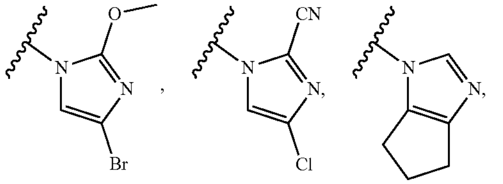
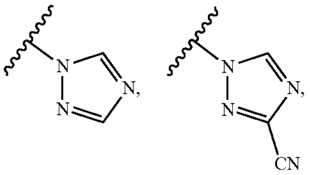
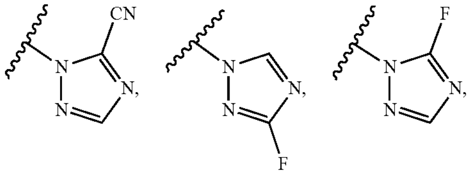
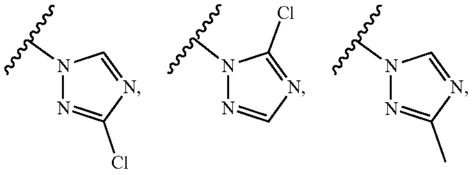
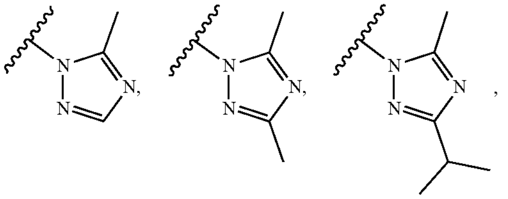
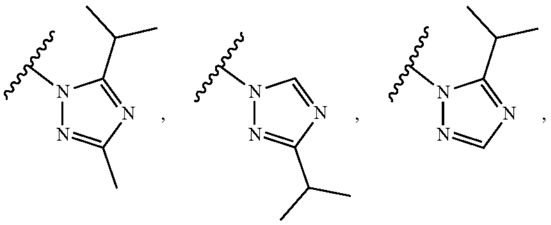
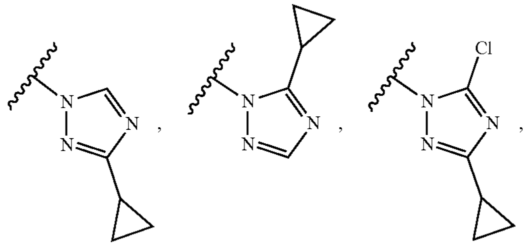

-continued
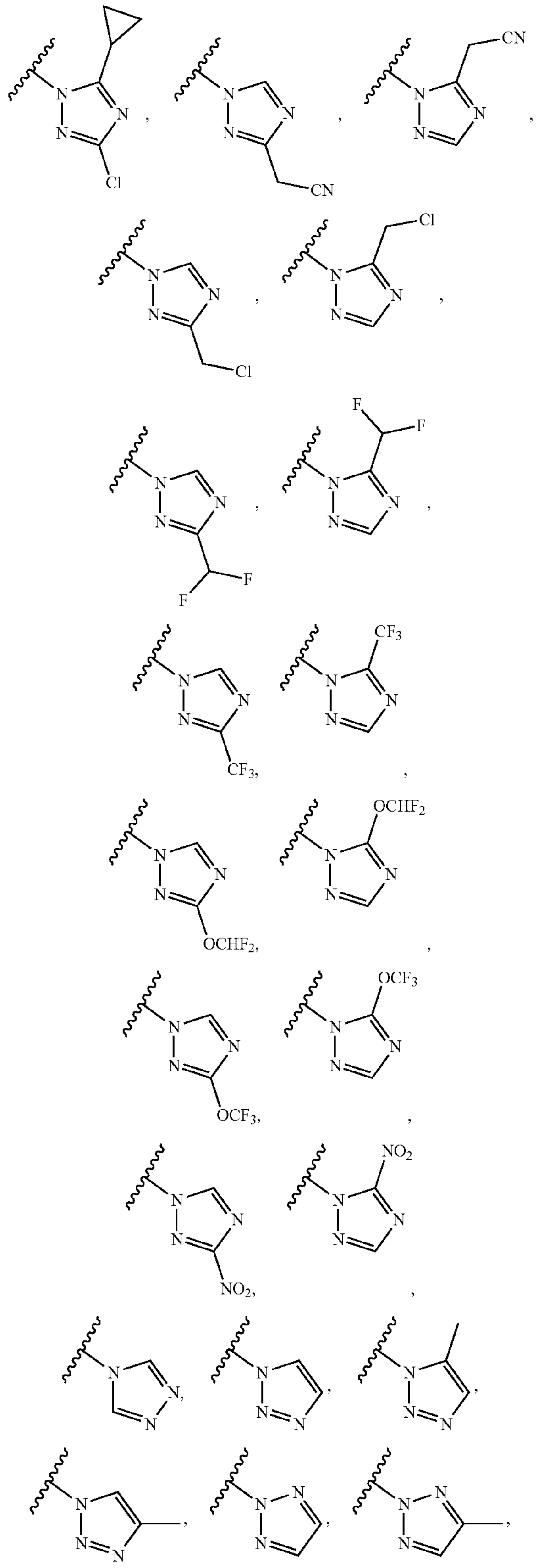
-continued
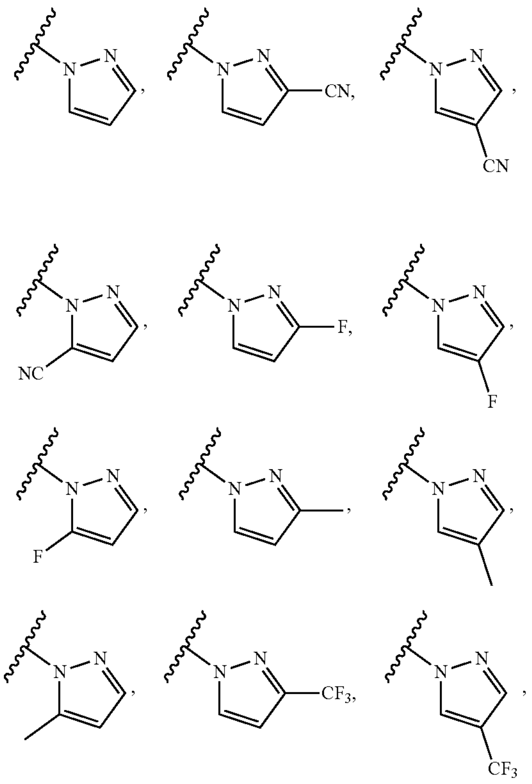
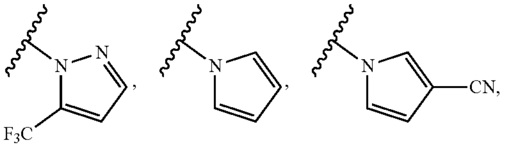
and
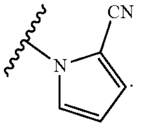
In some embodiments, $R^{19}$ is selected from
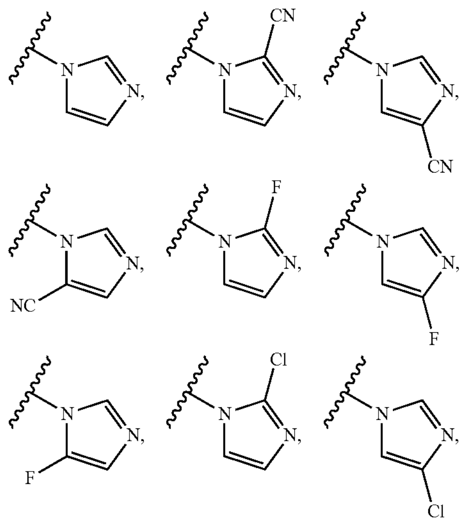

-continued
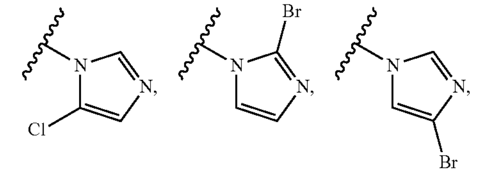
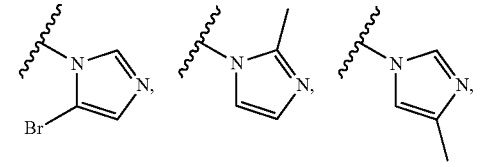
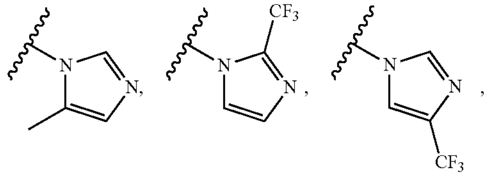
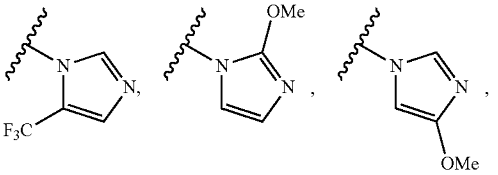
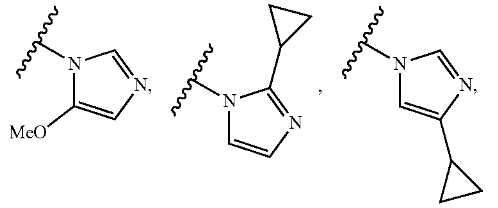
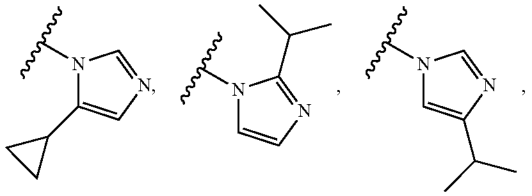
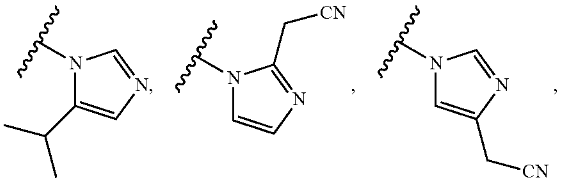
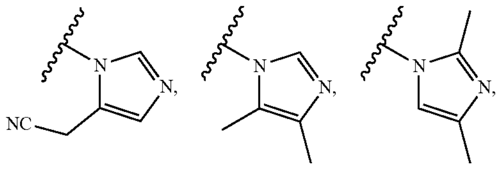
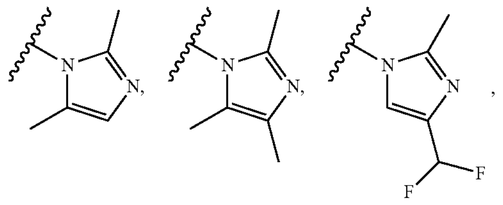
-continued
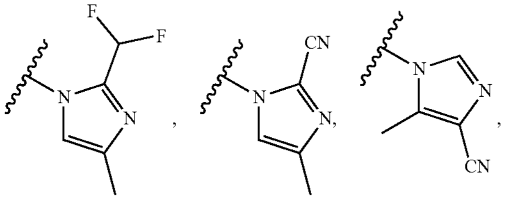
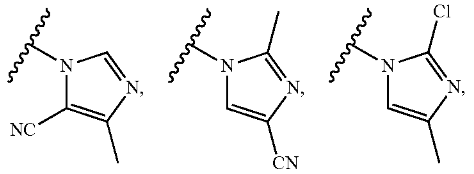
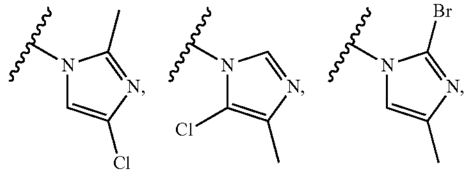
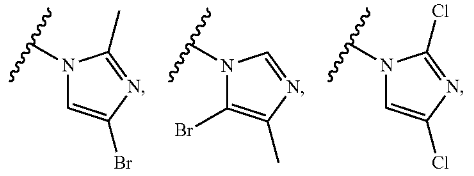
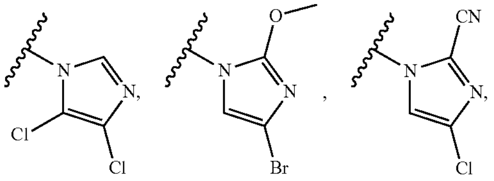
and
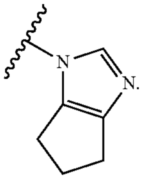
In some embodiments, $R^{19}$ is selected from
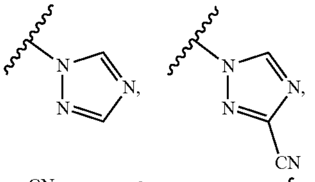
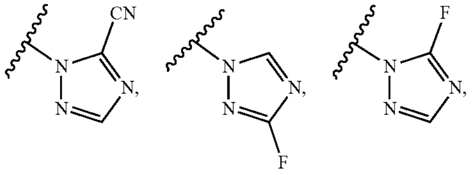
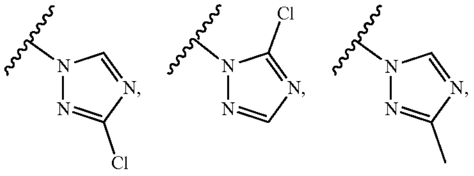

-continued
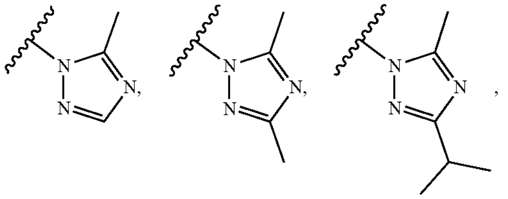
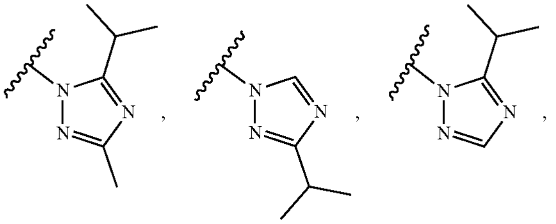
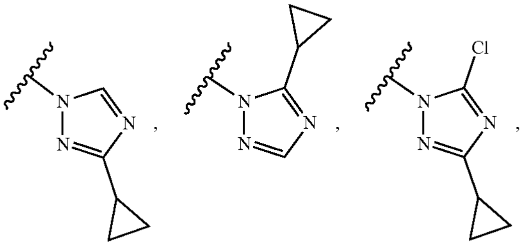
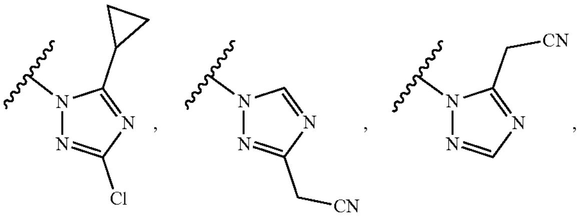
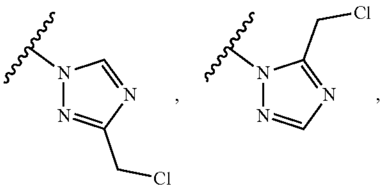
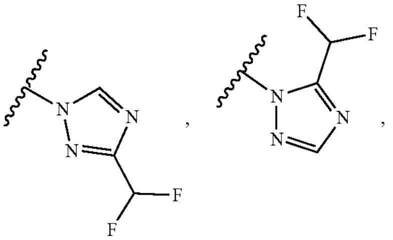
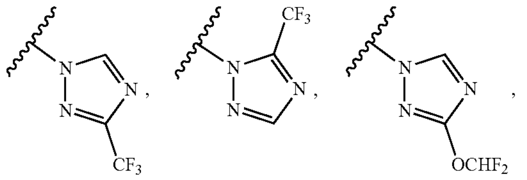
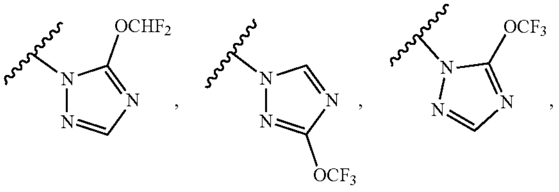
-continued
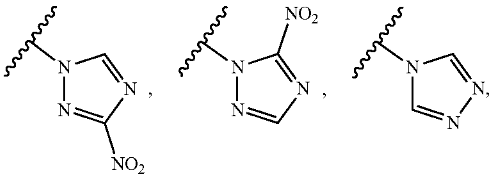
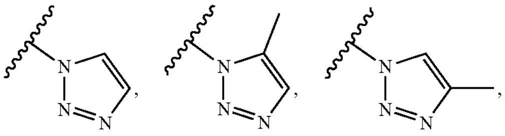
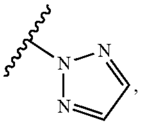
and
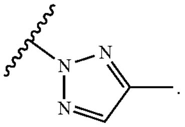
In some embodiments, $R^{19}$ is selected from
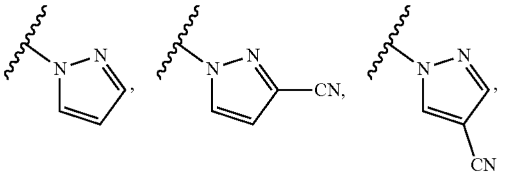
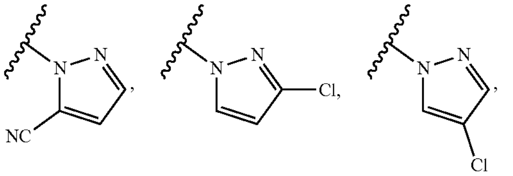
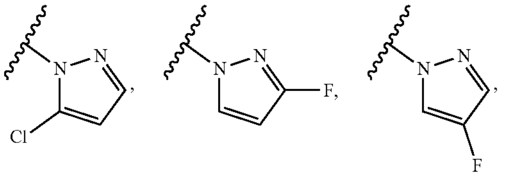
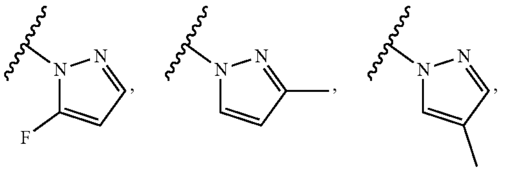
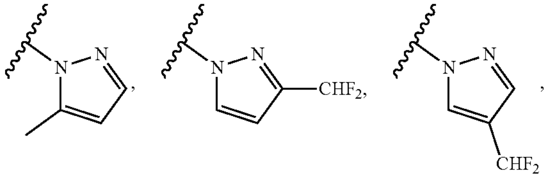
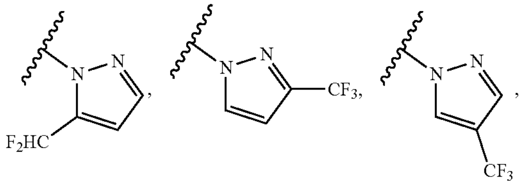
and -continued
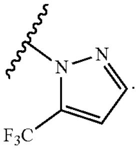.
In some embodiments $R^{19}$ is selected from
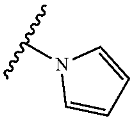, 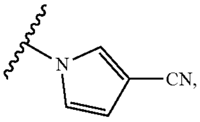, and
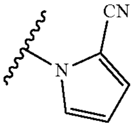.
In some embodiments, for a compound of Formula (I) or (II), $R^{19}$ is selected from
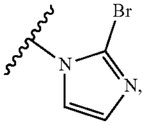, 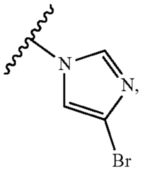, 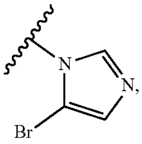,
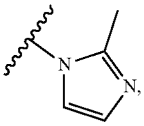, 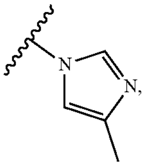, 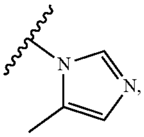,
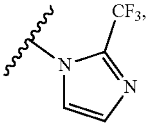, 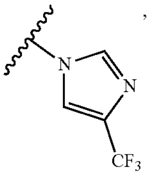, 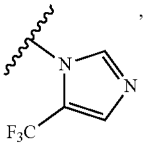,
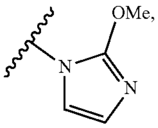, 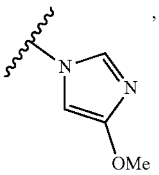, 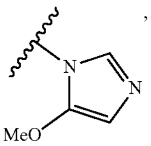,
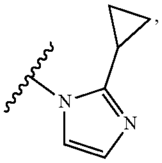, 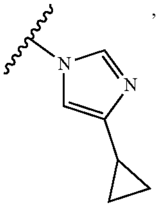, 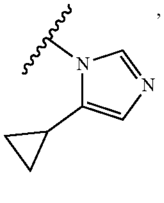,
-continued
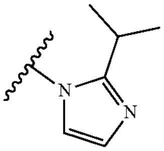, 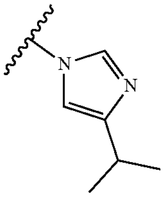, 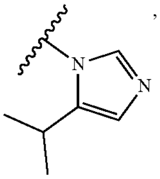,
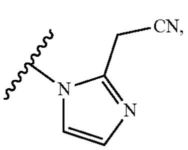, 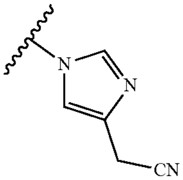, 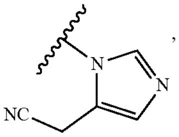,
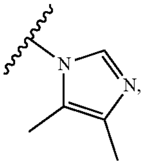, 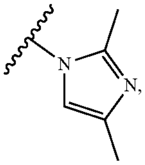, 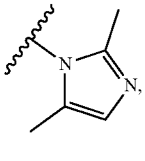,
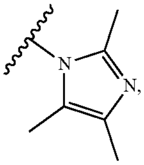, 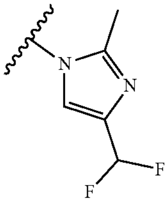, 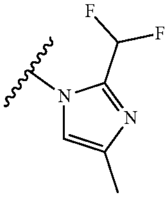,
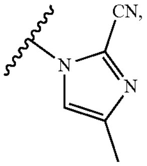, 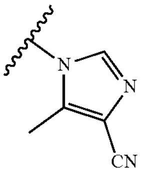, 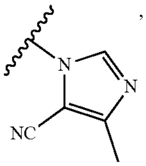,
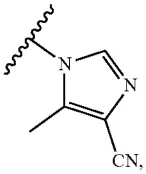, 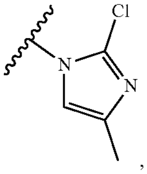, 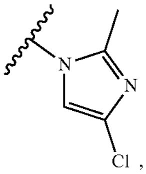,
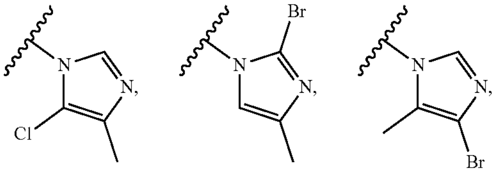
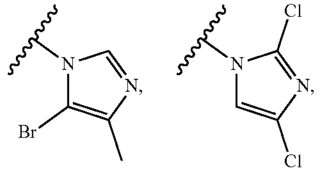
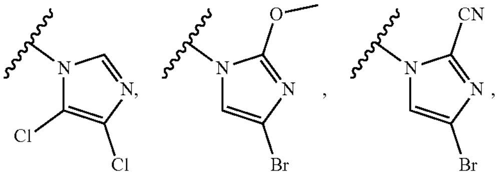 and -continued
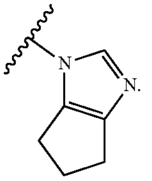
In some embodiments, $R^{19}$ is selected from
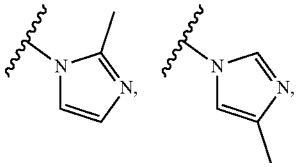
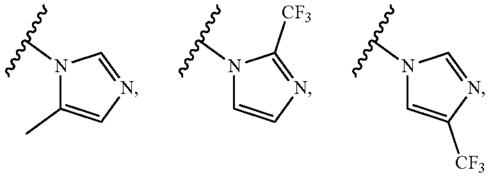
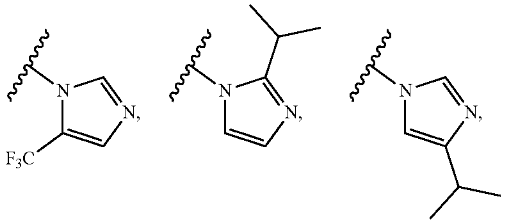
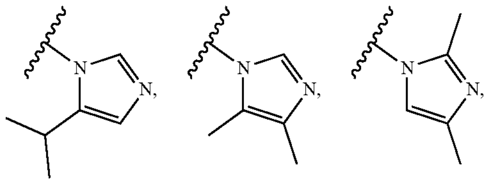
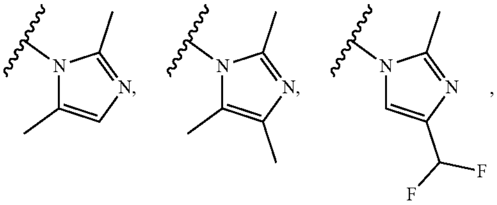
,
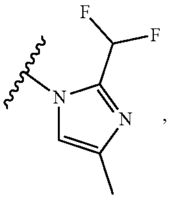
,
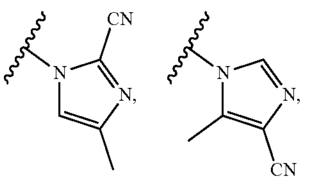
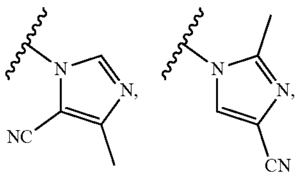
and
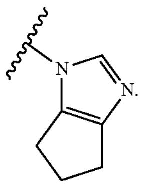
In some embodiments $R^{19}$ is selected from
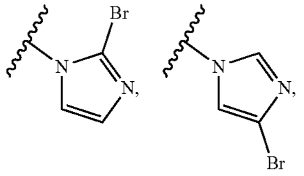
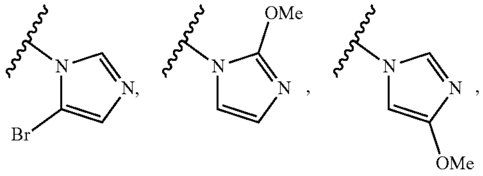
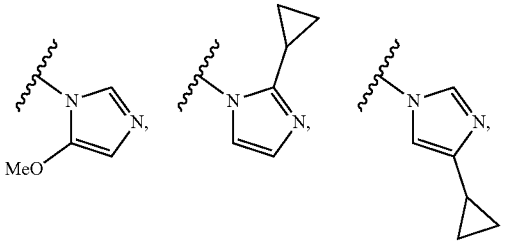
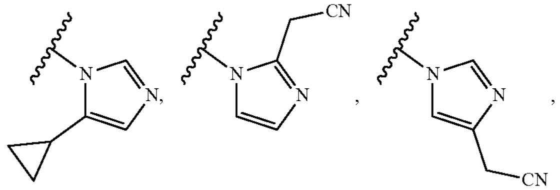
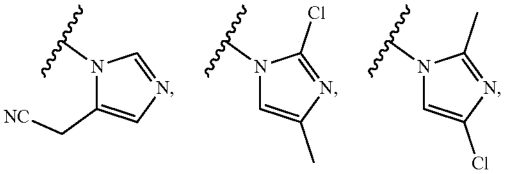
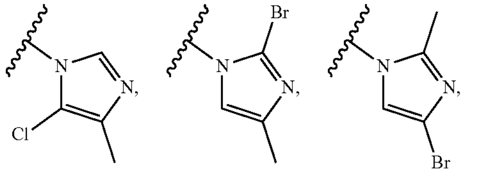
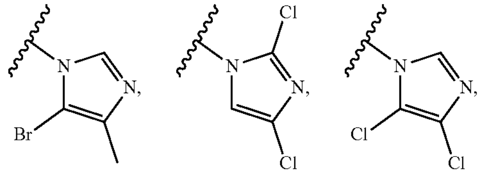
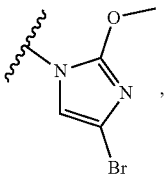
, and
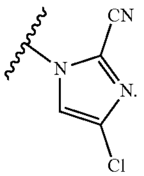

In some embodiments, $R^{19}$ is selected from
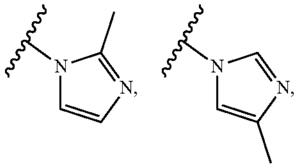
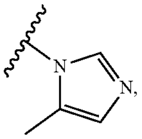
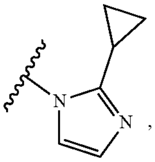
,
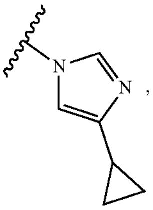
,
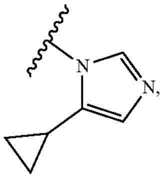
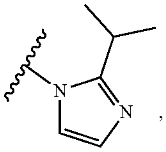
,
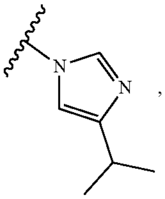
,
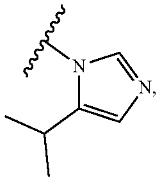
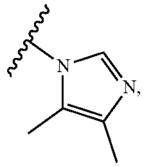
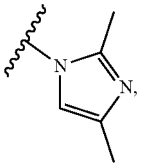
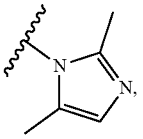
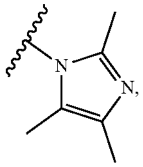
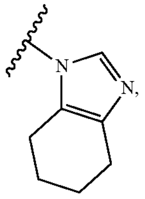
and
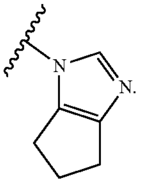
In some embodiments, $R^{19}$ is selected from
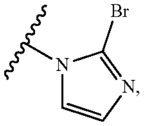
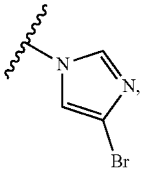
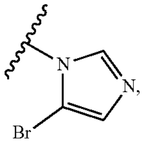
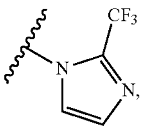
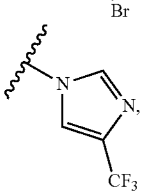
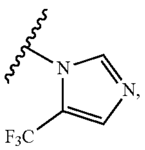
-continued
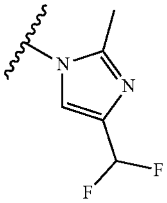
,
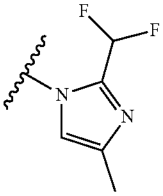
,
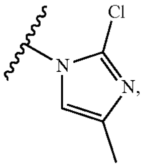
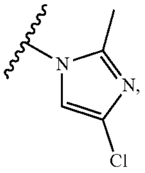
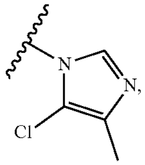
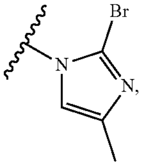
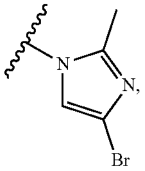
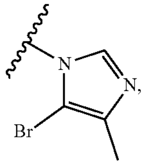
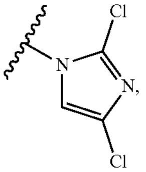
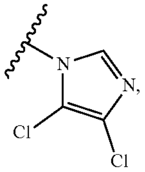
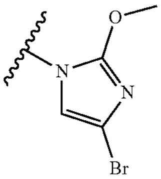
, and
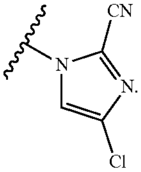
In some embodiments, $R^{19}$ is selected from
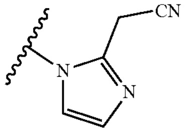
,
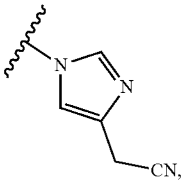
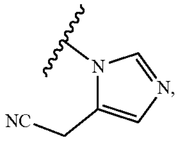
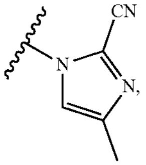
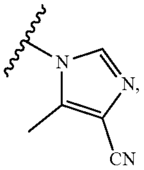
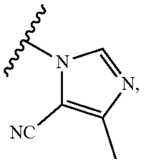
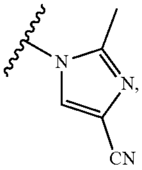
and
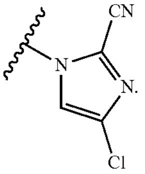

In some embodiments, $R^{19}$ is selected from

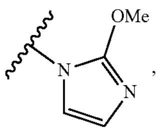,
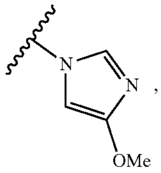, and
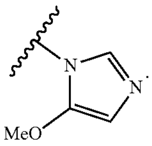.

In some embodiments, for a compound of Formula (II), $R^{4a}$ is selected from $C_{1-6}$ alkyl and $C_{2-6}$ alkenyl, each of which is optionally substituted. In some embodiments, $R^{4a}$ is selected from $C_{1-6}$ alkyl and $C_{2-6}$ alkenyl. In some embodiments, $R^{4a}$ is $C_{1-6}$ alkyl, such as $—CH_3$, $—CH_2CH_3$, and $—CH(CH_3)_2$. In some embodiments, $R^{4a}$ is $—CH_3$. In some embodiments, $R^{4a}$ is $—CH_2CH_3$. In some embodiments, $R^{4a}$ is $—CH(CH_3)_2$.

In some embodiments, for a compound of Formula (I) or (II), $R^2$ is selected from hydrogen, $C_{1-6}$ alkyl, $C_{2-6}$ alkenyl, $C_{3-10}$ carbocycle, 3- to 10-membered heterocycle, $—OR^{12}$, and $—N(R^{12})(R^{13})$, wherein each of $C_{1-6}$ alkyl, $C_{2-6}$ alkenyl, $C_{3-10}$ carbocycle, and 3- to 10-membered heterocycle is optionally substituted. In some embodiments, $R^2$ is selected from hydrogen, $—(C_{0-3}$ alkylene)-O—($C_{0-3}$ alkylene)-$R^{20}$, $C_{1-3}$ alkyl, and 3- to 10-membered heterocycle, wherein each $C_{0-3}$ alkylene, $C_{1-3}$ alkyl, and 3- to 10-membered heterocycle is optionally substituted. In some embodiments, $R^2$ is selected from hydrogen, $C_{1-3}$ alkyl, $—OR^{12}$, and 3- to 10-membered heterocycle, wherein each of $C_{1-3}$ alkyl and 3- to 10-membered heterocycle is optionally substituted. In some embodiments, $R^2$ is $OR^{12}$. In some embodiments, $R^2$ is $—O(C_{1-3}$ alkylene)(4- to 10-membered heterocycle), wherein 4- to 10-membered heterocycle is optionally substituted with one, two, or three substituents independently selected from halogen, $C_{1-3}$ alkyl, $C_{1-3}$ haloalkyl, and $=C(R^{21})_2$, wherein $R^{21}$ is independently selected at each occurrence from hydrogen, halogen, and $C_{1-3}$ alkyl. In some embodiments, $R^2$ is optionally substituted $—OCH_2$(hexahydro-1H-pyrrolizine). In some embodiments, $R^2$ is $—OCH_2$(hexahydro-1H-pyrrolizine) optionally substituted with one, two, or three substituents independently selected from halogen, $C_{1-3}$ alkyl, $C_{1-3}$ haloalkyl, and $=C(R^{21})_2$, wherein $R^{21}$ is independently selected at each occurrence from hydrogen, halogen, and $C_{1-3}$ alkyl.

In some embodiments, for a compound of Formula (I) or (II), $R^2$ is selected from

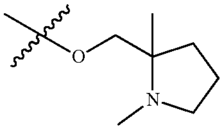,
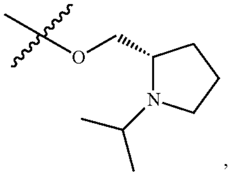,
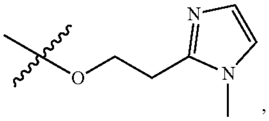,
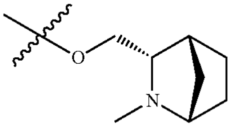,
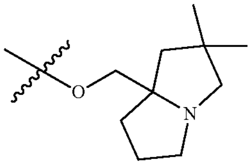,
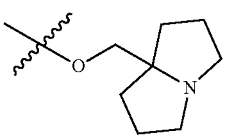,

-continued

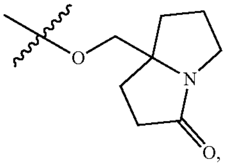
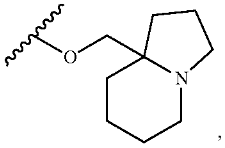,
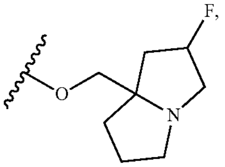
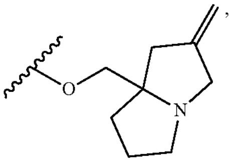
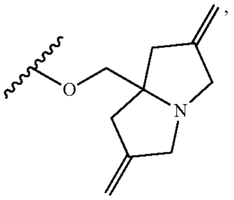
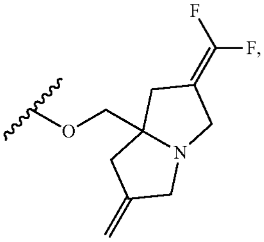
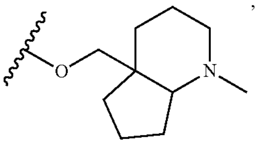,
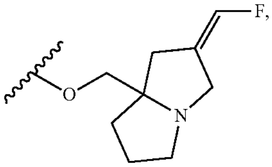
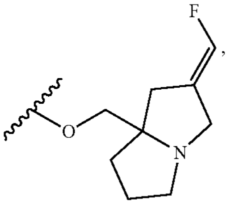
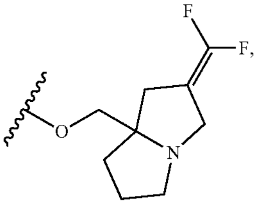
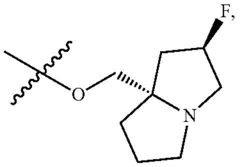
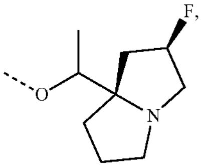
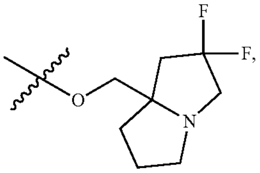
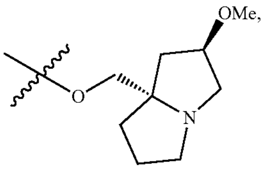
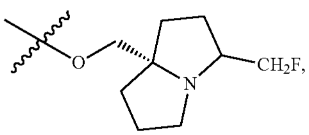
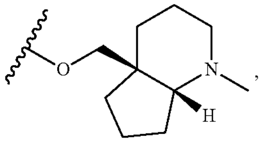
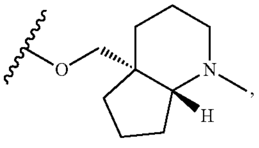
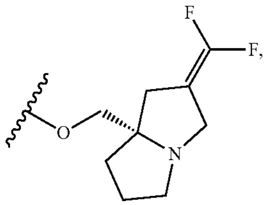

-continued
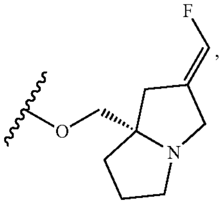
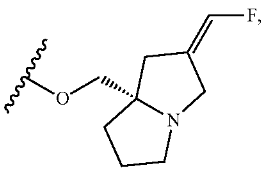
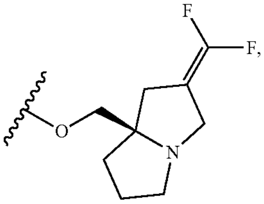
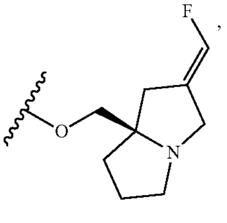
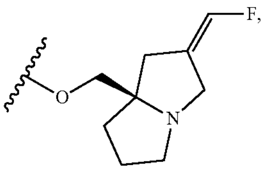
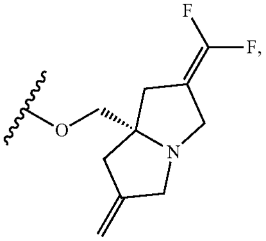
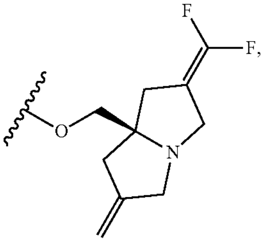
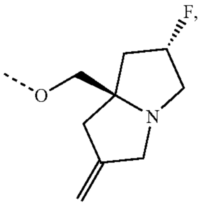
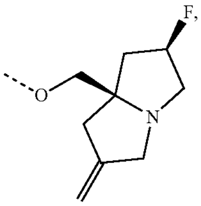
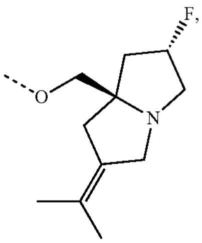
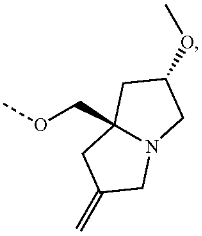
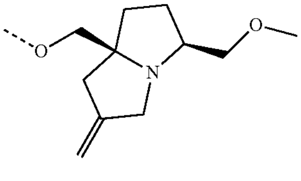
,
-continued
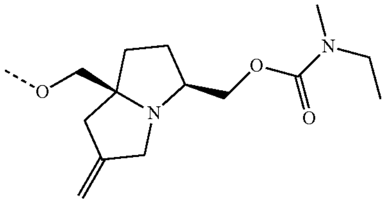
,
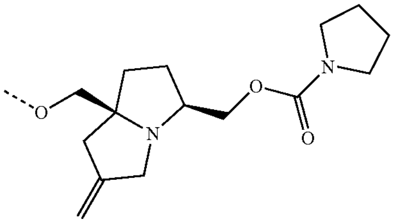
,
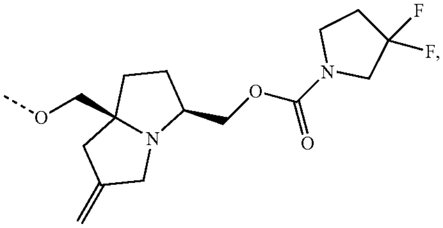
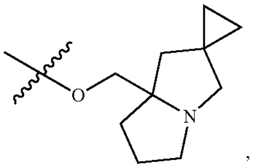
,
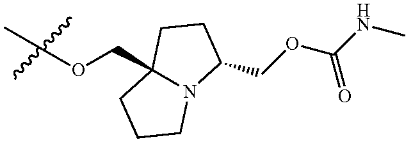
,
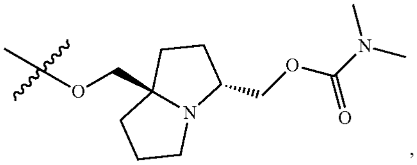
,
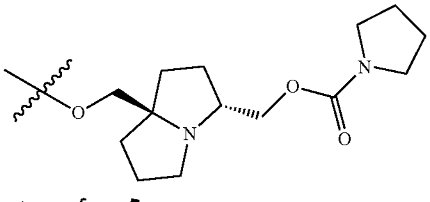
,
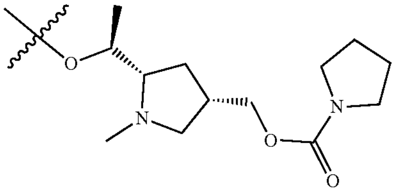
,
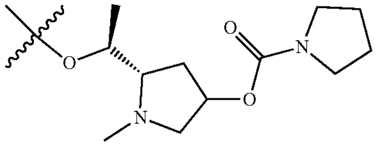
, -continued
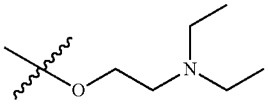, 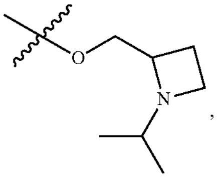,
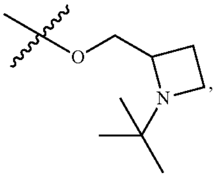, 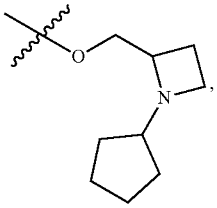,
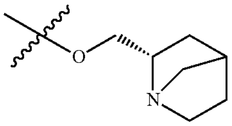, 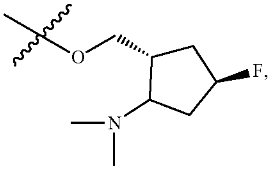
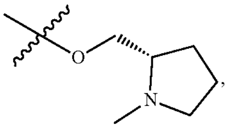, 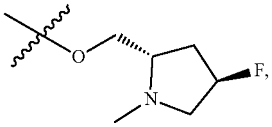
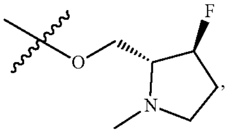, 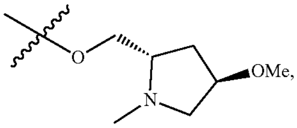
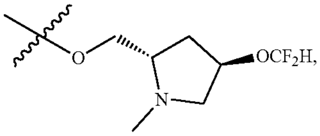
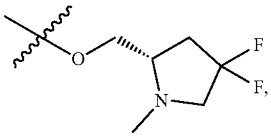 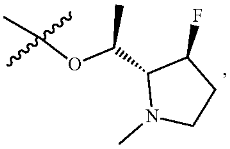,
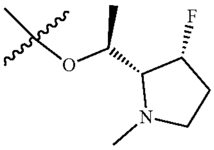, 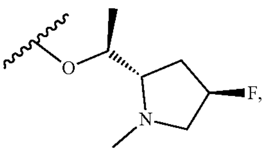
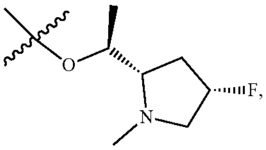
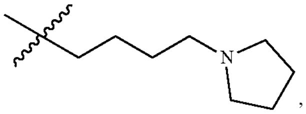,
-continued
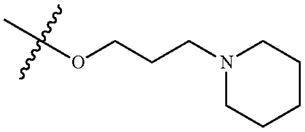, 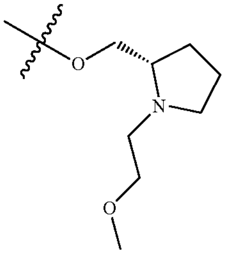,
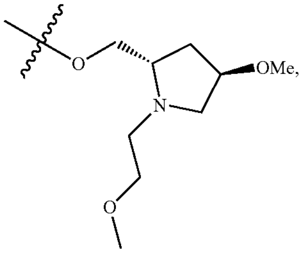 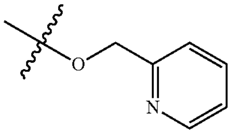,
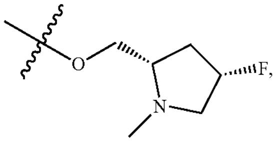 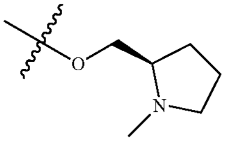,
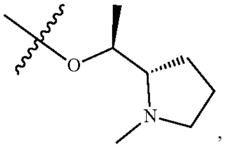, 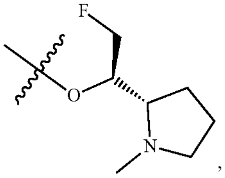,
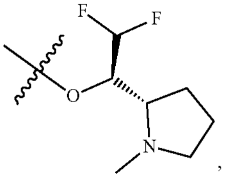, 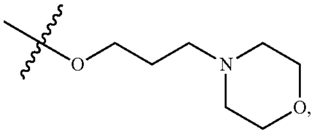
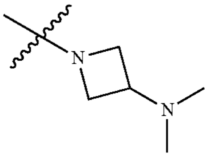, 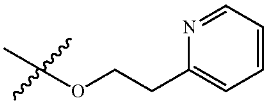,
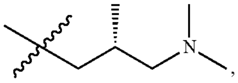 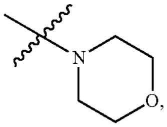
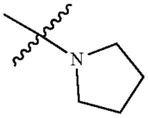, 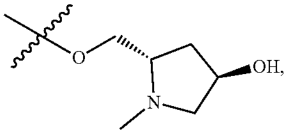
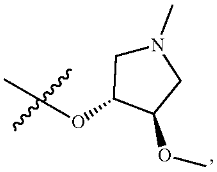 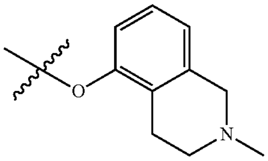

-continued
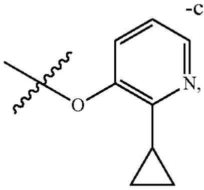
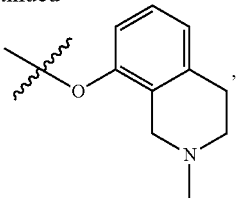
,
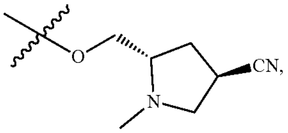
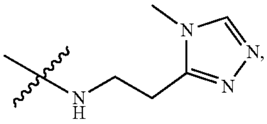
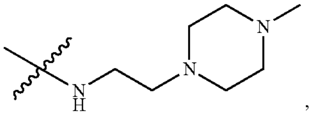
,
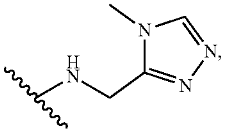
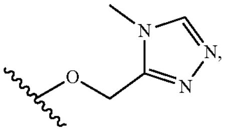
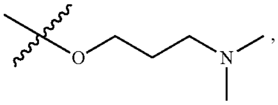
,
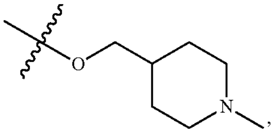
,
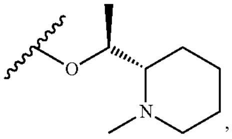
,
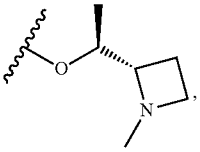
,
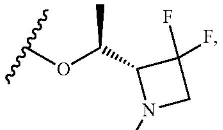
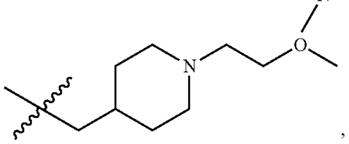
,
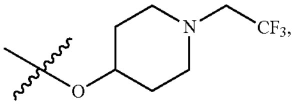
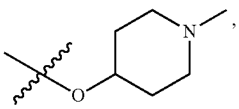
,
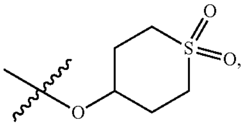
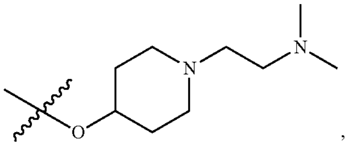
,
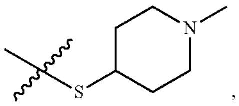
,
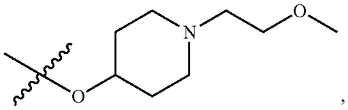
,
-continued
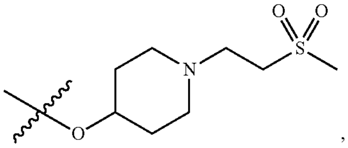
,
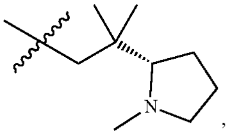
,
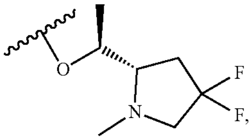
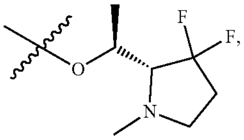
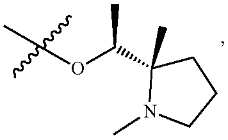
,
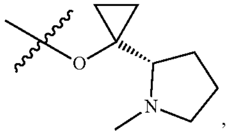
,
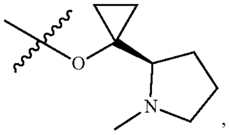
,
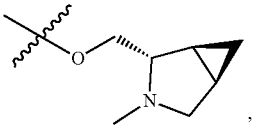
,
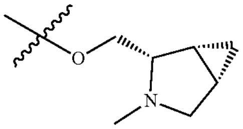
,
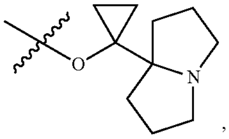
,
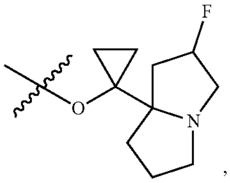
,
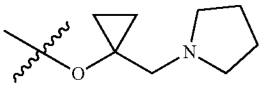
,
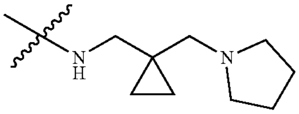
,
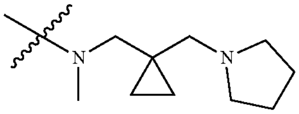
,
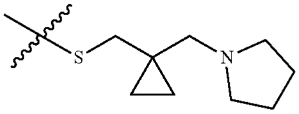
,
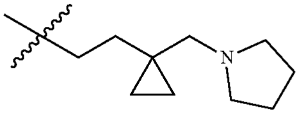
,
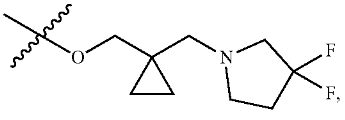
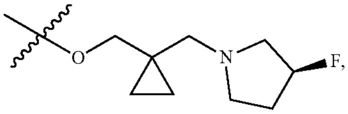

-continued
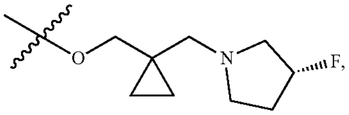
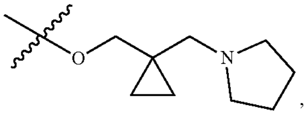
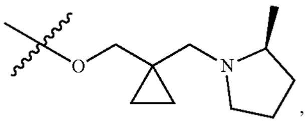
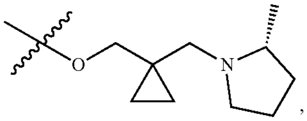
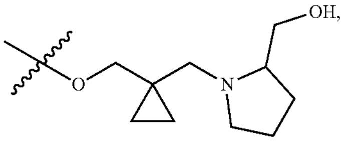
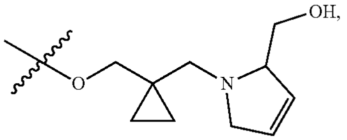
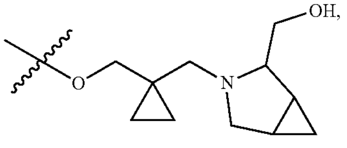
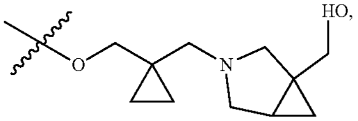
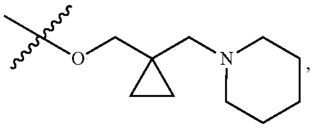
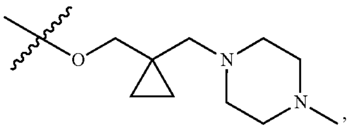
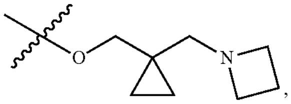
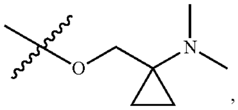
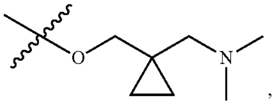
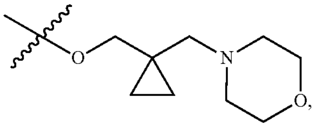
-continued
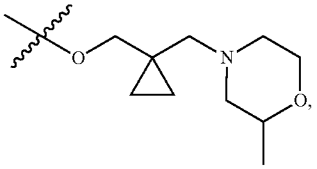
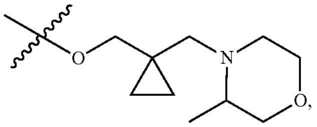
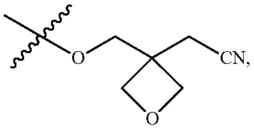
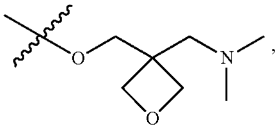
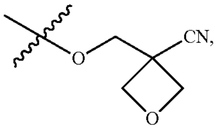
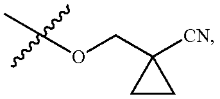
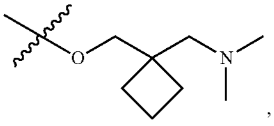
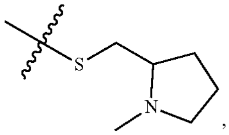
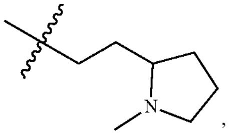
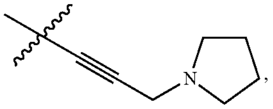
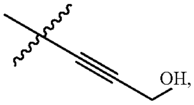
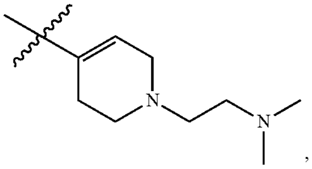
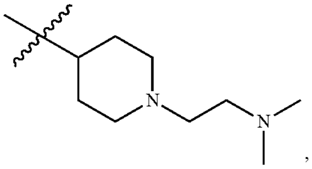
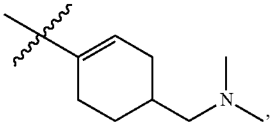
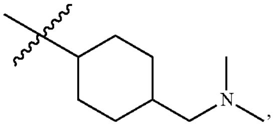
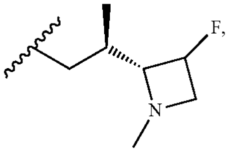
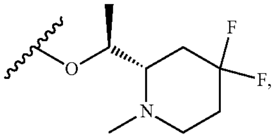

-continued
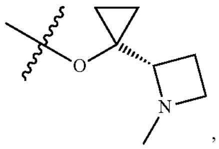,
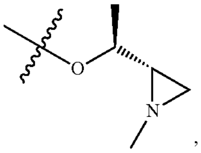,
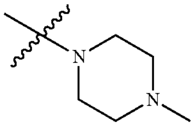,
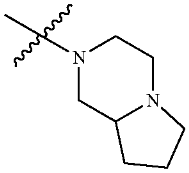,
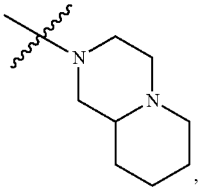,
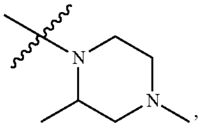,
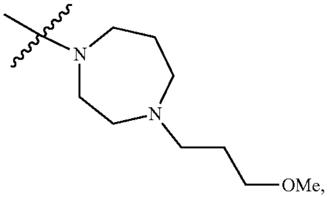,
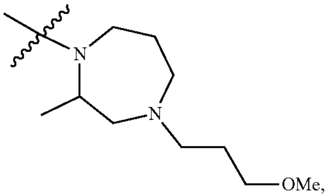,
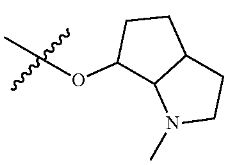,
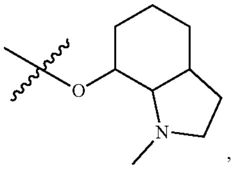,
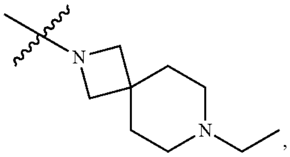,
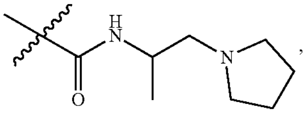,
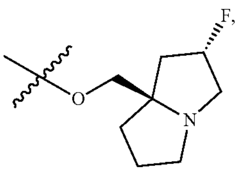
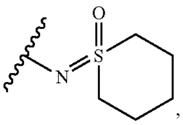,
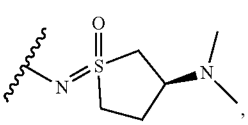,
-continued
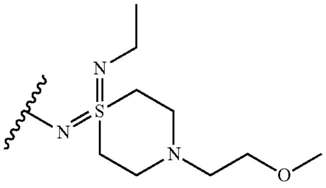, and
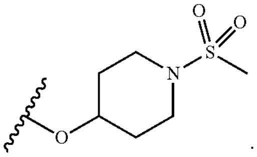.
In some embodiments, R is selected from
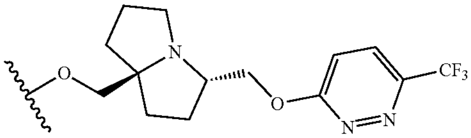 and
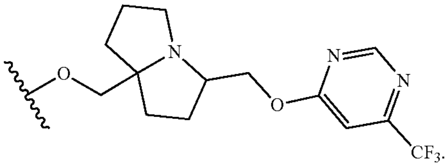
In some embodiments, $R^2$ is selected from
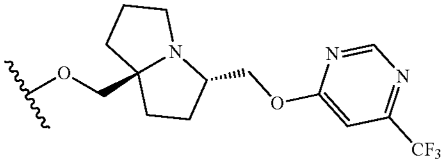 and
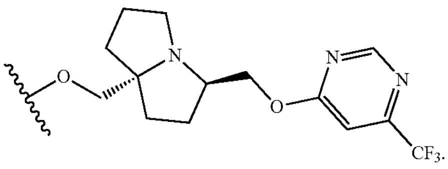
In some embodiments, $R^2$ is selected from
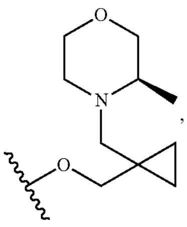,
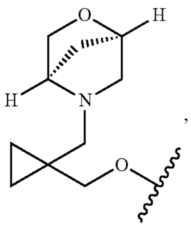, -continued
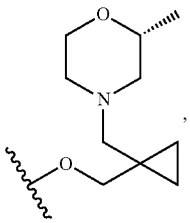
,
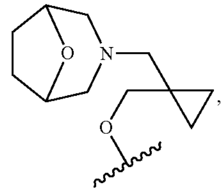
,
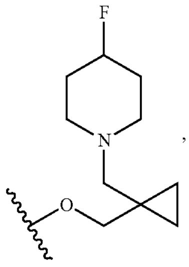
,
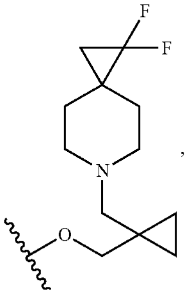
,
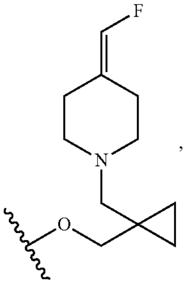
, and
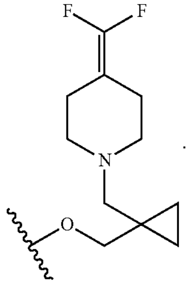
.
In some embodiments, $R^2$ is selected from
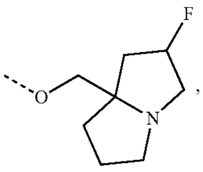
,
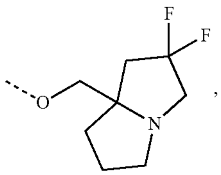
,
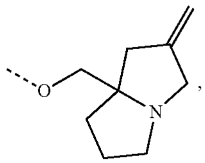
,
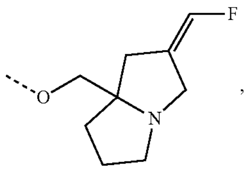
,
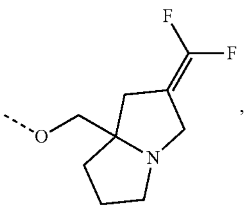
, and
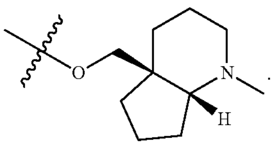
.
In some embodiments, $R^2$ is selected from
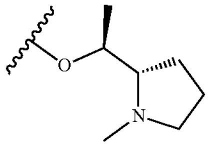
and
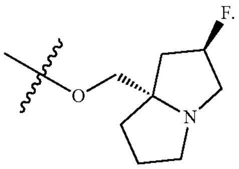
In some embodiments, $R^2$ is optionally substituted
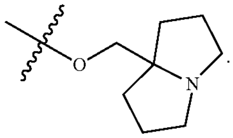 [SMILES: *OCC12CCCN1CCC2]
In some embodiments, $R^2$ is
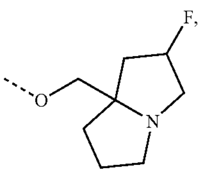
such as
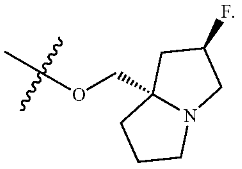
In some embodiments, $R^2$ is
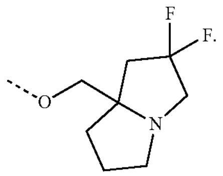
In some embodiments, $R^2$ is
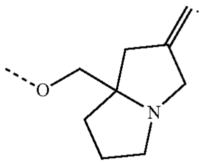
In some embodiments, $R^2$ is
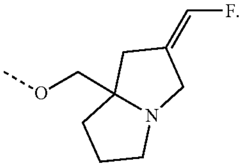

In some embodiments, $R^2$ is

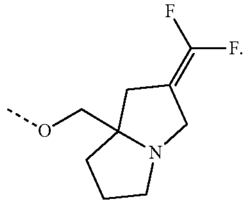

In some embodiments, $R^2$ is

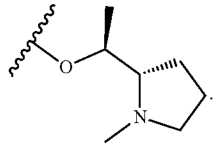 [SMILES: *O[C@@H](C)[C@@H]1CCCN1C]

In some embodiments, $R^2$ is

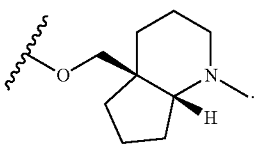 [SMILES: *OC[C@]12CCC[C@H]1N(C)CCC2]

In some embodiments, for a compound of Formula (I) or (II), $R^2$ is substituted with one, two, three, or four substituents independently selected from halogen, oxo, $C_{1-6}$ alkyl, —$OR^{22}$, —$N(R^{22})(R^{23})$, =$C(R^{21})_2$, and —$OC(O)N(R^{22})(R^{23})$, wherein $C_{1-6}$ alkyl is optionally substituted with one or more substituents independently selected from halogen, —CN, —$OR^{22}$, —$N(R^{22})(R^{23})$, and —$OC(O)N(R^{22})(R^{23})$. In some embodiments, $R^2$ is substituted with one, two, three, or four substituents independently selected from halogen, $C_{1-3}$ alkyl, $C_{1-3}$ haloalkyl, and =$C(R^{21})_2$, wherein $R^{21}$ is independently selected at each occurrence from hydrogen, halogen, and $C_{1-3}$ alkyl. In some embodiments, $R^2$ is substituted with one, two, three, or four substituents independently selected from halogen, $C_{1-3}$ alkyl, $C_{1-3}$ haloalkyl, =$CH_2$, =CHF, and =$CF_2$. In some embodiments, $R^2$ is substituted with halogen, such as fluorine.

In some embodiments, for a compound of Formula (I) or (II), $R^5$ is selected from hydrogen, halogen, —CN, $C_{1-6}$ alkyl, 2- to 6-membered heteroalkyl, —$C_{0-6}$ alkyl-($C_{3-12}$ carbocycle), —$C_{0-6}$ alkyl-(3- to 12-membered heterocycle), —$OR^{12}$, and —$N(R^{12})(R^{13})$, wherein each of $C_{1-6}$ alkyl, 2- to 6-membered heteroalkyl, —$C_{0-6}$ alkyl-($C_{3-12}$ carbocycle), and —$C_{0-6}$ alkyl-(3- to 12-membered heterocycle) is optionally substituted. In some embodiments, $R^5$ is selected from hydrogen, halogen, and $C_{1-3}$ alkyl. In some embodiments, $R^5$ is selected from hydrogen, halogen, and $C_{1-3}$ haloalkyl. In some embodiments, $R^5$ is selected from halogen and $C_{1-3}$ haloalkyl, such as $R^5$ is selected from —Cl and —$CF_3$. In some embodiments, $R^5$ is selected from hydrogen and halogen. In some embodiments, $R^5$ is hydrogen. In some embodiments, $R^5$ is halogen, such as fluorine. In some embodiments, $R^5$ is chlorine. In some embodiments, $R^5$ is —$CF_3$. In some embodiments, $R^5$ is —$CHF_2$. In some embodiments, $R^5$ is —$CH_2CN$.

In some embodiments, for a compound of Formula (I) or (II), $X^1$ is $CR^6$. In some embodiments, $X^1$ is N.

In some embodiments, for a compound of Formula (I) or (II), $R^6$ is selected from hydrogen, halogen, —CN, $C_{1-6}$ alkyl, 2- to 6-membered heteroalkyl, —$C_{0-6}$ alkyl-($C_{3-12}$ carbocycle), —$C_{0-6}$ alkyl-(3- to 12-membered heterocycle), —$OR^{12}$, and —$N(R^{12})(R^{13})$, wherein each of $C_{1-6}$ alkyl, 2- to 6-membered heteroalkyl, —$C_{0-6}$ alkyl-($C_{3-12}$ carbocycle), and —$C_{0-6}$ alkyl-(3- to 12-membered heterocycle) is optionally substituted. In some embodiments, $R^6$ is selected from hydrogen, halogen, and $C_{1-3}$ alkyl. In some embodiments, $R^6$ is selected from hydrogen, halogen, and $C_{1-3}$ haloalkyl. In some embodiments, $R^6$ is selected from halogen and $C_{1-3}$ haloalkyl, such as $R^6$ is selected from —Cl and —$CF_3$. In some embodiments, $R^6$ is selected from hydrogen and halogen. In some embodiments, $R^6$ is hydrogen. In some embodiments, $R^6$ is halogen, such as fluorine. In some embodiments, $R^6$ is chlorine. In some embodiments, $R^6$ is —$CF_3$. In some embodiments, $R^6$ is —$CHF_2$. In some embodiments, $R^6$ is —$CH_2CN$.

In some embodiments, for a compound of Formula (I) or (II), $R^8$ is selected from hydrogen, halogen, —CN, $C_{1-6}$ alkyl, 2- to 6-membered heteroalkyl, —$C_{0-6}$ alkyl-($C_{3-12}$ carbocycle), —$C_{0-6}$ alkyl-(3- to 12-membered heterocycle), —$OR^{12}$, and —$N(R^{12})(R^{13})$, wherein each of $C_{1-6}$ alkyl, 2- to 6-membered heteroalkyl, —$C_{0-6}$ alkyl-($C_{3-12}$ carbocycle), and —$C_{0-6}$ alkyl-(3- to 12-membered heterocycle) is optionally substituted. In some embodiments, $R^8$ is selected from hydrogen, halogen, and $C_{1-3}$ alkyl. In some embodiments, $R^8$ is selected from hydrogen and halogen. In some embodiments, $R^8$ is hydrogen. In some embodiments, $R^8$ is halogen, such as chlorine. In some embodiments, $R^8$ is fluorine. In some embodiments, $R^6$ and $R^8$ are independently selected from hydrogen, halogen, and $C_{1-3}$ haloalkyl. In some embodiments, $R^6$ and $R^8$ are independently selected from $C_{1-3}$ haloalkyl and halogen. In some embodiments, $R^6$ and $R^8$ are independently selected from hydrogen, halogen, and —$CF_3$. In some embodiments, $R^6$ and $R^8$ are independently selected from —Cl, —F, and —$CF_3$. In some embodiments, $R^6$ and $R^8$ are independently selected from hydrogen and halogen.

In some embodiments, for a compound of Formula (I) or (II), $R^7$ is selected from $C_{6-12}$ aryl and 5- to 12-membered heteroaryl, each of which is optionally substituted. In some embodiments, $R^7$ is selected from $C_{10}$ aryl and 9-membered heteroaryl, each of which is optionally substituted. In some embodiments, $R^7$ is selected from naphthalenyl and benzothiophenyl, each of which is optionally substituted. In some embodiments, $R^7$ is selected from $C_{3-10}$ cycloalkyl, 3- to 10-membered heterocycloalkyl, $C_{6-10}$ aryl, and 5- to 10-membered heteroaryl, each of which is optionally substituted. In some embodiments, $R^7$ is selected from bicyclic $C_{4-10}$ cycloalkyl, bicyclic 4- to 10-membered heterocycloalkyl, bicyclic $C_{7-10}$ aryl, and bicyclic 7- to 10-membered heteroaryl, each of which is optionally substituted. In some embodiments, $R^7$ is selected from bridged bicyclic $C_{4-10}$ cycloalkyl, bridged bicyclic 4- to 10-membered heterocycloalkyl, bridged bicyclic $C_{7-10}$ aryl, and bridged bicyclic 7- to 10-membered heteroaryl, each of which is optionally substituted. In some embodiments, $R^7$ is selected from fused bicyclic $C_{4-10}$ cycloalkyl, fused bicyclic 4- to 10-membered heterocycloalkyl, fused bicyclic $C_{7-10}$ aryl, and fused bicyclic 7- to 10-membered heteroaryl, each of which is optionally substituted. In some embodiments, $R^7$ is selected from $C_{6-10}$ aryl and 5- to 10-membered heteroaryl, each of which is optionally substituted. In some embodiments, $R^7$ is selected from naphthyl, isoquinolinyl, indazolyl, benzothiazolyl, benzothiophenyl, phenyl, and pyridinyl, each of which is optionally substituted. In some embodiments, $R^7$ is substituted with one, two, three, or four substituents independently selected from halogen, —CN, $C_{1-3}$ alkyl, $C_{1-3}$ haloalkyl, $C_{2-3}$ alkenyl, $C_{2-3}$ alkynyl, $—OR^{22}$, $—N(R^{22})(R^{23})$, and $C_{3-6}$ cycloalkyl. In some embodiments, $R^7$ is selected from $C_6$ aryl and 6-membered heteroaryl, each of which is substituted with one, two, three, four, or five substituents (e.g., $R^{20}$). In some embodiments, $R^7$ is optionally substituted with one or more substituents, such as one, two, three, four, five, six, or seven substituents (e.g., $R^{20}$).

In some embodiments, for a compound of Formula (I) or (II), $R^7$ is selected from:

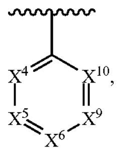
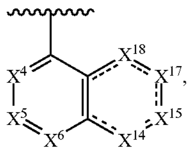
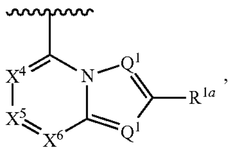
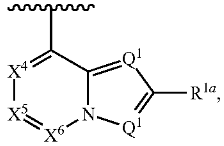
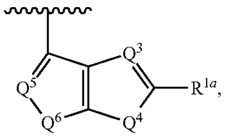
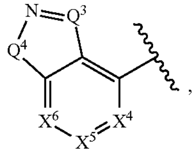
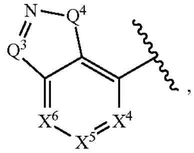
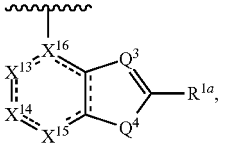
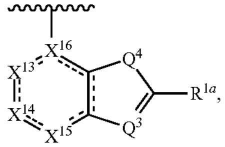
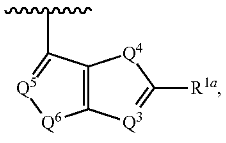
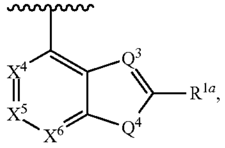
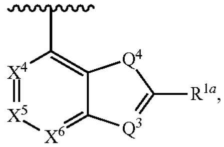
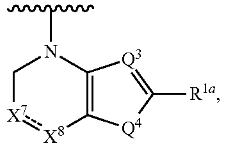
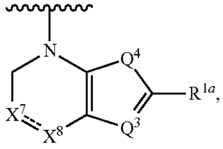
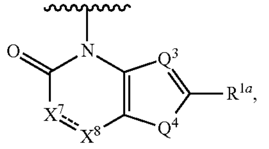
and
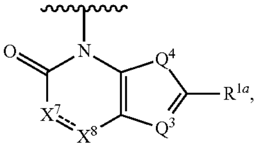

wherein:

$Q^1$, $Q^3$, and $Q^5$ are independently selected from N and $C(R^{1a})$;

$Q^4$ and $Q^6$ are independently selected from O, S, $C(R^{1a})_2$, and $N(R^{1b})$;

$X^4$, $X^5$, $X^6$, $X^9$, and $X^{10}$ are independently selected from $C(R^{1a})$ and N;

$X^7$ and $X^8$ are independently selected from $C(R^{1a})$, $C(R^{1a})_2$, N, and $N(R^{1b})$;

$X^{13}$ is selected from a bond, $C(R^{1a})$, N, C(O), $C(R^{1a})_2$, $C(O)C(R^{1a})_2$, $C(R^{1a})_2C(R^{1a})_2$, $C(R^{1a})_2N(R^{1b})$, and $N(R^{1b})$;

$X^{14}$, $X^{15}$, $X^{17}$, and $X^{18}$ are independently selected from C(O), $C(R^{1a})$, N, $C(R^{1a})_2$, and $N(R^{1b})$;

$X^{16}$ is selected from C, N, and $C(R^{1a})$;

each $R^{1a}$ is independently selected from hydrogen, halogen, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), -(2- to 6-membered heteroalkyl)-(3- to 12-membered heterocycle), $—OR^{12}$, $—SR^{12}$, $—N(R^{12})(R^{13})$, $—C(O)OR^{12}$, $—OC(O)N(R^{12})(R^{13})$, $—N(R^{12})C(O)N(R^{12})(R^{13})$, $—N(R^{12})C(O)OR^{12}$, $—N(R^{12})S(O)_2R^{12}$, $—C(O)R^{12}$, $—S(O)R^{12}$, $—OC(O)R^{12}$, $—C(O)N(R^{12})(R^{13})$, $—C(O)C(O)N(R^{12})(R^{13})$, $—N(R^{12})C(O)R^{12}$, $—S(O)_2R^{12}$, $—S(O)(NR^{12})R^{12}$, $—S(O)_2N(R^{12})(R^{13})$, and $—S({=}O)({=}NR^{12})N(R^{12})(R^{13})$, wherein each of $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), and -(2- to 6-membered heteroalkyl)-(3- to 12-membered heterocycle) is optionally substituted; or two Ria bonded to the same carbon are joined to form 3- to 10-membered heterocycle or $C_{3-10}$ carbocycle, wherein each of 3- to 10-membered heterocycle and $C_{3-10}$ carbocycle is optionally substituted; or two $R^{1a}$ bonded to adjacent atoms are joined to form 3- to 10-membered heterocycle or $C_{3-10}$ carbocycle, wherein each of 3- to 10-membered heterocycle and $C_{3-10}$ carbocycle is optionally substituted; or one $R^{1a}$ and one $R^{1b}$ are joined to form 3- to 10-membered heterocycle or $C_{3-10}$ carbocycle, wherein each of 3- to 10-membered heterocycle and $C_{3-10}$ carbocycle is optionally substituted;

each $R^{1b}$ is independently selected from hydrogen, $C_{1-6}$ alkyl, $C_{2-6}$ alkenyl, $C_{2-6}$ alkynyl, 3- to 10-membered heterocycle, and $C_{3-10}$ carbocycle, wherein each of $C_{1-6}$ alkyl, $C_{2-6}$ alkenyl, $C_{2-6}$ alkynyl, 3- to 10-membered heterocycle, and $C_{3-10}$ carbocycle is optionally substituted; and ----- indicates a single or double bond such that all valences are satisfied.

In some embodiments, $R^7$ is selected from

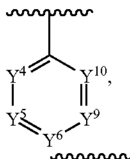
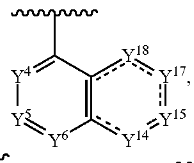
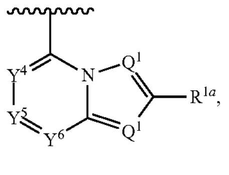
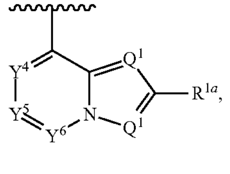
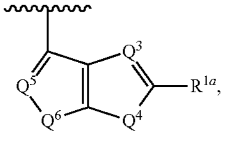

-continued
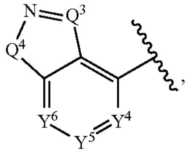
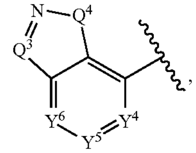
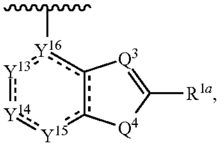
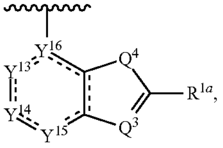
and
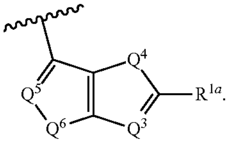
In some embodiments, $R^7$ is selected from
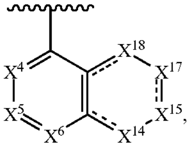
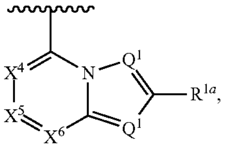
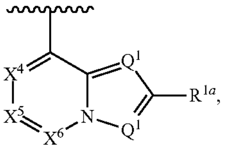
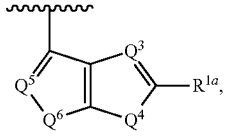
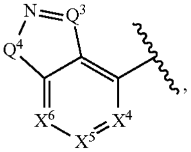
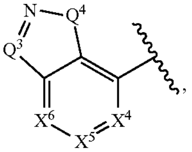
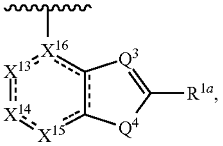
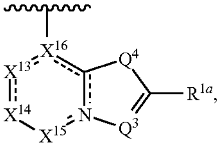
and
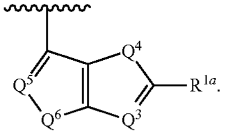
In some embodiments, $R^7$ is selected from
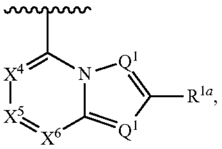
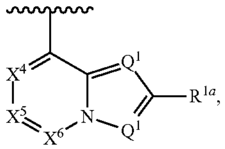
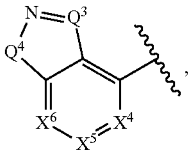
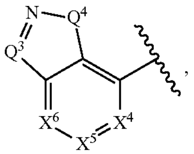
-continued
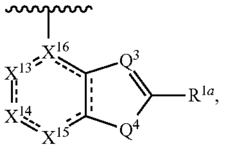
and
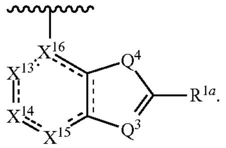
In some embodiments, $R^7$ is selected from
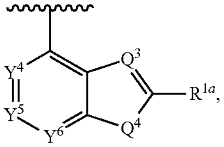
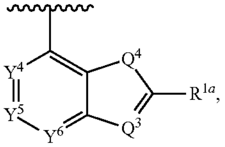
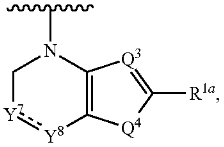
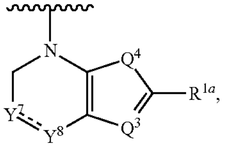
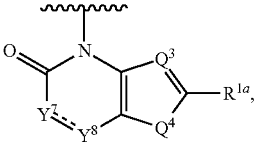
and
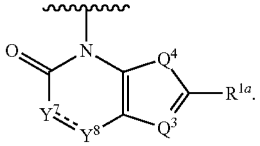
In some embodiments, for a compound of Formula (I) or (II), $R^7$ is selected from
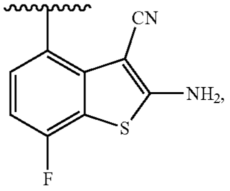
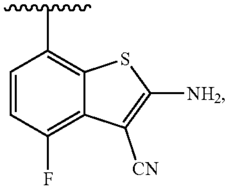
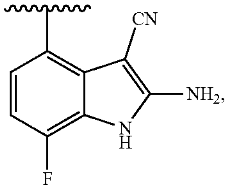
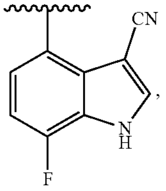
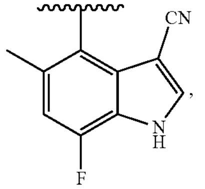
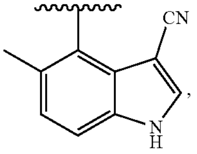
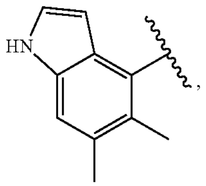
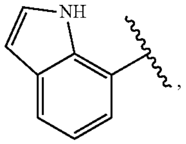

-continued
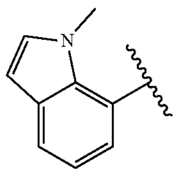,
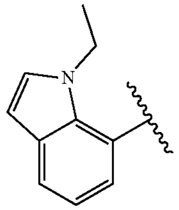,
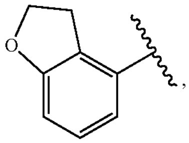,
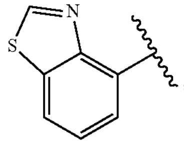,
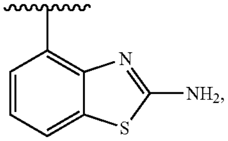,
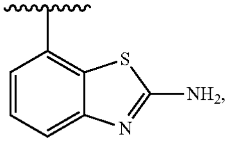,
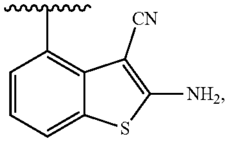,
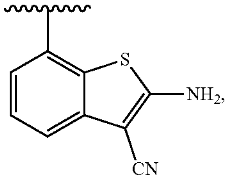,
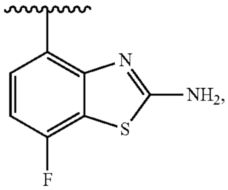,
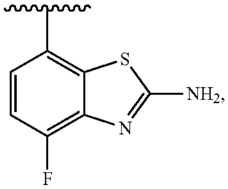,
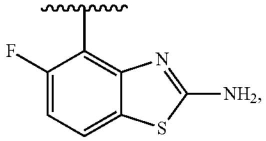,
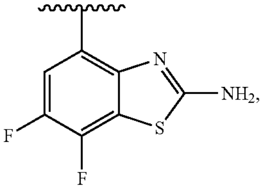,
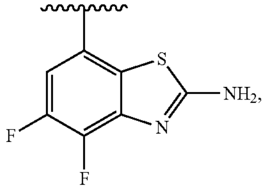,
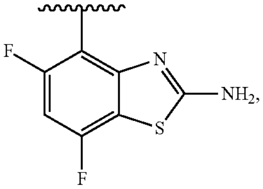,
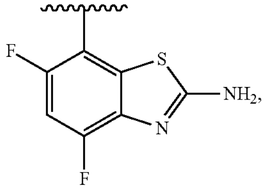,
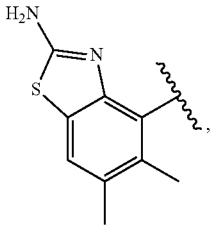,
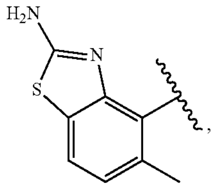,
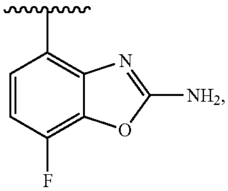,
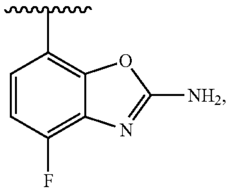,
-continued
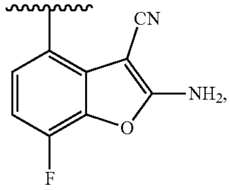,
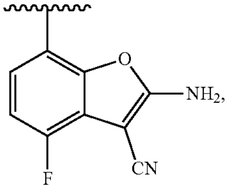,
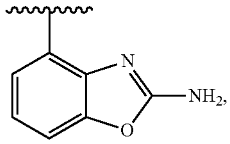,
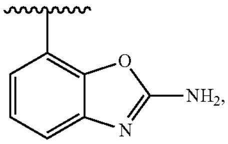,
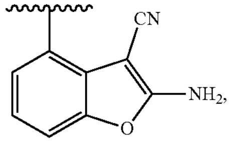,
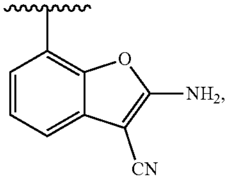,
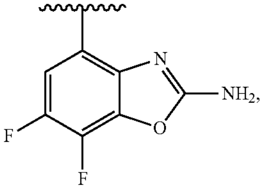,
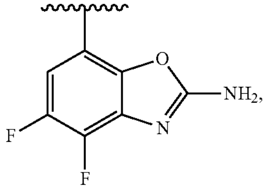,
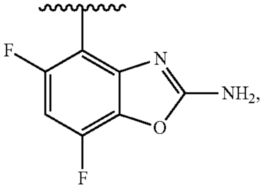,
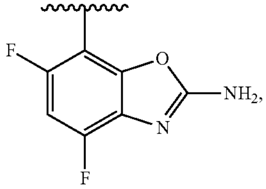,
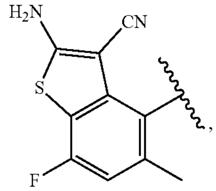,
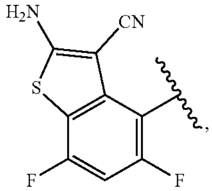,
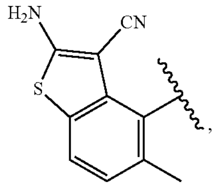,
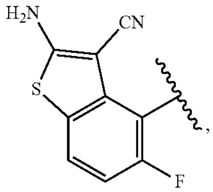,
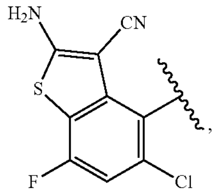,
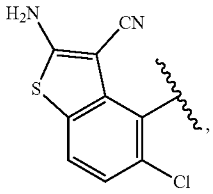,
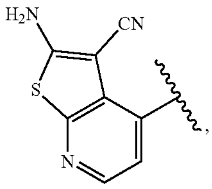,
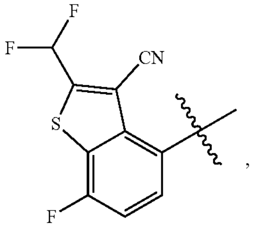, -continued
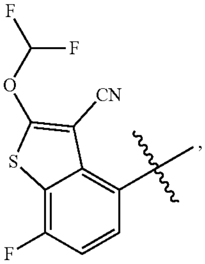,
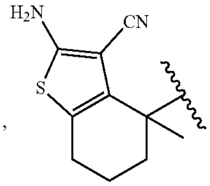,
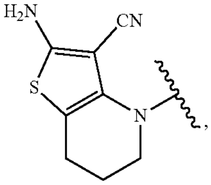,
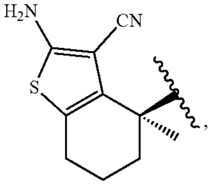,
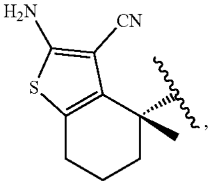,
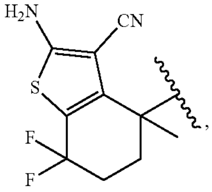,
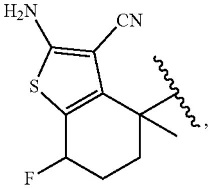,
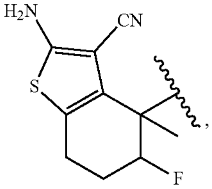,
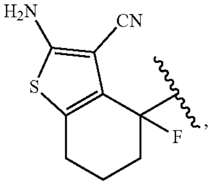,
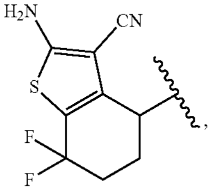,
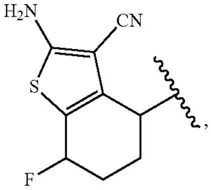,
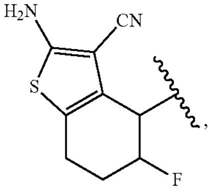,
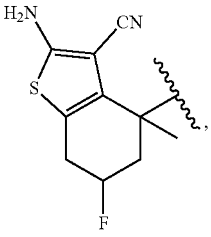,
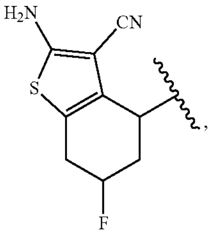,
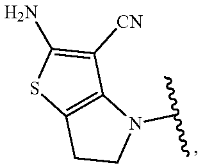,
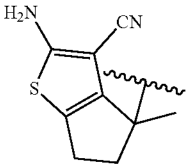,
-continued
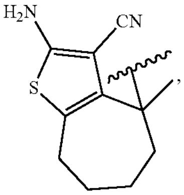,
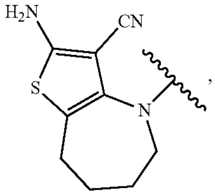,
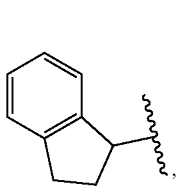,
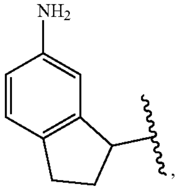,
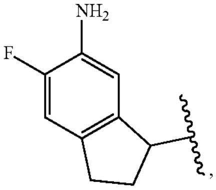,
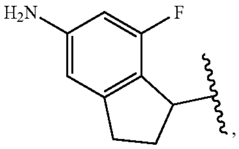,
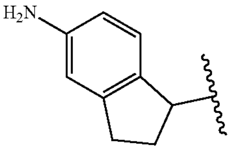,
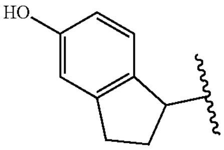,
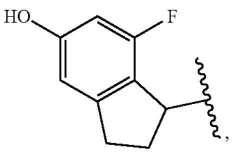,
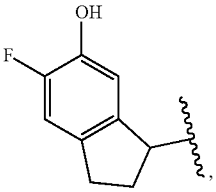,
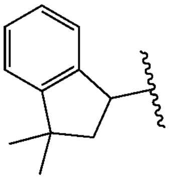,
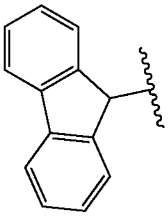,
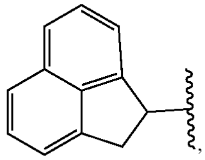,
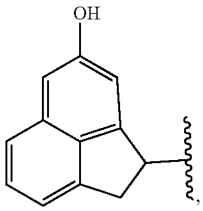,
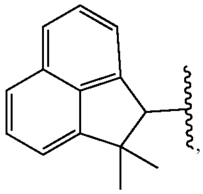,
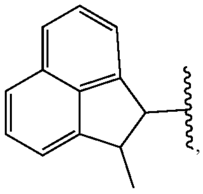,
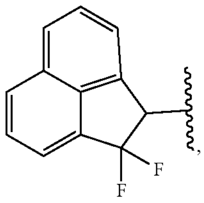, -continued
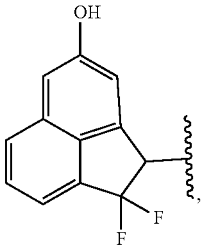, 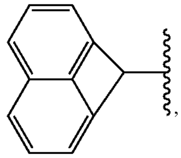,
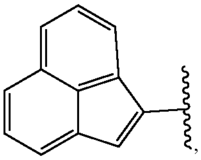, 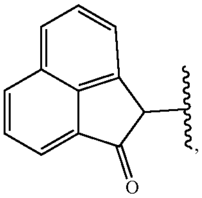,
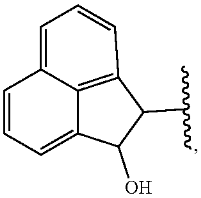, 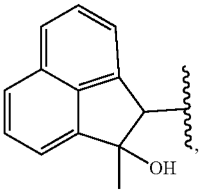,
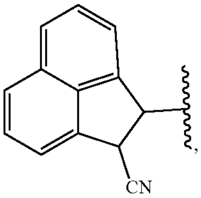, 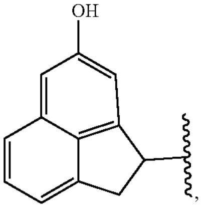,
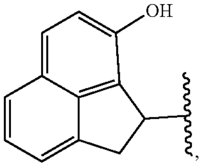, 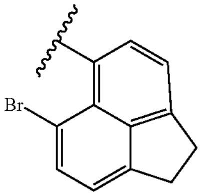,
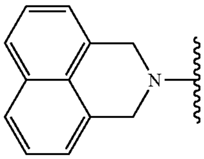, 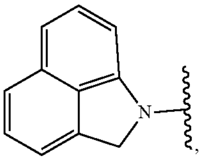,
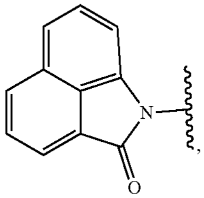, 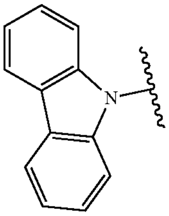, 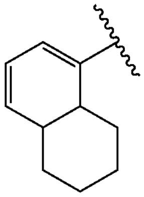,
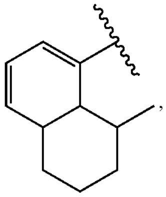, 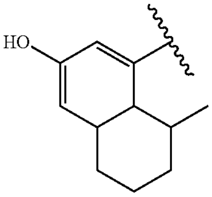,
-continued
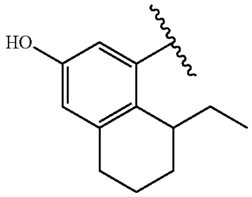, 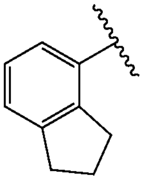,
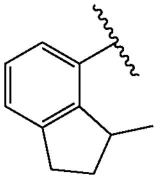, 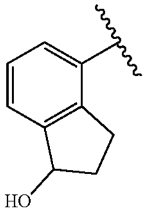,
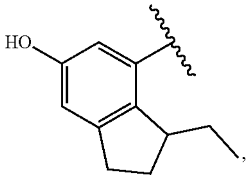, 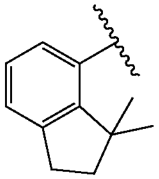,
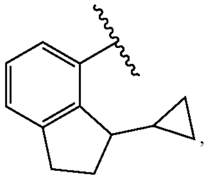, 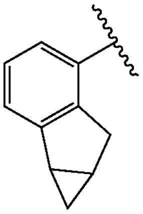,
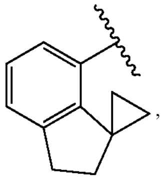, 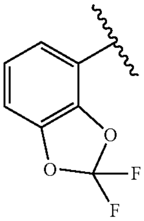, 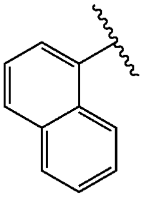,
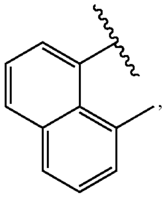, 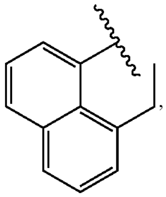, 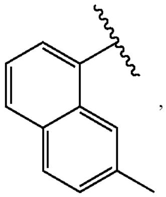,
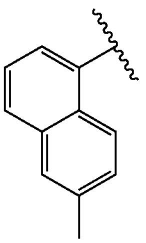, 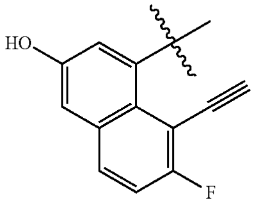,
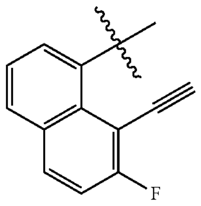, 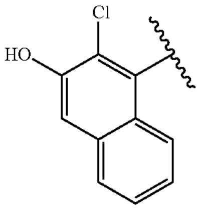, -continued
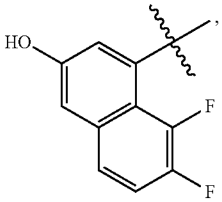
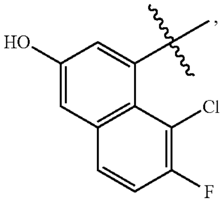
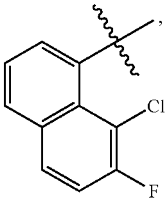
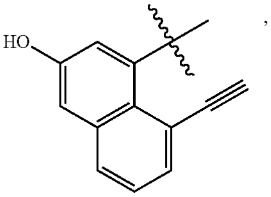
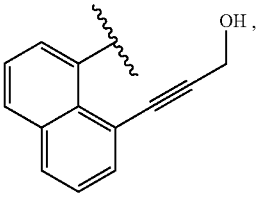
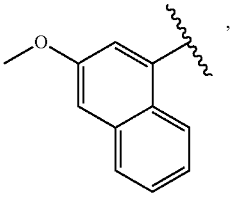
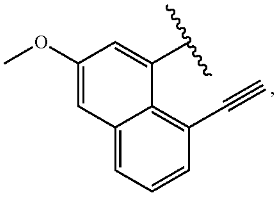
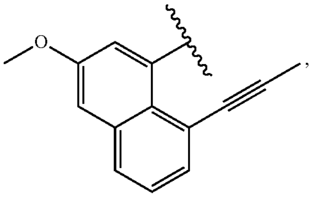
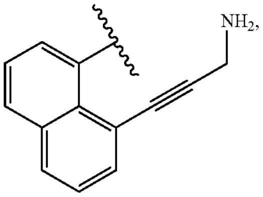
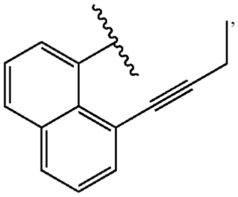
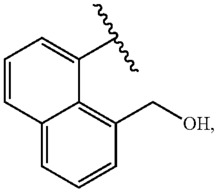
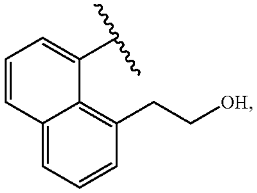
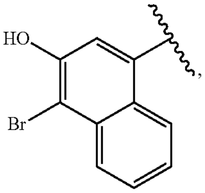
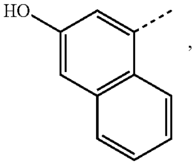
-continued
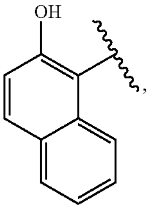
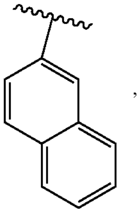
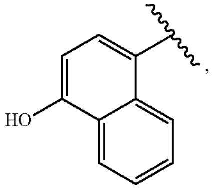
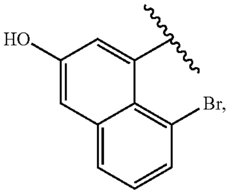
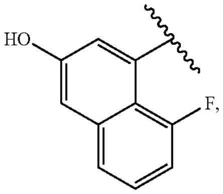
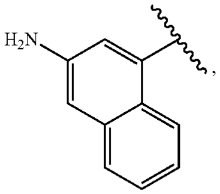
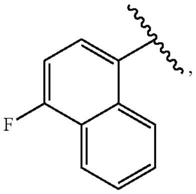
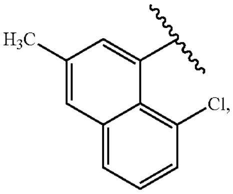
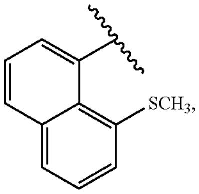
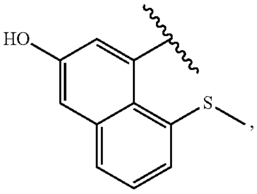
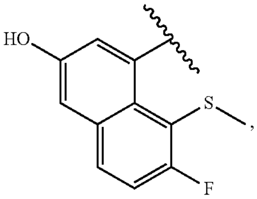
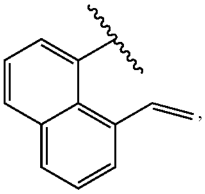
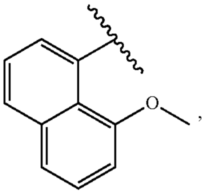
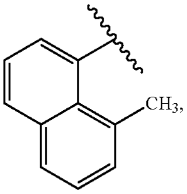
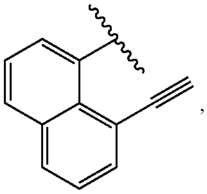
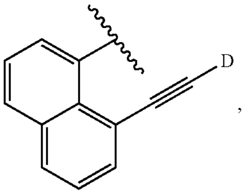
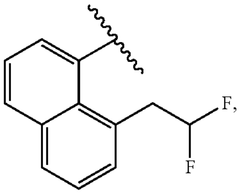

-continued
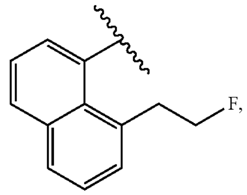 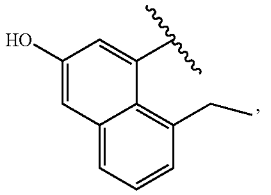
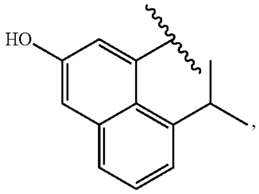 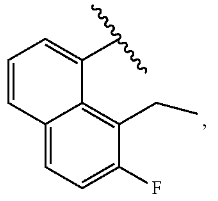
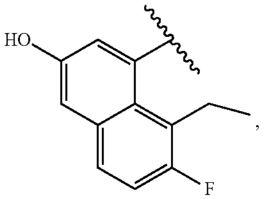 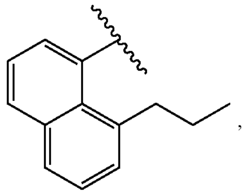
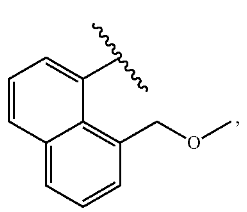 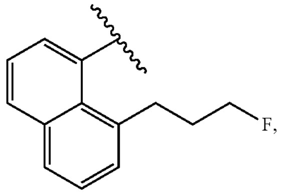
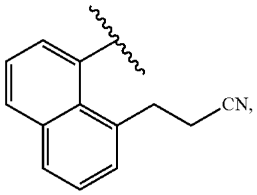 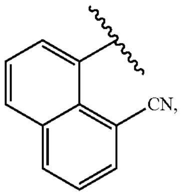
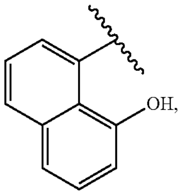 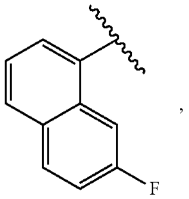
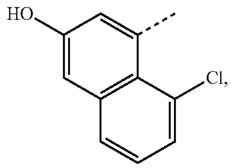 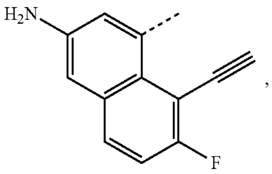
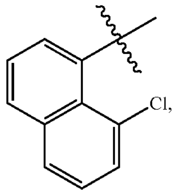 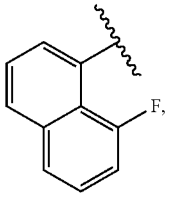 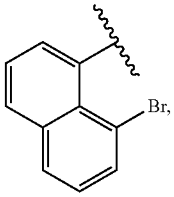
-continued
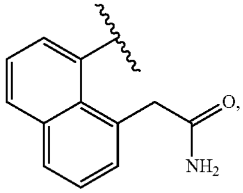 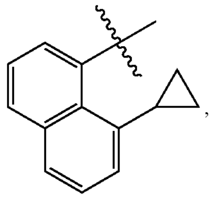
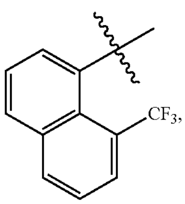 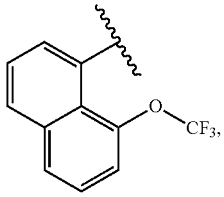
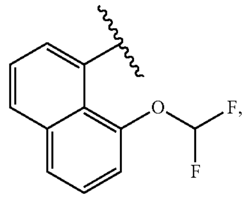 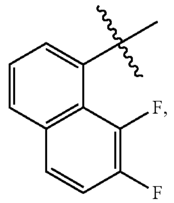
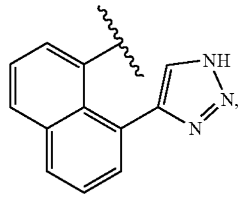 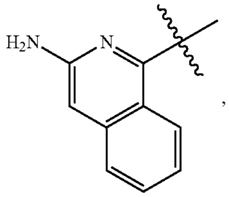
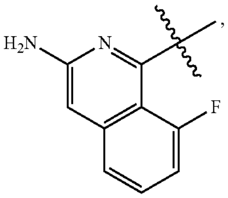 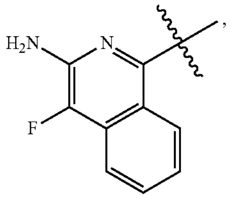
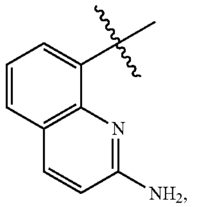 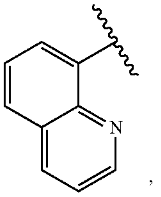 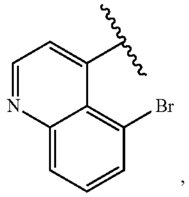
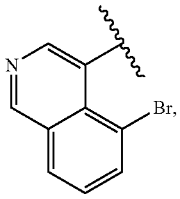 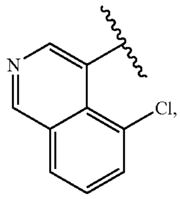
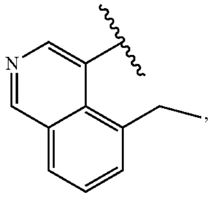 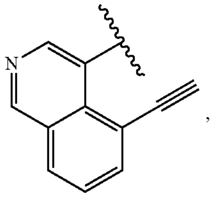

-continued
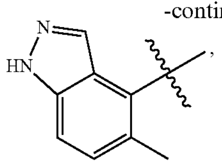, 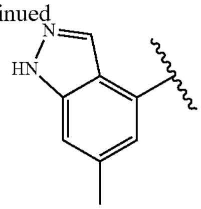,
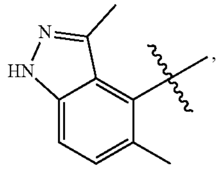, 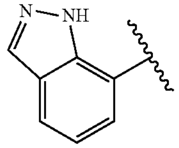,
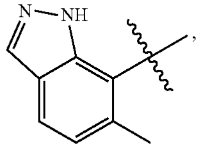, 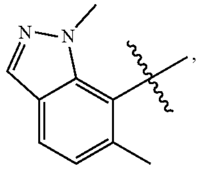,
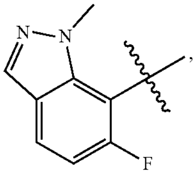, 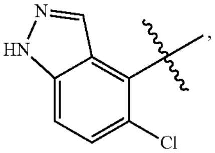,
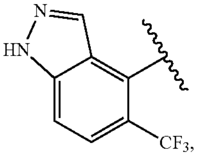, 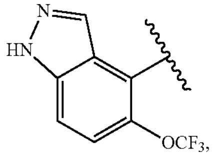,
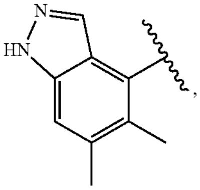, 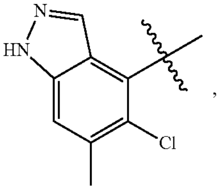,
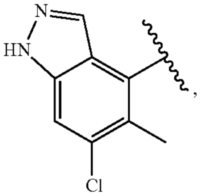, 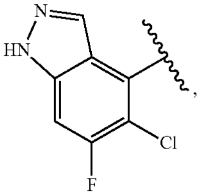,
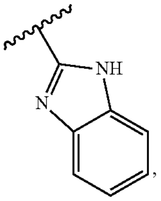, 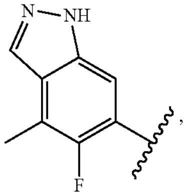,
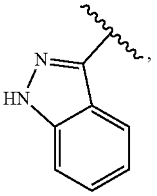, 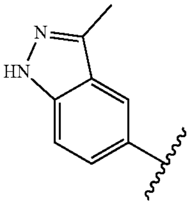
-continued
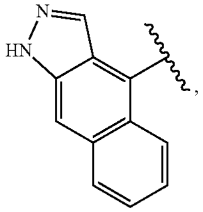, 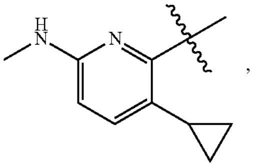,
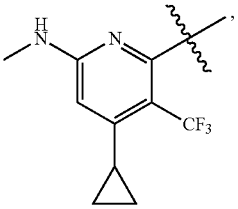, 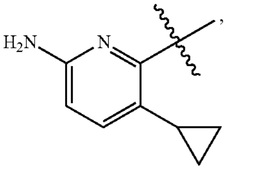,
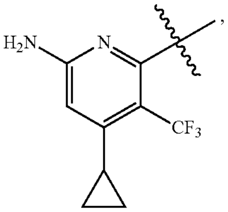, 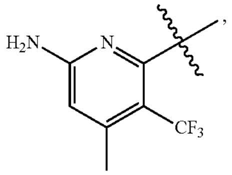,
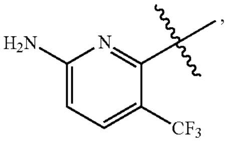, 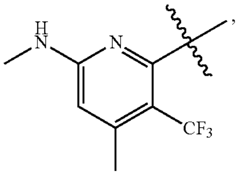,
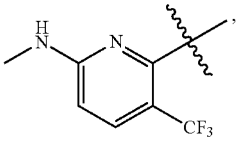, 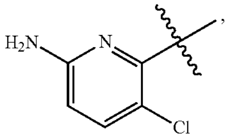,
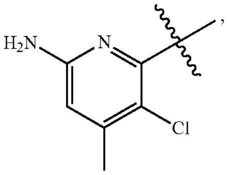, 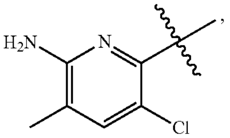,
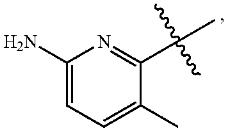, 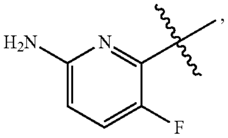,
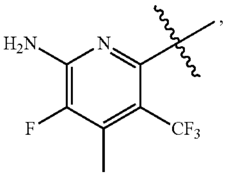, 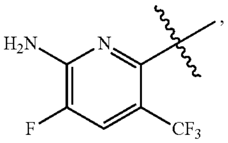,
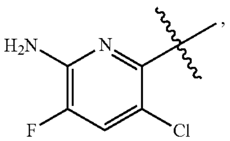, 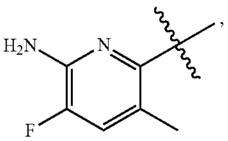, -continued
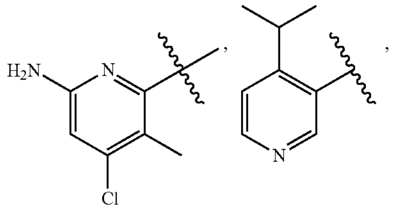
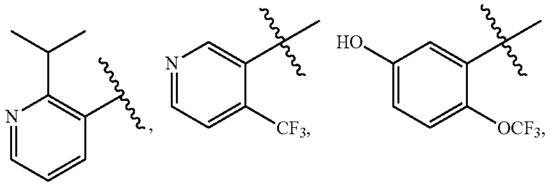
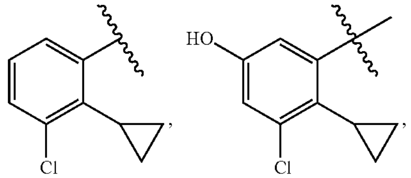
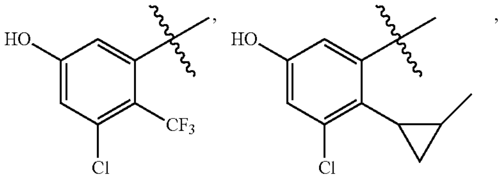
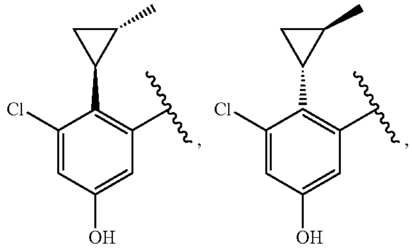
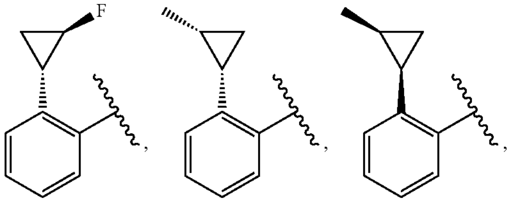
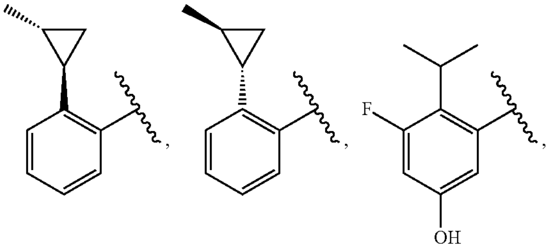
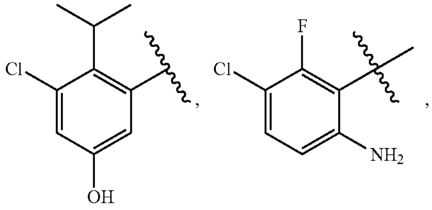
-continued
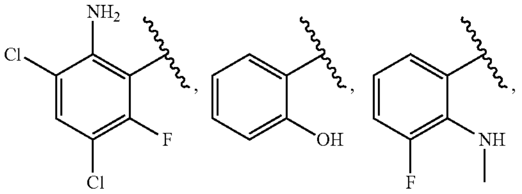
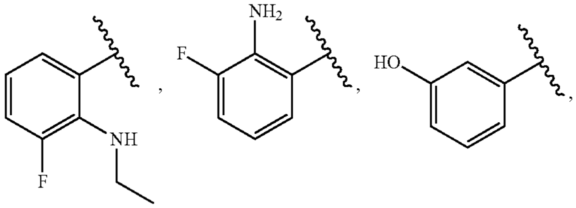
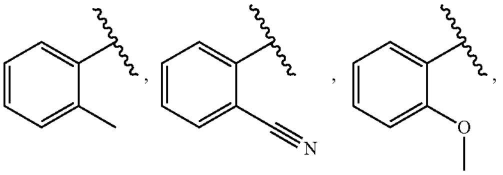
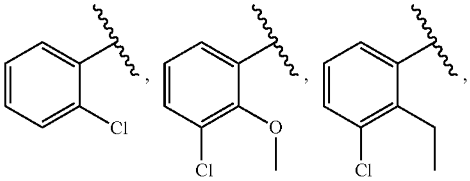
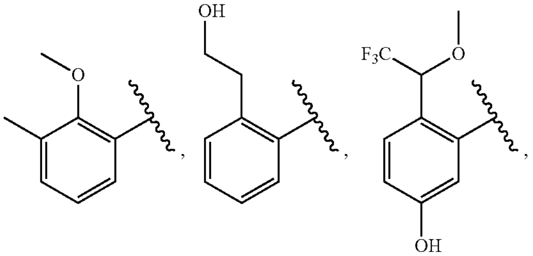
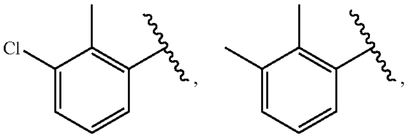
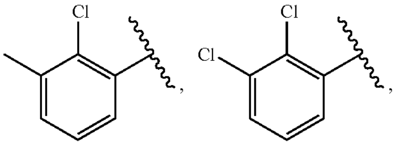
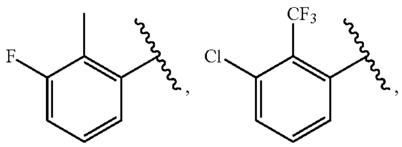
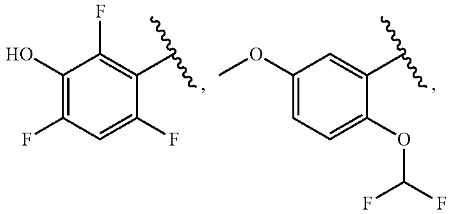

-continued
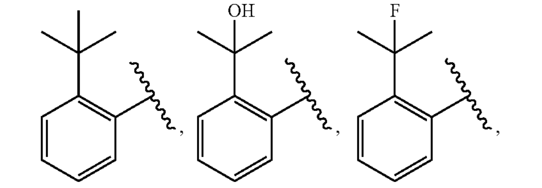
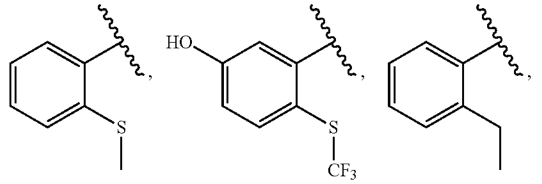
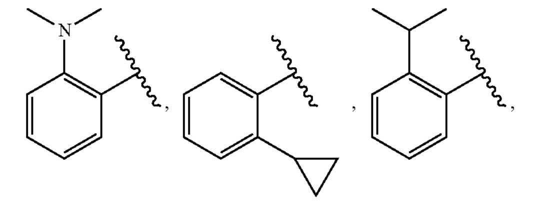
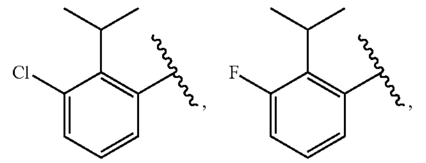
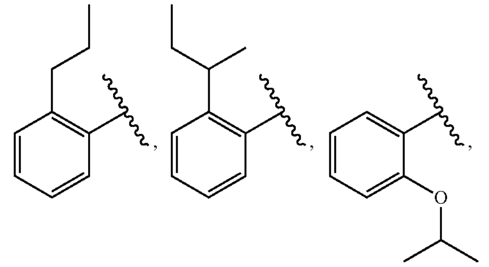
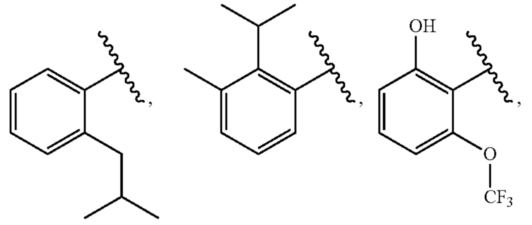
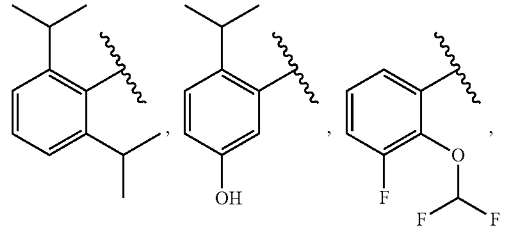
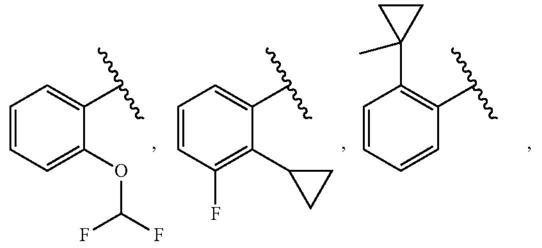
-continued
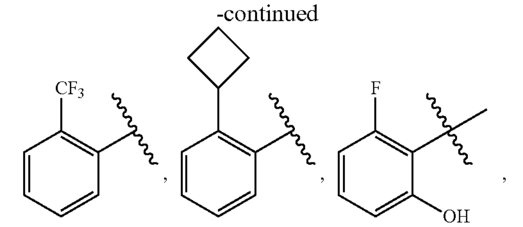
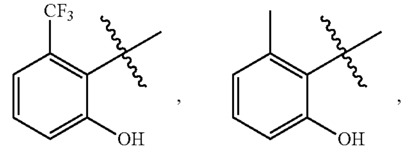
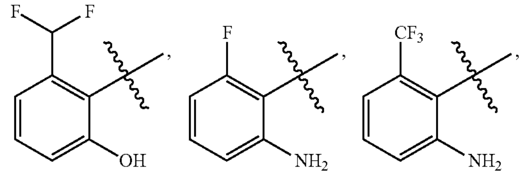
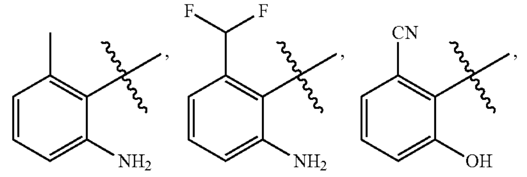
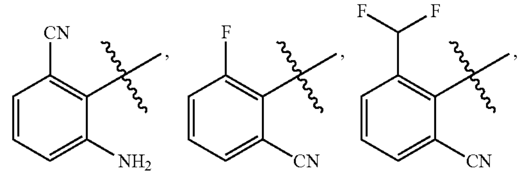
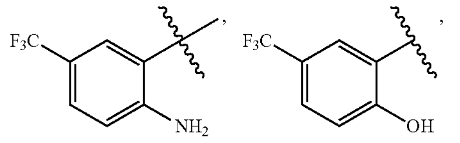
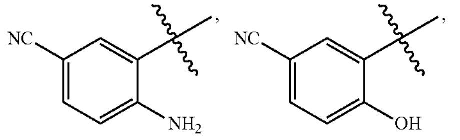
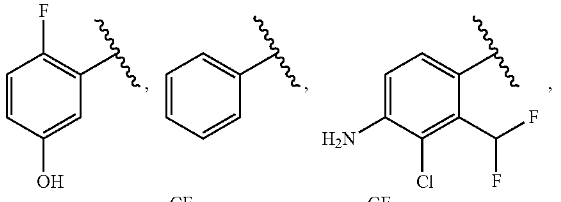
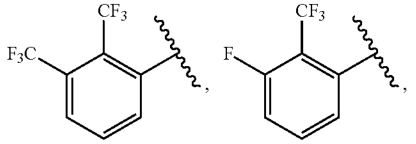
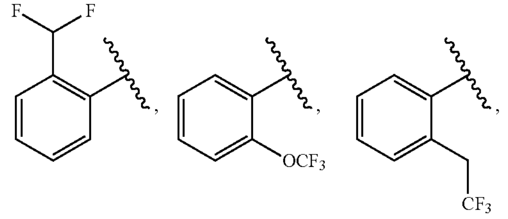

-continued
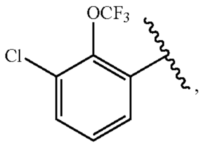,
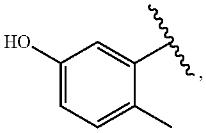,
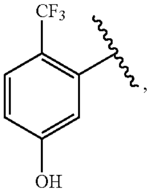,
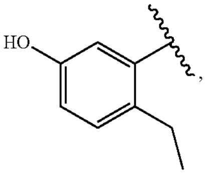,
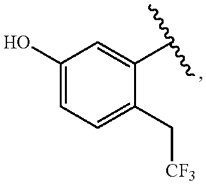,
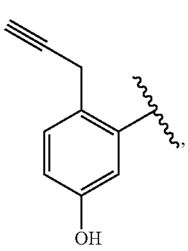,
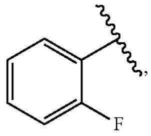,
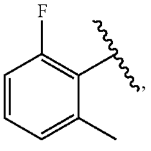,
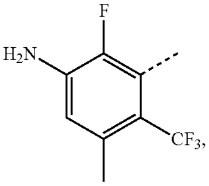,
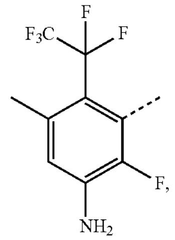,
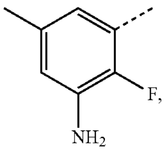,
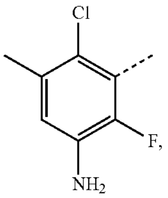,
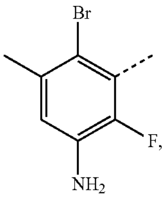,
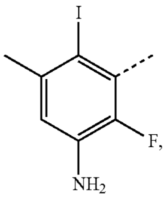,
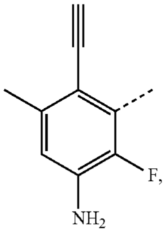,
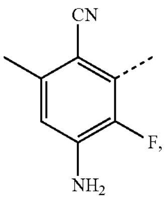,
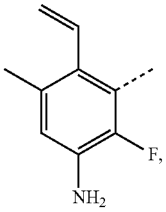,
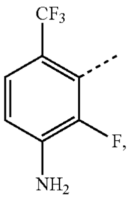,
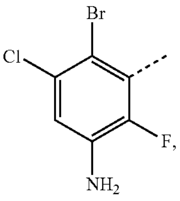,
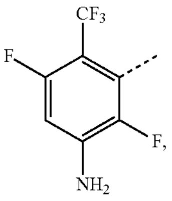,
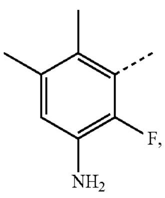,
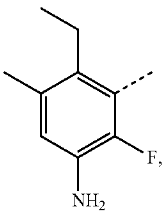, and
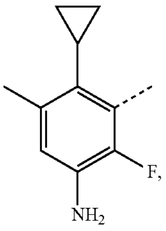
-continued
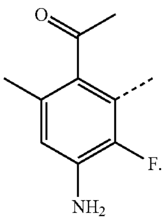.
In some embodiments, for a compound of Formula (I) or (II), $R^7$ is
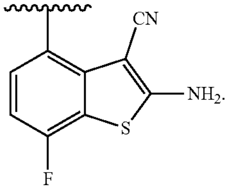 [SMILES: *c1ccc(F)c2sc(N)c(C#N)c12].
In some embodiments, $R^7$ is selected from
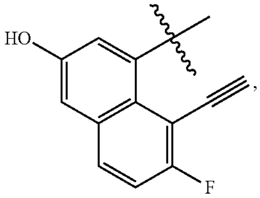,
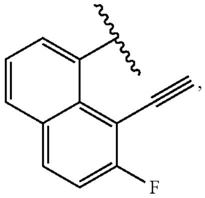,
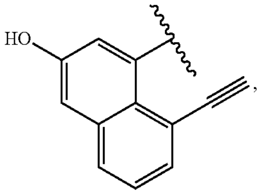,
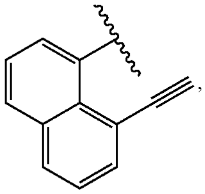,
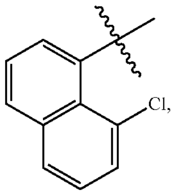,
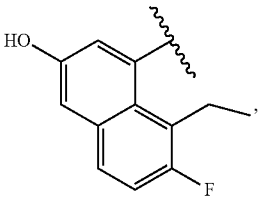,
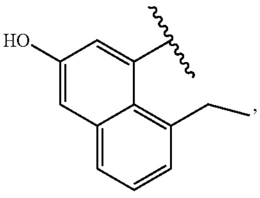,
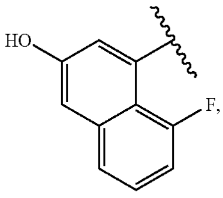,
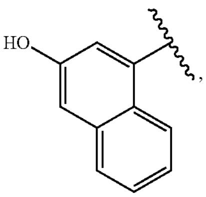,
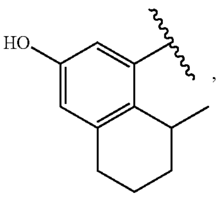, -continued
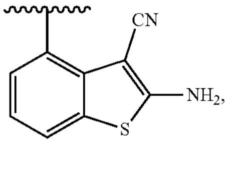 [SMILES: *c1cccc2sc(N)c(C#N)c12] 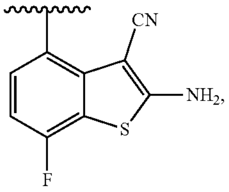
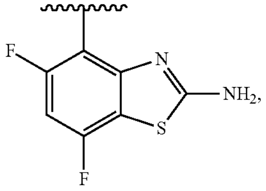 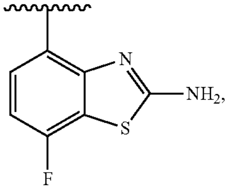
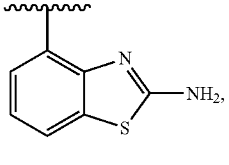 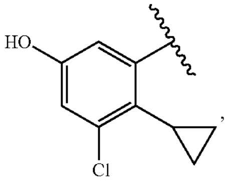
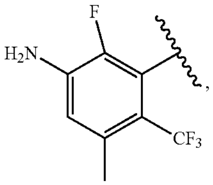 and 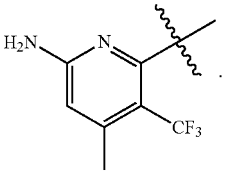
In some embodiments, $R^7$ is selected from
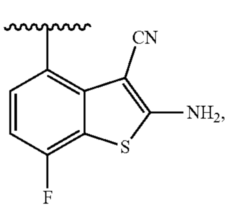 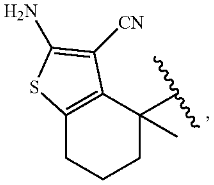
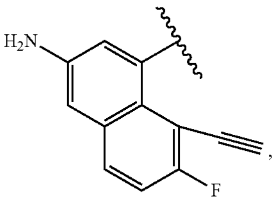 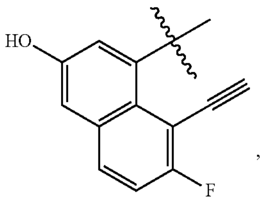
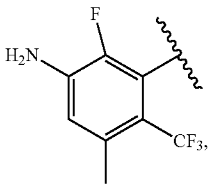 and 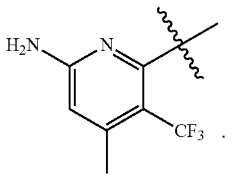
In some embodiments, $R^7$ is selected from
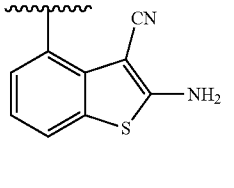 and 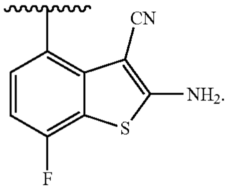 [SMILES: *c1ccc(F)c2sc(N)c(C#N)c12]
In some embodiments, $R^7$ is
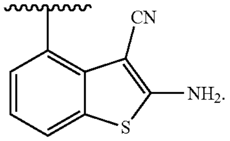
In some embodiments, $R^7$ is
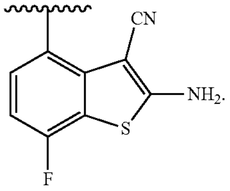
In some embodiments, $R^7$ is
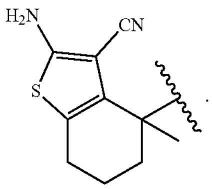 [SMILES: *C1(C)CCCc2sc(N)c(C#N)c21]
In some embodiments, $R^7$ is
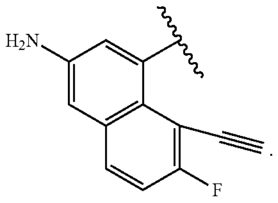 [SMILES: *c1cc(N)cc2ccc(F)c(C#C)c12]
In some embodiments, $R^7$ is
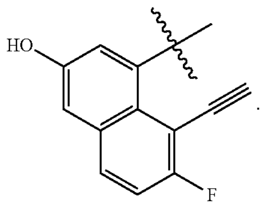 [SMILES: *c1cc(O)cc2ccc(F)c(C#C)c12]

In some embodiments, $R^7$ is

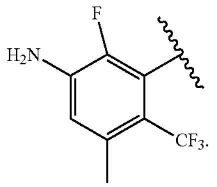 [SMILES: *c1c(F)c(N)cc(C)c1C(F)(F)F]

In some embodiments, $R^7$ is

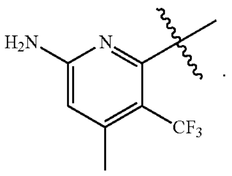 [SMILES: *c1nc(N)cc(C)c1C(F)(F)F]

In some embodiments, $R^7$ is

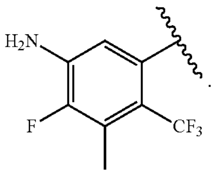 [SMILES: *c1cc(N)c(F)c(C)c1C(F)(F)F]

In some embodiments, for a compound of Formula (I) or (II), $R^7$ is substituted with one, two, three, or four substituents independently selected from halogen, —CN, $C_{1-6}$ alkyl, $C_{2-6}$ alkenyl, $C_{2-6}$ alkynyl, $C_{3-6}$ cycloalkyl, —$OR^{22}$, —$SR^{22}$, and —$N(R^{22})(R^{23})$, wherein each of $C_{1-6}$ alkyl, $C_{2-6}$ alkenyl, $C_{2-6}$ alkynyl, and $C_{3-6}$ cycloalkyl is optionally substituted with one, two, or three substituents independently selected from halogen, $C_{1-6}$ alkyl, $C_{1-6}$ haloalkyl, and —$OR^{22}$. In some embodiments, $R^7$ is substituted with one, two, three, or four substituents independently selected from halogen, —CN, $C_{1-3}$ alkyl, $C_{2-3}$ alkenyl, $C_{2-3}$ alkynyl, —$OR^{22}$, and —$N(R^{22})(R^{23})$. In some embodiments, $R^7$ is substituted with one, two, three, or four substituents independently selected from halogen, —CN, —$CH_3$, —C≡CH, —OH, and —$NH_2$. In some embodiments, $R^7$ is substituted with —F, —CN, and —$NH_2$. In some embodiments, $R^7$ is substituted with —F, —C≡CH, and —OH. In some embodiments, $R^7$ is substituted with —$CF_3$, —$CH_3$, and —$NH_2$. In some embodiments, $R^7$ is substituted with —$CF_3$ and —$NH_2$. In some embodiments, $R^7$ is substituted with —$CF_3$, —$CH_3$, —F, and —$NH_2$. In some embodiments, $R^7$ is substituted with —$CF_3$, —F, and —$NH_2$. In some embodiments, $R^7$ is substituted with one, two, three, or four substituents independently selected from halogen, —CN, —$CH_3$, —$CH_2CH_3$, —CH=$CH_2$, —$CF_3$, —C≡CH, —OH, —$NH_2$, and -cyclopropyl.

In some embodiments, for a compound of Formula (I) or (II):

$R^2$ is selected from hydrogen, $C_{1-3}$ alkyl, —$OR^{12}$, and 3- to 10-membered heterocycle, wherein each of $C_{1-3}$ alkyl and 3- to 10-membered heterocycle is optionally substituted; and $R^6$ and $R^8$ are independently selected from hydrogen, halogen, and $C_{1-3}$ haloalkyl.

In some embodiments, for a compound of Formula (I) or (II):

$R^2$ is selected from hydrogen, $C_{1-3}$ alkyl, —$OR^{12}$, and 3- to 10-membered heterocycle, wherein each of $C_{1-3}$ alkyl and 3- to 10-membered heterocycle is optionally substituted;

$R^5$ is hydrogen; and $R^6$ and $R^8$ are independently selected from hydrogen, halogen, and $C_{1-3}$ haloalkyl.

In some embodiments, for a compound of Formula (I) or (II):

$R^2$ is selected from hydrogen, $C_{1-3}$ alkyl, —$OR^{12}$, and 3- to 10-membered heterocycle, wherein each of $C_{1-3}$ alkyl and 3- to 10-membered heterocycle is optionally substituted;

$R^5$ is hydrogen;

$R^6$ and $R^8$ are independently selected from hydrogen, halogen, and $C_{1-3}$ haloalkyl; and $R^7$ is selected from naphthyl, isoquinolinyl, indazolyl, benzothiazolyl, benzothiophenyl, phenyl, and pyridinyl, each of which is optionally substituted.

In some embodiments, for a compound of Formula (I) or (II):

$R^2$ is selected from hydrogen, $C_{1-3}$ alkyl, —$OR^{12}$, and 3- to 10-membered heterocycle, wherein each of $C_{1-3}$ alkyl and 3- to 10-membered heterocycle is optionally substituted;

$R^6$ and $R^8$ are independently selected from hydrogen, halogen, and $C_{1-3}$ haloalkyl; and $R^7$ is selected from

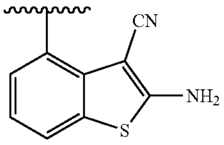
and
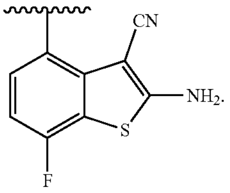

In some embodiments, for a compound of Formula (I) or (II):

$R^2$ is selected from hydrogen, $C_{1-3}$ alkyl, —$OR^{12}$, and 3- to 10-membered heterocycle, wherein each of $C_{1-3}$ alkyl and 3- to 10-membered heterocycle is optionally substituted;

$R^5$ is hydrogen;

$R^6$ and $R^8$ are independently selected from hydrogen, halogen, and $C_{1-3}$ haloalkyl; and $R^7$ is selected from

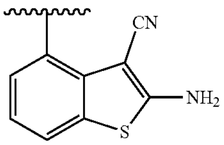
and
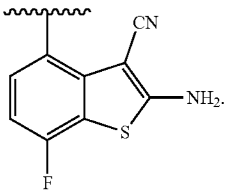

In some embodiments, for a compound of Formula (I) or (II):

$R^5$ is hydrogen;

$R^6$ is selected from halogen and $C_{1-3}$ haloalkyl;

$R^7$ is selected from naphthyl, isoquinolinyl, indazolyl, benzothiazolyl, benzothiophenyl, phenyl, and pyridinyl, each of which is optionally substituted; and $R^8$ is halogen.

In some embodiments, for a compound of Formula (I) or (II):

$R^2$ is selected from

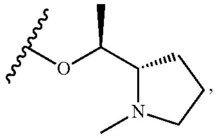,
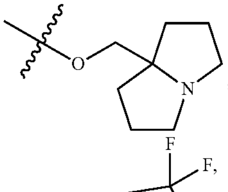,
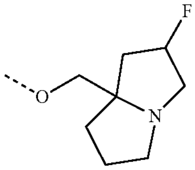,
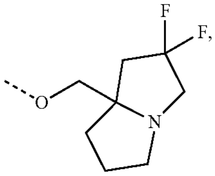
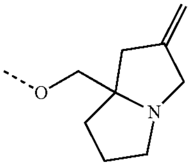,
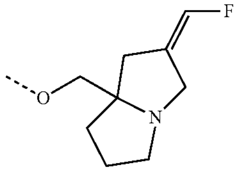,
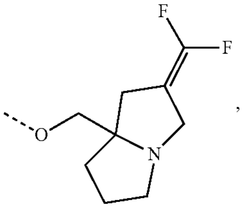, and
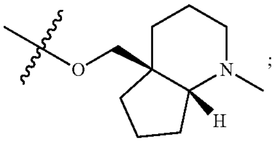;

$R^5$ is hydrogen;

$R^6$ is selected from halogen and $C_{1-3}$ haloalkyl;

$R^7$ is selected from naphthyl, isoquinolinyl, indazolyl, benzothiazolyl, benzothiophenyl, phenyl, and pyridinyl, each of which is optionally substituted; and $R^8$ is halogen.

In some embodiments, for a compound of Formula (I) or (II):

$R^2$ is selected from

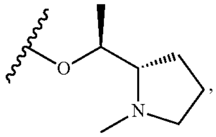,
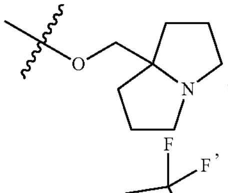,
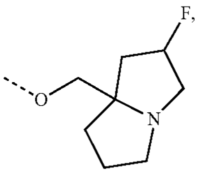
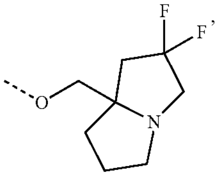
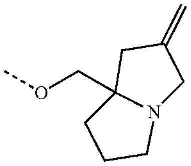,
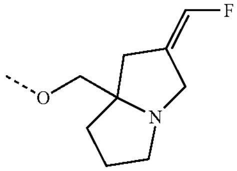,

-continued

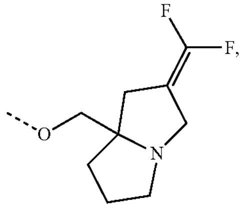 and
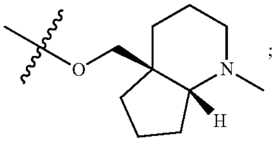;

$R^5$ is hydrogen;

$R^6$ is selected from halogen and $C_{1-3}$ haloalkyl;

$R^7$ is selected from

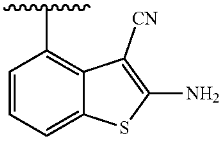 and
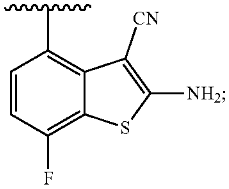

and $R^8$ is halogen.

In some embodiments, for a compound of Formula (I) or (II):

$R^2$ is selected from

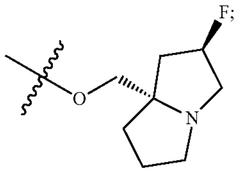 [SMILES: *OC[C@@]12CCCN1C[C@H](F)C2]

$R^5$ is hydrogen;

$R^6$ is selected from chlorine and $-CF_3$; and $R^8$ is fluorine.

In some embodiments, for a compound of Formula (I) or (II):

$R^2$ is selected from

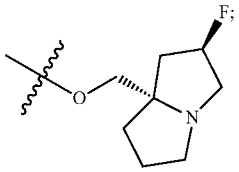 [SMILES: *OC[C@@]12CCCN1C[C@H](F)C2]

$R^5$ is hydrogen;

$R^6$ is selected from chlorine and $-CF_3$;

$R^7$ is selected from

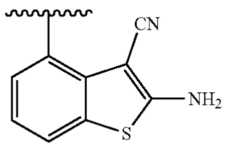 and 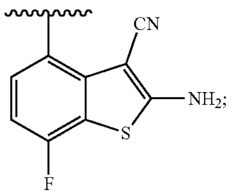 [SMILES: *c1ccc(F)c2sc(N)c(C#N)c12]

and $R^8$ is fluorine.

In some embodiments, for a compound of Formula (I) or (II):

$R^5$ is hydrogen;

$R^6$ is selected from chlorine and —$CF_3$; and $R^8$ is fluorine.

In some embodiments, for a compound of Formula (I) or (II):

$R^5$ is hydrogen;

$R^6$ is selected from chlorine and —$CF_3$;

$R^7$ is

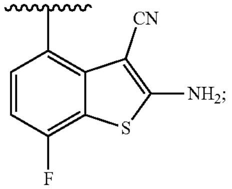

and $R^8$ is fluorine.

In some embodiments, for a compound of Formula (I) or (II):

$R^2$ is

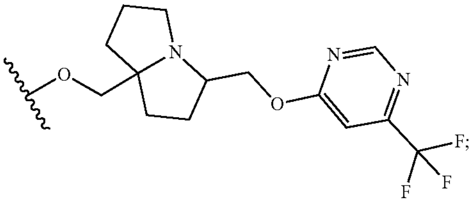 [SMILES: *OCC12CCCN1C(COc1cc(C(F)(F)F)ncn1)CC2]

$R^5$ is hydrogen;

$R^6$ is chlorine; and $R^8$ is fluorine.

In some embodiments, for a compound of Formula (I) or (II):

$R^2$ is

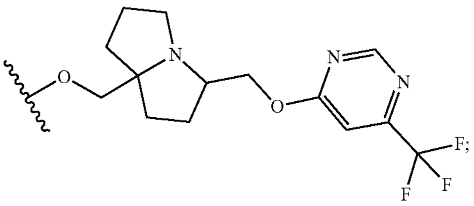 [SMILES: *OCC12CCCN1C(COc1cc(C(F)(F)F)ncn1)CC2]

$R^5$ is hydrogen;

$R^6$ is chlorine;

$R^7$ is

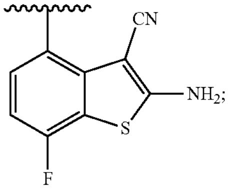 [SMILES: *c1ccc(F)c2sc(N)c(C#N)c12]

and $R^8$ is fluorine.

In some embodiments, for a compound of Formula (II):

$R^2$ is

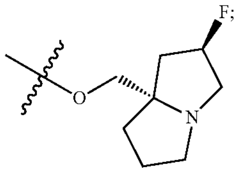 [SMILES: *OC[C@@]12CCCN1C[C@H](F)C2]

$R^{4a}$ is $C_{1-6}$ alkyl;

$L^2$ is pyrrolidin-1,3-diyl, optionally substituted with $C_{1-3}$ alkyl;

$R^{19}$ is selected from imidazole-1-yl and 1,2,4-triazol-1-yl, each of which is optionally substituted with one or two substituents independently selected from halogen, —CN, $C_{1-6}$ alkyl, —O($C_{1-6}$ alkyl), and $C_{3-6}$ cycloalkyl;

$R^5$ is hydrogen;

$R^6$ is selected from chlorine and —$CF_3$; and $R^8$ is fluorine.

In some embodiments, for a compound of Formula (II):

$R^2$ is selected from

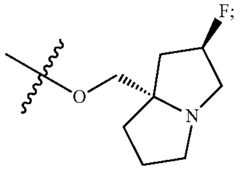 [SMILES: *OC[C@@]12CCCN1C[C@H](F)C2]

$R^{4a}$ is $C_{1-6}$ alkyl;

$L^2$ is pyrrolidin-1,3-diyl, optionally substituted with $C_{1-3}$ alkyl;

$R^{19}$ is selected from imidazole-1-yl and 1,2,4-triazol-1-yl, each of which is optionally substituted with one or two substituents independently selected from halogen, —CN, $C_{1-6}$ alkyl, —O($C_{1-6}$ alkyl), and $C_{3-6}$ cycloalkyl;

$R^5$ is hydrogen;

$R^6$ is selected from chlorine and —$CF_3$;

$R^7$ is

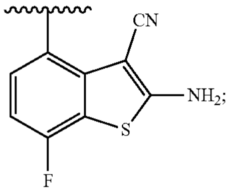 [SMILES: *c1ccc(F)c2sc(N)c(C#N)c12]

and $R^8$ is fluorine.

In some embodiments, for a compound of Formula (II):

$R^2$ is selected from

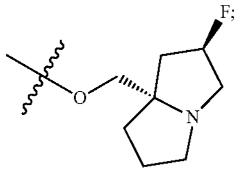 [SMILES: *OC[C@@]12CCCN1C[C@H](F)C2]

$R^{4a}$ is selected from —$CH_3$, —$CH_2CH_3$, and —$CH(CH_3)_2$;

$L^2$ is 2-methylpyrrolidin-1,3-diyl;

$R^{19}$ is 1,2,4-triazol-1-yl, optionally substituted with one or two substituents independently selected from halogen, —CN, and $C_{1-3}$ alkyl;

$R^5$ is hydrogen;

$R^6$ is selected from chlorine and —$CF_3$;

$R^7$ is

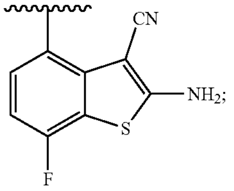 [SMILES: *c1ccc(F)c2sc(N)c(C#N)c12]

and $R^8$ is fluorine.

In some embodiments, for a compound of Formula (II):

$R^{4a}$ is selected from —$CH_3$, —$CH_2CH_3$, and —$CH(CH_3)_2$;

$L^2$ is pyrrolidin-1,3-diyl, optionally substituted with $C_{1-3}$ alkyl;

$R^{19}$ is selected from imidazole-1-yl and 1,2,4-triazol-1-yl, each of which is optionally substituted with one or two substituents independently selected from halogen, —CN, $C_{1-6}$ alkyl, —O($C_{1-6}$ alkyl), and $C_{3-6}$ cycloalkyl;

$R^5$ is hydrogen;

$R^6$ is selected from chlorine and —$CF_3$; and $R^8$ is fluorine.

In some embodiments, for a compound of Formula (II):

$R^{4a}$ is selected from —$CH_3$, —$CH_2CH_3$, and —$CH(CH_3)_2$;

$L^2$ is 2-methylpyrrolidin-1,3-diyl;

$R^{19}$ is selected from imidazole-1-yl and 1,2,4-triazol-1-yl, each of which is optionally substituted with one or two substituents independently selected from halogen, —CN, $C_{1-6}$ alkyl, —O($C_{1-6}$ alkyl), and $C_{3-6}$ cycloalkyl;

$R^5$ is hydrogen;

$R^6$ is selected from chlorine and —$CF_3$;

$R^7$ is

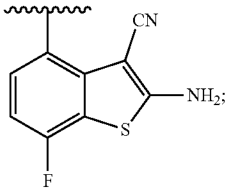 [SMILES: *c1ccc(F)c2sc(N)c(C#N)c12]

and $R^8$ is fluorine.

In some embodiments, for a compound of Formula (II):

$R^2$ is

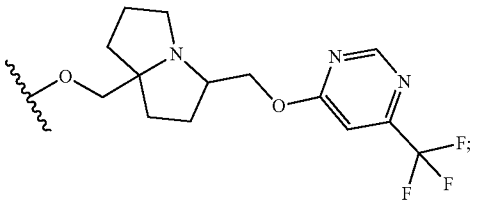 [SMILES: *OCC12CCCN1C(COc1cc(C(F)(F)F)ncn1)CC2]

$R^{4a}$ is selected from —$CH_3$, —$CH_2CH_3$, and —$CH(CH_3)_2$;

$L^2$ is 2-methylpyrrolidin-1,3-diyl;

$R^{19}$ is 2,4-dimethyl-imidazole-1-yl;

$R^5$ is hydrogen;

$R^6$ is chlorine; and $R^8$ is fluorine.

In some embodiments, for a compound of Formula (II):

$R^2$ is

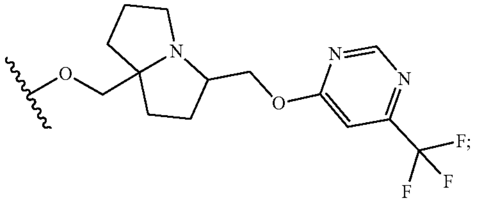 [SMILES: *OCC12CCCN1C(COc1cc(C(F)(F)F)ncn1)CC2]

$R^{4a}$ is selected from —$CH_3$, —$CH_2CH_3$, and —$CH(CH_3)_2$;

$L^2$ is 2-methylpyrrolidin-1,3-diyl;

$R^{19}$ is 2,4-dimethyl-imidazole-1-yl;

$R^5$ is hydrogen;

$R^6$ is chlorine;

$R^7$ is

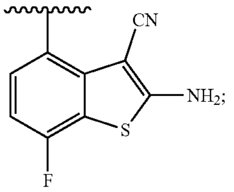 [SMILES: *c1ccc(F)c2sc(N)c(C#N)c12]

and $R^8$ is fluorine.

In certain aspects, the present disclosure provides a compound of the formula

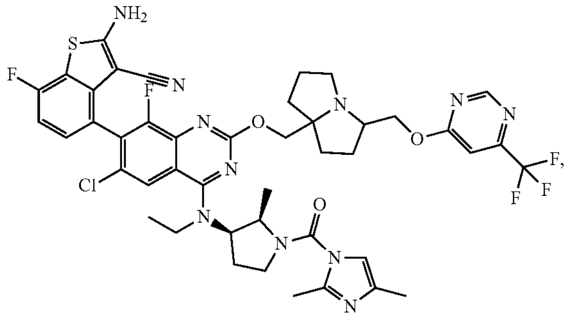 [SMILES: CCN(c1nc(OCC23CCCN2C(COc2cc(C(F)(F)F)ncn2)CC3)nc2c(F)c(-c3ccc(F)c4sc(N)c(C#N)c34)c(Cl)cc12)[C@@H]1CCN(C(=O)n2cc(C)nc2C)[C@@H]1C]

or a pharmaceutically acceptable salt or solvate thereof. In certain aspects, the present disclosure provides a pharmaceutical composition comprising a compound of the formula

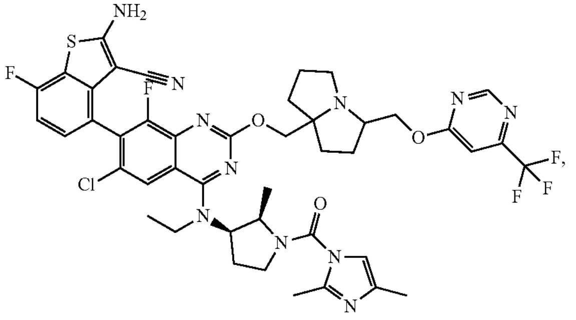 [SMILES: CCN(c1nc(OCC23CCCN2C(COc2cc(C(F)(F)F)ncn2)CC3)nc2c(F)c(-c3ccc(F)c4sc(N)c(C#N)c34)c(Cl)cc12)[C@@H]1CCN(C(=O)n2cc(C)nc2C)[C@@H]1C]

or a pharmaceutically acceptable salt or solvate thereof, and a pharmaceutically acceptable excipient.

Unless stated otherwise, an optionally substituted group of the present disclosure may be unsubstituted or substituted with one or more, such as one, two, three, four, or five, substituents independently selected from $R^{20}$. In some embodiments, an optionally substituted group of the present disclosure is unsubstituted or substituted with one, two, or three substituents independently selected from $R^{20}$. In some embodiments, $R^{20}$ is independently selected at each occurrence from:

halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, —$S(=O)(=NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein each of $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle is optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, a compound disclosed herein, such as a compound of Formula (I) or (II), exhibits selective and potent inhibition of K-Ras G12S and/or K-Ras G12C relative to wildtype K-Ras or other K-Ras mutants (e.g., K-Ras G12V or K-Ras G12D). In some embodiments, a subject warhead exhibits selective engagement of K-Ras G12S and/or K-Ras G12C relative to K-Ras G12D or wildtype K-Ras by at least 1-fold, and in some instances greater than 2-, 3-, 4-, 5-, 10-, 15-, or 20-fold, or even higher. In some embodiments, a subject warhead exhibits a selective and rapid engagement of K-Ras G12S and/or K-Ras G12C yielding at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, or even higher engagement of G12S and/or K-Ras G12C within, 10 mins, 20 mins, 30 mins, 1 hr, 2 hrs, 3 hrs, 4 hrs, 5 hrs, 6 hrs, 7 hrs, 8 hrs, 9 hrs, 10 hrs, 20 hrs, or 24 hours. In some embodiments, a selective and rapid engagement of K-Ras G12S and/or K-Ras G12C is evidenced by at least 50% engagement within 24 hours. In some embodiments, subject compounds specifically engage K-Ras G12S and/or K-Ras G12C covalently with essentially no detectable labeling of K-Ras G12D when assayed under comparable conditions.

The inclusion of a warhead of the present disclosure may enhance the efficacy or potency of K-Ras G12S and/or K-Ras G12C inhibition. In some embodiments, a subject compound comprising a subject warhead inhibits K-Ras G12S and/or K-Ras G12C with higher potency as evidenced by an IC50 value that is at least 10%, 20%, 50%, 100%, 200%, 300%, 400%, or at least 500% lower than the IC50 value of a corresponding control compound that does not comprise the warhead. In some embodiments, a subject compound comprising a subject warhead inhibits K-Ras G12S and/or K-Ras G12C with higher potency as evidenced by an IC50 value that is at least 1.1-times, 1.2-times, 1.5-times, 2-times, 3-times, 4-times, 5-times, 6-times, 7-times, 8-times, 9-times, 10-times, 15-times, or at least 20-times lower than the IC50 value of a corresponding control compound that does not comprise the warhead, as ascertained in a biochemical assay exemplified in Example 5.

The inclusion of a warhead of the present disclosure may enhance the efficacy or potency with which a subject compound inhibits the proliferation of cells that express a K-Ras G12S mutation and/or a K-Ras G12C mutation. In some embodiments, a subject compound comprising a subject warhead inhibits the proliferation of cells that express a K-Ras G12S mutation and/or a K-Ras G12C mutation with higher potency as evidenced by an IC50 value that is at least 10%, 20%, 50%, 100%, 200%, 300%, 400%, or at least 500% lower than the IC50 value of a corresponding control compound that does not comprise the warhead. In some embodiments, a subject compound comprising a subject warhead inhibits the proliferation of cells that express a K-Ras G12S mutation and/or a K-Ras G12C mutation with higher potency as evidenced by an IC50 value that is at least 1.1-times, 1.2-times, 1.5-times, 2-times, 3-times, 4-times, 5-times, 6-times, 7-times, 8-times, 9-times, 10-times, 15-times, or at least 20-times lower than the IC50 value of a corresponding control compound that does not comprise the warhead, as ascertained in a cellular inhibition assay exemplified in Example 9.

In some embodiments, a compound described herein, such as a compound of Formula (I) or (II), is provided as a substantially pure stereoisomer. In some embodiments, the stereoisomer is provided in at least 80% enantiomeric excess, such as at least 85%, at least 90%, at least 95%, at least 96%, at least 97%, at least 98%, at least 99%, or at least 99.9% enantiomeric excess.

In some embodiments, the present disclosure provides an atropisomer of a compound described herein, such as a compound of Formula (I) or (II). In some embodiments, the atropisomer is provided in enantiomeric excess. In some embodiments, the atropisomer is provided in at least 80% enantiomeric excess, such as at least 85%, at least 90%, at least 95%, at least 96%, at least 97%, at least 98%, at least 99%, or at least 99.9% enantiomeric excess. In some embodiments, the compound of Formula (I) or (II) is preferably used as a non-racemic mixture, wherein one atropisomer is present in excess of its corresponding enantiomer or epimer. Typically, such mixture contains a mixture of the two isomers in a ratio of at least 9:1, preferably at least 19:1. In some embodiments, the atropisomer is provided in at least 96% enantiomeric excess, meaning the compound has less than 2% of the corresponding enantiomer. In some embodiments, the atropisomer is provided in at least 96% diastereomeric excess, meaning the compound has less than 2% of the corresponding diastereomer.

The term "atropisomers" refers to conformational stereoisomers which occur when rotation about a single bond in the molecule is prevented, restricted, or greatly slowed as a result of steric interactions with other parts of the molecule and wherein the substituents at both ends of the single bond are asymmetrical (i.e., optical activity arises without requiring an asymmetric carbon center or stereocenter). Where the rotational barrier about the single bond is high enough, and interconversion between conformations is slow enough, separation and isolation of the isomeric species may be permitted. Atropisomers are enantiomers (or epimers) without a single asymmetric atom. Atropisomers are typically considered stable if the barrier to interconversion is high enough to permit the atropisomers to undergo little or no interconversion at room temperature for a least a week, preferably at least a year. In some embodiments, an atropisomeric compound of the disclosure does not undergo more than about 5% interconversion to its opposite atropisomer at room temperature during one week when the atropisomeric compound is in substantially pure form, which is generally a solid state. In some embodiments, an atropisomeric compound of the disclosure does not undergo more than about 5% interconversion to its opposite atropisomer at room temperature (approximately 25° C.) during one year. The present chemical entities, pharmaceutical compositions, and methods are meant to include all such possible atropisomers, including racemic mixtures, diastereomeric mixtures, epimeric mixtures, optically pure forms of single atropisomers, and intermediate mixtures.

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases or inorganic or organic acids to form a pharmaceutically acceptable salt. In some embodiments, such salts are prepared in situ during the final isolation and purification of the compounds described herein, or by separately reacting a purified compound in its free form with a suitable acid or base, and isolating the salt thus formed.

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1 and 2 and Example 1, the steps in some cases may be performed in a different order than the order shown in Schemes 1 and 2 and Example 1. Various modifications to these synthetic reaction schemes may be made and will be suggested to one skilled in the art having referred to the present disclosure. Numberings or R groups in each scheme typically have the same meanings as those defined elsewhere herein unless otherwise indicated.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

Scheme 1

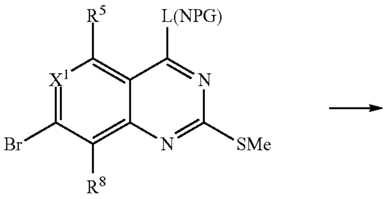

1a

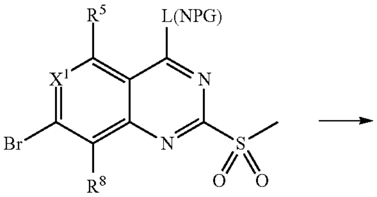

1b

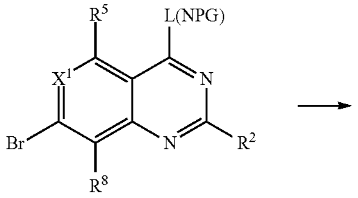

1c

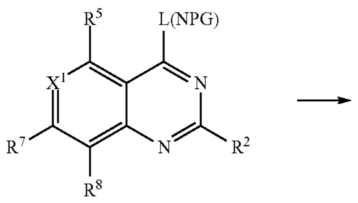

1d

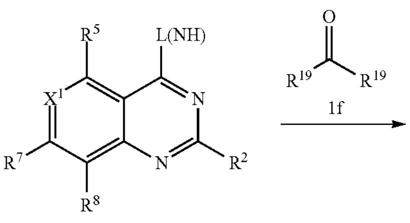

1e

-continued

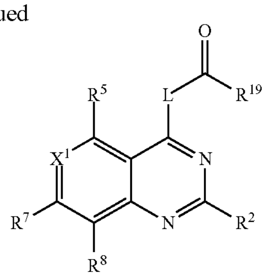

1g

In some embodiments, a compound of Formula 1g may be prepared according to Scheme 1. For example, oxidation of methyl sulfide 1a can provide sulfone 1b, which can be substituted with $R^2$ upon additional of a suitable alcohol to afford 1c (wherein L comprises a suitably-protected amine (e.g., PG is Boc, Bus, Cbz, or Fmoc)). Substitution of the aryl bromide with a suitable boronic ester can provide the corresponding $R^7$-substituted compound (1d). Removal of the N-protecting group to reveal amine 1e can be followed by reaction with compound if in the presence of a suitable base, such as DIPEA, to provide a compound of Formula 1g.

Scheme 2

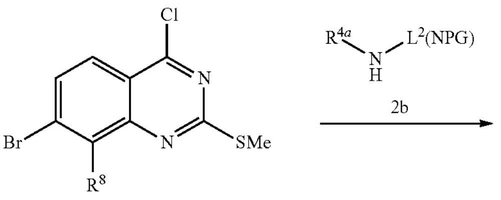

2a

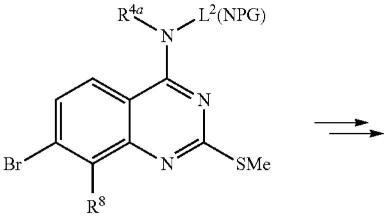

2c

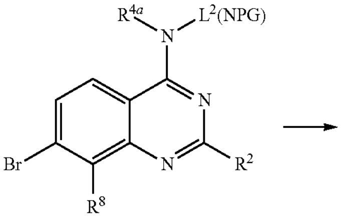

2d

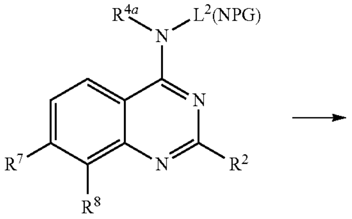

2e

-continued

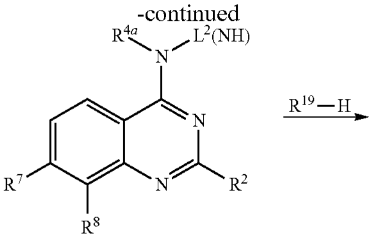

2f

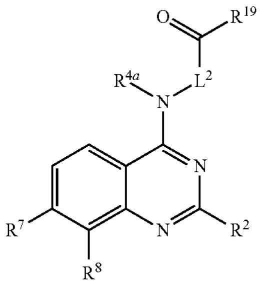

2g

In some embodiments, a compound of Formula 2g may be prepared according to Scheme 2. For example, heteroaryl amine 2c can be formed from chloride 2a via a nucleophilic aromatic substitution reaction with amine 2b (where $L^2$ of compound 2b comprises a suitably protected nitrogen atom (e.g., wherein PG is Boc, Bus, Cbz, or Fmoc)). Oxidation of the methyl sulfide can be followed by substitution with a suitable alcohol to install $R^2$ (2d). Substitution of aryl bromide 2d with a suitable boronic ester can provide the corresponding $R^7$-substituted compound (2e). Removal of the N-protecting group to reveal amine 2f can be followed by reaction with $R^{19}$—H in the presence of triphosgene (bis(trichloromethyl) carbonate (BTC) and pyridine to provide a compound of Formula 2g.

In some embodiments, a compound of the present disclosure, for example, a compound of a formula given in Table 1, was synthesized according to one of the general routes outlined in Schemes 1-2, Example 1, or by methods generally known in the art. In some embodiments, exemplary compounds may include, but are not limited to, a compound selected from Table 1, or a salt or solvate thereof.

TABLE 1

| No. | Structure | Chemical Name | $[M+H]^+$ |
|---|---|---|---|
| 101[1] | 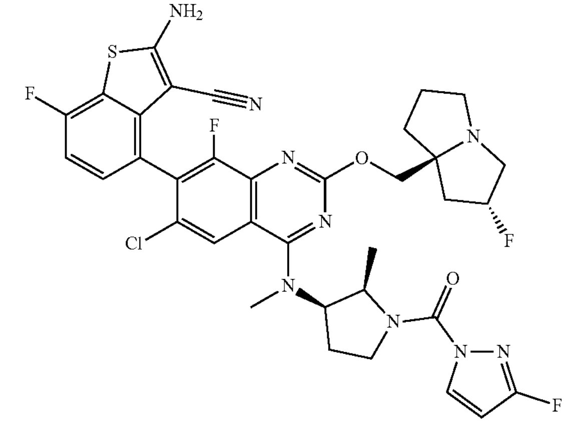 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccc(F)n1] | 2-amino-4-(6-chloro-8-fluoro-4-(((2R,3R)-1-(3-fluoro-1H-pyrazole-1-carbonyl)-2-methylpyrrolidin-3-yl)(methyl)amino)-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 759.2 |
| 102[1] | 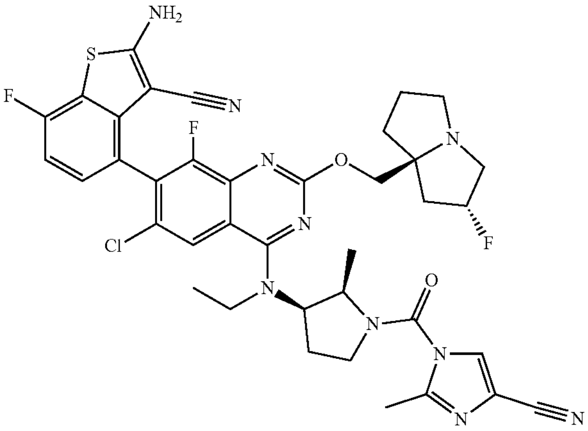 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cc(C#N)nc2C)[C@@H]1C] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carbonyl)-2-methyl-1H-imidazole-4-carbonitrile | 789.2 |

TABLE 1-continued

| No. | Structure | Chemical Name | [M + H]+ |
|---|---|---|---|
| 103[1] | 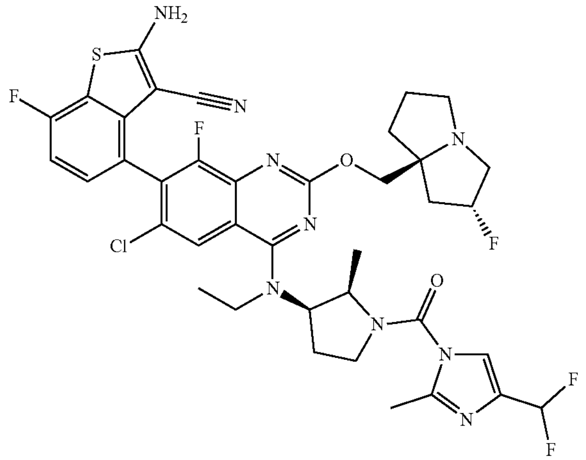 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cc(C(F)F)nc2C)[C@@H]1C] | 2-amino-4-(6-chloro-4-(((2R,3R)-1-(4-(difluoromethyl)-2-methyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 814.4 |
| 104[1] | 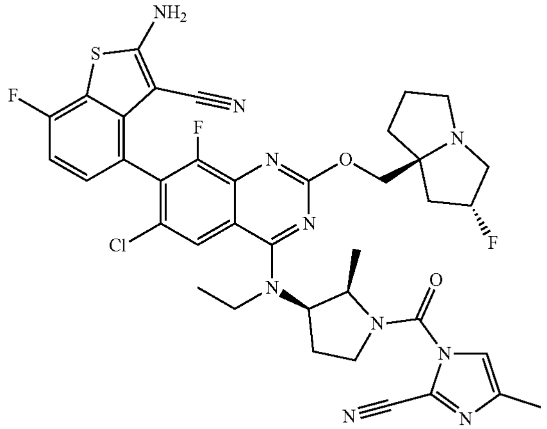 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cc(C)nc2C#N)[C@@H]1C] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carbonyl)-4-methyl-1H-imidazole-2-carbonitrile | 789.2 |
| 105[1] | 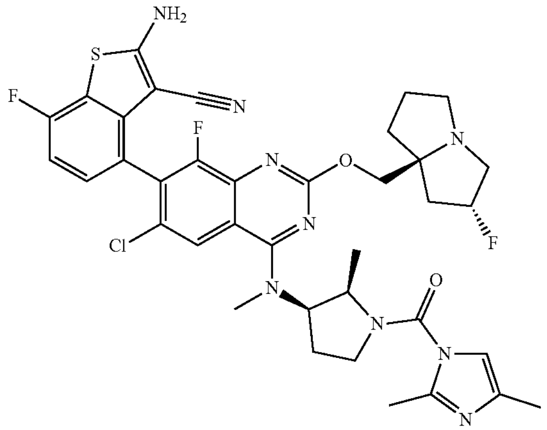 [SMILES: Cc1cn(C(=O)N2CC[C@@H](N(C)c3nc(OC[C@@]45CCCN4C[C@H](F)C5)nc4c(F)c(-c5ccc(F)c6sc(N)c(C#N)c56)c(Cl)cc34)[C@H]2C)c(C)n1] | 2-amino-4-(6-chloro-4-(((2R,3R)-1-(2,4-dimethyl-1H-imidazole-1-carbonyl)-2-methylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 764.2 |

TABLE 1-continued

| No. | Structure | Chemical Name | [M + H]$^+$ |
|---|---|---|---|
| 106[1] | 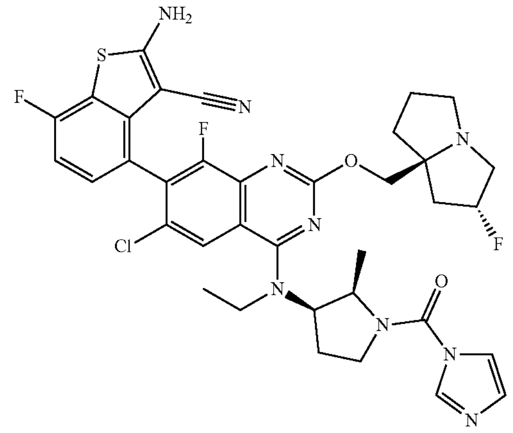 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2ccnc2)[C@@H]1C] | 4-(4-(((2R,3R)-1-(1H-imidazole-1-carbonyl)-2-methylpyrrolidin-3-yl)(ethyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile | 750.2 |
| 107[1] | 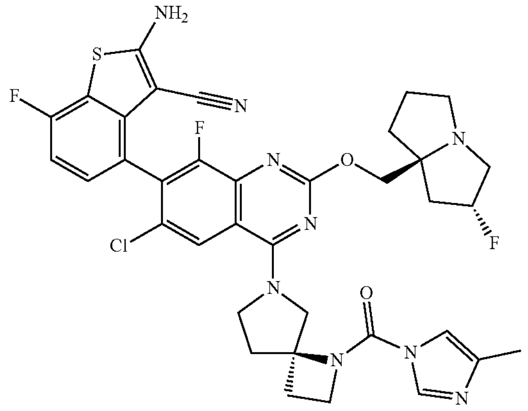 [SMILES: Cc1cn(C(=O)N2CC[C@@]23CCN(c2nc(OC[C@@]45CCCN4C[C@H](F)C5)nc4c(F)c(-c5ccc(F)c6sc(N)c(C#N)c56)c(Cl)cc24)C3)cn1] | 2-amino-4-(6-chloro-8-fluoro-2-(((2R,7aS)-2-fluorotetrahydro-1H-pyrrolizin-7a(5H)-yl)methoxy)-4-((R)-1-(4-methyl-1H-imidazole-1-carbonyl)-1,6-diazaspiro[3.4]octan-6-yl)quinazolin-7-yl)-7-fluorobenzo[b]thiophene-3-carbonitrile | 748.2 |
| 108[1] | 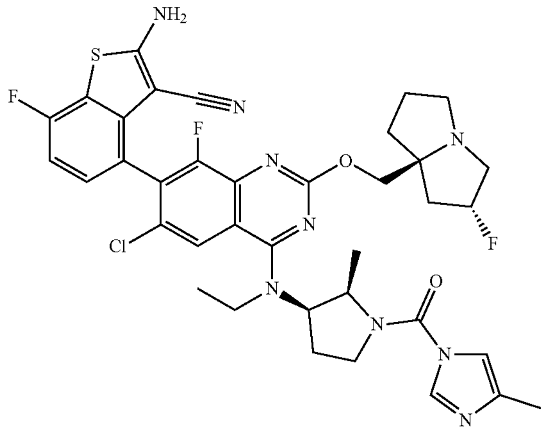 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cnc(C)c2)[C@@H]1C] | 2-amino-4-(6-chloro-4-(ethyl((2R,3R)-2-methyl-1-(4-methyl-1H-imidazole-1-carbonyl)pyrrolidin-3-yl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 764.2 |

TABLE 1-continued

| No. | Structure | Chemical Name | [M + H]+ |
| --- | --- | --- | --- |
| 109[3] | 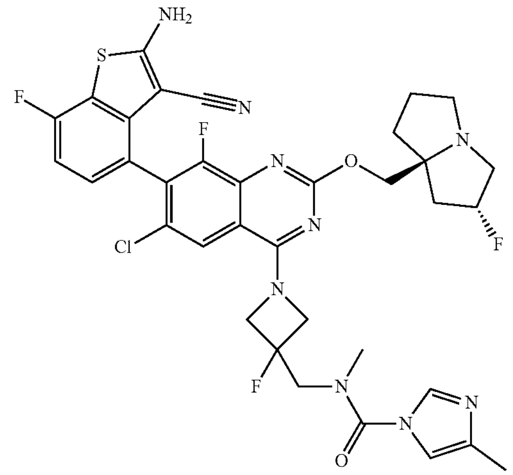 [SMILES: Cc1cn(C(=O)N(C)CC2(F)CN(c3nc(OC[C@@]45CCCN4C[C@H](F)C5)nc4c(F)c(-c5ccc(F)c6sc(N)c(C#N)c56)c(Cl)cc34)C2)cn1] | N-((1-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-3-fluoroazetidin-3-yl)methyl)-N,4-dimethyl-1H-imidazole-1-carboxamide | 754.2 |
| 110[1] | 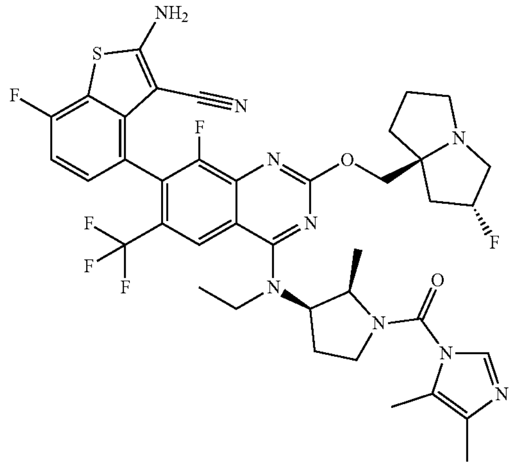 [SMILES: CCN(c1nc(OC[C@@]23CCCN2C[C@H](F)C3)nc2c(F)c(-c3ccc(F)c4sc(N)c(C#N)c34)c(C(F)(F)F)cc12)[C@@H]1CCN(C(=O)n2cnc(C)c2C)[C@@H]1C] | 2-amino-4-(4-(((2R,3R)-1-(4,5-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile | 812.2 |
| 111[2] | 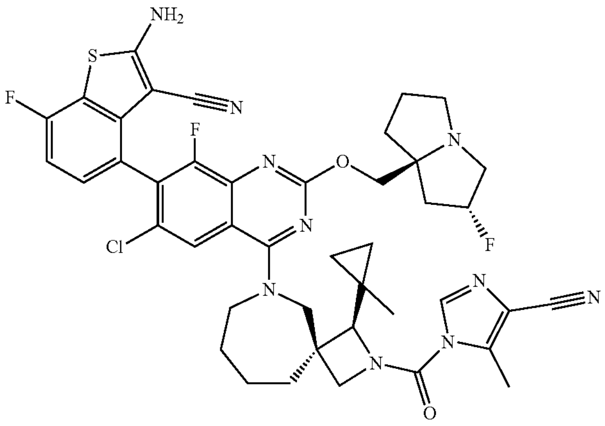 [SMILES: Cc1c(C#N)ncn1C(=O)N1C[C@]2(CCCCN(c3nc(OC[C@@]45CCCN4C[C@H](F)C5)nc4c(F)c(-c5ccc(F)c6sc(N)c(C#N)c56)c(Cl)cc34)C2)[C@H]1C1(C)CC1] | 1-((1R,4R)-6-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-1-(1-methylcyclopropyl)-2,6-diazaspiro[3.6]decane-2-carbonyl)-5-methyl-1H-imidazole-4-carbonitrile | 855.2 |

TABLE 1-continued

| No. | Structure | Chemical Name | [M + H]+ |
|---|---|---|---|
| 112[2] | 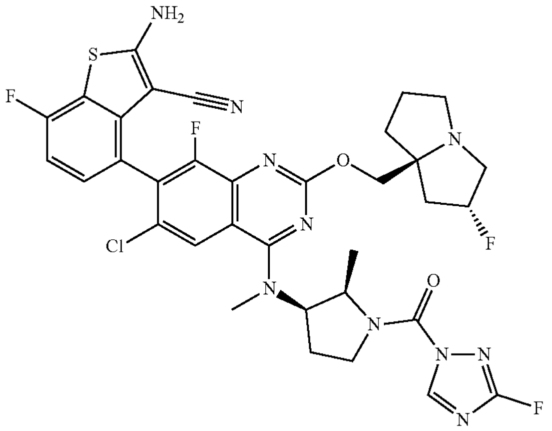 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1cnc(F)n1] | 2-amino-4-(6-chloro-8-fluoro-4-(((2R,3R)-1-(3-fluoro-1H-1,2,4-triazole-1-carbonyl)-2-methylpyrrolidin-3-yl)(methyl)amino)-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 755.2 |
| 113 | 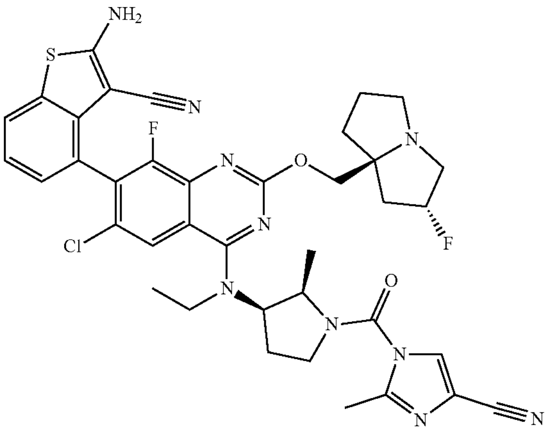 [SMILES: CCN(c1nc(OC[C@@]23CCCN2C[C@H](F)C3)nc2c(F)c(-c3cccc4sc(N)c(C#N)c34)c(Cl)cc12)[C@@H]1CCN(C(=O)n2cc(C#N)nc2C)[C@@H]1C] | 1-((2R,3R)-3-((7-(2-amino-3-cyanobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carbonyl)-2-methyl-1H-imidazole-4-carbonitrile | 771.2 |
| 114[1] | 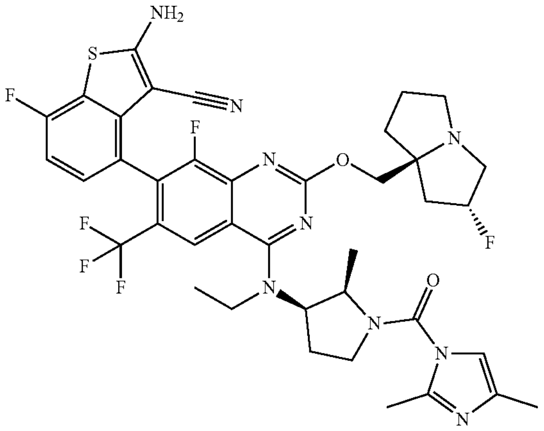 [SMILES: CCN(c1nc(OC[C@@]23CCCN2C[C@H](F)C3)nc2c(F)c(-c3ccc(F)c4sc(N)c(C#N)c34)c(C(F)(F)F)cc12)[C@@H]1CCN(C(=O)n2cc(C)nc2C)[C@@H]1C] | 2-amino-4-(4-(((2R,3R)-1-(2,4-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile | 812.2 |

TABLE 1-continued

| No. | Structure | Chemical Name | [M + H]+ |
|---|---|---|---|
| 115[2] | 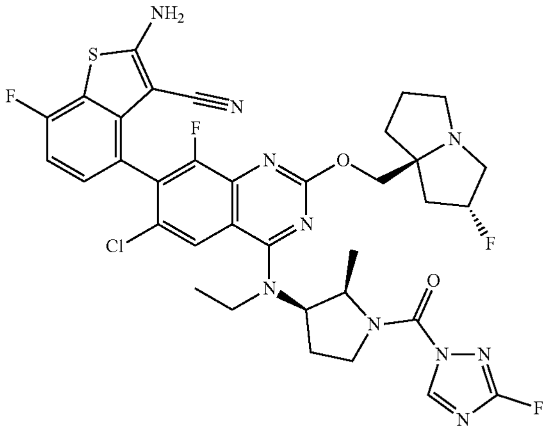 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cnc(F)n2)[C@@H]1C] | 2-amino-4-(6-chloro-4-(ethyl((2R,3R)-1-(3-fluoro-1H-1,2,4-triazole-1-carbonyl)-2-methylpyrrolidin-3-yl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 769.4 |
| 116[1] | 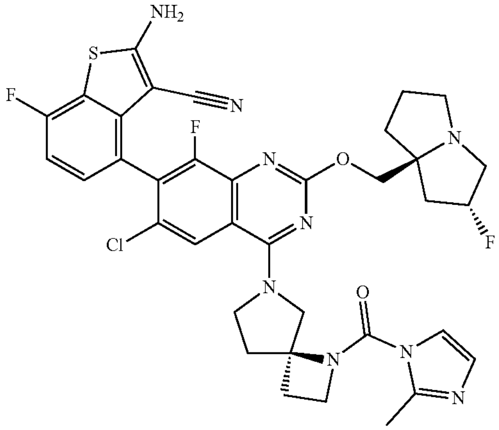 [SMILES: Cc1nccn1C(=O)N1CC[C@@]12CCN(c1nc(OC[C@@]34CCCN3C[C@H](F)C4)nc3c(F)c(-c4ccc(F)c5sc(N)c(C#N)c45)c(Cl)cc13)C2] | 2-amino-4-(6-chloro-8-fluoro-2-(((2R,7aS)-2-fluorotetrahydro-1H-pyrrolizin-7a(5H)-yl)methoxy)-4-((R)-1-(2-methyl-1H-imidazole-1-carbonyl)-1,6-diazaspiro[3.4]octan-6-yl)quinazolin-7-yl)-7-fluorobenzo[b]thiophene-3-carbonitrile | 748.2 |
| 117[1] | 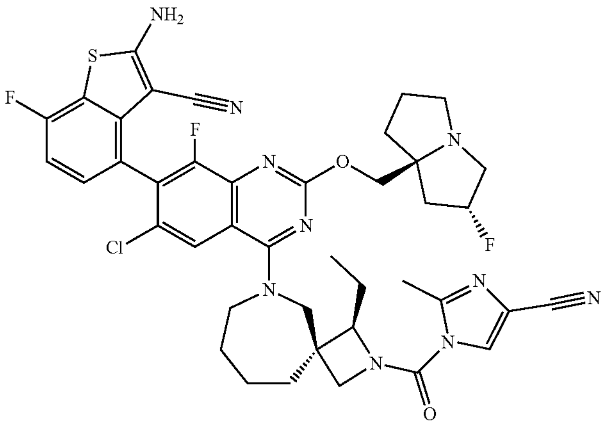 [SMILES: CC[C@H]1N(C(=O)n2cc(C#N)nc2C)C[C@]12CCCCN(c1nc(OC[C@@]34CCCN3C[C@H](F)C4)nc3c(F)c(-c4ccc(F)c5sc(N)c(C#N)c45)c(Cl)cc13)C2] | 1-((1R,4R)-6-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-1-ethyl-2,6-diazaspiro[3.6]decane-2-carbonyl)-2-methyl-1H-imidazole-4-carbonitrile | 829.2 |

TABLE 1-continued

| No. | Structure | Chemical Name | [M + H]+ |
|---|---|---|---|
| 118[3] | 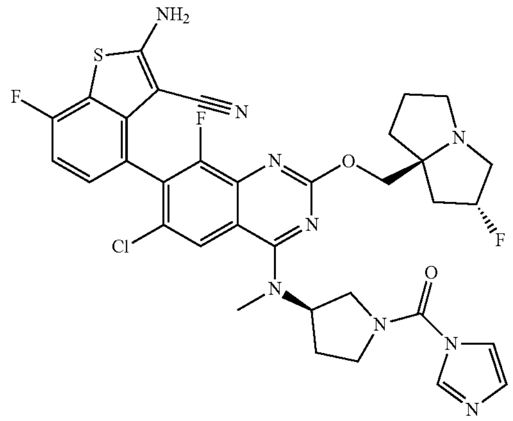 [SMILES: CN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2ccnc2)C1] | 4-(4-(((R)-1-(1H-imidazole-1-carbonyl)pyrrolidin-3-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile | 722.2 |
| 119[1] | 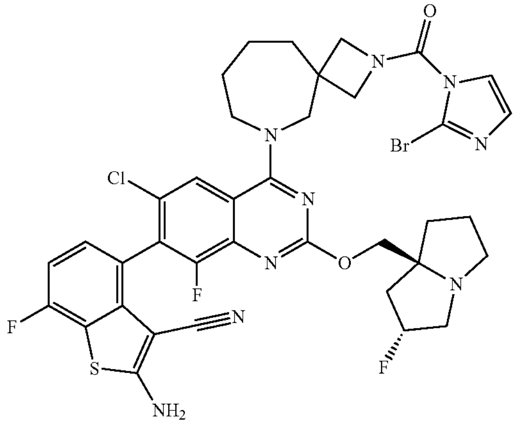 [SMILES: N#Cc1c(N)sc2c(F)ccc(-c3c(Cl)cc4c(N5CCCCC6(CN(C(=O)n7ccnc7Br)C6)C5)nc(OC[C@@]56CCCN5C[C@H](F)C6)nc4c3F)c12] | 2-amino-4-(4-(2-(2-bromo-1H-imidazole-1-carbonyl)-2,6-diazaspiro[3.6]decan-6-yl)-6-chloro-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 840.2 |
| 120[1] | 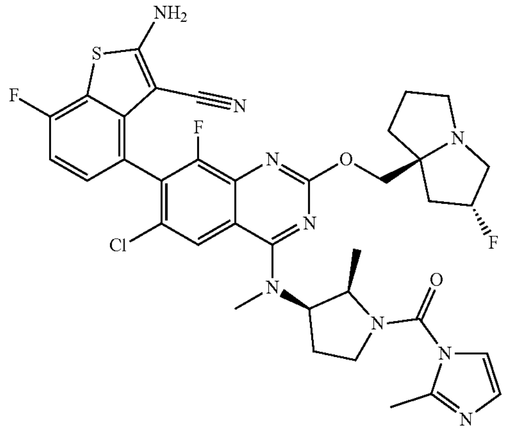 [SMILES: Cc1nccn1C(=O)N1CC[C@@H](N(C)c2nc(OC[C@@]34CCCN3C[C@H](F)C4)nc3c(F)c(-c4ccc(F)c5sc(N)c(C#N)c45)c(Cl)cc23)[C@H]1C] | 2-amino-4-(6-chloro-8-fluoro-2-(((2R,7aS)-2-fluorotetrahydro-1H-pyrrolizin-7a(5H)-yl)methoxy)-4-(methyl((2R,3R)-2-methyl-1-(2-methyl-1H-imidazole-1-carbonyl)pyrrolidin-3-yl)amino)quinazolin-7-yl)-7-fluorobenzo[b]thiophene-3-carbonitrile | 750.2 |

TABLE 1-continued

| No. | Structure | Chemical Name | [M + H]+ |
|---|---|---|---|
| 121[2] | 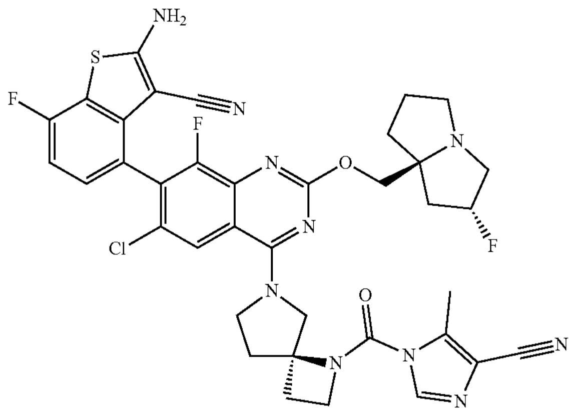 [SMILES: Cc1c(C#N)ncn1C(=O)N1CC[C@@]12CCN(c1nc(OC[C@@]34CCCN3C[C@H](F)C4)nc3c(F)c(-c4ccc(F)c5sc(N)c(C#N)c45)c(Cl)cc13)C2] | 1-((4R)-6-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-1,6-diazaspiro[3.4]octane-1-carbonyl)-5-methyl-1H-imidazole-4-carbonitrile | 773.2 |
| 122[2] | 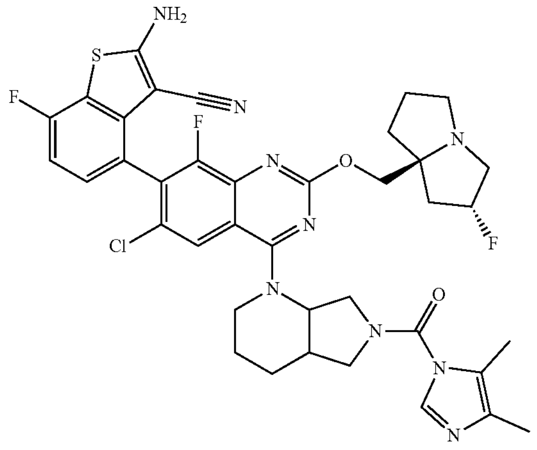 [SMILES: Cc1ncn(C(=O)N2CC3CCCN(c4nc(OC[C@@]56CCCN5C[C@H](F)C6)nc5c(F)c(-c6ccc(F)c7sc(N)c(C#N)c67)c(Cl)cc45)C3C2)c1C] | 2-amino-4-(6-chloro-4-(6-(4,5-dimethyl-1H-imidazole-1-carbonyl)octahydro-1H-pyrrolo[3,4-b]pyridin-1-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile (mixture of cis octahydro-1H-pyrrolo[3,4-b]pyridine isomers) | 775.8 |
| 123[1] | 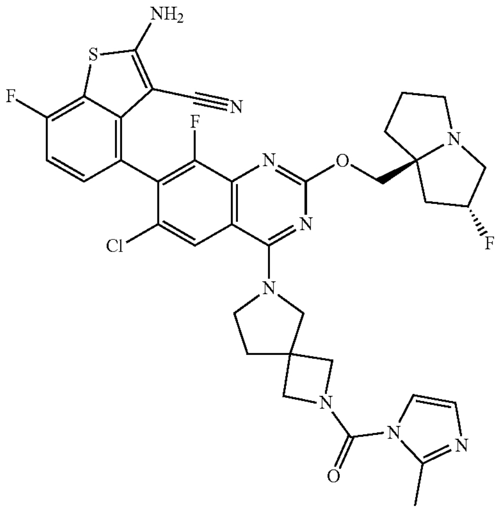 [SMILES: Cc1nccn1C(=O)N1CC2(CCN(c3nc(OC[C@@]45CCCN4C[C@H](F)C5)nc4c(F)c(-c5ccc(F)c6sc(N)c(C#N)c56)c(Cl)cc34)C2)C1] | 2-amino-4-(6-chloro-8-fluoro-2-(((2R,7aS)-2-fluorotetrahydro-1H-pyrrolizin-7a(5H)-yl)methoxy)-4-(2-(2-methyl-1H-imidazole-1-carbonyl)-2,6-diazaspiro[3.4]octan-6-yl)quinazolin-7-yl)-7-fluorobenzo[b]thiophene-3-carbonitrile | 748.2 |

TABLE 1-continued

| No. | Structure | Chemical Name | [M + H]+ |
|---|---|---|---|
| 124[1] | 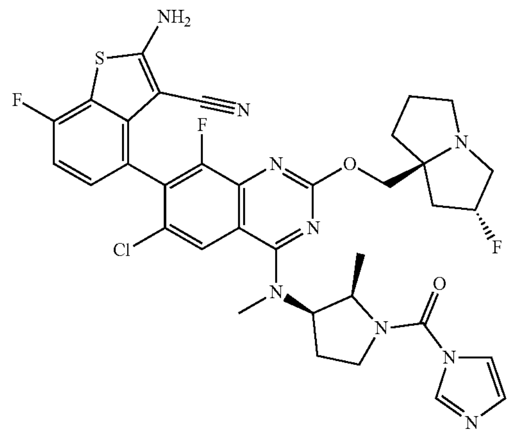 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1] | 4-(4-(((2R,3R)-1-(1H-imidazole-1-carbonyl)-2-methylpyrrolidin-3-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile | 736.2 |
| 125[2] | 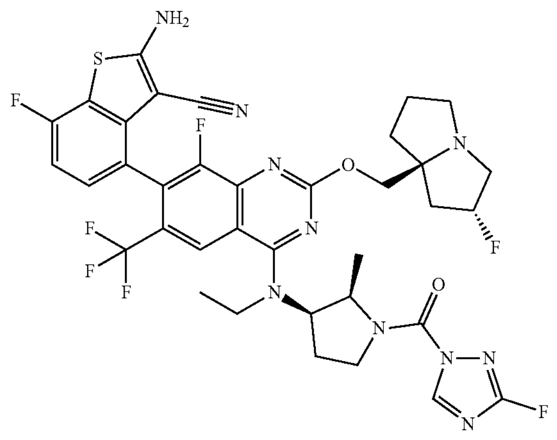 [SMILES: CCN(c1nc(OC[C@@]23CCCN2C[C@H](F)C3)nc2c(F)c(-c3ccc(F)c4sc(N)c(C#N)c34)c(C(F)(F)F)cc12)[C@@H]1CCN(C(=O)n2cnc(F)n2)[C@@H]1C] | 2-amino-4-(4-(ethyl((2R,3R)-1-(3-fluoro-1H-1,2,4-triazole-1-carbonyl)-2-methylpyrrolidin-3-yl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile (single cis pyrrolidine isomer) | 803.2 |
| 126[1] | 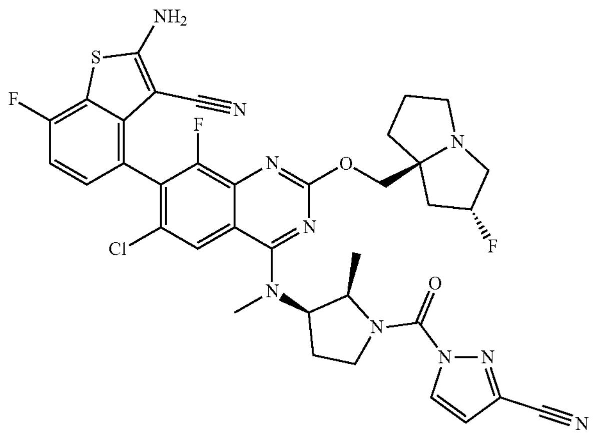 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccc(C#N)n1] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(methyl)amino)-2-methylpyrrolidine-1-carbonyl)-1H-pyrazole-3-carbonitrile | 761.2 |

TABLE 1-continued

| No. | Structure | Chemical Name | [M + H]+ |
|---|---|---|---|
| 127[1] | 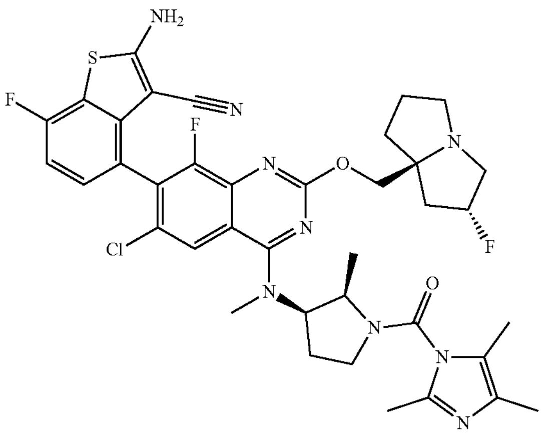 [SMILES: Cc1nc(C)n(C(=O)N2CC[C@@H](N(C)c3nc(OC[C@@]45CCCN4C[C@H](F)C5)nc4c(F)c(-c5ccc(F)c6sc(N)c(C#N)c56)c(Cl)cc34)[C@H]2C)c1C] | 2-amino-4-(6-chloro-8-fluoro-2-(((2R,7aS)-2-fluorotetrahydro-1H-pyrrolizin-7a(5H)-yl)methoxy)-4-(methyl((2R,3R)-2-methyl-1-(2,4,5-trimethyl-1H-imidazole-1-carbonyl)pyrrolidin-3-yl)amino)quinazolin-7-yl)-7-fluorobenzo[b]thiophene-3-carbonitrile | 778.2 |
| 128[2] | 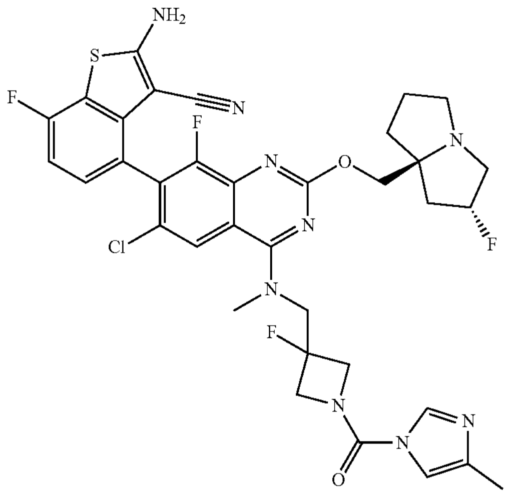 [SMILES: Cc1cn(C(=O)N2CC(F)(CN(C)c3nc(OC[C@@]45CCCN4C[C@H](F)C5)nc4c(F)c(-c5ccc(F)c6sc(N)c(C#N)c56)c(Cl)cc34)C2)cn1] | 2-amino-4-(6-chloro-8-fluoro-4-(((3-fluoro-1-(4-methyl-1H-imidazole-1-carbonyl)azetidin-3-yl)methyl)(methyl)amino)-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 754.2 |
| 129[2] | 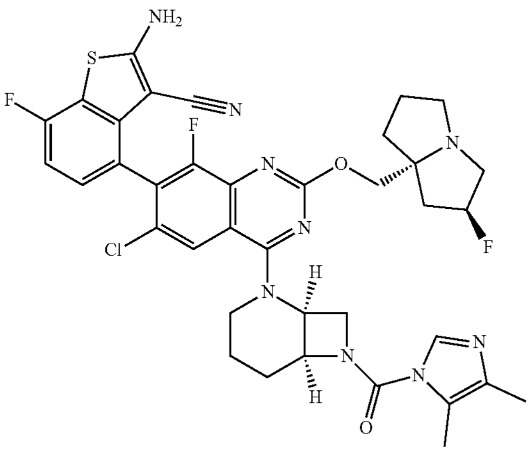 [SMILES: Cc1ncn(C(=O)N2C[C@H]3[C@@H]2CCCN3c2nc(OC[C@]34CCCN3C[C@@H](F)C4)nc3c(F)c(-c4ccc(F)c5sc(N)c(C#N)c45)c(Cl)cc23)c1C] | 2-amino-4-(6-chloro-4-((1S,6S)-7-(4,5-dimethyl-1H-imidazole-1-carbonyl)-2,7-diazabicyclo[4.2.0]octan-2-yl)-8-fluoro-2-(((2S,7aR)-2-fluorotetrahydro-1H-pyrrolizin-7a(5H)-yl)methoxy)quinazolin-7-yl)-7-fluorobenzo[b]thiophene-3-carbonitrile | 762.2 |

TABLE 1-continued

| No. | Structure | Chemical Name | [M + H]+ |
|---|---|---|---|
| 130[1] | 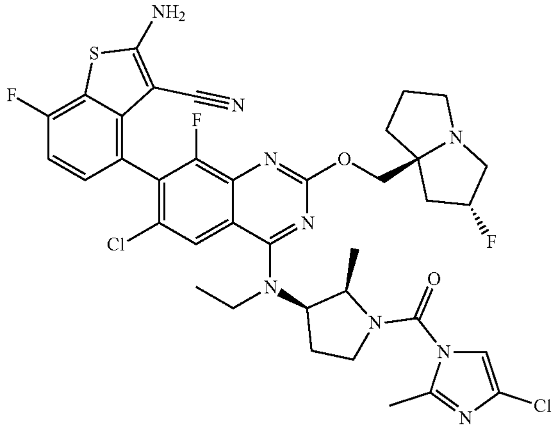 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cc(Cl)nc2C)[C@@H]1C] | 2-amino-4-(6-chloro-4-(((2R,3R)-1-(4-chloro-2-methyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 798.2 |
| 131[1] | 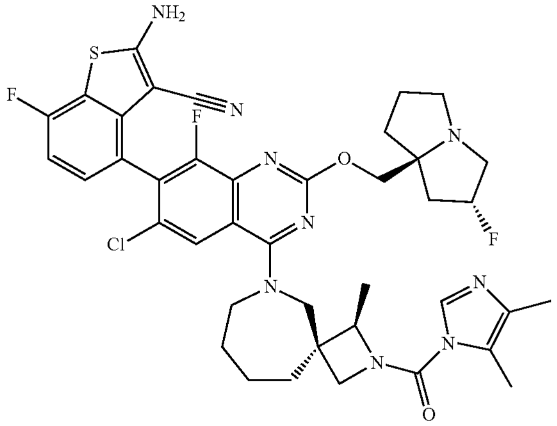 [SMILES: Cc1ncn(C(=O)N2C[C@]3(CCCCN(c4nc(OC[C@@]56CCCN5C[C@H](F)C6)nc5c(F)c(-c6ccc(F)c7sc(N)c(C#N)c67)c(Cl)cc45)C3)[C@H]2C)c1C] | 2-amino-4-(6-chloro-4-((1R,4R)-2-(4,5-dimethyl-1H-imidazole-1-carbonyl)-1-methyl-2,6-diazaspiro[3.6]decan-6-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 804.2 |
| 132[1] | 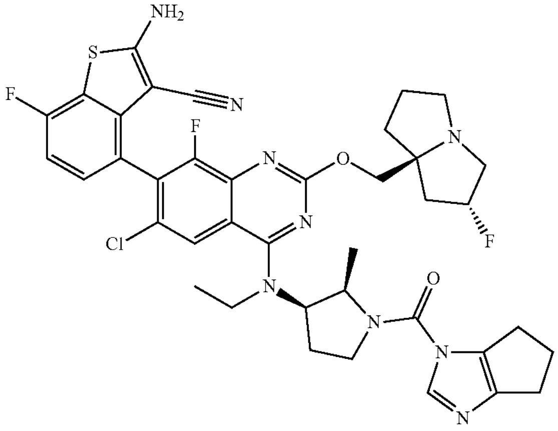 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cnc3c2CCC3)[C@@H]1C] | 2-amino-4-(6-chloro-4-(ethyl((2R,3R)-2-methyl-1-(1,4,5,6-tetrahydrocyclopenta[d]imidazole-1-carbonyl)pyrrolidin-3-yl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 790.2 |

TABLE 1-continued

| No. | Structure | Chemical Name | [M + H]+ |
|---|---|---|---|
| 133[2] | 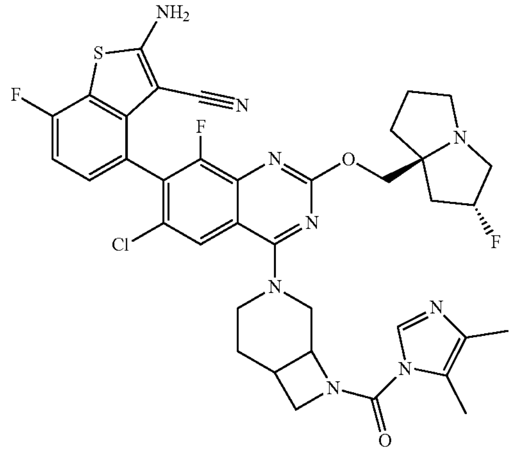 [SMILES: Cc1ncn(C(=O)N2CC3CCN(c4nc(OC[C@@]56CCCN5C[C@H](F)C6)nc5c(F)c(-c6ccc(F)c7sc(N)c(C#N)c67)c(Cl)cc45)CC32)c1C] | 2-amino-4-(6-chloro-4-(8-(4,5-dimethyl-1H-imidazole-1-carbonyl)-3,8-diazabicyclo[4.2.0]octan-3-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile (mixture of cis diazabicyclo[4.2.0]octane isomers) | 762.2 |
| 134[2] | 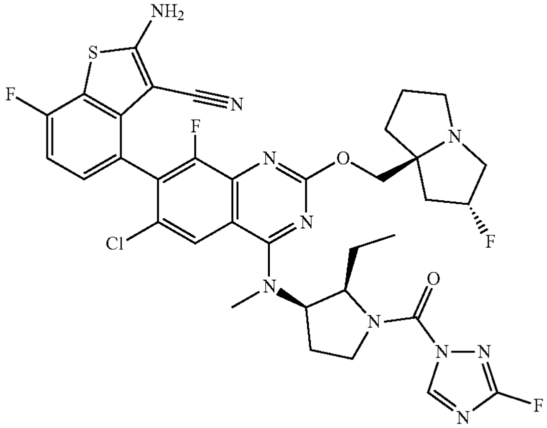 [SMILES: CC[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1cnc(F)n1] | 2-amino-4-(6-chloro-4-(((2R,3R)-2-ethyl-1-(3-fluoro-1H-1,2,4-triazole-1-carbonyl)pyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 769.2 |
| 135[1] | 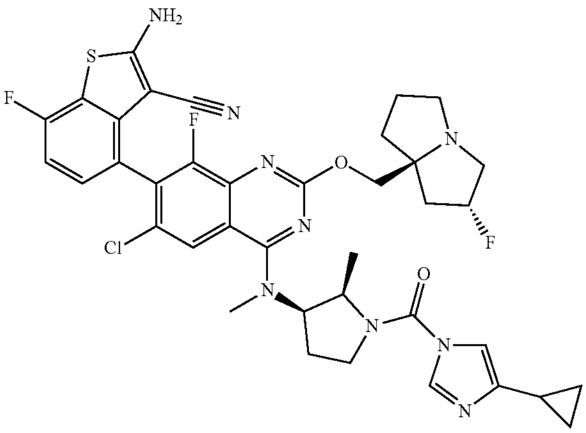 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1cnc(C2CC2)c1] | 2-amino-4-(6-chloro-4-(((2R,3R)-1-(4-cyclopropyl-1H-imidazole-1-carbonyl)-2-methylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 776.2 |

TABLE 1-continued

| No. | Structure | Chemical Name | [M + H]+ |
|---|---|---|---|
| 136[1] | 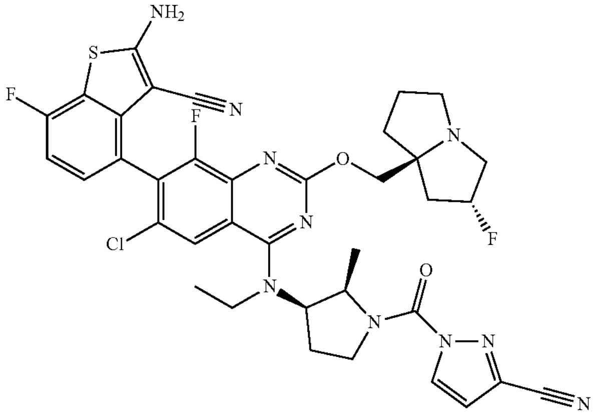 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2ccc(C#N)n2)[C@@H]1C] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carbonyl)-1H-pyrazole-3-carbonitrile | 775.2 |
| 137[1] | 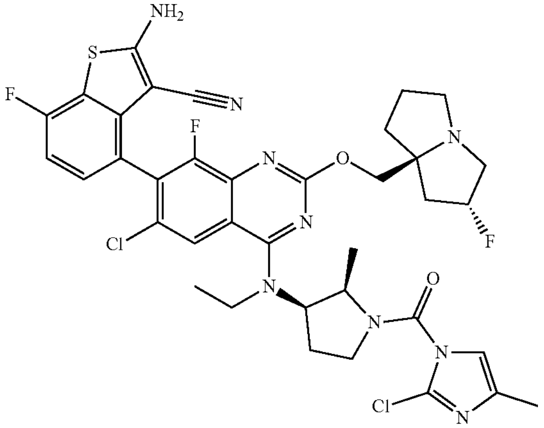 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cc(C)nc2Cl)[C@@H]1C] | 2-amino-4-(6-chloro-4-(((2R,3R)-1-(2-chloro-4-methyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 798.1 |
| 138[1] | 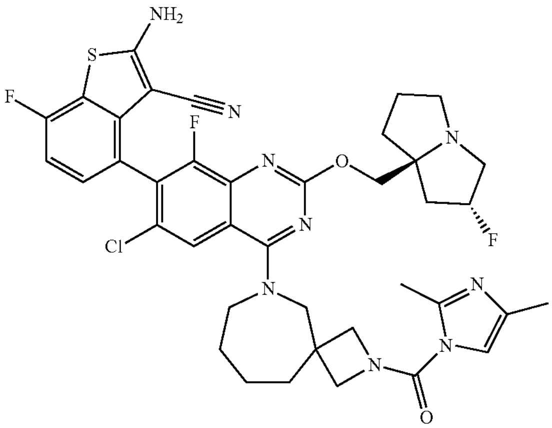 [SMILES: Cc1cn(C(=O)N2CC3(CCCCN(c4nc(OC[C@@]56CCCN5C[C@H](F)C6)nc5c(F)c(-c6ccc(F)c7sc(N)c(C#N)c67)c(Cl)cc45)C3)C2)c(C)n1] | 2-amino-4-(6-chloro-4-(2-(2,4-dimethyl-1H-imidazole-1-carbonyl)-2,6-diazaspiro[3.6]decan-6-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 790.2 |

TABLE 1-continued

| No. | Structure | Chemical Name | [M + H]+ |
|---|---|---|---|
| 139[1] | 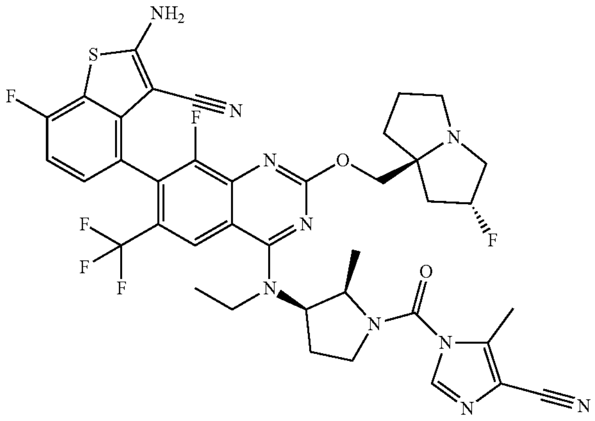 [SMILES: CCN(c1nc(OC[C@@]23CCCN2C[C@H](F)C3)nc2c(F)c(-c3ccc(F)c4sc(N)c(C#N)c34)c(C(F)(F)F)cc12)[C@@H]1CCN(C(=O)n2cnc(C#N)c2C)[C@@H]1C] | 1-((2R,3R)-3-((7-(2-amino-3-cyano-7-fluorobenzo[b]thiophen-4-yl)-8-fluoro-2-(((2R,7aS)-2-fluorotetrahydro-1H-pyrrolizin-7a(5H)-yl)methoxy)-6-(trifluoromethyl)quinazolin-4-yl)(ethyl)amino)-2-methylpyrrolidine-1-carbonyl)-5-methyl-1H-imidazole-4-carbonitrile | 823.2 |
| 140[2] | 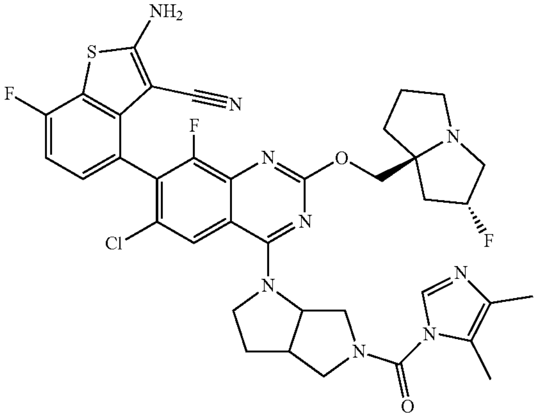 [SMILES: Cc1ncn(C(=O)N2CC3CCN(c4nc(OC[C@@]56CCCN5C[C@H](F)C6)nc5c(F)c(-c6ccc(F)c7sc(N)c(C#N)c67)c(Cl)cc45)C3C2)c1C] | 2-amino-4-(6-chloro-4-(5-(4,5-dimethyl-1H-imidazole-1-carbonyl)hexahydropyrrolo[3,4-b]pyrrol-1(2H)-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile (mixture of cis and trans octahydropyrrolo[3,4-b]pyrrole isomers) | 762.2 |
| 141[1] | 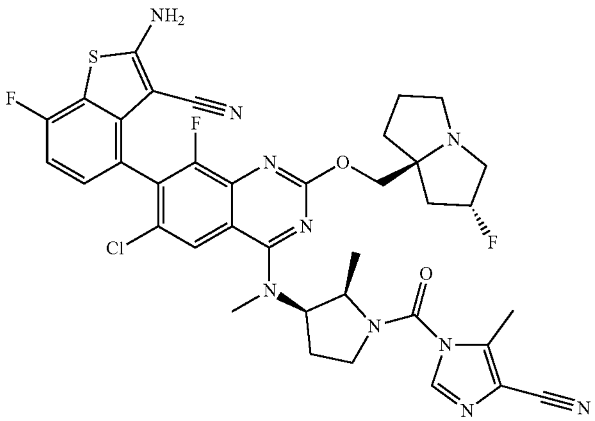 [SMILES: Cc1c(C#N)ncn1C(=O)N1CC[C@@H](N(C)c2nc(OC[C@@]34CCCN3C[C@H](F)C4)nc3c(F)c(-c4ccc(F)c5sc(N)c(C#N)c45)c(Cl)cc23)[C@H]1C] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(methyl)amino)-2-methylpyrrolidine-1-carbonyl)-5-methyl-1H-imidazole-4-carbonitrile | 775.2 |

TABLE 1-continued

| No. | Structure | Chemical Name | [M + H]+ |
|---|---|---|---|
| 142[1] | 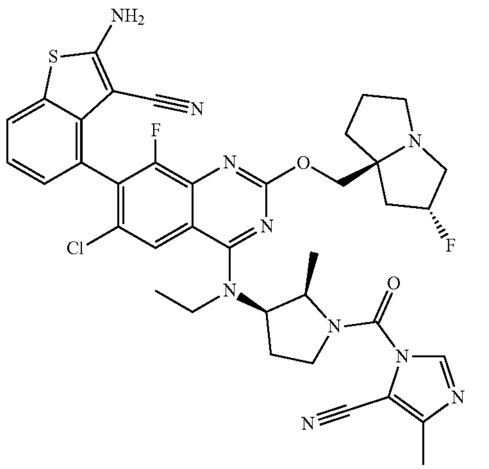 [SMILES: CCN(c1nc(OC[C@@]23CCCN2C[C@H](F)C3)nc2c(F)c(-c3cccc4sc(N)c(C#N)c34)c(Cl)cc12)[C@@H]1CCN(C(=O)n2cnc(C)c2C#N)[C@@H]1C] | 1-((2R,3R)-3-((7-(2-amino-3-cyanobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carbonyl)-4-methyl-1H-imidazole-5-carbonitrile | 771.3 |
| 143[1] | 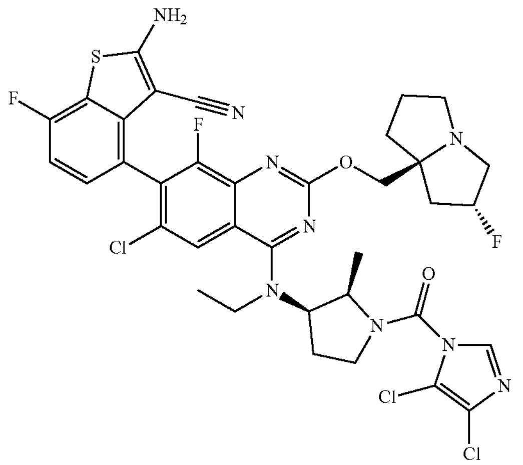 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cnc(Cl)c2Cl)[C@@H]1C] | 2-amino-4-(6-chloro-4-(((2R,3R)-1-(4,5-dichloro-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 818.1 |
| 144[1] | 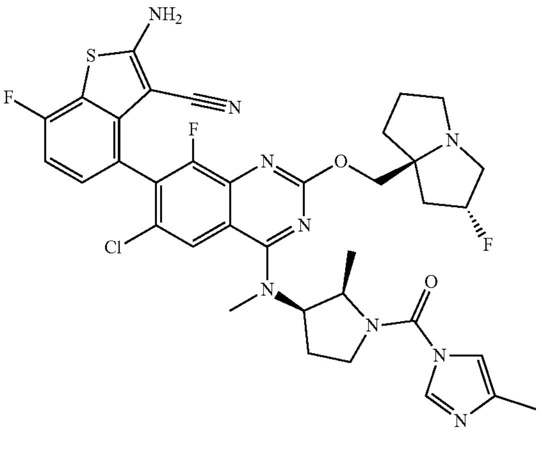 [SMILES: Cc1cn(C(=O)N2CC[C@@H](N(C)c3nc(OC[C@@]45CCCN4C[C@H](F)C5)nc4c(F)c(-c5ccc(F)c6sc(N)c(C#N)c56)c(Cl)cc34)[C@H]2C)cn1] | 2-amino-4-(6-chloro-8-fluoro-2-(((2R,7aS)-2-fluorotetrahydro-1H-pyrrolizin-7a(5H)-yl)methoxy)-4-(methyl((2R,3R)-2-methyl-1-(4-methyl-1H-imidazole-1-carbonyl)pyrrolidin-3-yl)amino)quinazolin-7-yl)-7-fluorobenzo[b]thiophene-3-carbonitrile | 750.2 |

TABLE 1-continued

| No. | Structure | Chemical Name | [M + H]+ |
|---|---|---|---|
| 145[1] | 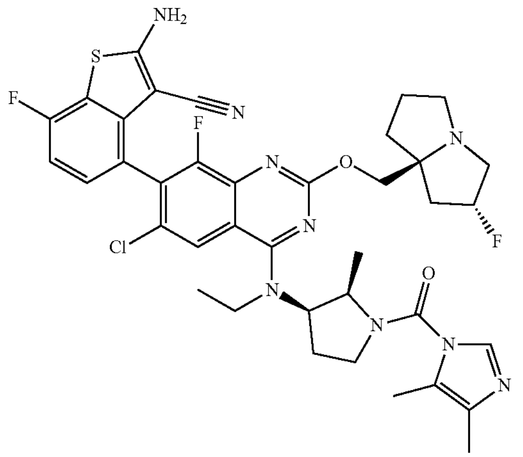 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cnc(C)c2C)[C@@H]1C] | 2-amino-4-(6-chloro-4-(((2R,3R)-1-(4,5-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 778.2 |
| 146[2] | 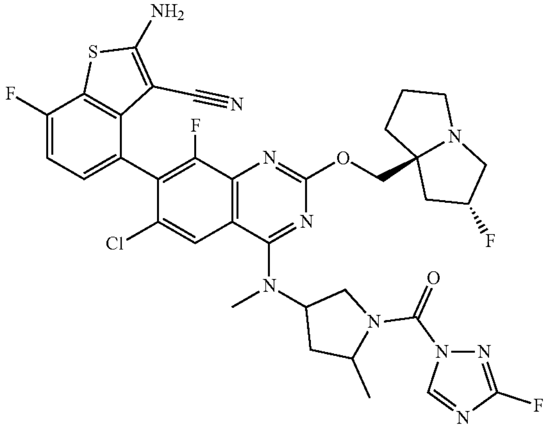 [SMILES: CC1CC(N(C)c2nc(OC[C@@]34CCCN3C[C@H](F)C4)nc3c(F)c(-c4ccc(F)c5sc(N)c(C#N)c45)c(Cl)cc23)CN1C(=O)n1cnc(F)n1] | 2-amino-4-(6-chloro-8-fluoro-4-((1-(3-fluoro-1H-1,2,4-triazole-1-carbonyl)-5-methylpyrrolidin-3-yl)(methyl)amino)-2-(((2R,7aS)-2-fluorotetrahydro-1H-pyrrolizin-7a(5H)-yl)methoxy)quinazolin-7-yl)-7-fluorobenzo[b]thiophene-3-carbonitrile (mixture of cis pyrrolidine isomers) | 755.2 |
| 147[2] | 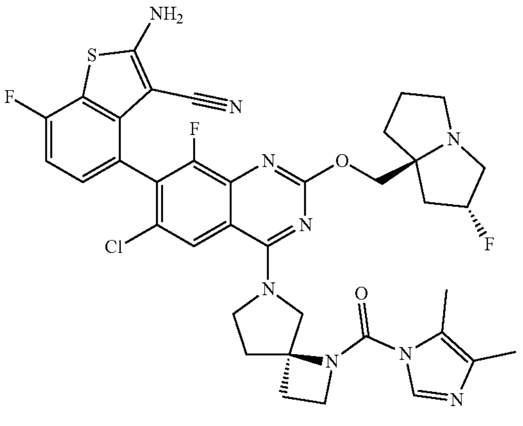 [SMILES: Cc1ncn(C(=O)N2CC[C@@]23CCN(c2nc(OC[C@@]45CCCN4C[C@H](F)C5)nc4c(F)c(-c5ccc(F)c6sc(N)c(C#N)c56)c(Cl)cc24)C3)c1C] | 2-amino-4-(6-chloro-4-((R)-1-(4,5-dimethyl-1H-imidazole-1-carbonyl)-1,6-diazaspiro[3.4]octan-6-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 762.2 |

TABLE 1-continued

| No. | Structure | Chemical Name | [M + H]+ |
|---|---|---|---|
| 148[1] | 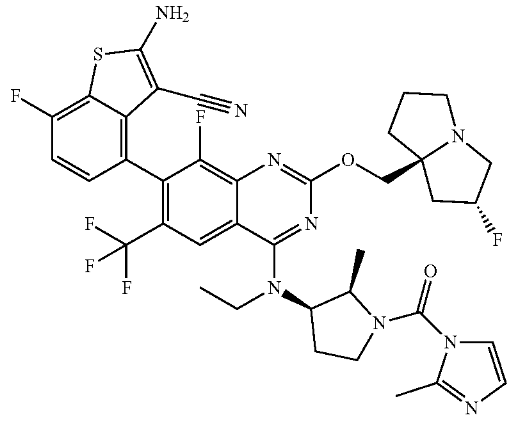 [SMILES: CCN(c1nc(OC[C@@]23CCCN2C[C@H](F)C3)nc2c(F)c(-c3ccc(F)c4sc(N)c(C#N)c34)c(C(F)(F)F)cc12)[C@@H]1CCN(C(=O)n2ccnc2C)[C@@H]1C] | 2-amino-4-(4-(ethyl((2R,3R)-2-methyl-1-(2-methyl-1H-imidazole-1-carbonyl)pyrrolidin-3-yl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile | 798.2 |
| 149[1] | 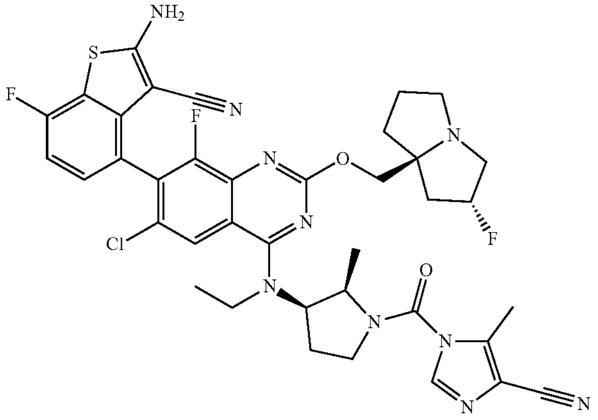 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cnc(C#N)c2C)[C@@H]1C] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carbonyl)-5-methyl-1H-imidazole-4-carbonitrile | 789.2 |
| 150[2] | 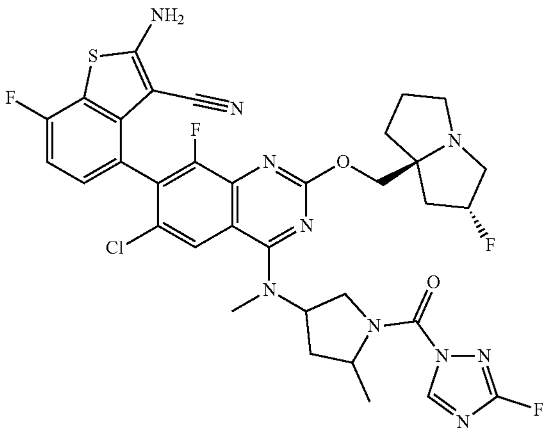 [SMILES: CC1CC(N(C)c2nc(OC[C@@]34CCCN3C[C@H](F)C4)nc3c(F)c(-c4ccc(F)c5sc(N)c(C#N)c45)c(Cl)cc23)CN1C(=O)n1cnc(F)n1] | 2-amino-4-(6-chloro-8-fluoro-4-((1-(3-fluoro-1H-1,2,4-triazole-1-carbonyl)-5-methylpyrrolidin-3-yl)(methyl)amino)-2-(((2R,7aS)-2-fluorotetrahydro-1H-pyrrolizin-7a(5H)-yl)methoxy)quinazolin-7-yl)-7-fluorobenzo[b]thiophene-3-carbonitrile (mixture of trans pyrrolidine isomers) | 755.2 |

TABLE 1-continued

| No. | Structure | Chemical Name | [M + H]+ |
|---|---|---|---|
| 151[2] | 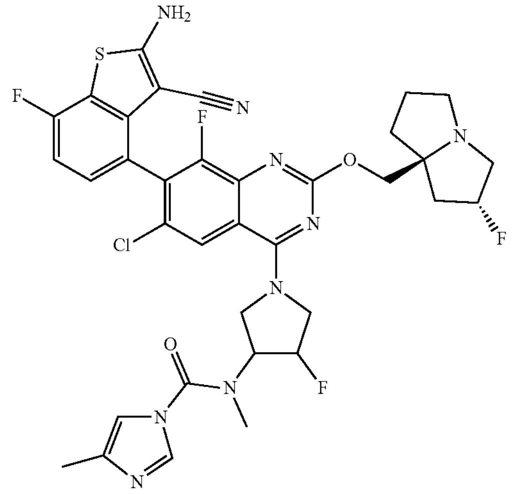 [SMILES: Cc1cn(C(=O)N(C)C2CN(c3nc(OC[C@@]45CCCN4C[C@H](F)C5)nc4c(F)c(-c5ccc(F)c6sc(N)c(C#N)c56)c(Cl)cc34)CC2F)cn1] | N-(1-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-4-fluoropyrrolidin-3-yl)-N,4-dimethyl-1H-imidazole-1-carboxamide (mixture of trans pyrrolidine isomers) | 754.2 |
| 152[1] | 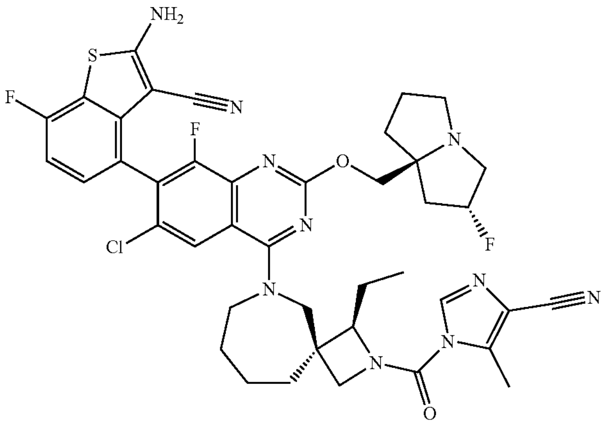 [SMILES: CC[C@H]1N(C(=O)n2cnc(C#N)c2C)C[C@]12CCCCN(c1nc(OC[C@@]34CCCN3C[C@H](F)C4)nc3c(F)c(-c4ccc(F)c5sc(N)c(C#N)c45)c(Cl)cc13)C2] | 1-((1R,4R)-6-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-1-ethyl-2,6-diazaspiro[3.6]decane-2-carbonyl)-5-methyl-1H-imidazole-4-carbonitrile | 829.2 |
| 153[2] | 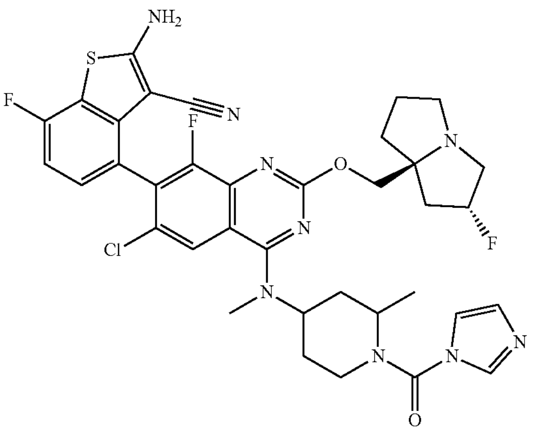 [SMILES: CC1CC(N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1] | 4-(4-((1-(1H-imidazole-1-carbonyl)-2-methylpiperidin-4-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile (mixture of trans piperidine isomers) | 750.2 |

TABLE 1-continued

| No. | Structure | Chemical Name | [M + H]+ |
|---|---|---|---|
| 154[1] | 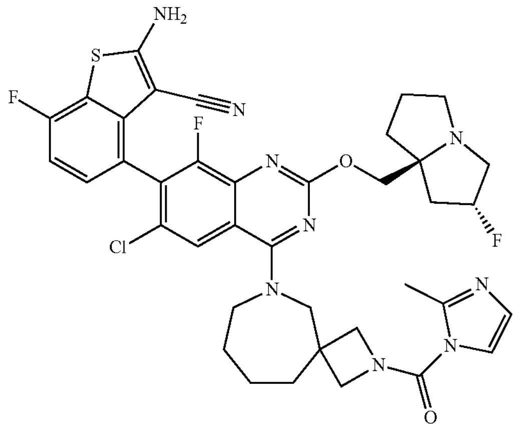 [SMILES: Cc1nccn1C(=O)N1CC2(CCCCN(c3nc(OC[C@@]45CCCN4C[C@H](F)C5)nc4c(F)c(-c5ccc(F)c6sc(N)c(C#N)c56)c(Cl)cc34)C2)C1] | 2-amino-4-(6-chloro-8-fluoro-2-(((2R,7aS)-2-fluorotetrahydro-1H-pyrrolizin-7a(5H)-yl)methoxy)-4-(2-(2-methyl-1H-imidazole-1-carbonyl)-2,6-diazaspiro[3.6]decan-6-yl)quinazolin-7-yl)-7-fluorobenzo[b]thiophene-3-carbonitrile | 776.2 |
| 155[2] | 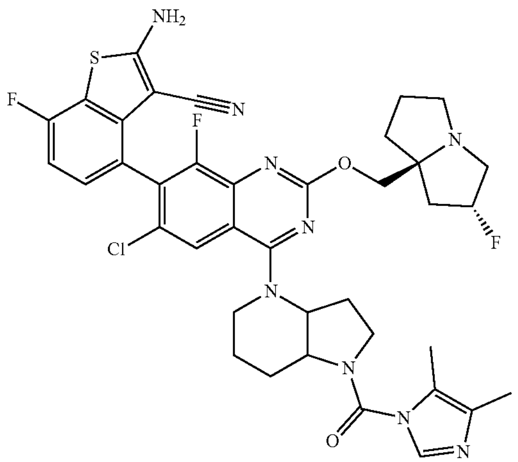 [SMILES: Cc1ncn(C(=O)N2CCC3C2CCCN3c2nc(OC[C@@]34CCCN3C[C@H](F)C4)nc3c(F)c(-c4ccc(F)c5sc(N)c(C#N)c45)c(Cl)cc23)c1C] | 2-amino-4-(6-chloro-4-(1-(4,5-dimethyl-1H-imidazole-1-carbonyl)octahydro-4H-pyrrolo[3,2-b]pyridin-4-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile (mixture of cis octahydro-4H-pyrrolo[3,2-b]pyridine isomers) | 776.2 |
| 156[2] | 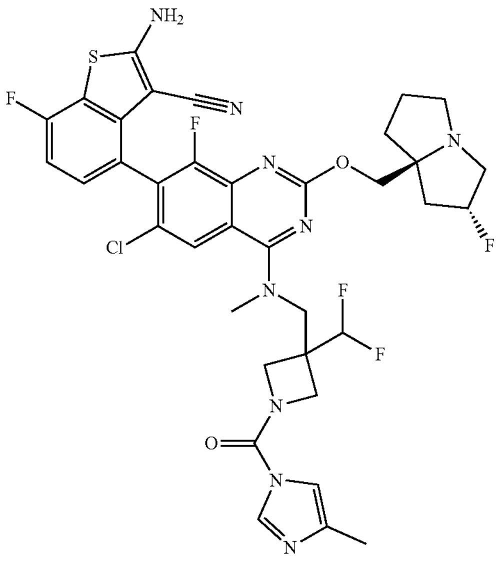 [SMILES: Cc1cn(C(=O)N2CC(CN(C)c3nc(OC[C@@]45CCCN4C[C@H](F)C5)nc4c(F)c(-c5ccc(F)c6sc(N)c(C#N)c56)c(Cl)cc34)(C(F)F)C2)cn1] | 2-amino-4-(6-chloro-4-(((3-(difluoromethyl)-1-(4-methyl-1H-imidazole-1-carbonyl)azetidin-3-yl)methyl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 786.2 |

TABLE 1-continued

| No. | Structure | Chemical Name | [M + H]+ |
| --- | --- | --- | --- |
| 157[2] | 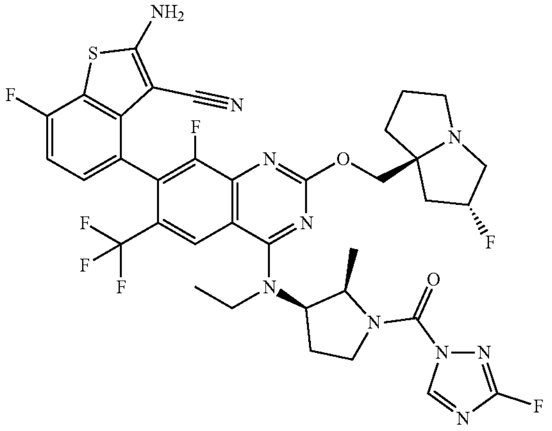 [SMILES: CCN(c1nc(OC[C@@]23CCCN2C[C@H](F)C3)nc2c(F)c(-c3ccc(F)c4sc(N)c(C#N)c34)c(C(F)(F)F)cc12)[C@@H]1CCN(C(=O)n2cnc(F)n2)[C@@H]1C] | 2-amino-4-(4-(ethyl((2R,3R)-1-(3-fluoro-1H-1,2,4-triazole-1-carbonyl)-2-methylpyrrolidin-3-yl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile (single cis pyrrolidine isomer) | 803.2 |
| 158[1] | 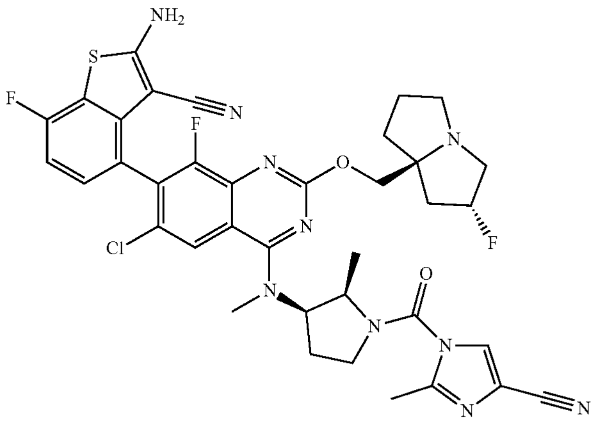 [SMILES: Cc1nc(C#N)cn1C(=O)N1CC[C@@H](N(C)c2nc(OC[C@@]34CCCN3C[C@H](F)C4)nc3c(F)c(-c4ccc(F)c5sc(N)c(C#N)c45)c(Cl)cc23)[C@H]1C] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(methyl)amino)-2-methylpyrrolidine-1-carbonyl)-2-methyl-1H-imidazole-4-carbonitrile | 775.2 |
| 159[1] | 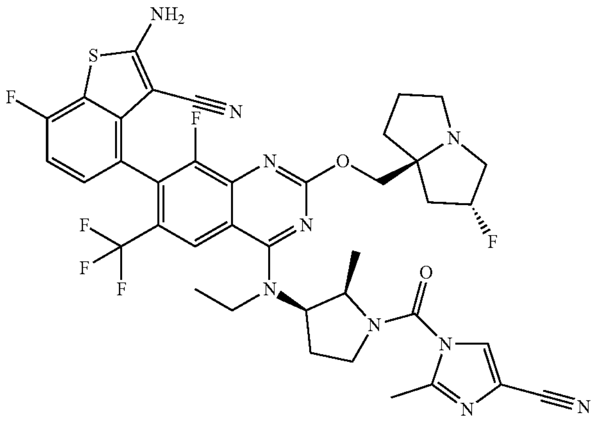 [SMILES: CCN(c1nc(OC[C@@]23CCCN2C[C@H](F)C3)nc2c(F)c(-c3ccc(F)c4sc(N)c(C#N)c34)c(C(F)(F)F)cc12)[C@@H]1CCN(C(=O)n2cc(C#N)nc2C)[C@@H]1C] | 1-((2R,3R)-3-((7-(2-amino-3-cyano-7-fluorobenzo[b]thiophen-4-yl)-8-fluoro-2-(((2R,7aS)-2-fluorotetrahydro-1H-pyrrolizin-7a(5H)-yl)methoxy)-6-(trifluoromethyl)quinazolin-4-yl)(ethyl)amino)-2-methylpyrrolidine-1-carbonyl)-2-methyl-1H-imidazole-4-carbonitrile | 823.2 |

TABLE 1-continued

| No. | Structure | Chemical Name | [M + H]+ |
|---|---|---|---|
| 160[2] | 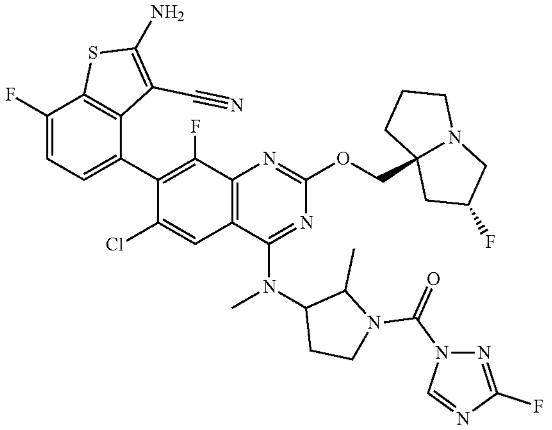 [SMILES: CC1C(N(C)c2nc(OC[C@@]34CCCN3C[C@H](F)C4)nc3c(F)c(-c4ccc(F)c5sc(N)c(C#N)c45)c(Cl)cc23)CCN1C(=O)n1cnc(F)n1] | 2-amino-4-(6-chloro-8-fluoro-4-((1-(3-fluoro-1H-1,2,4-triazole-1-carbonyl)-2-methylpyrrolidin-3-yl)(methyl)amino)-2-(((2R,7aS)-2-fluorotetrahydro-1H-pyrrolizin-7a(5H)-yl)methoxy)quinazolin-7-yl)-7-fluorobenzo[b]thiophene-3-carbonitrile (trans pyrrolidine) | 755.2 |
| 161[1] | 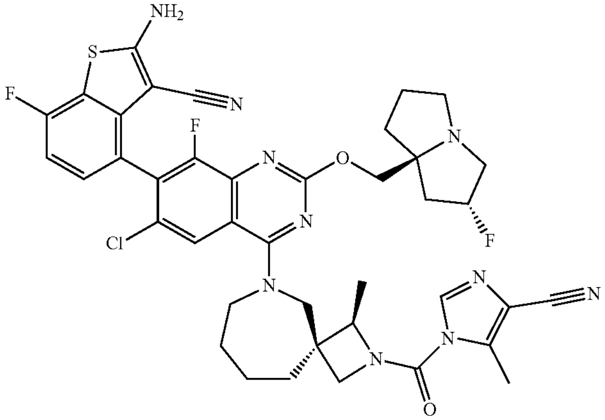 [SMILES: Cc1c(C#N)ncn1C(=O)N1C[C@]2(CCCCN(c3nc(OC[C@@]45CCCN4C[C@H](F)C5)nc4c(F)c(-c5ccc(F)c6sc(N)c(C#N)c56)c(Cl)cc34)C2)[C@H]1C] | 1-((1R,4R)-6-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-1-methyl-2,6-diazaspiro[3.6]decane-2-carbonyl)-5-methyl-1H-imidazole-4-carbonitrile | 815.2 |
| 162[1] | 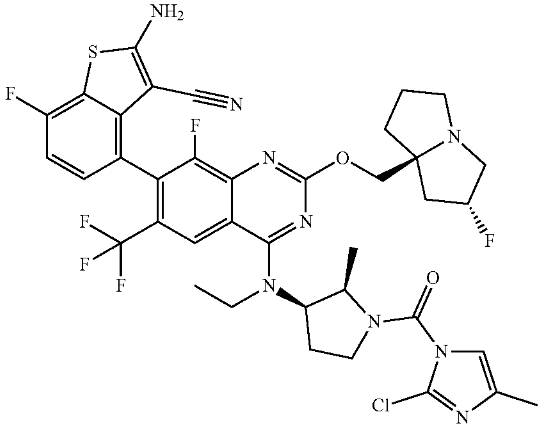 | 2-amino-4-(4-(((2R,3R)-1-(2-chloro-4-methyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile | 832.2 |

TABLE 1-continued

| No. | Structure | Chemical Name | [M + H]+ |
|---|---|---|---|
| 163[1] | 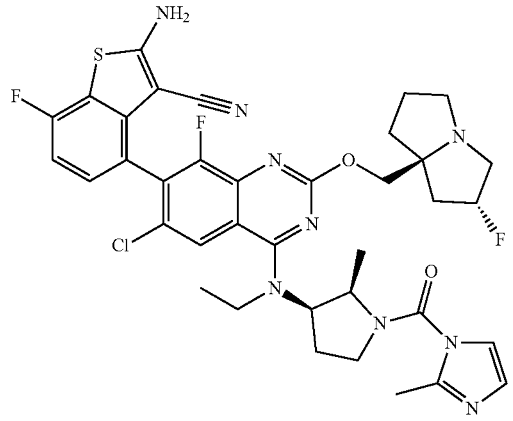 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2ccnc2C)[C@@H]1C] | 2-amino-4-(6-chloro-4-(ethyl((2R,3R)-2-methyl-1-(2-methyl-1H-imidazole-1-carbonyl)pyrrolidin-3-yl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 764.2 |
| 164[2] | 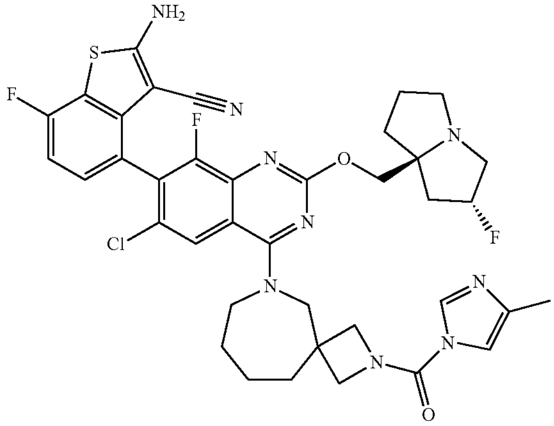 [SMILES: Cc1cn(C(=O)N2CC3(CCCCN(c4nc(OC[C@@]56CCCN5C[C@H](F)C6)nc5c(F)c(-c6ccc(F)c7sc(N)c(C#N)c67)c(Cl)cc45)C3)C2)cn1] | 2-amino-4-(6-chloro-8-fluoro-2-(((2R,7aS)-2-fluorotetrahydro-1H-pyrrolizin-7a(5H)-yl)methoxy)-4-(2-(4-methyl-1H-imidazole-1-carbonyl)-2,6-diazaspiro[3.6]decan-6-yl)quinazolin-7-yl)-7-fluorobenzo[b]thiophene-3-carbonitrile | 776.2 |
| 165[1] | 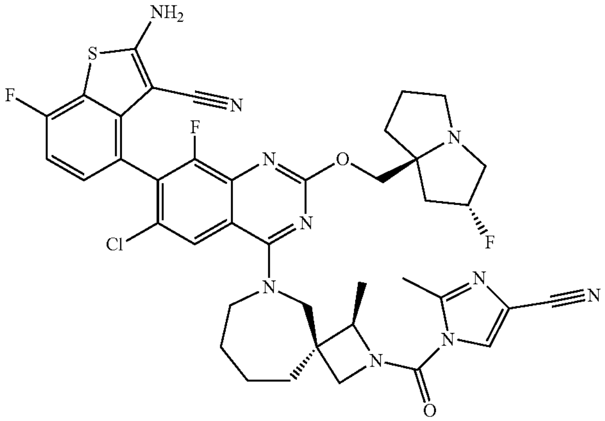 [SMILES: Cc1nc(C#N)cn1C(=O)N1C[C@]2(CCCCN(c3nc(OC[C@@]45CCCN4C[C@H](F)C5)nc4c(F)c(-c5ccc(F)c6sc(N)c(C#N)c56)c(Cl)cc34)C2)[C@H]1C] | 1-((1R,4R)-6-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-1-methyl-2,6-diazaspiro[3.6]decane-2-carbonyl)-2-methyl-1H-imidazole-4-carbonitrile | 815.2 |

TABLE 1-continued

| No. | Structure | Chemical Name | [M + H]+ |
|---|---|---|---|
| 166[1] | 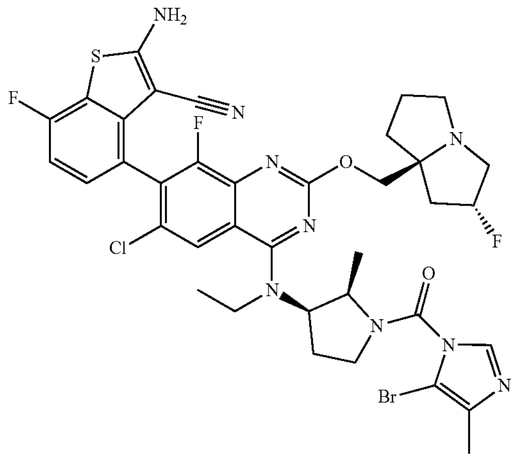 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cnc(C)c2Br)[C@@H]1C] | 2-amino-4-(4-(((2R,3R)-1-(5-bromo-4-methyl-1H-imidazole-1-carbonyl)-2-methylpyrrolidin-3-yl)(ethyl)amino)-6-chloro-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 842.1 |
| 167[1] | 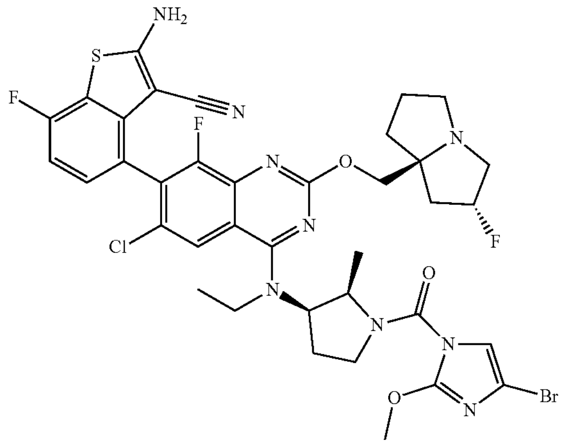 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cc(Br)nc2OC)[C@@H]1C] | 2-amino-4-(4-(((2R,3R)-1-(4-bromo-2-methoxy-1H-imidazole-1-carbonyl)-2-methylpyrrolidin-3-yl)(ethyl)amino)-6-chloro-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 858.2 |
| 168[2] | 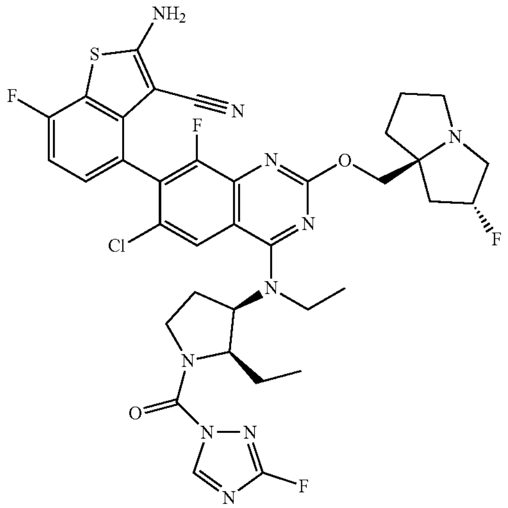 [SMILES: CC[C@@H]1[C@H](N(CC)c2nc(OC[C@@]34CCCN3C[C@H](F)C4)nc3c(F)c(-c4ccc(F)c5sc(N)c(C#N)c45)c(Cl)cc23)CCN1C(=O)n1cnc(F)n1] | 2-amino-4-(6-chloro-4-(ethyl((2R,3R)-2-ethyl-1-(3-fluoro-1H-1,2,4-triazole-1-carbonyl)pyrrolidin-3-yl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 783.2 |

TABLE 1-continued

| No. | Structure | Chemical Name | [M + H]+ |
| --- | --- | --- | --- |
| 169[2] | 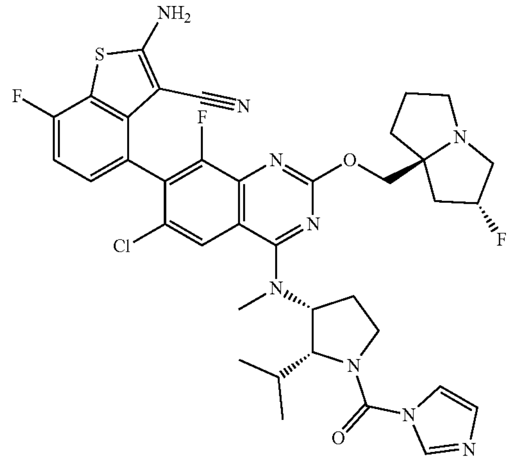 [SMILES: CC(C)[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1] | 4-(4-(((2R,3R)-1-(1H-imidazole-1-carbonyl)-2-isopropylpyrrolidin-3-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile | 764.2 |
| 170[1] | 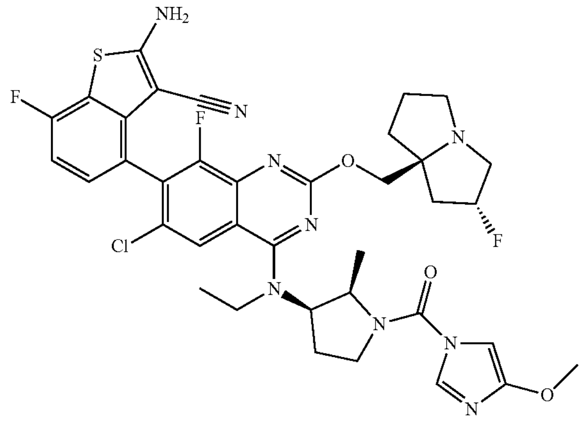 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cnc(OC)c2)[C@@H]1C] | 2-amino-4-(6-chloro-4-(ethyl((2R,3R)-1-(4-methoxy-1H-imidazole-1-carbonyl)-2-methylpyrrolidin-3-yl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 780.2 |
| 171[1] | 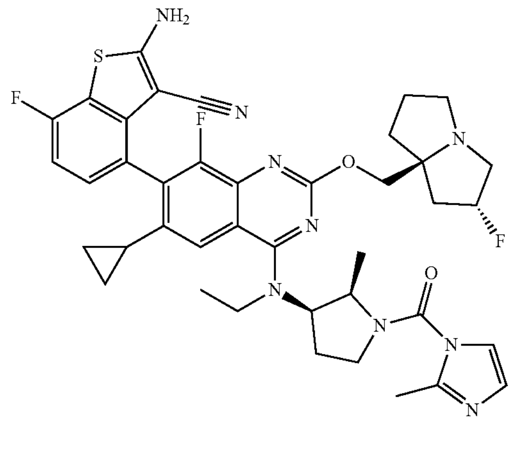 [SMILES: CCN(c1nc(OC[C@@]23CCCN2C[C@H](F)C3)nc2c(F)c(-c3ccc(F)c4sc(N)c(C#N)c34)c(C3CC3)cc12)[C@@H]1CCN(C(=O)n2ccnc2C)[C@@H]1C] | 2-amino-4-(6-cyclopropyl-4-(ethyl((2R,3R)-2-methyl-1-(2-methyl-1H-imidazole-1-carbonyl)pyrrolidin-3-yl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 770.3 |

TABLE 1-continued

| No. | Structure | Chemical Name | [M + H]+ |
|---|---|---|---|
| 172[1] | 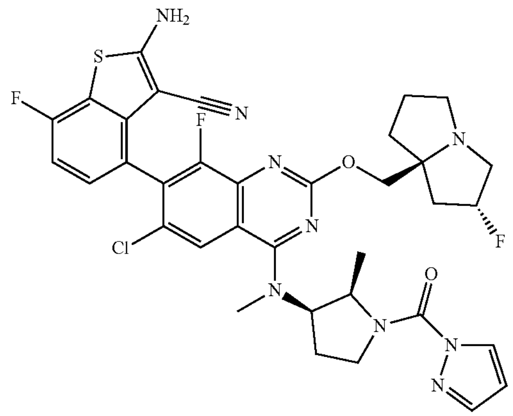 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1cccn1] | 2-amino-4-(6-chloro-8-fluoro-2-(((2R,7aS)-2-fluorotetrahydro-1H-pyrrolizin-7a(5H)-yl)methoxy)-4-(methyl((2R,3R)-2-methyl-1-(1H-pyrazole-1-carbonyl)pyrrolidin-3-yl)amino)quinazolin-7-yl)-7-fluorobenzo[b]thiophene-3-carbonitrile | 736.2 |
| 173[2] | 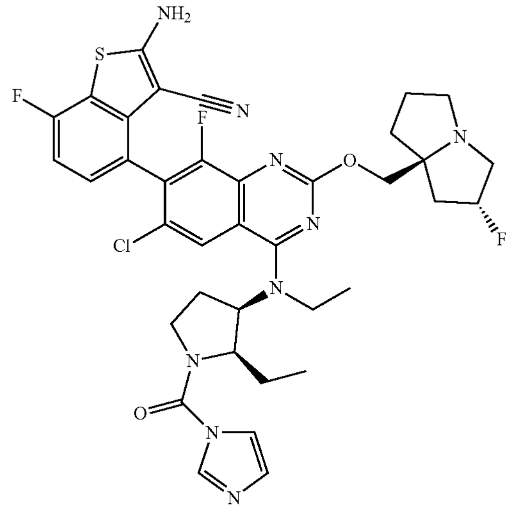 [SMILES: CC[C@@H]1[C@H](N(CC)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1] | 2-amino-4-(6-chloro-4-(ethyl((2R,3R)-2-ethyl-1-(1H-imidazole-1-carbonyl)pyrrolidin-3-yl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 764.2 |
| 174[2] | 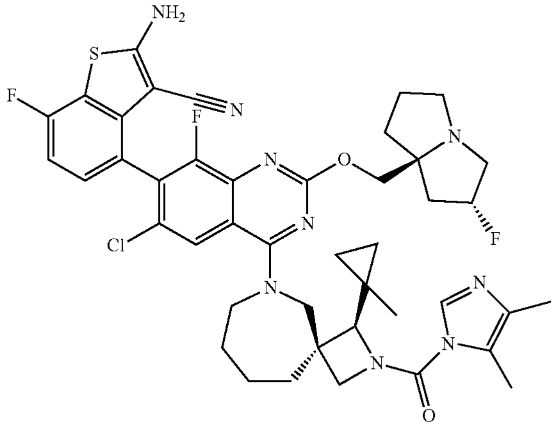 [SMILES: Cc1ncn(C(=O)N2C[C@]3(CCCCN(c4nc(OC[C@@]56CCCN5C[C@H](F)C6)nc5c(F)c(-c6ccc(F)c7sc(N)c(C#N)c67)c(Cl)cc45)C3)[C@H]2C2(C)CC2)c1C] | 2-amino-4-(6-chloro-4-((1R,4R)-2-(4,5-dimethyl-1H-imidazole-1-carbonyl)-1-(1-methylcyclopropyl)-2,6-diazaspiro[3.6]decan-6-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 844.2 |

TABLE 1-continued

| No. | Structure | Chemical Name | [M + H]+ |
|---|---|---|---|
| 175[1] | 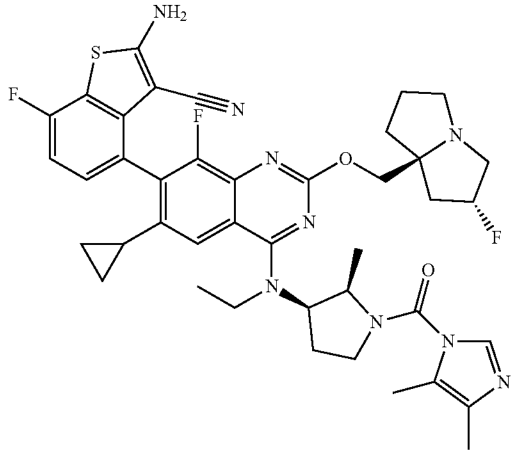 [SMILES: CCN(c1nc(OC[C@@]23CCCN2C[C@H](F)C3)nc2c(F)c(-c3ccc(F)c4sc(N)c(C#N)c34)c(C3CC3)cc12)[C@@H]1CCN(C(=O)n2cnc(C)c2C)[C@@H]1C] | 2-amino-4-(6-cyclopropyl-4-(((2R,3R)-1-(4,5-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 784.3 |
| 176[1] | 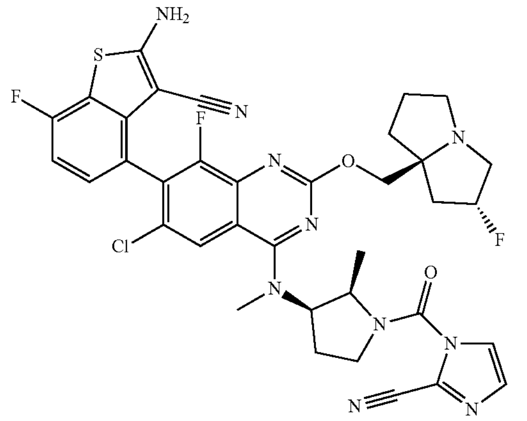 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1C#N] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(methyl)amino)-2-methylpyrrolidine-1-carbonyl)-1H-imidazole-2-carbonitrile | 761.2 |
| 177[1] | 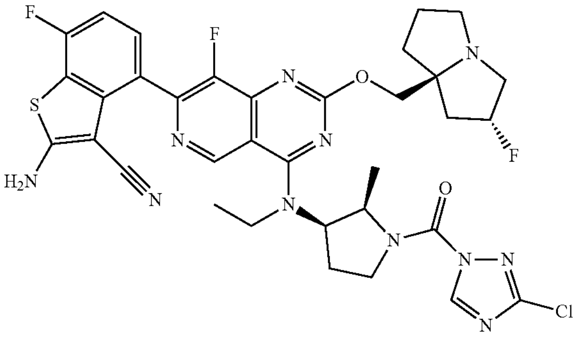 [SMILES: CCN(c1nc(OC[C@@]23CCCN2C[C@H](F)C3)nc2c(F)c(-c3ccc(F)c4sc(N)c(C#N)c34)ncc12)[C@@H]1CCN(C(=O)n2cnc(Cl)n2)[C@@H]1C] | 2-amino-4-(4-(((2R,3R)-1-(3-chloro-1H-1,2,4-triazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)pyrido[4,3-d]pyrimidin-7-yl)-7-fluorobenzo[b]thiophene-3-carbonitrile | 752.4 |

TABLE 1-continued

| No. | Structure | Chemical Name | [M + H]+ |
|---|---|---|---|
| 178[1] | 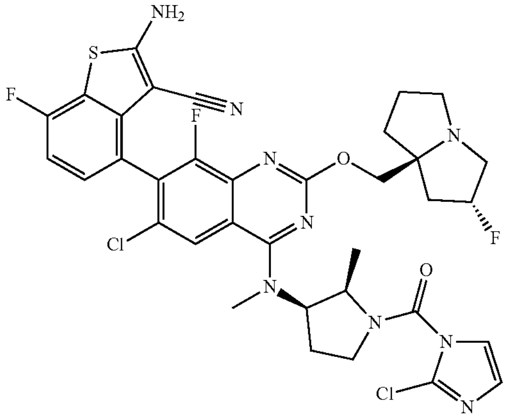 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1Cl] | 2-amino-4-(6-chloro-4-(((2R,3R)-1-(2-chloro-1H-imidazole-1-carbonyl)-2-methylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 770.1 |
| 179[3] | 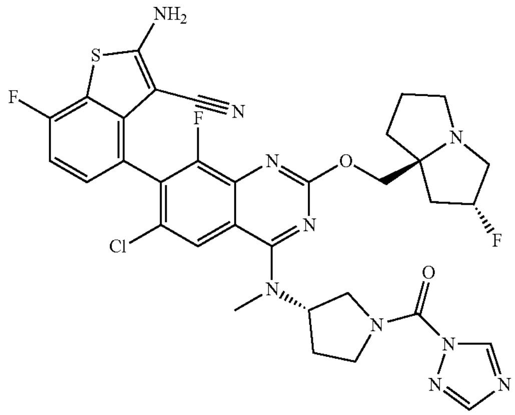 [SMILES: CN(c1nc(OC[C@@]23CCCN2C[C@H](F)C3)nc2c(F)c(-c3ccc(F)c4sc(N)c(C#N)c34)c(Cl)cc12)[C@H]1CCN(C(=O)n2cncn2)C1] | 4-(4-(((S)-1-(1H-1,2,4-triazole-1-carbonyl)pyrrolidin-3-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile | 723.2 |
| 180[1] | 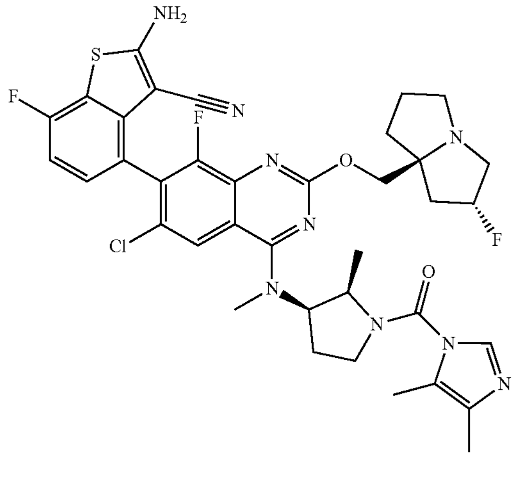 [SMILES: Cc1ncn(C(=O)N2CC[C@@H](N(C)c3nc(OC[C@@]45CCCN4C[C@H](F)C5)nc4c(F)c(-c5ccc(F)c6sc(N)c(C#N)c56)c(Cl)cc34)[C@H]2C)c1C] | 2-amino-4-(6-chloro-4-(((2R,3R)-1-(4,5-dimethyl-1H-imidazole-1-carbonyl)-2-methylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 764.2 |

TABLE 1-continued

| No. | Structure | Chemical Name | [M + H]+ |
|---|---|---|---|
| 181[3] | 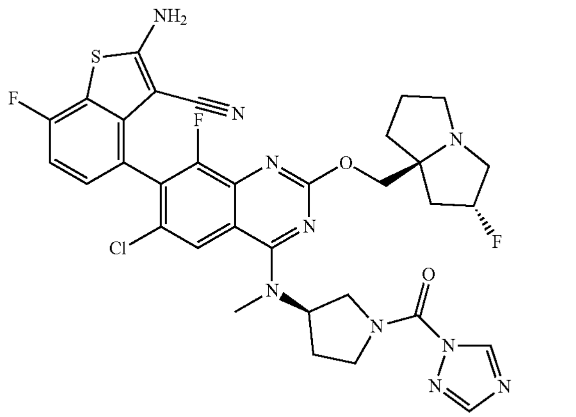 [SMILES: CN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2cncn2)C1] | 4-(4-(((R)-1-(1H-1,2,4-triazole-1-carbonyl)pyrrolidin-3-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile | 723.2 |
| 182[2] | 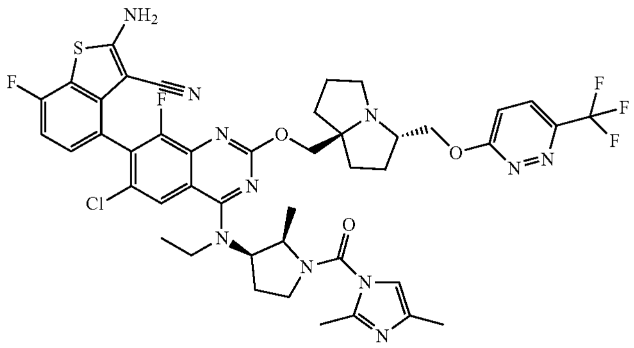 [SMILES: CCN(c1nc(OC[C@@]23CCCN2[C@H](COc2ccc(C(F)(F)F)nn2)CC3)nc2c(F)c(-c3ccc(F)c4sc(N)c(C#N)c34)c(Cl)cc12)[C@@H]1CCN(C(=O)n2cc(C)nc2C)[C@@H]1C] | 2-amino-4-(6-chloro-4-(((2R,3R)-1-(2,4-dimethyl-1H-imidazole-1-carbonyl)-2-methylpyrrolidin-3-yl)(ethyl)amino)-8-fluoro-2-(((3S,7aS)-3-(((6-(trifluoromethyl)pyridazin-3-yl)oxy)methyl)tetrahydro-1H-pyrrolizin-7a(5H)-yl)methoxy)quinazolin-7-yl)-7-fluorobenzo[b]thiophene-3-carbonitrile | 936.1 |
| 183[1] | 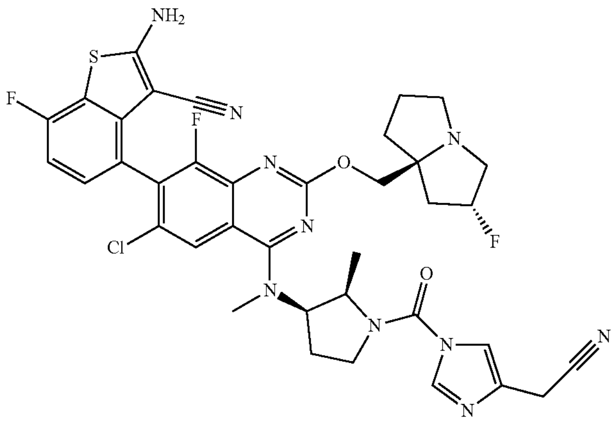 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1cnc(CC#N)c1] | 2-amino-4-(6-chloro-4-(((2R,3R)-1-(4-(cyanomethyl)-1H-imidazole-1-carbonyl)-2-methylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 775.2 |

TABLE 1-continued

| No. | Structure | Chemical Name | [M + H]+ |
| --- | --- | --- | --- |
| 184[1] | 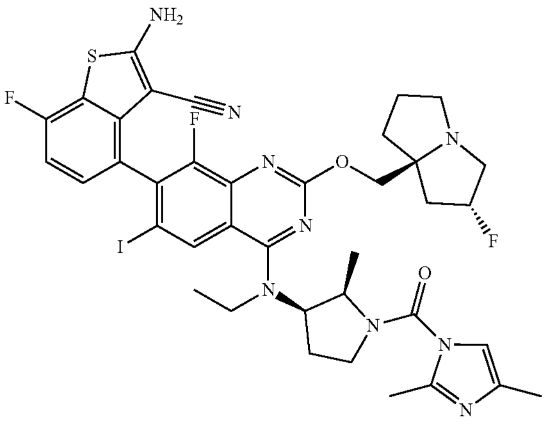 [SMILES: CCN(c1nc(OC[C@@]23CCCN2C[C@H](F)C3)nc2c(F)c(-c3ccc(F)c4sc(N)c(C#N)c34)c(I)cc12)[C@@H]1CCN(C(=O)n2cc(C)nc2C)[C@@H]1C] | 2-amino-4-(4-(((2R,3R)-1-(2,4-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)-6-iodoquinazolin-7-yl)-7-fluorobenzo[b]thiophene-3-carbonitrile | 870.2 |
| 185[1] | 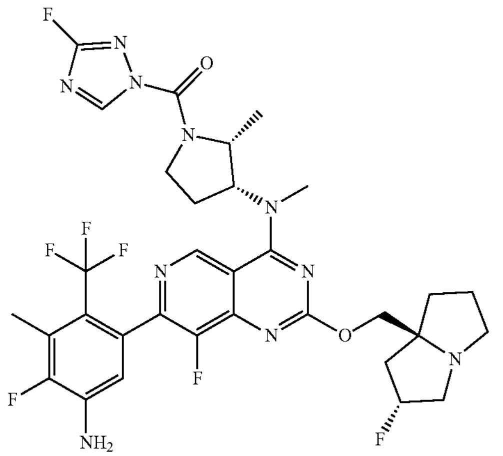 [SMILES: Cc1c(F)c(N)cc(-c2ncc3c(N(C)[C@@H]4CCN(C(=O)n5cnc(F)n5)[C@@H]4C)nc(OC[C@@]45CCCN4C[C@H](F)C5)nc3c2F)c1C(F)(F)F] | ((2R,3R)-3-((7-(5-amino-4-fluoro-3-methyl-2-(trifluoromethyl)phenyl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-2-methylpyrrolidin-1-yl)(3-fluoro-1H-1,2,4-triazol-1-yl)methanone | 784.3 |
| 186[1] | 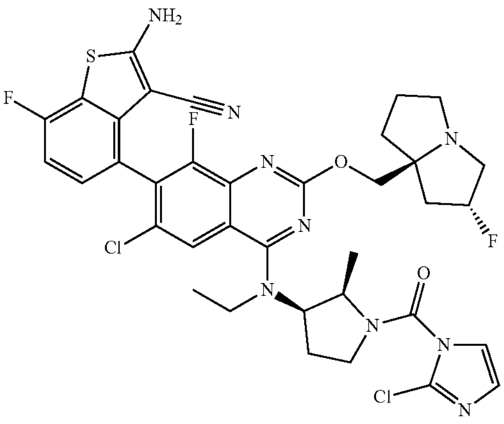 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2ccnc2Cl)[C@@H]1C] | 2-amino-4-(6-chloro-4-(((2R,3R)-1-(2-chloro-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 784.2 |

TABLE 1-continued

| No. | Structure | Chemical Name | [M + H]+ |
|---|---|---|---|
| 187[2] | 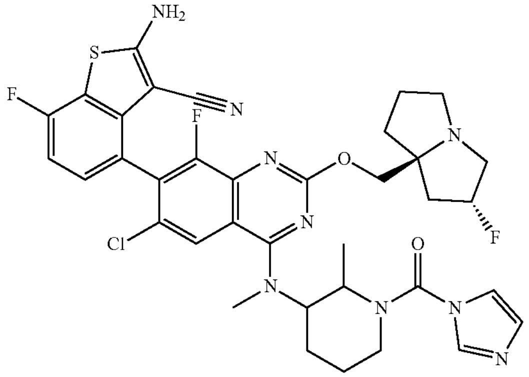 [SMILES: CC1C(N(C)c2nc(OC[C@@]34CCCN3C[C@H](F)C4)nc3c(F)c(-c4ccc(F)c5sc(N)c(C#N)c45)c(Cl)cc23)CCCN1C(=O)n1ccnc1] | 4-(4-((1-(1H-imidazole-1-carbonyl)-2-methylpiperidin-3-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile (single cis piperidine isomer) | 750.2 |
| 188[1] | 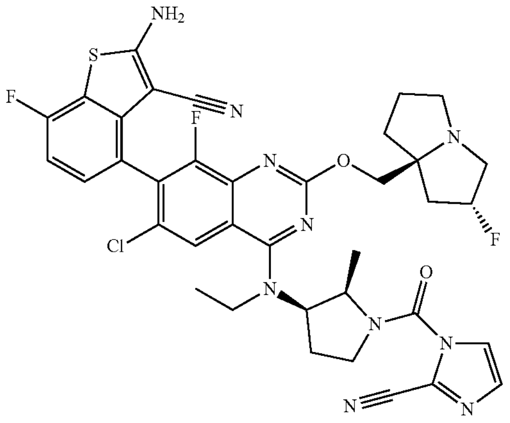 [SMILES: CCN(c1nc(OC[C@@]23CCCN2C[C@H](F)C3)nc2c(F)c(-c3ccc(F)c4sc(N)c(C#N)c34)c(Cl)cc12)[C@@H]1CCN(C(=O)n2ccnc2C#N)[C@@H]1C] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carbonyl)-1H-imidazole-2-carbonitrile | 775.2 |
| 189[2] | 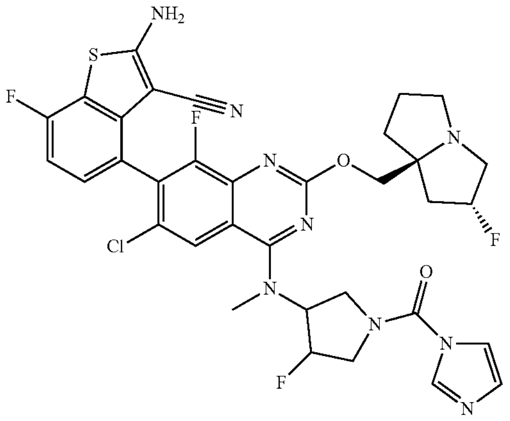 [SMILES: CN(c1nc(OC[C@@]23CCCN2C[C@H](F)C3)nc2c(F)c(-c3ccc(F)c4sc(N)c(C#N)c34)c(Cl)cc12)C1CN(C(=O)n2ccnc2)CC1F] | 2-amino-4-(6-chloro-8-fluoro-4-((4-fluoro-1-(1H-imidazole-1-carbonyl)pyrrolidin-3-yl)(methyl)amino)-2-(((2R,7aS)-2-fluorotetrahydro-1H-pyrrolizin-7a(5H)-yl)methoxy)quinazolin-7-yl)-7-fluorobenzo[b]thiophene-3-carbonitrile (single trans pyrrolidine isomer) | 740.2 |

TABLE 1-continued

| No. | Structure | Chemical Name | [M + H]+ |
|---|---|---|---|
| 190[1] | 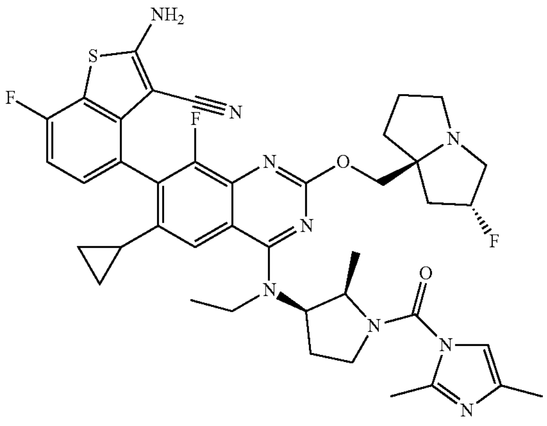 [SMILES: CCN(c1nc(OC[C@@]23CCCN2C[C@H](F)C3)nc2c(F)c(-c3ccc(F)c4sc(N)c(C#N)c34)c(C3CC3)cc12)[C@@H]1CCN(C(=O)n2cc(C)nc2C)[C@@H]1C] | 2-amino-4-(6-cyclopropyl-4-(((2R,3R)-1-(2,4-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 784.3 |
| 191[2] | 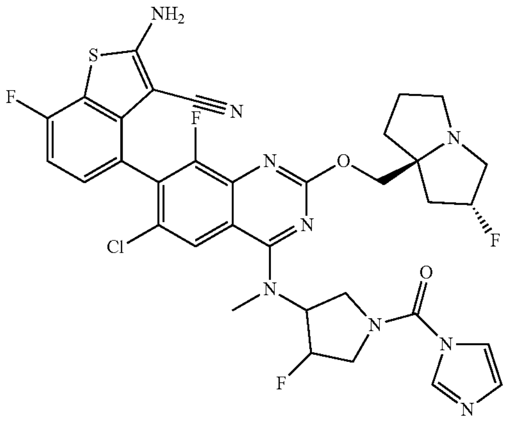 [SMILES: CN(c1nc(OC[C@@]23CCCN2C[C@H](F)C3)nc2c(F)c(-c3ccc(F)c4sc(N)c(C#N)c34)c(Cl)cc12)C1CN(C(=O)n2ccnc2)CC1F] | 2-amino-4-(6-chloro-8-fluoro-4-((4-fluoro-1-(1H-imidazole-1-carbonyl)pyrrolidin-3-yl)(methyl)amino)-2-(((2R,7aS)-2-fluorotetrahydro-1H-pyrrolizin-7a(5H)-yl)methoxy)quinazolin-7-yl)-7-fluorobenzo[b]thiophene-3-carbonitrile (single trans pyrrolidine isomer) | 740.1 |
| 192[2] | 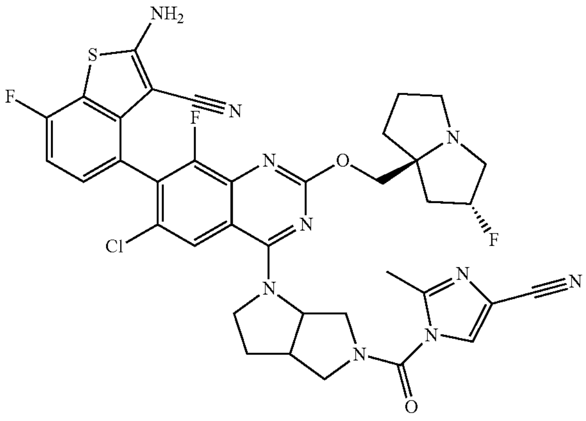 [SMILES: Cc1nc(C#N)cn1C(=O)N1CC2CCN(c3nc(OC[C@@]45CCCN4C[C@H](F)C5)nc4c(F)c(-c5ccc(F)c6sc(N)c(C#N)c56)c(Cl)cc34)C2C1] | 1-(1-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)octahydropyrrolo[3,4-b]pyrrole-5-carbonyl)-2-methyl-1H-imidazole-4-carbonitrile | 773.2 |

TABLE 1-continued

| No. | Structure | Chemical Name | [M + H]+ |
|---|---|---|---|
| 193[1] | 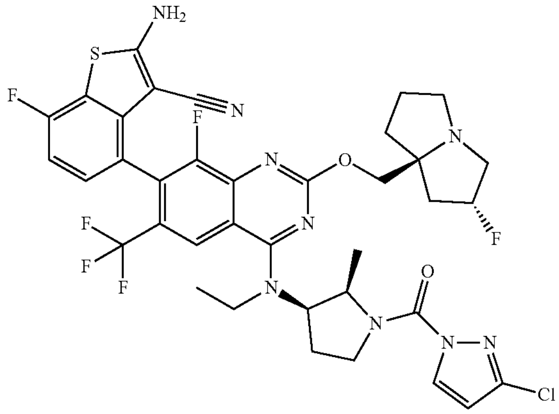 [SMILES: CCN(c1nc(OC[C@@]23CCCN2C[C@H](F)C3)nc2c(F)c(-c3ccc(F)c4sc(N)c(C#N)c34)c(C(F)(F)F)cc12)[C@@H]1CCN(C(=O)n2ccc(Cl)n2)[C@@H]1C] | 2-amino-4-(4-(((2R,3R)-1-(3-chloro-1H-pyrazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile | 818.5 |
| 194[1] | 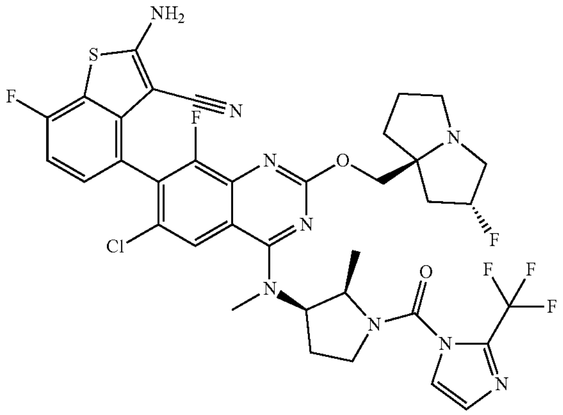 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1C(F)(F)F] | 2-amino-4-(6-chloro-8-fluoro-2-(((2R,7aS)-2-fluorotetrahydro-1H-pyrrolizin-7a(5H)-yl)methoxy)-4-(methyl((2R,3R)-2-methyl-1-(2-(trifluoromethyl)-1H-imidazole-1-carbonyl)pyrrolidin-3-yl)amino)quinazolin-7-yl)-7-fluorobenzo[b]thiophene-3-carbonitrile | 804.2 |
| 195[1] | 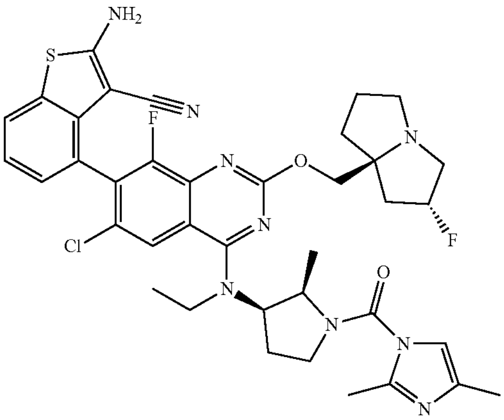 [SMILES: CCN(c1nc(OC[C@@]23CCCN2C[C@H](F)C3)nc2c(F)c(-c3cccc4sc(N)c(C#N)c34)c(Cl)cc12)[C@@H]1CCN(C(=O)n2cc(C)nc2C)[C@@H]1C] | 2-amino-4-(6-chloro-4-(((2R,3R)-1-(2,4-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)benzo[b]thiophene-3-carbonitrile | 760.1 |

TABLE 1-continued

| No. | Structure | Chemical Name | [M + H]+ |
|---|---|---|---|
| 196[1] | 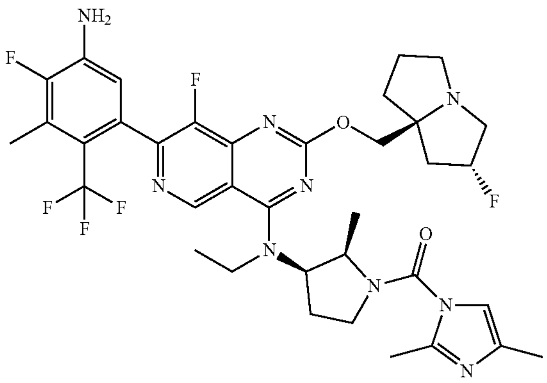 [SMILES: CCN(c1nc(OC[C@@]23CCCN2C[C@H](F)C3)nc2c(F)c(-c3cc(N)c(F)c(C)c3C(F)(F)F)ncc12)[C@@H]1CCN(C(=O)n2cc(C)nc2C)[C@@H]1C] | ((2R,3R)-3-((7-(5-amino-4-fluoro-3-methyl-2-(trifluoromethyl)phenyl)-8-fluoro-2-(((2R,7aS)-2-fluorotetrahydro-1H-pyrrolizin-7a(5H)-yl)methoxy)pyrido[4,3-d]pyrimidin-4-yl)(ethyl)amino)-2-methylpyrrolidin-1-yl)(2,4-dimethyl-1H-imidazol-1-yl)methanone | 746.4 |
| 197[1] | 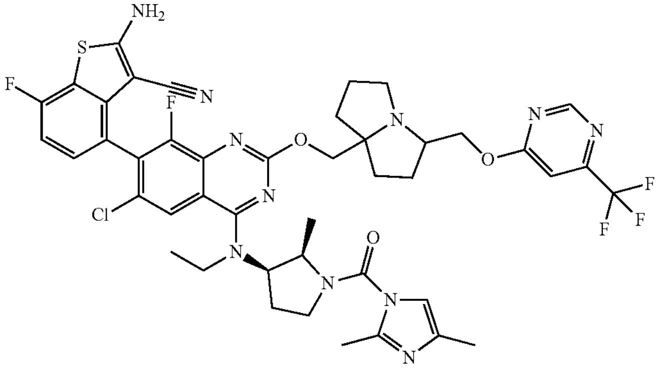 [SMILES: CCN(c1nc(OCC23CCCN2C(COc2cc(C(F)(F)F)ncn2)CC3)nc2c(F)c(-c3ccc(F)c4sc(N)c(C#N)c34)c(Cl)cc12)[C@@H]1CCN(C(=O)n2cc(C)nc2C)[C@@H]1C] | 2-amino-4-(6-chloro-4-(((2R,3R)-1-(2,4-dimethyl-1H-imidazole-1-carbonyl)-2-methylpyrrolidin-3-yl)(ethyl)amino)-8-fluoro-2-((3-(((6-(trifluoromethyl)pyrimidin-4-yl)oxy)methyl)tetrahydro-1H-pyrrolizin-7a(5H)-yl)methoxy)quinazolin-7-yl)-7-fluorobenzo[b]thiophene-3-carbonitrile (single trans hexahydro-1H-pyrrolizine isomer | 936.2 |
| 198[2] | 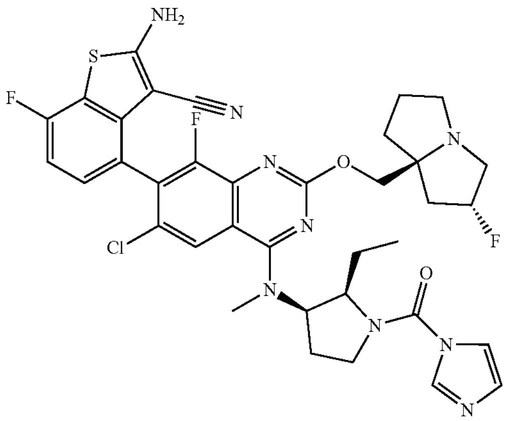 [SMILES: CC[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1] | 2-amino-4-(6-chloro-4-(((2R,3R)-2-ethyl-1-(1H-imidazole-1-carbonyl)pyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 750.2 |
| 199[1] | 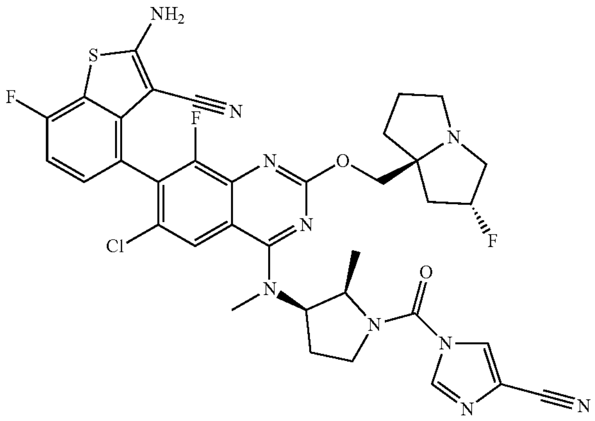 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1cnc(C#N)c1] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(methyl)amino)-2-methylpyrrolidine-1-carbonyl)-1H-imidazole-4-carbonitrile | 761.2 |

TABLE 1-continued

| No. | Structure | Chemical Name | [M + H]+ |
|---|---|---|---|
| 200[2] | 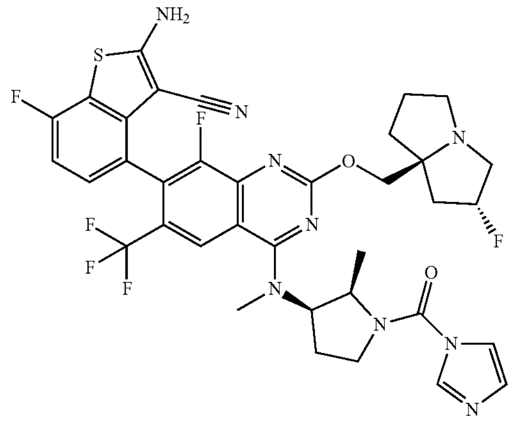 [SMILES: C[C@@H]1[C@H](N(C)c2nc(OC[C@@]34CCCN3C[C@H](F)C4)nc3c(F)c(-c4ccc(F)c5sc(N)c(C#N)c45)c(C(F)(F)F)cc23)CCN1C(=O)n1ccnc1] | 4-(4-(((2R,3R)-1-(1H-imidazole-1-carbonyl)-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile | 770.2 |
| 201[1] | 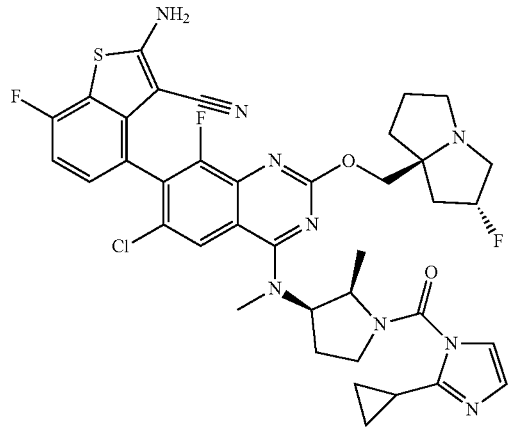 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1C1CC1] | 2-amino-4-(6-chloro-4-(((2R,3R)-1-(2-cyclopropyl-1H-imidazole-1-carbonyl)-2-methylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 776.2 |
| 202[2] | 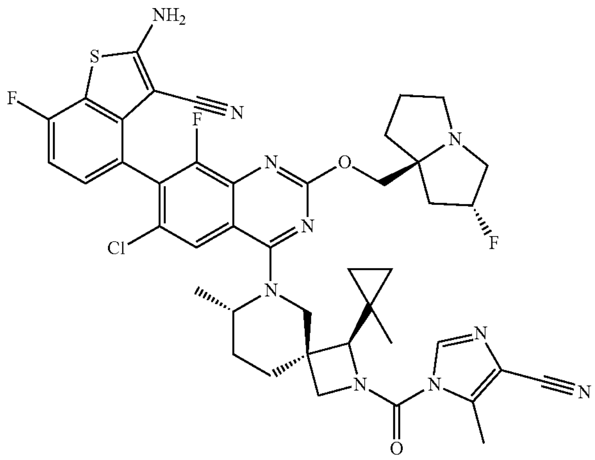 [SMILES: Cc1c(C#N)ncn1C(=O)N1C[C@]2(CC[C@H](C)N(c3nc(OC[C@@]45CCCN4C[C@H](F)C5)nc4c(F)c(-c5ccc(F)c6sc(N)c(C#N)c56)c(Cl)cc34)C2)[C@H]1C1(C)CC1] | 1-((1R,4R,7S)-6-(7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-7-methyl-1-(1-methylcyclopropyl)-2,6-diazaspiro[3.5]nonane-2-carbonyl)-5-methyl-1H-imidazole-4-carbonitrile | 855.3 |

TABLE 1-continued

| No. | Structure | Chemical Name | [M + H]+ |
|---|---|---|---|
| 203[2] | 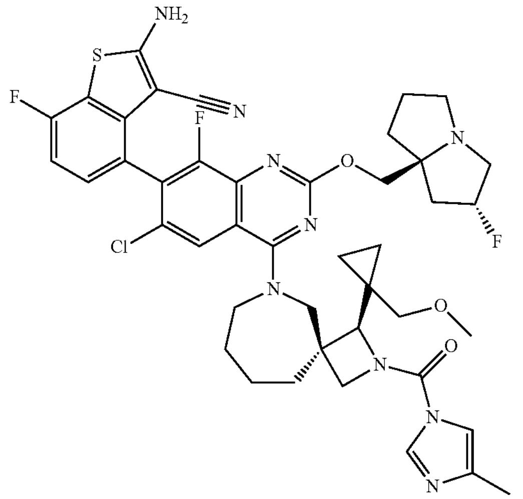 [SMILES: COCC1([C@H]2N(C(=O)n3cnc(C)c3)C[C@]23CCCCN(c2nc(OC[C@@]45CCCN4C[C@H](F)C5)nc4c(F)c(-c5ccc(F)c6sc(N)c(C#N)c56)c(Cl)cc24)C3)CC1] | 2-amino-4-(6-chloro-8-fluoro-2-(((2R,7aS)-2-fluorotetrahydro-1H-pyrrolizin-7a(5H)-yl)methoxy)-4-((1S,4R)-1-(1-(methoxymethyl)cyclopropyl)-2-(4-methyl-1H-imidazole-1-carbonyl)-2,6-diazaspiro[3.6]decan-6-yl)quinazolin-7-yl)-7-fluorobenzo[b]thiophene-3-carbonitrile | 860.2 |
| 204[4] | 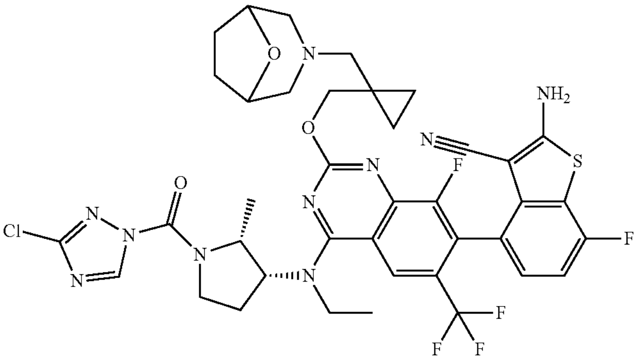 [SMILES: CCN(c1nc(OCC2(CN3CC4CCC(C3)O4)CC2)nc2c(F)c(-c3ccc(F)c4sc(N)c(C#N)c34)c(C(F)(F)F)cc12)[C@@H]1CCN(C(=O)n2cnc(Cl)n2)[C@@H]1C] | 4-(2-((1-((8-oxa-3-azabicyclo[3.2.1]octan-3-yl)methyl)cyclopropyl)methoxy)-4-(((2R,3R)-1-(3-chloro-1H-1,2,4-triazole-1-carbonyl)-2-methylpyrrolidin-3-yl)(ethyl)amino)-8-fluoro-6-(trifluoromethyl)quinazolin-7-yl)-2-amino-7-fluorobenzo[b]thiophene-3-carbonitrile | 857.5 |
| 205[1] | 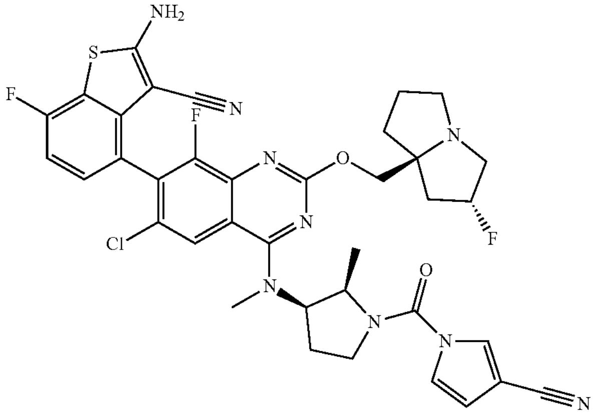 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccc(C#N)c1] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(methyl)amino)-2-methylpyrrolidine-1-carbonyl)-1H-pyrrole-3-carbonitrile | 760.2 |

TABLE 1-continued

| No. | Structure | Chemical Name | [M + H]+ |
|---|---|---|---|
| 206[2] | 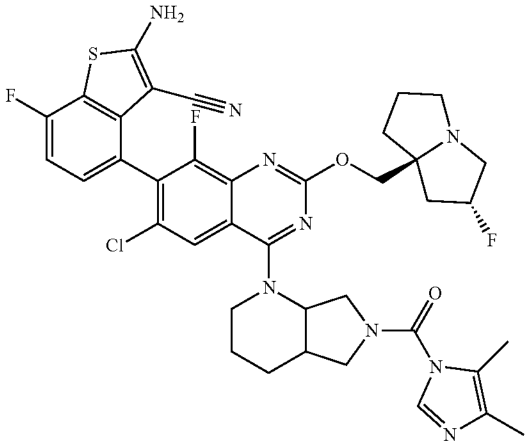 [SMILES: Cc1ncn(C(=O)N2CC3CCCN(c4nc(OC[C@@]56CCCN5C[C@H](F)C6)nc5c(F)c(-c6ccc(F)c7sc(N)c(C#N)c67)c(Cl)cc45)C3C2)c1C] | 2-amino-4-(6-chloro-4-(6-(4,5-dimethyl-1H-imidazole-1-carbonyl)octahydro-1H-pyrrolo[3,4-b]pyridin-1-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 776.2 |
| 207[2] | 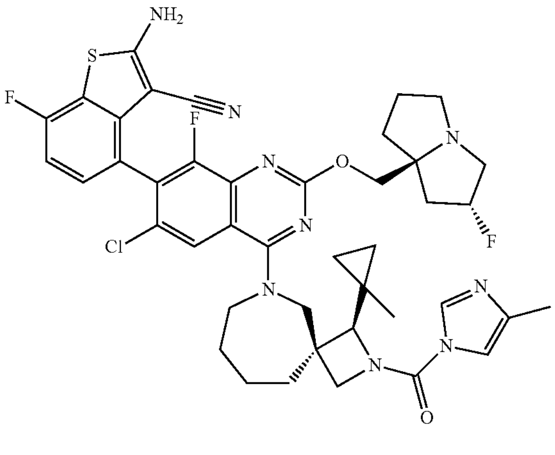 [SMILES: Cc1cn(C(=O)N2C[C@]3(CCCCN(c4nc(OC[C@@]56CCCN5C[C@H](F)C6)nc5c(F)c(-c6ccc(F)c7sc(N)c(C#N)c67)c(Cl)cc45)C3)[C@H]2C2(C)CC2)cn1] | 2-amino-4-(6-chloro-8-fluoro-2-(((2R,7aS)-2-fluorotetrahydro-1H-pyrrolizin-7a(5H)-yl)methoxy)-4-((1R,4R)-2-(4-methyl-1H-imidazole-1-carbonyl)-1-(1-methylcyclopropyl)-2,6-diazaspiro[3.6]decan-6-yl)quinazolin-7-yl)-7-fluorobenzo[b]thiophene-3-carbonitrile | 830.2 |
| 208[1] | 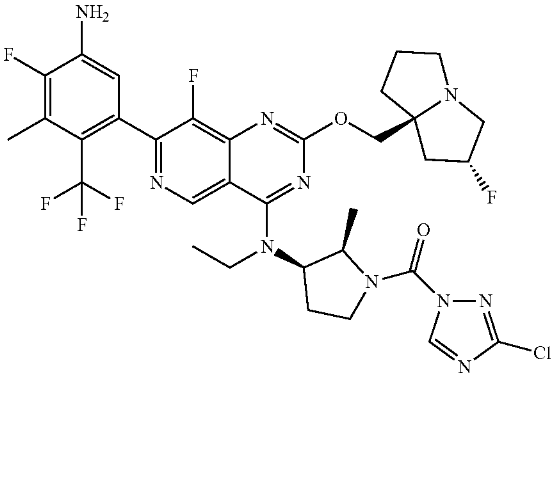 [SMILES: CCN(c1nc(OC[C@@]23CCCN2C[C@H](F)C3)nc2c(F)c(-c3cc(N)c(F)c(C)c3C(F)(F)F)ncc12)[C@@H]1CCN(C(=O)n2cnc(Cl)n2)[C@@H]1C] | ((2R,3R)-3-((7-(5-amino-4-fluoro-3-methyl-2-(trifluoromethyl)phenyl)-8-fluoro-2-(((2R,7aS)-2-fluorotetrahydro-1H-pyrrolizin-7a(5H)-yl)methoxy)pyrido[4,3-d]pyrimidin-4-yl)(ethyl)amino)-2-methylpyrrolidin-1-yl)(3-chloro-1H-1,2,4-triazol-1-yl)methanone | 753.4 |

TABLE 1-continued

| No. | Structure | Chemical Name | [M + H]+ |
|---|---|---|---|
| 209[2] | 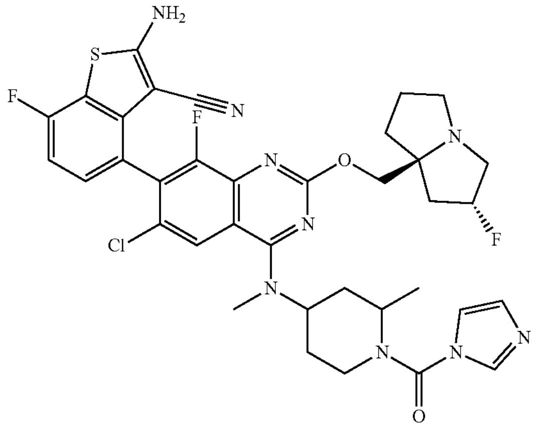 [SMILES: CC1CC(N(C)c2nc(OC[C@@]34CCCN3C[C@H](F)C4)nc3c(F)c(-c4ccc(F)c5sc(N)c(C#N)c45)c(Cl)cc23)CCN1C(=O)n1ccnc1] | 4-(4-((1-(1H-imidazole-1-carbonyl)-2-methylpiperidin-4-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile (single cis piperidine isomer) | 750.2 |
| 210[1] | 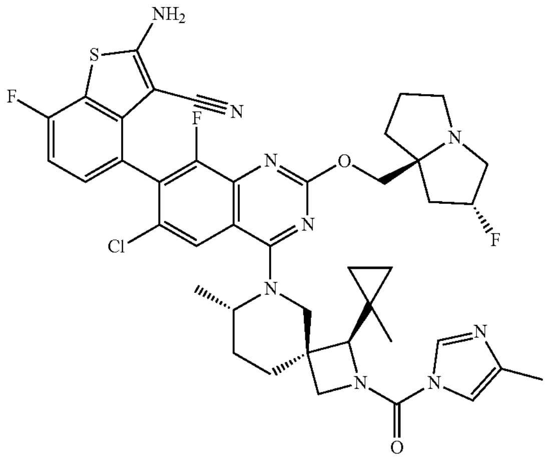 [SMILES: Cc1cn(C(=O)N2C[C@]3(CC[C@H](C)N(c4nc(OC[C@@]56CCCN5C[C@H](F)C6)nc5c(F)c(-c6ccc(F)c7sc(N)c(C#N)c67)c(Cl)cc45)C3)[C@H]2C2(C)CC2)cn1] | 2-amino-4-(6-chloro-8-fluoro-2-(((2R,7aS)-2-fluorotetrahydro-1H-pyrrolizin-7a(5H)-yl)methoxy)-4-((1R,4R,7S)-7-methyl-2-(4-methyl-1H-imidazole-1-carbonyl)-1-(1-methylcyclopropyl)-2,6-diazaspiro[3.5]nonan-6-yl)quinazolin-7-yl)-7-fluorobenzo[b]thiophene-3-carbonitrile | 830.2 |
| 211[1] | 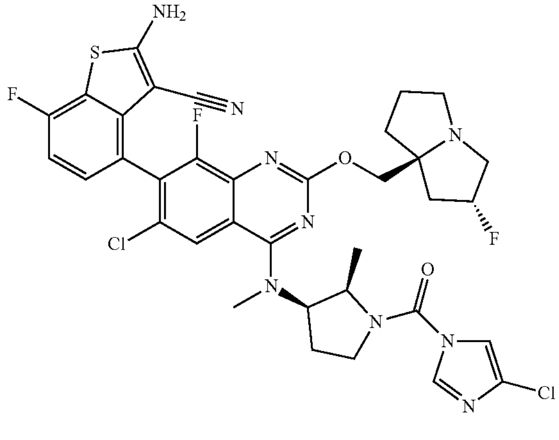 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1cnc(Cl)c1] | 2-amino-4-(6-chloro-4-(((2R,3R)-1-(4-chloro-1H-imidazole-1-carbonyl)-2-methylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 770.2 |

TABLE 1-continued

| No. | Structure | Chemical Name | [M + H]+ |
|---|---|---|---|
| 212[4] | 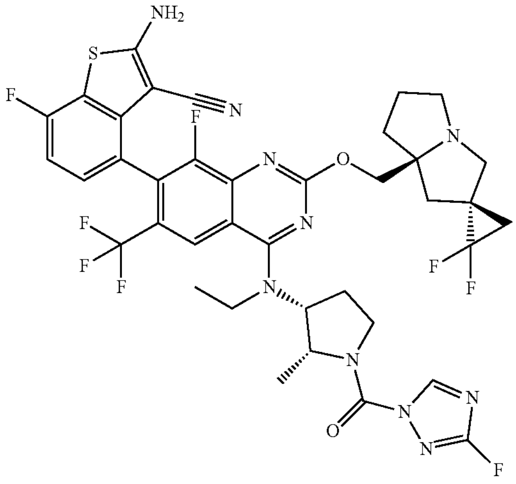 [SMILES: CCN(c1nc(OC[C@@]23CCCN2C[C@@]2(CC2(F)F)C3)nc2c(F)c(-c3ccc(F)c4sc(N)c(C#N)c34)c(C(F)(F)F)cc12)[C@@H]1CCN(C(=O)n2cnc(F)n2)[C@@H]1C] | 2-amino-4-(2-(((1S,7a'S)-2,2-difluorodihydro-1'H,3'H-spiro[cyclopropane-1,2'-pyrrolizin]-7a'(5'H)-yl)methoxy)-4-(ethyl((2R,3R)-1-(3-fluoro-1H-1,2,4-triazole-1-carbonyl)-2-methylpyrrolidin-3-yl)amino)-8-fluoro-6-(trifluoromethyl)quinazolin-7-yl)-7-fluorobenzo[b]thiophene-3-carbonitrile | 847.5 |
| 213[1] | 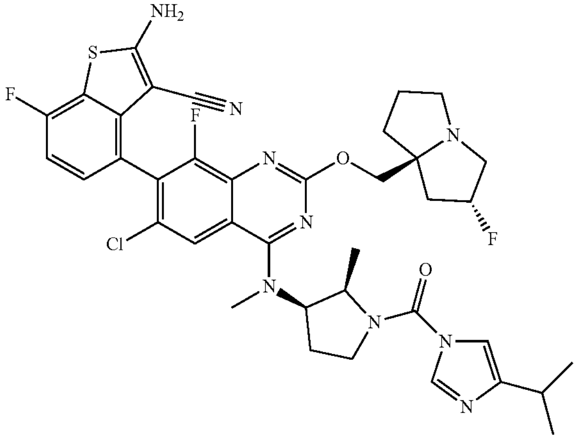 [SMILES: CC(C)c1cn(C(=O)N2CC[C@@H](N(C)c3nc(OC[C@@]45CCCN4C[C@H](F)C5)nc4c(F)c(-c5ccc(F)c6sc(N)c(C#N)c56)c(Cl)cc34)[C@H]2C)cn1] | 2-amino-4-(6-chloro-8-fluoro-2-(((2R,7aS)-2-fluorotetrahydro-1H-pyrrolizin-7a(5H)-yl)methoxy)-4-(((2R,3R)-1-(4-isopropyl-1H-imidazole-1-carbonyl)-2-methylpyrrolidin-3-yl)(methyl)amino)quinazolin-7-yl)-7-fluorobenzo[b]thiophene-3-carbonitrile | 778.2 |
| 214[2] | 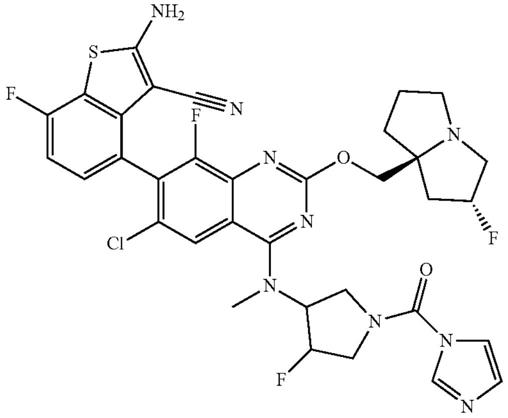 [SMILES: CN(c1nc(OC[C@@]23CCCN2C[C@H](F)C3)nc2c(F)c(-c3ccc(F)c4sc(N)c(C#N)c34)c(Cl)cc12)C1CN(C(=O)n2ccnc2)CC1F] | 2-amino-4-(6-chloro-8-fluoro-4-((4-fluoro-1-(1H-imidazole-1-carbonyl)pyrrolidin-3-yl)(methyl)amino)-2-(((2R,7aS)-2-fluorotetrahydro-1H-pyrrolizin-7a(5H)-yl)methoxy)quinazolin-7-yl)-7-fluorobenzo[b]thiophene-3-carbonitrile (racemic cis pyrrolidine isomers) | 740.2 |

TABLE 1-continued

| No. | Structure | Chemical Name | [M + H]+ |
| --- | --- | --- | --- |
| 215[1] | 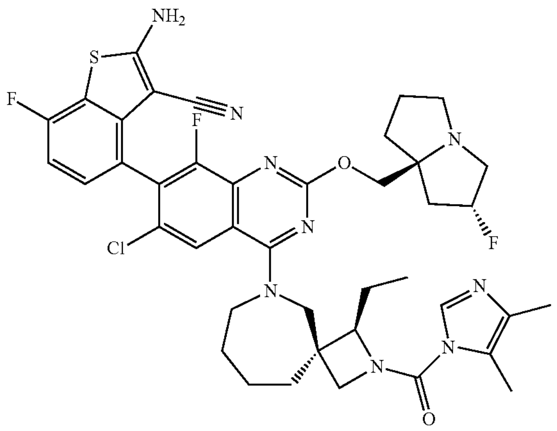 [SMILES: CC[C@H]1N(C(=O)n2cnc(C)c2C)C[C@]12CCCCN(c1nc(OC[C@@]34CCCN3C[C@H](F)C4)nc3c(F)c(-c4ccc(F)c5sc(N)c(C#N)c45)c(Cl)cc13)C2] | 2-amino-4-(6-chloro-4-((1R,4R)-2-(4,5-dimethyl-1H-imidazole-1-carbonyl)-1-ethyl-2,6-diazaspiro[3.6]decan-6-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 818.2 |
| 216[2] | 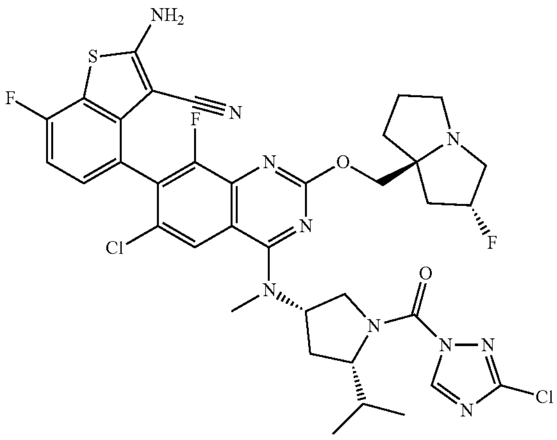 [SMILES: CC(C)[C@@H]1C[C@H](N(C)c2nc(OC[C@@]34CCCN3C[C@H](F)C4)nc3c(F)c(-c4ccc(F)c5sc(N)c(C#N)c45)c(Cl)cc23)CN1C(=O)n1cnc(Cl)n1] | 2-amino-4-(6-chloro-4-(((3S,5S)-1-(3-chloro-1H-1,2,4-triazole-1-carbonyl)-5-isopropylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile | 799.1 |
| 217[1] | 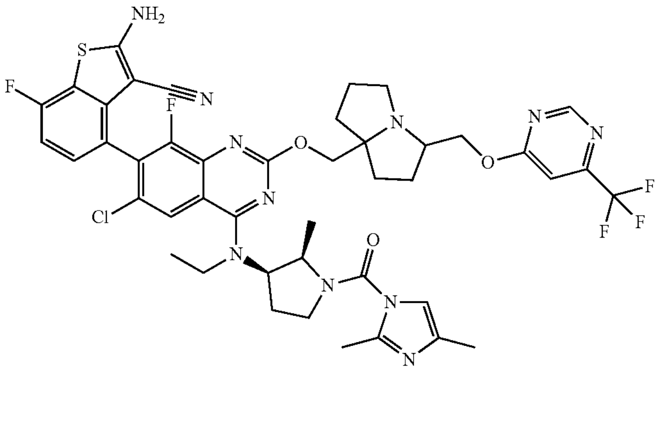 [SMILES: CCN(c1nc(OCC23CCCN2C(COc2cc(C(F)(F)F)ncn2)CC3)nc2c(F)c(-c3ccc(F)c4sc(N)c(C#N)c34)c(Cl)cc12)[C@@H]1CCN(C(=O)n2cc(C)nc2C)[C@@H]1C] | 2-amino-4-(6-chloro-4-(((2R,3R)-1-(2,4-dimethyl-1H-imidazole-1-carbonyl)-2-methylpyrrolidin-3-yl)(ethyl)amino)-8-fluoro-2-((3-(((6-(trifluoromethyl)pyrimidin-4-yl)oxy)methyl)tetrahydro-1H-pyrrolizin-7a(5H)-yl)methoxy)quinazolin-7-yl)-7-fluorobenzo[b]thiophene-3-carbonitrile (single trans hexahydro-1H-pyrrolizine isomer) | 936.5 |

TABLE 1-continued

| No. | Structure | Chemical Name | [M + H]$^+$ |
| --- | --- | --- | --- |
| 218[3] | 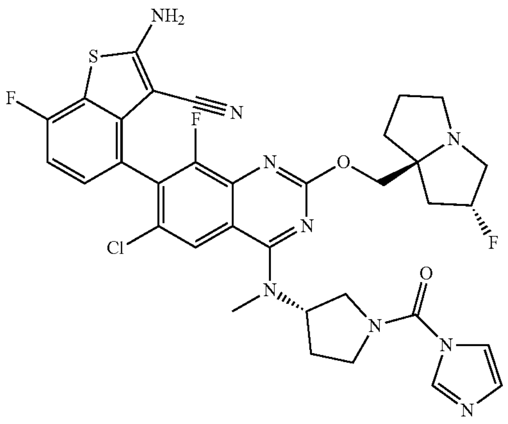 [SMILES: CN(c1nc(OC[C@@]23CCCN2C[C@H](F)C3)nc2c(F)c(-c3ccc(F)c4sc(N)c(C#N)c34)c(Cl)cc12)[C@H]1CCN(C(=O)n2ccnc2)C1] | 4-(4-(((S)-1-(1H-imidazole-1-carbonyl)pyrrolidin-3-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile | 722.2 |
| 219[4] | 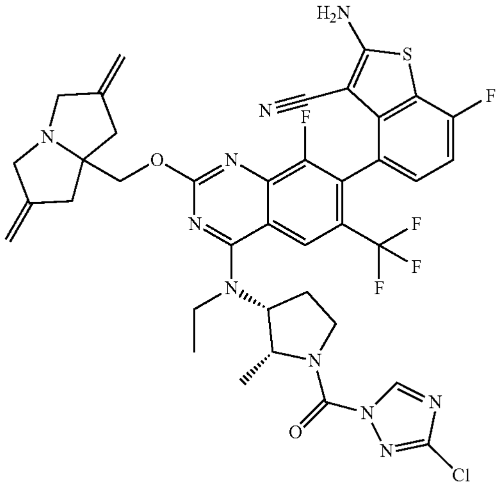 [SMILES: C=C1CN2CC(=C)CC2(COc2nc(N(CC)[C@@H]3CCN(C(=O)n4cnc(Cl)n4)[C@@H]3C)c3cc(C(F)(F)F)c(-c4ccc(F)c5sc(N)c(C#N)c45)c(F)c3n2)C1] | 2-amino-4-(4-(((2R,3R)-1-(3-chloro-1H-1,2,4-triazole-1-carbonyl)-2-methylpyrrolidin-3-yl)(ethyl)amino)-2-((2,6-dimethylenetetrahydro-1H-pyrrolizin-7a(5H)-yl)methoxy)-8-fluoro-6-(trifluoromethyl)quinazolin-7-yl)-7-fluorobenzo[b]thiophene-3-carbonitrile | 825.1 |
| 220[1] | 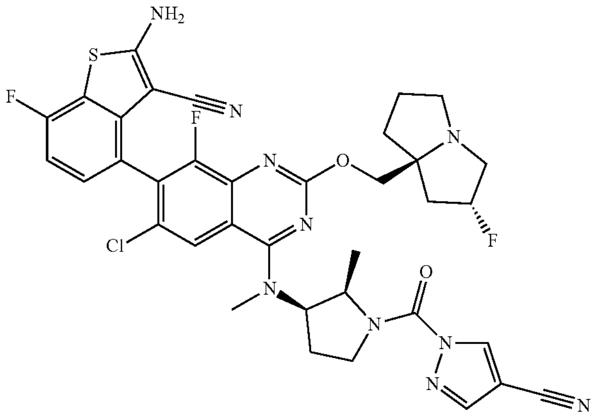 [SMILES: C[C@@H]1[C@H](N(C)c2nc(OC[C@@]34CCCN3C[C@H](F)C4)nc3c(F)c(-c4ccc(F)c5sc(N)c(C#N)c45)c(Cl)cc23)CCN1C(=O)n1cc(C#N)cn1] | 1-((2R,3R)-3-((7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)(methyl)amino)-2-methylpyrrolidine-1-carbonyl)-1H-pyrazole-4-carbonitrile | 761.2 |

Compounds of Table 1 are depicted with flat, wedged, and/or hashed wedged bonds. It is understood that compounds depicted in Table 1 encompass all possible stereoisomers, including atropisomers, of the compounds of Table 1. In some instances, the relative stereochemistry at one or more stereocenters of a compound has been determined; in some instances, the absolute stereochemistry has been determined. In some instances, a single compound number represents a mixture of stereoisomers, including atropisomers. In some instances, a single compound number represents a single stereoisomer, such as a single atropisomer. As such, it is understood that if two or more compound numbers in Table 1 are provided with the same depicted structure, then different stereoisomers or mixtures of stereoisomers of the depicted structure are represented by each compound number. [1]Compound provided as a substantially pure single atropisomer at $R^7$; [2]compound provided as substantially pure R atropisomer at $R^7$; [3]compound provided as a mixture of atropisomers at $R^7$; [4]compound provided as substantially pure S atropisomer at $R^7$.

In some embodiments, the compounds of the present disclosure exhibit one or more functional characteristics disclosed herein. For example, a subject compound binds to a Ras protein, KRAS protein or a mutant form thereof. In some embodiments, a subject compound binds specifically and also inhibits a Ras protein, KRAS protein or a mutant form thereof. In some embodiments, a subject compound selectively inhibits a KRAS mutant relative to a wildtype KRAS. In some embodiments, the IC50 of a subject compound for a KRAS mutant (e.g., G12S and/or G12C) is less than about 5 μM, less than about 1 μM, less than about 500 nM, less than 250 nM, less than 100 nM, less than 50 nM, or even less, as measured in an in vitro assay known in the art or exemplified herein. In some embodiments, a subject compound covalently binds to a KRAS mutant (e.g., KRAS G12S and/or KRAS G12C).

In some embodiments, a compound of the present disclosure is capable of reducing Ras signaling output. Such reduction may be evidenced by one or more of the following: (i) an increase in steady state level of GDP-bound Ras protein; (ii) a reduction in steady state level of GTP-bound Ras protein; (iii) a reduction of phosphorylated AKTs473, (iv) a reduction of phosphorylated ERKT202/y204, (v) a reduction of phosphorylated S6S235/236, and (vi) reduction (e.g., inhibition) of cell growth of Ras-driven tumor cells (e.g., those derived from a tumor cell line disclosed herein). In some cases, the reduction in Ras signaling output can be evidenced by two, three, four, five, or all of (i)-(vi) above.

It shall be understood that different aspects of the disclosure can be appreciated individually, collectively, or in combination with each other. Various aspects described herein may be applied to any of the particular applications disclosed herein. The compositions of matter, including compounds of any formulae disclosed in the compound section, of the present disclosure may be utilized in the method section, including methods of use and production disclosed herein, or vice versa.

Methods

The compounds described herein, or a pharmaceutically acceptable salt or solvate thereof, are Ras inhibitors capable of inhibiting a Ras protein, such as wild-type Ras or a Ras mutant protein (e.g., G12S, G12C, G12D, G12V, G13C, and/or G13D) from K-Ras, H-Ras or N-Ras. Compounds, including pharmaceutically acceptable salts or solvates thereof, disclosed herein have a wide range of applications in therapeutics, diagnostics, and other biomedical research.

In certain aspects, the present disclosure provides a method of treating cancer in a subject in need thereof, comprising administering to the subject a therapeutically effective amount of a compound described herein, or a pharmaceutically acceptable salt or solvate thereof.

In certain aspects, the present disclosure provides a method of treating a cancer comprising amplified wildtype Ras or a Ras mutant (e.g., G12S, G12C, G12D, G12V, G13C, and/or G13D) protein in a subject, comprising inhibiting amplified wildtype Ras or the Ras mutant protein of said subject by administering to said subject a compound, wherein the compound is characterized in that upon contacting the Ras protein, the Ras protein activity or function is inhibited (e.g., partially inhibited or completely inhibited), such that said inhibited Ras protein exhibits reduced Ras signaling output (e.g., compared to a corresponding Ras protein not contacted by the compound).

In certain aspects, the present disclosure provides a method of modulating activity of a Ras protein (e.g., K-Ras, mutant K-Ras, K-Ras G12S, K-Ras G12C, K-Ras G12D, K-Ras G12V, K-Ras G13C, and/or K-Ras G13D), comprising contacting a Ras protein with an effective amount of a compound described herein, or a pharmaceutically acceptable salt or solvate thereof, thereby modulating the activity of the Ras protein.

In certain aspects, the present disclosure provides a method of inhibiting cell growth, comprising administering an effective amount of a compound described herein, or a pharmaceutically acceptable salt or solvate thereof, to a cell expressing a Ras (e.g., K-Ras) protein, thereby inhibiting growth of said cells. In some embodiments, the subject method comprises administering an additional agent to said cell.

In certain aspects, the present disclosure provides a method of treating a disease mediated at least in part by a Ras protein, such as K-Ras or a mutant thereof, in a subject in need thereof, comprising administering to the subject an effective amount of a compound disclosed herein, or a pharmaceutically acceptable salt or solvate thereof. In some embodiments, the disease is cancer, such as a solid tumor or a hematological cancer. In some embodiments, the method further comprises administering an additional agent to the subject, such as a SHP2 inhibitor, a SOS inhibitor, an EGFR inhibitor, a MEK inhibitor, an ERK inhibitor, a CDK4/6 inhibitor, a BRAF inhibitor, or a combination thereof.

In certain aspects, the present disclosure provides a method of inhibiting activity of a Ras protein, such as K-Ras or a mutant thereof, comprising contacting the Ras protein with a compound disclosed herein, or a pharmaceutically acceptable salt or solvate thereof. In some embodiments, the compound exhibits an IC50 against the Ras protein of less than 10 μM, such as less than 5 μM, 1 μM, 500 nM, 100 nM, 50 nM, 10 nM, 5 nM, 1 nM, 500 μM, 50 μM, 10 μM or less.

In certain aspects, the present disclosure provides a method of treating a Ras-mediated cancer in a subject in need thereof, comprising administering to the subject a SHP2 inhibitor, a SOS inhibitor, an EGFR inhibitor, a MEK inhibitor, an ERK inhibitor, a CDK4/6 inhibitor, or a BRAF inhibitor and an effective amount of a compound disclosed herein, such as a compound of Formula (I) or (II), or a pharmaceutically acceptable salt or solvate thereof. In some embodiments, the cancer is a solid tumor. In some embodiments, the cancer is a hematological cancer.

In practicing any of the methods disclosed herein, the Ras target to which a subject compound binds, either covalently or reversibly, can be a Ras mutant (e.g., G12S, G12C, G12D, G12V, G13C, and/or G13D), including a mutant of K-Ras, H-Ras, or N-Ras. In some embodiments, the methods of treating cancer can be applied to treat a solid tumor or a hematological cancer. In some embodiments, the cancer being treated can be, without limitation, prostate cancer, brain cancer, colon cancer, rectal cancer, renal-cell carcinoma, liver cancer, various lung cancers including non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer selected from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and preleukemia. In some embodiments is a method of treating cancer in a subject in need thereof, comprising administering to the subject a therapeutically effective amount of a compound described herein, or a pharmaceutically acceptable salt or solvate thereof, wherein the cancer is one or more cancers selected from the group consisting of chronic lymphocytic leukemia (CLL), acute myeloid leukemia (AML), T-cell acute lymphoblastic leukemia (T-ALL), B cell acute lymphoblastic leukemia (B-ALL), and/or acute lymphoblastic leukemia (ALL).

Any of the treatment methods disclosed herein can be administered alone or in combination or in conjunction with another therapy or another agent. By "combination" it is meant to include (a) formulating a subject composition containing a subject compound together with another agent, or (b) using the subject composition separate from the another agent as an overall treatment regimen. By "conjunction" it is meant that the another therapy or agent is administered either simultaneously, concurrently or sequentially with a subject composition comprising a compound disclosed herein, with no specific time limits, wherein such conjunctive administration provides a therapeutic effect.

In some embodiments, a subject treatment method is combined with surgery, cellular therapy, chemotherapy, radiation, and/or immunosuppressive agents. Additionally, compositions of the present disclosure can be combined with other therapeutic agents, such as other anti-cancer agents, anti-allergic agents, anti-nausea agents (or anti-emetics), pain relievers, cytoprotective agents, immunostimulants, and combinations thereof. In one embodiment, a subject treatment method is combined with a chemotherapeutic agent.

Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). Additional chemotherapeutic agents contemplated for use in combination include busulfan (Myleran®), busulfan injection (Busulfex®), cladribine (Leustatin®), cyclophosphamide (Cytoxan® or Neosar®), cytarabine, cytosine arabinoside (Cytosar-U®), cytarabine liposome injection (DepoCyt®), daunorubicin hydrochloride (Cerubidine®), daunorubicin citrate liposome injection (DaunoXome®), dexamethasone, doxorubicin hydrochloride (Adriamycin®, Rubex®), etoposide (Vepesid®), fludarabine phosphate (Fludara®), hydroxyurea (Hydrea®), Idarubicin (Idamycin®), mitoxantrone (Novantrone®), Gemtuzumab Ozogamicin (Mylotarg®), anastrozole (Arimidex®), bicalutamide (Casodex®), bleomycin sulfate (Blenoxane®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), dacarbazine (DTIC-Dome®), dactinomycin (Actinomycin D, Cosmegan), dexamethasone, docetaxel (Taxotere®), 5-fluorouracil (Adrucil®, Efudex®), flutamide (Eulexin®), tezacitibine, Gemcitabine (difluorodeoxycitidine), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/M4X-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with a compound of the present disclosure include: anthracyclines; alkylating agents; antimetabolites; drugs that inhibit either the calcium dependent phosphatase calcineurin or the p70S6 kinase FK506 or inhibit the p70S6 kinase; mTOR inhibitors; immunomodulators; anthracyclines; vinca alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary antimetabolites include, without limitation, pyrimidine analogs, purine analogs and adenosine deaminase inhibitors: methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), azacitidine (Vidaza®), decitabine and gemcitabine (Gemzar®). Preferred antimetabolites include, cytarabine, clofarabine and fludarabine.

Exemplary alkylating agents include, without limitation, nitrogen mustards, ethylenimine derivatives, alkyl sulfonates, nitrosoureas and triazenes: uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™, ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In certain aspects, compositions provided herein can be administered in combination with radiotherapy, such as radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation it may be uniform or not uniform. For example, when radiation may not be uniform, narrower regions of a body such as the neck may receive a higher dose than broader regions such as the hips.

Where desirable, an immunosuppressive agent can be used in conjunction with a subject treatment method. Exemplary immunosuppressive agents include but are not limited to cyclosporin, azathioprine, methotrexate, mycophenolate, and FK506, antibodies, or other immunoablative agents such as CAMPATH, anti-CD3 antibodies (e.g., muromonab, otelixizumab) or other antibody therapies, cytoxin, fludarabine, cyclosporin, FK506, rapamycin, mycophenolic acid, steroids, FR901228, cytokines, and irradiation, peptide vaccine, and any combination thereof. In accordance with the presently disclosed subject matter, the above-described various methods can comprise administering at least one immunomodulatory agent. In certain embodiments, the at least one immunomodulatory agent is selected from the group consisting of immunostimulatory agents, checkpoint immune blockade agents (e.g., blockade agents or inhibitors of immune checkpoint genes, such as, for example, PD-1, PD-L1, CTLA-4, IDO, TIM3, LAG3, TIGIT, BTLA, VISTA, ICOS, KIRs and CD39), radiation therapy agents, chemotherapy agents, and combinations thereof. In some embodiments, the immunostimulatory agents are selected from the group consisting of IL-12, an agonist costimulatory monoclonal antibody, and combinations thereof. In one embodiment, the immunostimulatory agent is IL-12. In some embodiments, the agonist costimulatory monoclonal antibody is selected from the group consisting of an anti-4-1BB antibody (e.g., urelumab, PF-05082566), an anti-OX40 antibody (pogalizumab, tavolixizumab, PF-04518600), an anti-ICOS antibody (BMS986226, MEDI-570, GSK3359609, JTX-2011), and combinations thereof. In one embodiment, the agonist costimulatory monoclonal antibody is an anti-4-1 BB antibody. In some embodiments, the checkpoint immune blockade agents are selected from the group consisting of anti-PD-L1 antibodies (atezolizumab, avelumab, durvalumab, BMS-936559), anti-CTLA-4 antibodies (e.g., tremelimumab, ipilimumab), anti-PD-1 antibodies (e.g., pembrolizumab, nivolumab, cemiplimab), anti-LAG3 antibodies (e.g., C9B7W, 410C9), anti-B7-H3 antibodies (e.g., DS-5573a), anti-TIM3 antibodies (e.g., F38-2E2), and combinations thereof. In one embodiment, the checkpoint immune blockade agent is an anti-PD-L1 antibody. In some cases, a compound of the present disclosure can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. Alternatively, compositions comprising a compound described herein can be administered with immunostimulants. Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with modified cells provided herein. Cytokines can be utilized to boost function of modified T lymphocytes (including adoptively transferred tumor-specific cytotoxic T lymphocytes) to expand within a tumor microenvironment. In some cases, IL-2 can be used to facilitate expansion of the modified cells described herein. Cytokines such as IL-15 can also be employed. Other relevant cytokines in the field of immunotherapy can also be utilized, such as IL-2, IL-7, IL-12, IL-15, IL-21, or any combination thereof. An interleukin can be IL-2, or aldesleukin. Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg.

In some embodiments, a compound described herein, such as a compound, salt, or solvate of Formula (I) or (II), is administered in combination or in conjunction with one or more pharmacologically active agents selected from (1) an inhibitor of MEK (e.g., MEK1, MEK2) or of mutants thereof (e.g., trametinib, cobimetinib, binimetinib, selumetinib, refametinib, AZD6244); (2) an inhibitor of epidermal growth factor receptor (EGFR) and/or of mutants thereof (e.g., afatinib, erlotinib, gefitinib, lapatinib, cetuximab panitumumab, osimertinib, olmutinib, EGF-816); (3) an immunotherapeutic agent (e.g., checkpoint immune blockade agents, as disclosed herein); (4) a taxane (e.g., paclitaxel, docetaxel); (5) an anti-metabolite (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); (6) an inhibitor of FGFR1 and/or FGFR2 and/or FGFR3 and/or FGFR4 and/or of mutants thereof (e.g., nintedanib); (7) a mitotic kinase inhibitor (e.g., a CDK4/6 inhibitor, such as, for example, palbociclib, ribociclib, abemaciclib); (8) an anti-angiogenic drug (e.g., an anti-VEGF antibody, such as, for example, bevacizumab); (9) a topoisomerase inhibitor (e.g. epipodophyllotoxins such as for example etoposide and etopophos, teniposide, amsacrin, topotecan, irinotecan, mitoxantrone); (10) a platinum-containing compound (e.g. cisplatin, oxaliplatin, carboplatin); (11) an inhibitor of ALK and/or of mutants thereof (e.g. crizotinib, alectinib, entrectinib, brigatinib); (12) an inhibitor of c-MET and/or of mutants thereof (e.g., K252a, SU11274, PHA665752, PF2341066); (13) an inhibitor of BCR-ABL and/or of mutants thereof (e.g., imatinib, dasatinib, nilotinib); (14) an inhibitor of ErbB2 (Her2) and/or of mutants thereof (e.g., afatinib, lapatinib, trastuzumab, pertuzumab); (15) an inhibitor of AXL and/or of mutants thereof (e.g., R428, amuvatinib, XL-880); (16) an inhibitor of NTRK1 and/or of mutants thereof (e.g., merestinib); (17) an inhibitor of RET and/or of mutants thereof (e.g., BLU-667, Lenvatinib); (18) an inhibitor of A-Raf and/or B-Raf and/or C-Raf and/or of mutants thereof (RAF-709, LY-3009120, sorafenib, vemurafenib, dabrafenib, encorafenib, regorafenib, GDC-879); (19) an inhibitor of ERK and/or of mutants thereof (e.g., ulixertinib, MK-8353, LTT462, AZD0364, SCH772984, BIX02189, LY3214996, ravoxertinib); (20) an MDM2 inhibitor (e.g., HDM-201, NVP-CGM097, RG-71 12, MK-8242, RG-7388, SAR405838, AMG-232, DS-3032, RG-7775, APG-115); (21) an inhibitor of mTOR (e.g., rapamycin, temsirolimus, everolimus, ridaforolimus); (22) an inhibitor of BET (e.g., I-BET 151, I-BET 762, OTX-015, TEN-010, CPI-203, CPI-0610, olionon, RVX-208, ABBC-744, LY294002, AZD5153, MT-1, MS645); (23) an inhibitor of IGF1/2 and/or of IGF1-R (e.g., xentuzumab, MEDI-573); (24) an inhibitor of CDK9 (e.g., DRB, flavopiridol, CR8, AZD 5438, purvalanol B, AT7519, dinaciclib, SNS-032); (25) an inhibitor of farnesyl transferase (e.g., tipifarnib); (26) an inhibitor of SHIP pathway including SHIP2 inhibitor, as well as SHIP1 inhibitors; (27) an inhibitor of SRC (e.g., dasatinib); (28) an inhibitor of JAK (e.g. tofacitinib); (29) a PARP inhibitor (e.g. Olaparib, Rucaparib, Niraparib, Talazoparib), (30) a BTK inhibitor (e.g. Ibrutinib, Acalabrutinib, Zanubrutinib), (31) a ROS1 inhibitor (e.g., entrectinib), (32) an inhibitor of Src, FLT3, HDAC, VEGFR, PDGFR, LCK, Bcr-Abl or AKT, (33) an inhibitor of KRAS G12C mutant (e.g., including but not limited to AMG510, MRTX849, and any covalent inhibitors binding to the cysteine residue 12 of KRAS, the structures of which are publicly known) (e.g., an inhibitor of Ras G12C as described in US20180334454, US20190144444, US20150239900, U.S. Ser. No. 10/246,424, US20180086753, WO2018143315, WO2018206539, WO20191107519, WO2019141250, WO2019150305, U.S. Pat. No. 9,862,701, US20170197945, US20180086753, U.S. Ser. No. 10/144,724, US20190055211, US20190092767, US20180127396, US20180273523, U.S. Ser. No. 10/280,172, US20180319775, US20180273515, US20180282307, US20180282308, WO2019051291, WO2019213526, WO2019213516, WO2019217691, WO2019241157, WO2019217307, WO2020047192, WO2017087528, WO2018218070, WO2018218069, WO2018218071, WO2020027083, WO2020027084, WO2019215203, WO2019155399, WO2020035031, WO2014160200, WO2018195349, WO2018112240, WO2019204442, WO2019204449, WO2019104505, WO2016179558, WO2016176338, or related patents and applications, each of which is incorporated by reference in its entirety), (34) an SHC inhibitor (e.g., PP2, AID371185), (35) a GAB inhibitor (e.g., GAB-0001), (36) a GRB inhibitor, (37) a PI-3 kinase inhibitor (e.g., idelalisib, copanlisib, duvelisib, alpelisib, taselisib, perifosine, buparlisib, umbralisib, NVP-BEZ235-AN), (38) a MARPK inhibitor, (39) a CDK4/6 inhibitor (e.g., palbociclib, ribociclib, abemaciclib), (40) a MAPK inhibitor (e.g., VX-745, VX-702, RO-4402257, SCIO-469, BIRB-796, SD-0006, PH-797804, AMG-548, LY2228820, SB-681323, GW-856553, RWJ67657, BCT-197), or (41) a SHP pathway inhibitor, such as a SHP2 inhibitor (e.g., RMC-4630, ERAS-601,

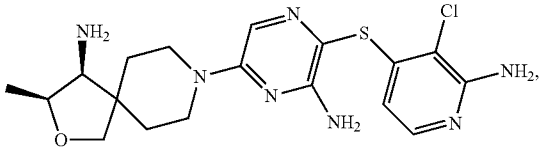

TNO155

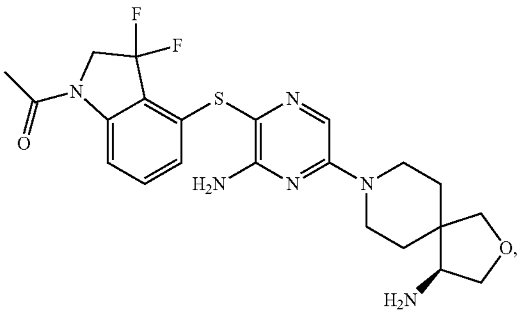

JAB-3068

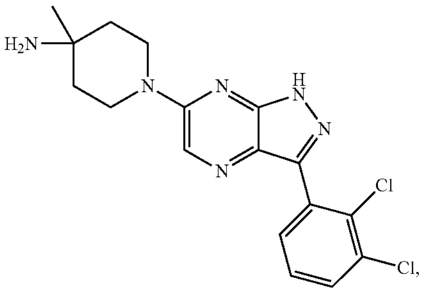

IACS-13909/BBP-398

-continued

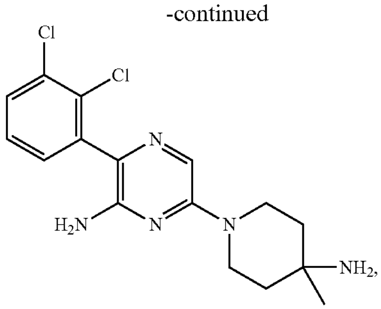

and

SHP099

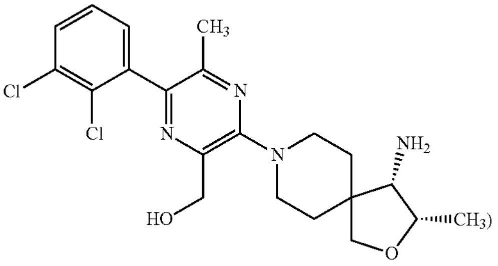

RMC-4550 or a SHP1 inhibitor. In some embodiments, a Ras inhibitor described herein, such as a compound, salt, or solvate of Formula (I) or (II), is administered in combination or in conjunction with one or more checkpoint immune blockade agents (e.g., anti-PD-1 and/or anti-PD-L1 antibody, anti-CLTA-4 antibody). In some embodiments, a Ras inhibitor described herein, such as a compound, salt, or solvate of Formula (I) or (II), is administered in combination or in conjunction with one or more pharmacologically active agents comprising an inhibitor against one or more targets selected from: MEK, epidermal growth factor receptor (EGFR), FGFR1, FGFR2, FGFR3, mitotic kinase, topoisomerase, ALK, ALK5, c-MET, ErbB2, AXL, NTRK1, RET, A-Raf, B-Raf, C-Raf, ERK, MDM2, mTOR, BET, IGF1/2, IGF1-R, CDK9, SHIP1, SHIP2, SHP2, SRC, JAK, PARP, BTK, FLT3, HDAC, VEGFR, PDGFR, LCK, Bcr-Abl, AKT, KRAS G12C mutant, and ROS1. In some embodiments, a Ras inhibitor described herein, such as a compound, salt, or solvate of Formula (I) or (II), is administered in combination or in conjunction with one or more additional pharmacologically active agents comprising an inhibitor of SOS (e.g., SOS1, SOS2) or of mutants thereof, such as

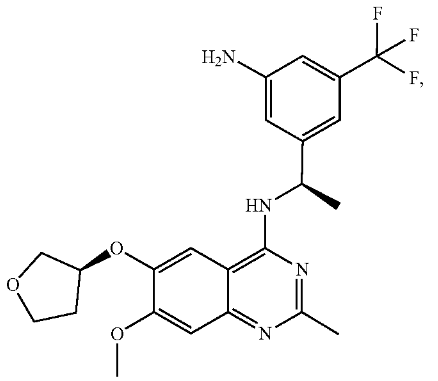

BI-3406

-continued

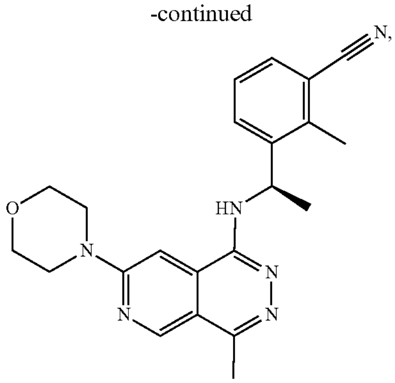

MRTX0902

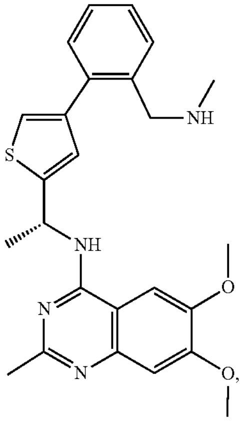

BAY 293

RMC-5845, or BI-1701963. In some embodiments, a Ras inhibitor described herein, such as a compound, salt, or solvate of Formula (I) or (II), is administered in combination or in conjunction with an inhibitor of SOS described in WO2021092115, WO2018172250, WO2019201848, WO2019122129, WO2018115380, WO2021127429, WO2020180768, or WO2020180770, each of which is herein incorporated by reference in its entirety for all purposes.

In some embodiments, a Ras inhibitor described herein, such as a compound, salt, or solvate of Formula (I) or (II), is administered in combination or in conjunction with one or more checkpoint immune blockade agents (e.g., anti-PD-1 and/or anti-PD-L1 antibody, anti-CLTA-4 antibody).

In some embodiments, a compound described herein, such as a compound, salt, or solvate of Formula (I) or (II), and one or more pharmacologically active agents are administered either simultaneously, concurrently or sequentially with no specific time limits, wherein such administration provides therapeutically effective levels of the two or more compounds in the body of the patient.

In some embodiments, a compound described herein, such as a compound, salt, or solvate of Formula (I) or (II), and one or more pharmacologically active agents are administered sequentially in any order by a suitable route, such as infusion or orally. The dosing regimen may vary depending upon the stage of the disease, physical fitness of the patient, safety profiles of the individual drugs, and tolerance of the individual drugs, as well as other criteria known to the attending physician and medical practitioner(s) administering the combination. The compound of the present disclosure and other pharmacologically active agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In some cases, a treatment regime may be dosed according to a body weight of a subject. In subjects who are determined obese (BMI>35) a practical weight may need to be utilized. BMI is calculated by: BMI=weight (kg)/[height $(m)]^2$. Body weight may be calculated for men as 50 kg+2.3*(number of inches over 60 inches) or for women 45.5 kg+2.3*(number of inches over 60 inches). An adjusted body weight may be calculated for subjects who are more than 20% of their ideal body weight. An adjusted body weight may be the sum of an ideal body weight+(0.4*(Actual body weight−ideal body weight)). In some cases, a body surface area may be utilized to calculate a dosage. A body surface area (BSA) may be calculated by: BSA $(m^2)=\sqrt{}$Height (cm)*Weight (kg)/3600.

In certain aspects, the present disclosure provides a method of modulating activity of a Ras (e.g., K-Ras) protein, comprising contacting a Ras protein with an effective amount of a compound described herein, or a pharmaceutically acceptable salt or solvate thereof, thereby modulating the activity of the Ras (e.g., K-Ras) protein. In some embodiments, the subject method comprises administering an additional agent or therapy.

In certain aspects, the present disclosure provides a method of modulating activity of a Ras protein, comprising contacting a Ras protein with an effective amount of a compound described, or a pharmaceutically acceptable salt or solvate thereof, wherein said modulating comprises inhibiting the Ras (e.g., K-Ras) protein activity. In certain aspects, the present disclosure provides a method of modulating activity of a Ras protein, such as Ras mutant (e.g., G12S, G12C, G12D, G12V, G13C, and/or G13D) proteins of K-Ras, H-Ras, and N-Ras, comprising contacting the Ras protein with an effective amount of a compound described herein, or a pharmaceutically acceptable salt or solvate thereof.

In certain aspects, the present disclosure provides a method of reducing Ras signaling output in a cell by contacting the cell with a compound described herein. A reduction in Ras signaling can be evidenced by one or more of the following: (i) an increase in steady state level of GDP-bound modified protein; (ii) a reduction in steady state level of GTP-bound Ras protein; (iii) a reduction of phosphorylated AKTs473, (iv) a reduction of phosphorylated ERKT202/y204, (v) a reduction of phosphorylated S6S235/236, (vi) a reduction of cell growth of a tumor cell expressing a Ras mutant (e.g., G12S, G12C, G12D, G12V, G13C, and/or G13D) protein, and (vii) a reduction in Ras interaction with a Ras-pathway signaling protein. Non-limiting examples of Ras-pathway signaling proteins include SOS (including SOS1 and SOS2), RAF, SHC, SHP (including SHP1 and SHP2), MEK, MAPK, ERK, GRB, RASA1, and GNAQ. In some embodiments, the reduction in Ras signaling output can be evidenced by two, three, four, five, six, or all of (i)-(vii) above. In some embodiments, the reduction of any one or more of (i)-(vii) can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to a control not treated with a subject compound. A reduction in cell growth can be demonstrated with the use of tumor cells or cell lines. A tumor cell line can be derived from a tumor in one or more tissues, e.g., pancreas, lung, ovary, biliary tract, intestine (e.g., small intestine, large intestine, colon), endometrium, stomach, hematopoietic tissue (e.g., lymphoid tissue), etc. Examples of tumor cell lines comprising a K-Ras mutation include, but are not limited to, A549 (e.g., K-Ras G12S), AGS (e.g., K-Ras G12D), ASPC1 (e.g., K-Ras G12D), Calu-6 (e.g., K-Ras Q61K), CFPAC-1 (e.g., K-Ras G12V), CL40 (e.g., K-Ras G12D), COL0678 (e.g., K-Ras G12D), COR-L23 (e.g., K-Ras G12V), DAN-G (e.g., K-Ras G12V), GP2D (e.g., K-Ras G12D), GSU (e.g., K-Ras G12F), HCT116 (e.g., K-Ras G13D), HEC1A (e.g., K-Ras G12D), HEC1B (e.g., K-Ras G12F), HEC50B (e.g., K-Ras G12F), HEYA8 (e.g., K-Ras G12D or G13D), HPAC (e.g., K-Ras G12D), HPAFII (e.g., K-Ras G12D), HUCCT1 (e.g., K-Ras G12D), KARPAS620 (e.g., K-Ras G13D), KOPN8 (e.g., K-Ras G13D), KP-3 (e.g., K-Ras G12V), KP-4 (e.g., K-Ras G12D), L3.3 (e.g., K-Ras G12D), LoVo (e.g., K-Ras G13D), LS180 (e.g., K-Ras G12D), LS513 (e.g., K-Ras G12D), MCAS (e.g., K-Ras G12D), NB4 (e.g., K-Ras A18D), NCI-H1355 (e.g., K-Ras G13C), NCI-H1573 (e.g., K-Ras G12A), NCI-H1944 (e.g., K-Ras G13D), NCI-H2009 (e.g., K-Ras G12A), NCI-H441 (e.g., K-Ras G12V), NCI-H747 (e.g., K-Ras G13D), NOMO-1 (e.g., K-Ras G12D), OV7 (e.g., K-Ras G12D), PANC0203 (e.g., K-Ras G12D), PANC0403 (e.g., K-Ras G12D), PANC0504 (e.g., K-Ras G12D), PANC0813 (e.g., K-Ras G12D), PANC1 (e.g., K-Ras G12D), Panc-10.05 (e.g., K-Ras G12D), PaTu-8902 (e.g., K-Ras G12V), PK1 (e.g., K-Ras G12D), PK45H (e.g., K-Ras G12D), PK59 (e.g., K-Ras G12D), SK-CO-1 (e.g., K-Ras G12V), SKLU1 (e.g., K-Ras G12D), SKM-1 (e.g., K-Ras K117N), SNU1 (e.g., K-Ras G12D), SNU1033 (e.g., K-Ras G12D), SNU1197 (e.g., K-Ras G12D), SNU407 (e.g., K-Ras G12D), SNU410 (e.g., K-Ras G12D), SNU601 (e.g., K-Ras G12D), SNU61 (e.g., K-Ras G12D), SNU8 (e.g., K-Ras G12D), SNU869 (e.g., K-Ras G12D), SNU-C2A (e.g., K-Ras G12D), SU.86.86 (e.g., K-Ras G12D), SUIT2 (e.g., K-Ras G12D), SW1990 (e.g., K-Ras G12D), SW403 (e.g., K-Ras G12V), SW480 (e.g., K-Ras G12V), SW620 (e.g., K-Ras G12V), SW948 (e.g., K-Ras Q61L), T3M10 (e.g., K-Ras G12D), TCC-PAN2 (e.g., K-Ras G12R), TGBC11TKB (e.g., K-Ras G12D), and MIA Pa-Ca (e.g., MIA Pa-Ca 2 (e.g., K-Ras G12C)).

In an aspect is provided a modified Ras mutant protein comprising a compound described herein (or a remnant of a compound described herein wherein the remnant of said compound is modified from a stand-alone compound described herein upon covalently bonding to an amino acid) covalently bonded to the amino acid corresponding to position 12 or 13 of SEQ ID No: 1. In some embodiments, such covalently bonded modified Ras mutant protein exhibits a reduced Ras signaling output (e.g., compared to a corresponding unmodified Ras mutant absent of the covalently bonded compound). In some embodiments, the modified Ras mutant protein comprises a compound described herein covalently bonded to the amino acid residue corresponding to position 12 or 13 of SEQ ID No: 1. In some embodiments, the modified Ras mutant protein comprises a compound described herein covalently bonded to the amino acid residue corresponding to position 12 or 13 of SEQ ID No: 1, wherein the Ras mutant protein is a human protein selected from KRAS G12S, KRAS G12C, KRAS G12D, KRAS G12V, KRAS G13C, and KRAS G13D. In some embodiments, the modified Ras mutant protein comprises a compound described herein covalently bonded to the amino acid residue corresponding to position 12 or 13 of SEQ ID No: 1, wherein the Ras mutant protein is a human KRAS mutant protein (e.g., G12S, G12C, G12D, G12V, G13C, and/or G13D). In some embodiments, the modified Ras mutant protein comprises a compound described herein covalently bonded to the amino acid residue corresponding to position 12 or 13 of SEQ ID No: 1, wherein the Ras mutant protein is a human KRAS G12S protein. In some embodiments, the modified Ras mutant protein comprises a compound described herein covalently bonded to the amino acid residue corresponding to position 12 or 13 of SEQ ID No: 1, wherein the Ras mutant protein is a human KRAS G12C protein. In some embodiments, the modified Ras mutant protein comprises a compound described herein covalently bonded to a protein of SEQ ID No. 4. In some embodiments, the modified Ras mutant protein comprises a compound described herein covalently bonded to a protein of SEQ ID No. 9. In some embodiments, the modified Ras mutant protein comprises a compound described herein covalently bonded to the serine residue at position 12 of SEQ ID No. 4. In some embodiments, the modified Ras mutant protein comprises a compound described herein covalently bonded to the cysteine residue at position 12 of SEQ ID No. 9. In some embodiments, the modified Ras mutant protein comprises a compound described herein covalently bonded to the amino acid residue corresponding to position 12 or 13 of SEQ ID No: 5, wherein the Ras mutant protein is a mammalian Ras protein (including human protein) selected from NRAS G12C, NRAS G12S, NRAS G13C, and NRAS G13S. In some embodiments, the modified Ras mutant protein comprises a compound described herein covalently bonded to the amino acid residue corresponding to position 12 or 13 of SEQ ID No: 7, wherein the Ras mutant protein is a mammalian protein (including human protein) selected from HRAS G12C, HRAS G12S, HRAS G13C, and HRAS G13S. It will be understood that a compound described herein may be modified upon covalently binding an amino acid (e.g., mutant amino acid other than G) corresponding to position 12 or 13 of human KRAS (e.g., SEQ ID. No: 1). A subject compound of the present disclosure encompasses a compound described herein immediately prior to covalently bonding the Ras mutant protein as well as the resulting compound covalently bonded to the modified Ras mutant protein.

In some embodiments, the modified Ras mutant protein described herein is formed by contacting a compound described herein with the serine residue of an unmodified Ras G12S mutant protein, wherein the compound comprises a moiety susceptible to reacting with a nucleophilic serine residue corresponding to position 12 of SEQ ID No: 4. In some embodiments, the compound comprises a staying group and a leaving group, wherein said contacting results in release of the leaving group and formation of said modified protein. In some embodiments, the compound selectively labels the serine residue corresponding to position 12 of SEQ ID No. 4 (a G12S mutant) relative to a valine (G12V) residue or glycine residue (wildtype KRAS) at the same position. In some embodiments, the compound selectively labels the serine residue as compared to (i) an aspartate residue of a K-Ras G12D mutant protein, said aspartate corresponding to residue 12 of SEQ ID NO: 2, and/or (ii) a valine residue of a K-Ras G12V mutant protein, said valine corresponding to residue 12 of SEQ ID NO: 3, by at least 1, 2, 3, 4, 5, or 10 fold or more, when assayed under comparable conditions.

In some embodiments, the modified Ras mutant protein described herein is formed by contacting a compound described herein with the cysteine residue of an unmodified Ras G12C mutant protein, wherein the compound comprises a moiety susceptible to reacting with a nucleophilic cysteine residue corresponding to position 12 of SEQ ID No: 9. In some embodiments, the compound comprises a staying group and a leaving group, wherein said contacting results in release of the leaving group and formation of said modified protein. In some embodiments, the compound selectively labels the cysteine residue corresponding to position 12 of SEQ ID No. 9 (a G12C mutant) relative to a valine (G12V) residue or glycine residue (wildtype KRAS) at the same position. In some embodiments, the compound selectively labels the cysteine residue as compared to (i) an aspartate residue of a K-Ras G12D mutant protein, said aspartate corresponding to residue 12 of SEQ ID NO: 2, and/or (ii) a valine residue of a K-Ras G12V mutant protein, said valine corresponding to residue 12 of SEQ ID NO: 3, by at least 1, 2, 3, 4, 5, or 10 fold or more, when assayed under comparable conditions.

In embodiments of the modified Ras mutant protein described herein, the compound covalently binds to the serine residue of an unmodified Ras G12S protein corresponding to position 12 of SEQ ID No: 4 in vitro. In embodiments of the modified Ras mutant protein described herein, the compound covalently binds to the serine residue of an unmodified K-Ras G12S protein corresponding to position 12 of SEQ ID No: 4 in vivo. In embodiments of the modified Ras mutant protein described herein, the compound covalently binds to the cysteine residue of an unmodified Ras G12C protein corresponding to position 12 of SEQ ID No: 9 in vitro. In embodiments of the modified Ras mutant protein described herein, the compound covalently binds to the cysteine residue of an unmodified K-Ras G12C protein corresponding to position 12 of SEQ ID No: 9 in vivo. In embodiments of the modified Ras mutant protein described herein, the compound covalently binds to both the serine residue and the cysteine residue of an unmodified K-Ras G12S and K-Ras G12C protein, respectively, at position 12 of the respective protein in vitro or in vivo.

In an aspect is provided a method of treating cancer in a subject comprising a Ras mutant protein (e.g., KRAS G12D, KRAS G12C, KRAS G12S, KRAS G12V, KRAS G13D, KRAS G13C, NRAS G12D, NRAS G12C, NRAS G12S, NRAS G13D, NRAS G13C, HRAS G12D, HRAS G12C, HRAS G12S, HRAS G13D, or HRAS G13C), the method comprising modifying the Ras mutant protein of said subject by administering to said subject a compound described herein, wherein the compound is characterized in that upon contacting a Ras mutant protein, said Ras mutant protein is modified covalently at a residue corresponding to residue 12 or 13 of SEQ ID No: 1, such that said modified Ras mutant protein exhibits reduced Ras signaling output (e.g., compared to a control, such as an unmodified Ras mutant protein not covalently bonded with any compound such as a compound disclosed herein).

In some aspects, a subject compound exhibits one or more of the following characteristics: it is capable of reacting with a mutant residue (e.g., KRAS G12D, KRAS G12C, KRAS G12S, KRAS G12V, KRAS G13D, KRAS G13C, NRAS G12D, NRAS G12C, NRAS G12S, NRAS G13D, NRAS G13C, HRAS G12D, HRAS G12C, HRAS G12S, HRAS G13D, or HRAS G13C) of a Ras mutant protein and covalently modifying such Ras mutant and/or it comprises a moiety susceptible to reacting with a nucleophilic amino acid residue corresponding to position 12 or 13 of SEQ ID No: 1. In some embodiments, a subject compound, when used to modify a Ras mutant protein, reduces the signaling output of the Ras protein. In some embodiments, a subject compound exhibits an IC50 against a mutant Ras as ascertained by reduction of Ras::SOS1 interaction of less than 10 μM, such as less than 5 μM, 1 μM, 500 nM, 100 nM, 50 nM, 10 nM, 5 nM, 1 nM, 500 μM, 50 μM, 10 μM or less.

In some embodiments, a modified Ras mutant protein disclosed herein exhibits a reduced Ras signaling output. A reduction of signaling output can be ascertained by a wide variety of methods known in the art. For example, phosphorylation of a substrate or a specific amino acid residue thereof can be detected and/or quantified using one or more techniques, such as kinase activity assays, phospho-specific antibodies, Western blot, enzyme-linked immunosorbent assays (ELISA), cell-based ELISA, intracellular flow cytometry, mass spectrometry, and multi-analyte profiling. A host of readout can evidence a reduction of Ras signaling output, including without limitation: (i) an increase in steady state level of GDP-bound modified protein; (ii) a reduction in steady state level of GTP-bound Ras protein; (iii) a reduction of phosphorylated AKTs473, (iv) a reduction of phosphorylated ERK T202/Y204, (v) a reduction of phosphorylated S6 S235/236, (vi) a reduction of cell growth of a tumor cell expressing a Ras mutant protein (e.g., KRAS G12D, KRAS G12C, KRAS G12S, KRAS G12V, KRAS G13D, KRAS G13C, NRAS G12D, NRAS G12C, NRAS G12S, NRAS G13D, NRAS G13C, HRAS G12D, HRAS G12C, HRAS G12S, HRAS G13D, or HRAS G13C), and (vii) a reduction in Ras interaction with a Ras-pathway signaling protein. In some embodiments, a reduction is evidenced by 2, 3, 4 or more of items (i)-(vii). In some embodiments, the reduction in Ras signaling output can be evidenced by any one of (i)-(vii) as compared to control unmodified corresponding Ras protein that is not covalently bonded to any compound disclosed herein. For example, a control Ras protein, as described herein, can be a Ras protein (e.g., wildtype or mutated) that is not complexed with any subject compound of the present disclosure. The increase in item (i) or reduction in items (ii) through (vi) can be at least about 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to the control Ras protein. In some embodiments, a reduction in Ras interaction with a Ras-pathway signaling protein is established by a reduced interaction with SOS (including SOS1 and SOS2), RAF, SHC, SHP (including SHP1 and SHP2), MEK, MAPK, ERK, GRB, RASA1, or GNAQ.

Signaling output measured in terms of IC50 values can be obtained and a ratio of IC50 against one mutant relative to another mutant can be calculated. For instance, a selective reduction of K-Ras G12S or K-Ras G12C signaling output can be evidenced by a ratio greater than one. In particular, a selective reduction of K-Ras G12S or K-Ras G12C signaling relative to K-Ras G12D signaling or wildtype K-Ras signaling is evidenced if the ratio of IC50 (against K-Ras G12D or wildtype) to IC50 (against K-Ras G12S or K-Ras G12C) is greater than 1.

It will be understood that when a compound described herein selectively labels the serine and/or cysteine residue of a K-Ras G12S or K-Ras G12C protein compared to another K-Ras protein(s) (e.g., WT, G12D, or G12V), the compound labels the K-Ras G12S or K-Ras G12C protein with greater speed or to a greater degree or by any other quantifiable measurement compared to the other K-Ras protein (e.g., WT, G12D, G12V), under similar or identical reaction conditions for the proteins being compared. In some embodiments, the greater labeling of K-Ras G12S and/or K-Ras G12C can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to another K-Ras protein (e.g., WT, G12D, or G12V).

In some embodiments, the compounds described herein, or a pharmaceutically acceptable salt or solvate thereof, are Ras modulators (including Ras inhibitors) capable of covalently modifying a Ras protein. Ras proteins being modified can be Ras G12S mutants or G12C mutants from K-Ras, H-Ras or N-Ras. The compounds disclosed herein, or pharmaceutically acceptable salts or solvates thereof, have a wide range of applications in therapeutics, diagnostics, and other biomedical research.

In an aspect is provided a method of treating cancer in a subject comprising a Ras G12S mutant protein, comprising modifying the Ras G12S mutant protein of said subject by administering to said subject a compound described herein, wherein said compound is characterized in that upon contacting the Ras G12S mutant protein, the Ras G12S mutant protein is modified covalently at a serine residue corresponding to residue 12 of SEQ ID No: 4, such that said modified K-Ras G12S protein exhibits reduced Ras signaling output (e.g., compared to a corresponding unmodified Ras protein unbound to the covalent compound).

In an aspect is provided a method of treating cancer in a subject comprising a Ras G12C mutant protein, comprising modifying the Ras G12C mutant protein of said subject by administering to said subject a compound described herein, wherein said compound is characterized in that upon contacting the Ras G12C mutant protein, the Ras G12C mutant protein is modified covalently at a cysteine residue corresponding to residue 12 of SEQ ID No: 9, such that said modified K-Ras G12C protein exhibits reduced Ras signaling output (e.g., compared to a corresponding unmodified Ras protein unbound to the covalent compound).

In an aspect is provided a method of modulating activity of a Ras protein (e.g., K-Ras, mutant K-Ras, K-Ras G12S, K-Ras G12C), comprising contacting a Ras protein with an effective amount of a compound described herein, or a pharmaceutically acceptable salt or solvate thereof, thereby modulating the activity of the Ras protein.

In practicing any of the methods disclosed herein, the Ras target to which a subject compound binds covalently can be a Ras mutant (e.g., KRAS G12D, KRAS G12C, KRAS G12S, KRAS G12V, KRAS G13D, KRAS G13C, NRAS G12D, NRAS G12C, NRAS G12S, NRAS G13D, NRAS G13C, HRAS G12D, HRAS G12C, HRAS G12S, HRAS G13D, or HRAS G13C).

Pharmaceutical Compositions and Methods of Administration

In an aspect is provided a pharmaceutical composition comprising a compound described herein, or a pharmaceutically acceptable salt or solvate thereof, and a pharmaceutically acceptable excipient.

In some embodiments, a compound described herein, or a pharmaceutically acceptable salt or solvate thereof, is administered to a subject in a biologically compatible form suitable for administration to treat or prevent diseases, disorders, or conditions. Administration of a compound described herein can be in any pharmacological form including a therapeutically effective amount of a compound described herein, or a pharmaceutically acceptable salt or solvate thereof, alone or in combination with a pharmaceutically acceptable carrier.

In some embodiments, a compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, $21^{st}$ Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable excipients. The excipient(s) (or carrier(s)) is acceptable or suitable if the excipient is compatible with the other ingredients of the composition and not deleterious to the recipient (i.e., the subject) of the composition.

In some embodiments of the methods described herein, a compound described herein is administered either alone or in combination with pharmaceutically acceptable carriers, excipients or diluents, in a pharmaceutical composition. Administration of a compound or composition described herein can be affected by any method that enables delivery of the compound to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, a compound described herein can be administered locally to the area in need of treatment, by, for example, local infusion during surgery, topical application such as creams or ointments, injection, catheter, or implant. The administration can also be by direct injection at the site of a diseased tissue or organ. In some embodiments, a compound described herein, or a pharmaceutically acceptable salt or solvate thereof, is administered orally.

In some embodiments of the methods described herein, a pharmaceutical composition suitable for oral administration is presented as a discrete unit such as a capsule, cachet or tablet, each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary, or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments of the methods described herein, pharmaceutical compositions are formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compound which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

EXAMPLES

The following examples are provided for illustrative purposes only and not to limit the scope of the claims provided herein. Unless noted otherwise, all materials, such as reagents, starting materials and solvents, were purchased from commercial suppliers, such as Sigma-Aldrich, VWR, and the like, and were used without further purification. Reactions were run under nitrogen atmosphere, unless noted otherwise. The progress of reactions was monitored by thin layer chromatography (TLC), analytical high performance liquid chromatography (anal. HPLC), and mass spectrometry, the details of which may be provided in specific examples.

Reactions were worked up as described specifically in each preparation; commonly, reaction mixtures were purified by extraction and other purification methods such as temperature- and solvent-dependent crystallization, and precipitation. In addition, reaction mixtures were routinely purified by preparative HPLC, for example, using Microsorb C18 or Microsorb BDS column packings and conventional eluents. Progress of reactions was typically monitored by liquid chromatography mass spectrometry (LCMS). Characterization of isomers was typically done by Nuclear Overhauser effect spectroscopy (NOE). Characterization of reaction products was routinely carried out by mass spectrometry and/or $^1$H-NMR spectroscopy. For NMR measurement, samples were dissolved in deuterated solvent ($CD_3OD$, $CDCl_3$, or DMSO-d).

Example 1a: Synthesis of (R)-2-amino-4-(6-chloro-8-fluoro-2-(((2R,7aS)-2-fluorotetrahydro-1H-pyrrolizin-7a(5H)-yl)methoxy)-4-((R)-1-(4-methyl-1H-imidazole-1-carbonyl)-1,6-diazaspiro[3.4]octan-6-yl)quinazolin-7-yl)-7-fluorobenzo[b]thiophene-3-carbonitrile (107)

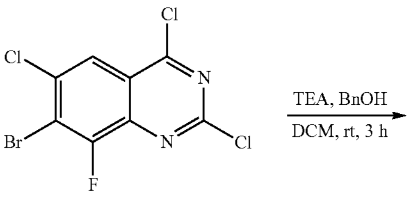

1-1

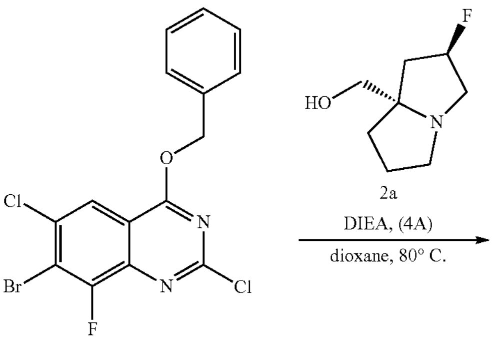

1-2

-continued

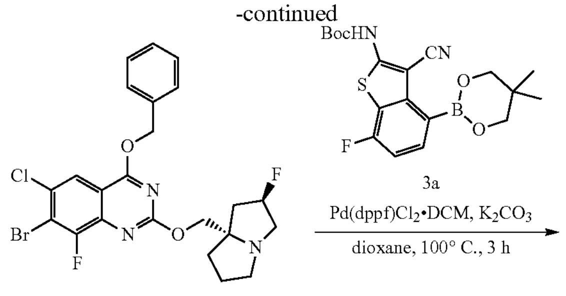

1-3

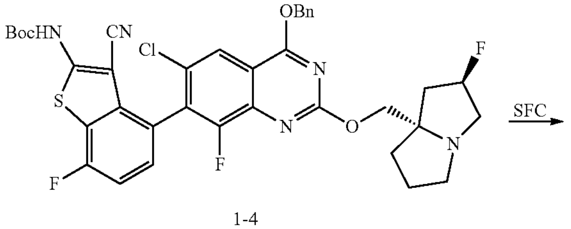

1-4

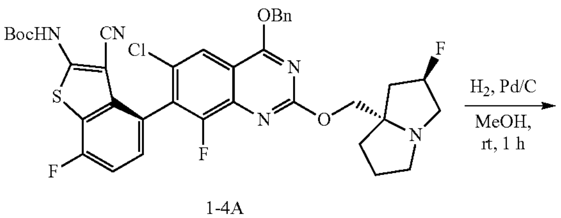

1-4A

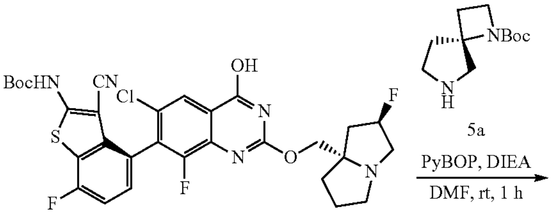

1-5

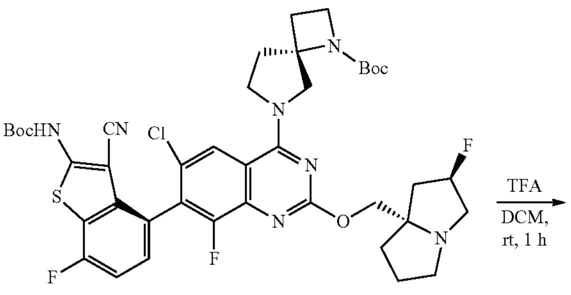

1-6

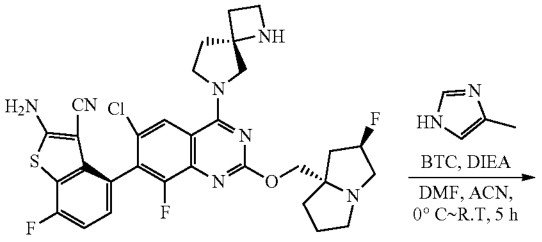

1-7

-continued

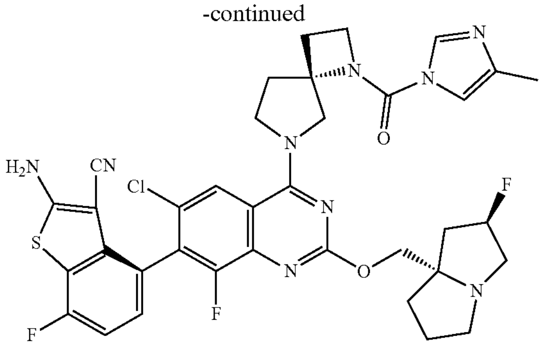

107

Step 1: To a solution of 7-bromo-2,4,6-trichloro-8-fluoroquinazoline (1-1, 5 g, 15.1 mmol) and TEA (4.59 g, 45.40 mmol) in DCM (50 mL) was added benzyl alcohol (1.96 g, 18.2 mmol). The mixture was stirred at room temperature for 3 h, then poured into water (100 mL) and extracted with DCM (100 mL×3). The organic layer was washed with brine (50 mL), dried over anhydrous sodium sulfate, filtered and the filtrate was concentrated to dryness under reduced pressure, then the residue was purified by silica gel column chromatography (petroleum ether/ethyl acetate=10:1) to give 4-(benzyloxy)-7-bromo-2,6-dichloro-8-fluoro quinazoline (1-2, 4 g) as a yellow solid. MS m/z (ESI): 401.0 $[M+H]^+$.

Step 2: A mixture of 1-2 (5 g, 12.44 mmol), ((2R,7aS)-2-fluorotetrahydro-1H-pyrrolizin-7a(5H)-yl)methanol (2a, 5.94 g, 37.31 mmol), 4 Å molecular sieves (500 mg) and DIEA (4.82 g, 37.31 mmol) in dioxane (30 mL) was stirred at 80° C. for 16 h. After cooling to room temperature, solid was removed by filtration and the filtrate was diluted with ethyl acetate (100 mL), washed with brine (50 ml×3), dried over anhydrous sodium sulfate, filtered and the filtrate was concentrated to dryness under reduced pressure. The residue was purified by silica gel column chromatography (petroleum ether/ethyl acetate=1:1) to give 4-(benzyloxy)-7-bromo-6-chloro-8-fluoro-2-(((2R,7aS)-2-fluorotetrahydro-1H-pyrrolizin-7a(5H)-yl)methoxy)quinazoline (1-3, 2.3 g) as a white solid. MS m/z (ESI): 523.8 $[M+H]^+$.

Step 3: To a solution of 1-3 (2 g, 3.82 mmol), tert-butyl (3-cyano-4-(5,5-dimethyl-1,3,2-dioxaborinan-2-yl)-7-fluoro benzo[b]thiophen-2-yl)carbamate (3a, 2.32 g, 5.73 mmol) and $K_2CO_3$ (3.16 g, 22.94 mmol) in dioxane (30 mL) was added Pd(dppf)$Cl_2$ (624 mg, 0.76 mmol). The mixture was stirred at 100° C. for 3 h. After cooling to room temperature, the mixture was poured into water (100 mL) and extracted with ethyl acetate (100 mL×3). The organic layer was washed with brine (100 mL), dried over anhydrous sodium sulfate, filtered and the filtrate was concentrated to dryness under reduced pressure. The residue was purified by silica gel column chromatography (MeOH:DCM=15:1) to give tert-butyl (4-(4-(benzyloxy)-6-chloro-8-fluoro-2-(((2R,7aS)-2-fluorotetrahydro-1H-pyrrolizin-7a(5H)-yl)methoxy)quinazolin-7-yl)-3-cyano-7-fluorobenzo[b]thiophen-2-yl)carbamate (1-4, 1.4 g) as a yellow solid. MS m/z (ESI): 736.3 $[M+H]^+$.

The atropoisomeric mixture 1-4 (4 g, 5.44 mmol) was purified by SFC to obtain enantiopure tert-butyl((R)-4-(4-(benzyloxy)-6-chloro-8-fluoro-2-(((2R,7aS)-2-fluorotetrahydro-1H-pyrrolizin-7a(5H)-yl)methoxy)quinazolin-7-yl)-3-cyano-7-fluorobenzo[b]thiophen-2-yl)carbamate (1-4A, 1.8 g) as a yellow solid.

Step 4: To a solution of 1-4A (1.8 g, 2.44 mmol) in MeOH (50 mL) was added 10% Pd/C (180 mg). The mixture was stirred at 25° C. for 0.5 h under $H_2$, then filtered and the filtrate concentrated to dryness under reduced pressure to give tert-butyl ((R)-4-(6-chloro-8-fluoro-2-(((2R,7aS)-2-fluorotetrahydro-1H-pyrrolizin-7a(5H)-yl)methoxy)-4-hydroxyquinazolin-7-yl)-3-cyano-7-fluorobenzo[b]thiophen-2-yl)carbamate (1-5, 1.4 g) as a grey solid. MS m/z (ESI): 646.4 $[M+H]^+$.

Step 5: To a solution of 1-5 (700 mg, 1.09 mmol), tert-butyl (R)-1,6-diazaspiro[3.4]octane-1-carboxylate (5a, 299 mg, 1.41 mmol), and PyBop (847 mg, 1.63 mmol) in DMF (5 mL) was added DIEA (210 mg, 1.63 mmol). The mixture was stirred at 25° C. for 1 h, then treated with water (50 mL) and extracted with ethyl acetate (100 mL×3). The organic layer was washed with brine (100 mL), dried over anhydrous sodium sulfate, filtered and the filtrate was concentrated to dryness under reduced pressure. The residue was purified by silica gel column chromatography (DCM/MeOH=15/1) to give tert-butyl (R)-6-(7-((R)-2-((tert-butoxycarbonyl) amino)-3-cyano-7-fluorobenzo [b]thiophen-4-yl)-6-chloro-8-fluoro-2-(((2R,7aS)-2-fluorotetrahydro-1H-pyrrolizin-7a(5H)-yl)methoxy)quinazolin-4-yl)-1,6-diazaspiro[3.4]octane-1-carboxylate (1-6, 700 mg) as a yellow solid. MS m/z (ESI): 840.3 $[M+H]^+$.

Step 6: To a solution of 1-6 (1.3 g, 1.55 mmol) in DCM (5 mL) was added TFA (5 mL). The reaction mixture was stirred at 20° C. for 30 min, then concentrated under reduced pressure and treated with saturated aqueous $NaHCO_3$ solution (200 mL) and DCM/MeOH=10/1 (300 mL). The organic layer was collected and washed with brine, dried over anhydrous sodium sulfate, filtered, and the filtrated concentrated to give (R)-2-amino-4-(6-chloro-8-fluoro-2-(((2R,7aS)-2-fluorotetrahydro-1H-pyrrolizin-7a(5H)-yl)methoxy)-4-((S)-1,6-diazaspiro[3.4]octan-6-yl)quinazolin-7-yl)-7-fluorobenzo[b]thiophene-3-carbonitrile (1-7, 830 mg) as a yellow solid. MS m/z (ESI): 640.6 $[M+H]^+$.

Step 7: To a stirred solution of 4-methyl-1H-imidazole (500 mg, 6.09 mmol) in ACN (10 mL) at 0° C. were added BTC (128 mg, 0.435 mmol) and DIEA (1 mL, 10.4 mmol). The mixture was stirred at 0° C. for 1 hour, then added to a solution of 1-7 (60 mg, 0.087 mmol) and DIEA (67 mg, 0.522 mmol) in DMF (2 mL). The mixture was stirred at room temperature for 10 min, then diluted with EtOAc (100 mL) and washed with brine (50 mL). The organic phase was dried over anhydrous sodium sulfate, filtered and the filtrate was concentrated. The residue was purified by prep-HPLC to give (R)-2-amino-4-(6-chloro-8-fluoro-2-(((2R,7aS)-2-fluorotetrahydro-1H-pyrrolizin-7a(5H)-yl)methoxy)-4-((R)-1-(4-methyl-1H-imidazole-1-carbonyl)-1,6-diazaspiro[3.4]octan-6-yl)quinazolin-7-yl)-7-fluorobenzo[b]thiophene-3-carbonitrile (107, 50.03 mg) as an off-white solid. MS m/z (ESI): 748.4 $[M+H]^+$. $^1H$ NMR (400 MHz, DMSO-$d_6$) δ 8.23-7.92 (m, 4H), 7.35-7.00 (m, 3H), 5.27 (d, J=53.6 Hz, 1H), 4.73-4.53 (m, 1H), 4.48-4.30 (m, 2H), 4.23-3.94 (m, 5H), 3.14-2.95 (m, 3H), 2.89-2.77 (m, 2H), 2.63-2.54 (m, 1H), 2.44-2.68 (m, 3H), 2.11 (s, 3H), 2.08-1.97 (m, 2H), 1.88-1.66 (m, 3H).

Example 1b: Synthesis of 1-((1R,4R)-6-(7-((R)-2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-1-ethyl-2,6-diazaspiro[3.6]decane-2-carbonyl)-2-methyl-1H-imidazole-4-carbonitrile (117)

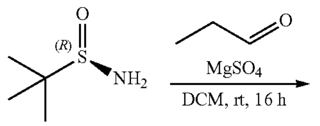

2-1

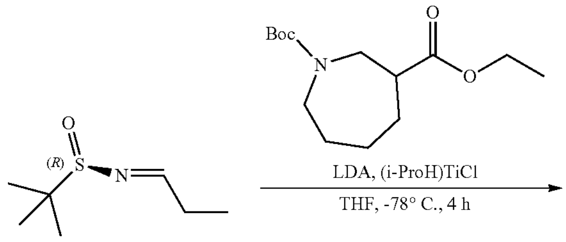

2-2

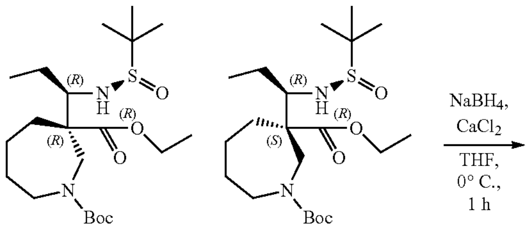

2-3-P1 2-3-P2

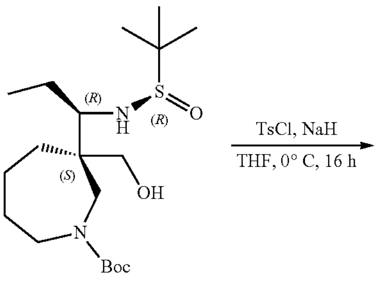

2-4

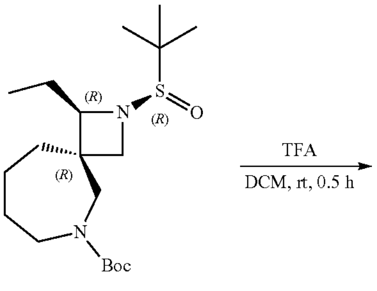

2-5

-continued

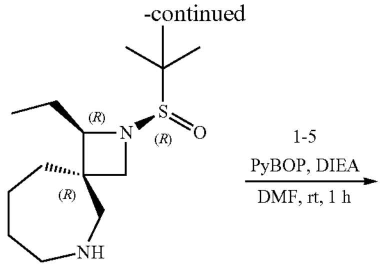

2-6

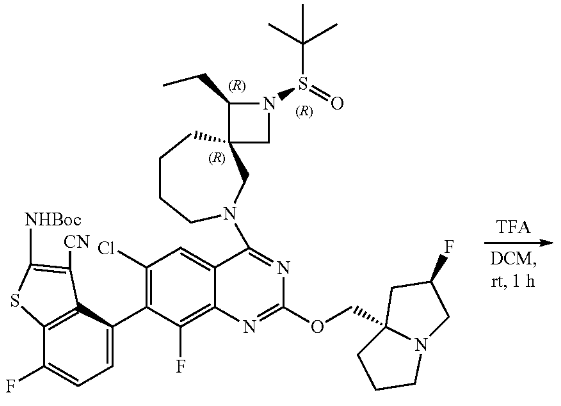

2-7

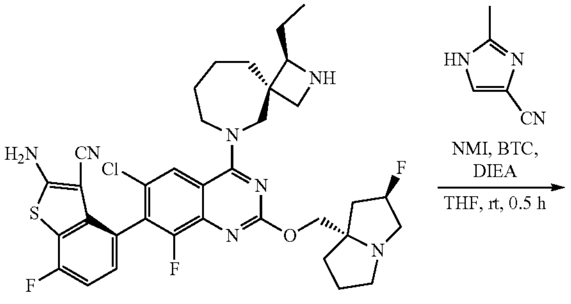

2-8

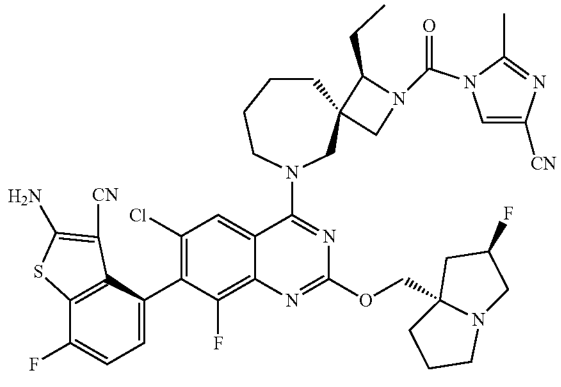

117

Step 1: A solution of (R)-2-methylpropane-2-sulfinamide (2-1, 10 g, 82.508 mmol), propionaldehyde (23.960 g, 412.534 mmol) and $MgSO_4$ (49.480 g, 412.540 mmol) in DCM (300 mL) was stirred at 25° C. for 16 hrs. The mixture was filtered and concentrated to dryness under reduced pressure. The residue was purified by silica gel flash column chromatography (EtOAc/petroleum ether=0~7%) to give (R,E)-2-methyl-N-propylidenepropane-2-sulfinamide (2-2, 5.3 g) as a colorless oil. MS m/z (ESI): 162.1 $[M+H]^+$.

Step 2: To a solution of diisopropylamine (3.14 g, 31.03 mmol) in THF (50 mL) was added n-BuLi (1.99 g, 31.07 mmol) at −78° C. The reaction mixture was stirred at −78° C. for 45 min, then added to a solution of 1-(tert-butyl) 3-ethyl azepane-1,3-dicarboxylate (3.367 g, 13.09 mmol) in THF (5 mL) at −78° C. The reaction mixture was stirred at −78° C. for 1 h, then added to a solution of (i-ProH)TiCl (9.706 g, 37.248 mmol, 1M) at −78° C. The reaction mixture was stirred at −78° C. for 1 h, then added to a solution of 2-2 (2.0 g, 12.43 mmol) in THF (5 mL) at −78° C. The reaction mixture was stirred at −78° C. for 1 h, then diluted with saturated $NH_4Cl$ aqueous solution (50 mL) and EtOAc (50 mL) and filtered with diatomite. The organic layer was collected and washed with brine, dried over anhydrous sodium sulfate, filtered, and the filtrated was concentrated to dryness under reduced pressure. The residue was purified by silica gel flash column chromatography (EtOAc/petroleum ether=0~14%, 25%) to give 1-(tert-butyl) 3-ethyl (R)-3-((R)-1-(((R)-tert-butylsulfinyl)amino)propyl)azepane-1,3-dicarboxylate (2-3-P1, 500 mg) and 1-(tert-butyl) 3-ethyl (S)-3-((R)-1-(((R)-tert-butylsulfinyl) amino)propyl) azepane-1,3-dicarboxylate (2-3-P2, 800 mg), each as a colorless oil. MS m/z (ESI): 433.3 $[M+H]^+$.

Step 3: To a solution of 2-3-P2 (900 mg, 2.08 mmol) in EtOH (10 mL) were added $CaCl_2$ (462.13 mg, 4.16 mmol) and $NaBH_4$ (315.05 mg, 8.33 mmol) at 0° C. The mixture was stirred at 25° C. for 16 h, then quenched with an aqueous solution of citric acid (10 mL) and water (20 mL). The mixture was extracted with EtOAc (20 mL×3) and the combined organic layer was washed with brine (30 mL), dried over anhydrous sodium sulfate, filtered and the filtrate was concentrated in vacuo. The residue was purified by silica gel flash column chromatography (EtOAc/petroleum ether=0~35%) to give tert-butyl (S)-3-((R)-1-(((R)-tert-butylsulfinyl)amino)propyl)-3-(hydroxymethyl) azepane-1-carboxylate (2-4, 566 mg) as a white solid. MS m/z (ESI): 391.1 $[M+H]^+$.

Step 4: To a solution of 2-4 (460 mg, 1.179 mmol) and TsCl (336.15 mg, 1.769 mmol) in dry THF (10 mL) was added NaH (188.72 mg, 7.863 mmol, 60%) at 0° C. and the resulting mixture was warmed to room temperature and stirred for 16 h. The mixture was diluted with saturated $NH_4Cl$ aqueous solution (25 mL), extracted with EtOAc (25 mL×3), and the combined organic layer was washed with brine (30 mL), dried over anhydrous sodium sulfate, filtered and the filtrate was concentrated in vacuo. The residue was purified by silica gel flash column chromatography (EtOAc/petroleum ether=0~35%) to give tert-butyl (1R,4R)-2-((R)-tert-butylsulfinyl)-1-ethyl-2,6-diazaspiro[3.6]decane-6-carboxylate (2-5, 420 mg) as a colorless oil. MS m/z (ESI): 373.2 $[M+H]^+$.

Step 5: To a solution of 2-5 (200 mg, 0.54 mmol) in DCM (2.5 mL) was added TFA (767.5 mg, 6.73 mmol). The mixture was stirred at 25° C. for 0.5 h, then solvent was removed under reduced pressure. The residue was treated with saturated $NaHCO_3$ aqueous solution (20 mL) and extracted with EtOAc (15 mL×3). The organic layer was washed with saturated $NaHCO_3$ aqueous solution (25 mL) and brine (25 mL), dried over anhydrous sodium sulfate, filtered and the filtrate was concentrated to dryness under reduced pressure to afford (1R,4R)-2-((R)-tert-butylsulfinyl)-1-ethyl-2,6-diazaspiro[3.6]decane (2-6, 160 mg, crude) as a yellow oil. MS m/z (ESI): 273.1 $[M+H]^+$.

Step 6: To a solution of 2-6 (200 mg, 0.775 mmol) and PyBop (605 mg, 1.163 mmol) in DMF (3 mL) was added 1-5 (500 mg, 0.775 mmol) and DIEA (401 mg, 3.101 mmol). The mixture was stirred at room temperature for 1 h, then poured into water (30 mL) and extracted with ethyl acetate (80 mL×3). The organic layer was washed with brine (30 mL), dried over anhydrous sodium sulfate, filtered and the filtrate was concentrated to dryness under reduced pressure. The residue was purified by prep-TLC ($DCM/NH_3$-MeOH=15:1) to give tert-butyl ((R)-4-(4-((1R,4R)-2-((R)-tert-butylsulfinyl)-1-ethyl-2,6-diazaspiro[3.6]decan-6-yl)-6-chloro-8-fluoro-2-(((2R,7aS)-2-fluorotetrahydro-1H-pyrrolizin-7a(5H)-yl)methoxy)quinazolin-7-yl)-3-cyano-7-fluorobenzo[b]thiophen-2-yl)carbamate (2-7, 310 mg) as a yellow solid. MS m/z (ESI): 901.9 $[M+H]^+$.

Step 7: To a solution of 2-7 (310 mg, 0.344 mmol) in dioxane was added HCl (4M in dioxane, 5 mL). The reaction mixture was stirred for 2 h., then solvent was removed in vacuo and the residue was diluted with DCM:MeOH=10:1. Saturated $NaHCO_3$ aqueous solution was added to adjust the pH to 8. The organic layer was collected, concentrated in vacuo, and the residue was purified by preparative TLC ($DCM:NH_3/MeOH$=10:1) to give (R)-2-amino-4-(6-chloro-4-((1R,4S)-1-ethyl-2,6-diazaspiro[3.6]decan-6-yl)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile (2-8, 134 mg) as a yellow solid. MS m/z (ESI): 696.3 $[M+H]^+$.

Step 8: To a solution of 2-methyl-1H-imidazole-4-carbonitrile (200 mg, 1.87 mmol) and NMI (61 mg, 0.75 mmol) in THF (10 mL) at 0° C. was added BTC (111 mg, 0.374 mmol). The mixture was stirred at 0° C. for 1.5 h, then a portion of the mixture (1.0 mL) was added to a solution of 2-8 (25 mg, 0.078 mmol) and DIEA (28 mg, 0.216 mmol) in THF (1 mL). The mixture was stirred for 0.5 h, then diluted with $H_2O$ (20 mL) and extracted with EtOAc (20 mL×3). The organic layer was dried over anhydrous sodium sulfate, filtered and the filtrate was concentrated to dryness under reduced pressure. The residue was purified by prep-HPLC (formic acid as modifier) to give 1-((1R,4R)-6-(7-((R)-2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-1-ethyl-2,6-diazaspiro[3.6]decane-2-carbonyl)-2-methyl-1H-imidazole-4-carbonitrile (117, 5.99 mg) as a white solid. MS m/z (ESI): 829.3 $[M+H]^+$. $^1H$ NMR (400 MHz, DMSO-d6) δ 8.39 (m, 1H), 8.10 (m, 2H), 8.00 (m, 1H), 7.26-7.23 (m, 1H), 7.17-7.12 (m, 1H), 5.24 (d, J=54.4 Hz, 1H), 4.38-4.30 (m, 2H), 4.08-3.95 (m, 5H), 3.72-3.7 (m, 1H), 3.07 (m, 2H), 2.99 (m, 1H), 2.85-2.79 (m, 1H), 2.46 (m, 3H), 2.09-1.76 (m, 13H), 1.67 (m, 2H), 0.94 (m, 3H).

Example 1c: Synthesis of 2-amino-4-((S)-4-(ethyl ((2R,3R)-1-(3-fluoro-1H-1,2,4-triazole-1-carbonyl)-2-methylpyrrolidin-3-yl)amino)-8-fluoro-2-(((2R, 7aS)-2-fluorotetrahydro-1H-pyrrolizin-7a(5H)-yl) methoxy)-6-(trifluoromethyl)quinazolin-7-yl)-7-fluorobenzo[b]thiophene-3-carbonitrile (125)

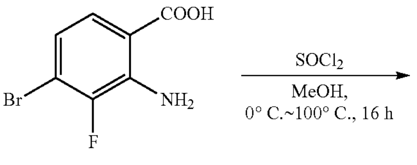

3-1

-continued
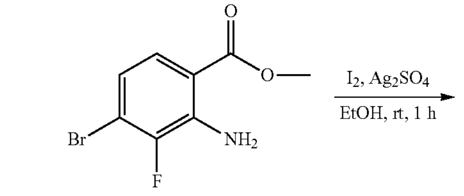
3-2
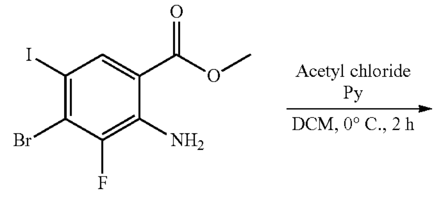
3-3
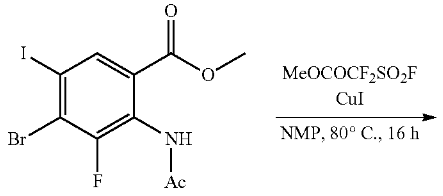
3-4
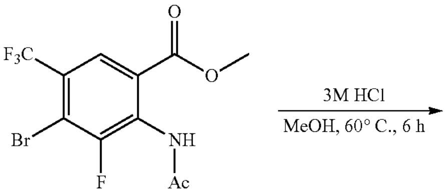
3-5
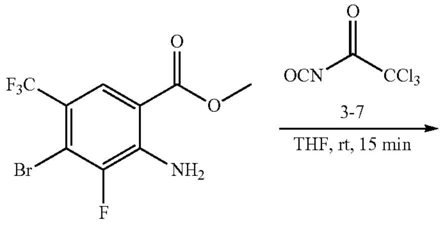
3-6
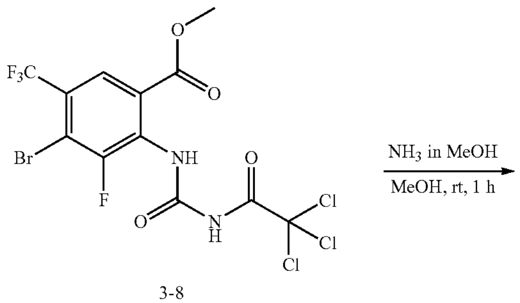
3-8
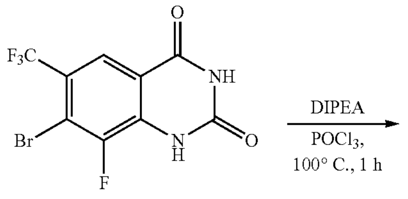
3-9
-continued
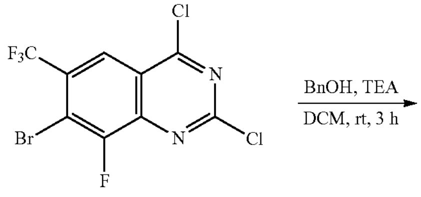
3-10
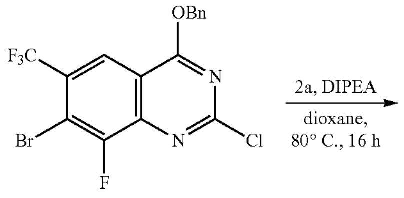
3-11
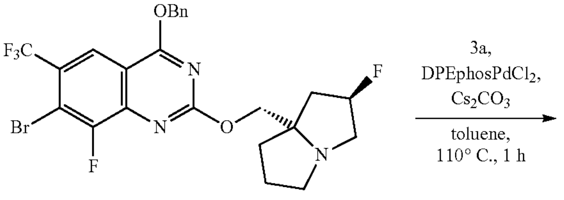
3-12
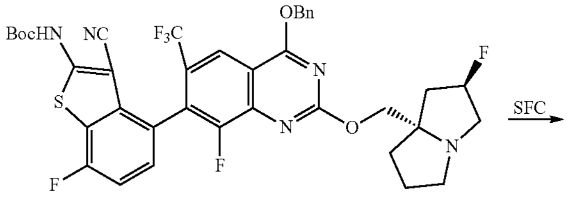
3-13
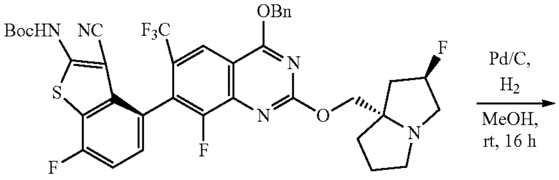
3-13B
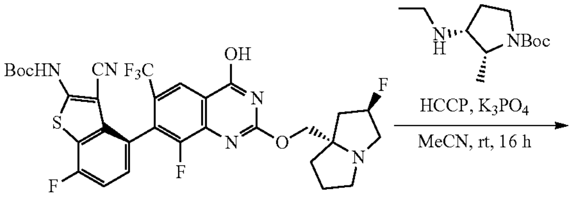
3-14
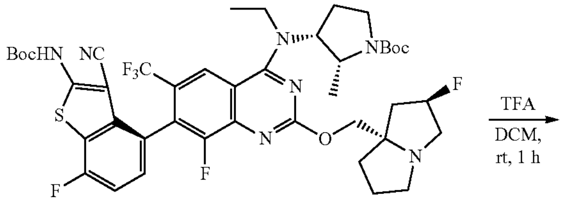
3-15

-continued

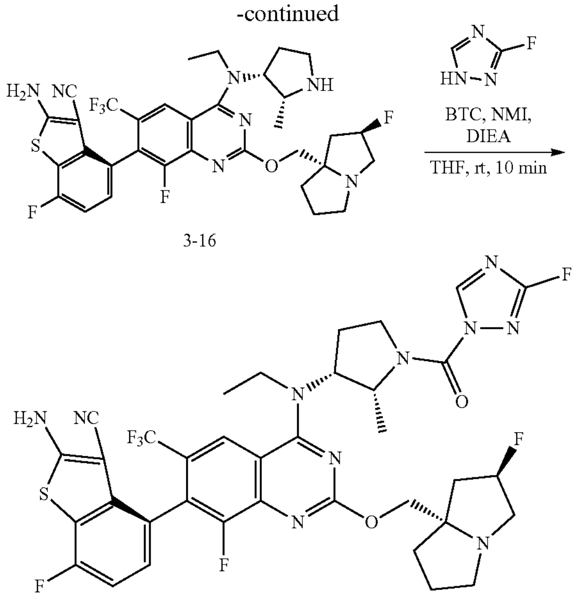

3-16

125

Step 1: To a stirring solution of 2-amino-4-bromo-3-fluorobenzoic acid (3-1, 105 g, 448.72 mmol) in methanol (1 L) was added dropwise $SOCl_2$ (327.6 mL, 4487.2 mmol) at 0° C. The resulting mixture was then heated to 100° C. and stirred at 100° C. for 16 hours. The solvent was evaporated and water was added to the residue. The solid was filtered, then the filter cake was dissolved in DCM (800 mL) and washed with saturated sodium bicarbonate aqueous solution (300 mL×3). The organic layer was dried with sodium sulfate, filtered, and the filtrate was concentrated under vacuum to give methyl 2-amino-4-bromo-3-fluorobenzoate (3-2, 97.5 g) as a yellow solid. MS (ESI) m/z=248.0 $[M+H]^+$.

Step 2: To a mixture of iodine (140.4 g, 552.63 mmol) and silver sulfate (104.7 g, 335.52 mmol) in ethanol (2 L) was added 3-2 (97.5 g, 394.68 mmol) and the resulting mixture was stirred at room temperature for 1 h. The solid was filtered and washed with DCM (200 mL), then the filtrate was concentrated under vacuum. The residue was dissolved in DCM (800 mL) and washed with 10% sodium thiosulfate solution (400 mL) and brine (400 mL). The organic layer was dried over sodium sulfate, filtered, and the filtrate was concentrated under vacuum to give methyl 2-amino-4-bromo-3-fluoro-5-iodobenzoate (3-3, 135 g) as a yellow solid. MS (ESI) m/z=375.8 $[M+H]^+$.

Step 3: To a solution of 3-3 (135 g, 361.93 mmol) and pyridine (84.7 g, 1085.79 mmol) in DCM (2 L) was added acetyl chloride (42.9 g, 542.93 mmol) slowly at 0° C. and the reaction mixture was warmed to room temperature and stirred for 2 h. The pH of the reaction mixture was adjusted with 1N hydrochloric acid to <7, then the mixture was washed with saturated sodium bicarbonate aqueous to pH>8. The combined organic phase was washed with water and brine, dried over saturated sodium sulfate, filtered and the filtrate was concentrated under vacuum to give methyl 2-acetamido-4-bromo-3-fluoro-5-iodobenzoate (3-4, 140 g) as a yellow solid. MS (ESI) m/z=415.8 $[M+H]^+$.

Step 4: To a solution of 3-4 (140.00 g, 336 mmol) and methyl 2,2-difluoro-2-(fluorosulfonyl)acetate (323.8 g, 1687 mmol) in N-methyl-2-pyrrolidone (1.5 L) was added CuI (257 g, 1350 mmol). The mixture was stirred at 80° C. for 16 hours, then cooled to room temperature and quenched with water. The mixture was filtered and the filtrate was extracted with ethyl acetate (1L×3). The organic layer was dried over sodium sulfate, filtered, and the filtrate was concentrated and the crude material was purified by silica gel column chromatography (petroleum ether:EtOAc=6:1) to give methyl 2-acetamido-4-bromo-3-fluoro-5-(trifluoromethyl) benzoate (3-5, 78.00 g) as a yellow solid. MS (ESI) m/z=358.0 $[M+H]^+$.

Step 5: To a solution of 3-5 (78.0 g, 218.5 mmol) in MeOH (800 mL) was added 4M HCl in methanol (240 mL) and the resulting mixture was heated at 60° C. for 6 hours. The mixture was cooled to room temperature and the pH adjusted to 8-9 with saturated $NaHCO_3$ aqueous solution. The crude product was extracted with ethyl acetate (500 mL×3) and the combined organic layer was dried over sodium sulfate, filtered, and the filtrate was concentrated under vacuum to give crude methyl 2-amino-4-bromo-3-fluoro-5-(trifluoro methyl)benzoate (3-6, 62.00 g, 90% yield) as a yellow solid.

Step 6: To a mixture of 3-6 (62 g, 196.8 mmol) in THF (700 mL) was added 2,2,2-trichloroacetyl isocyanate (3-7, 56 g, 295.2 mmol). After 15 minutes, the reaction mixture was evaporated to give methyl 2-amino-4-bromo-3-fluoro-5-(trifluoromethyl)benzoate (3-8, 84.00 g,) as a yellow solid.

Step 7: To a solution of 3-8 (84.00 g, 167.3 mmol) in methanol (600 mL) was added $NH_3$ in methanol (7N, 120 mL) and the resulting mixture was stirred for 1 hour. The mixture was concentrated under vacuum. The crude residue was triturated with a solution of petroleum ether/EtOAc=4:1 and the solid was collected by filtration and dried in vacuo to give 7-bromo-8-fluoro-6-(trifluoromethyl)quinazoline-2,4(1H,3H)-dione (3-9, 40.1 g) as a white solid.

Step 8: To a solution of 3-9 (2.00 g, 6 mmol) in $POCl_3$ (20 mL) was added DIEA (4 mL) and the resulting mixture was heated to 100° C. and stirred for 1 hour. The mixture was concentrated under vacuum, then the crude product was diluted with ethyl acetate (100 mL) and poured into ice water. The organic layer was separated, dried over anhydrous sodium sulfate, filtered, and the filtrate was concentrated in vacuo. The residue was purified by silica gel column chromatography to give 7-bromo-2,4-dichloro-8-fluoro-6-(trifluoromethyl) quinazoline (3-10, 1.2 g) as a white solid. $^1H$-NMR (400 MHz, DMSO-$d_6$) δ 8.17 (s, 1H).

Step 9: To a solution of 3-10 (1.2 g, 3.3 mmol) in DCM (12 mL) was added triethylamine (1 g, 9.9 mmol) and benzyl alcohol (0.43 g, 4 mmol). The resulting mixture was stirred for 16 h, then diluted with DCM (100 mL) and washed with brine (50 mL). The organic layer was dried over sodium sulfate, filtered, the filtrate was concentrated in vacuo and purified by silica gel column to give 4-(benzyloxy)-7-bromo-2-chloro-8-fluoro-6-(trifluoromethyl)quinazoline (3-11, 700 mg) as a white solid. MS (ESI) m/z=436.9 $[M+H]^+$.

Step 10: To a solution of 3-11 (700 mg, 1.6 mmol) in dioxane (10 mL) were added 2a (770 mg, 4.8 mmol), DIEA (624 mg, 4.8 mmol) and 4 Å molecular sieve powder (630 mg). The mixture was heated to 80° C. and stirred for 16 hours. After cooling to room temperature, the mixture was diluted with EtOAc (20 mL). The solid was filtered and the filtrate was washed with brine (50 mL). The filter cake was washed with DCM (20 mL×3), then the combined organic layer was dried over anhydrous sodium sulfate, filtered and the filtrate was concentrated in vacuo. The crude product was purified by silica gel column chromatography to give the 4-(benzyloxy)-7-bromo-8-fluoro-2-(((2R,7aS)-2-fluoro tetrahydro-1H-pyrrolizin-7a(5H)-yl)methoxy)-6-(trifluoromethyl) quinazoline (3-12, 500 mg) as a white solid. MS (ESI) m/z=560.0 [M+H]$^+$.

Step 11: To a solution of 3-12 (1.7 g, 3 mmol) in toluene (20 mL) were added 3a (1.85 g, 4.5 mmol), $Cs_2CO_3$ (3 g, 4.5 mmol) and DPEPhos $PdCl_2$ (437 mg, 0.6 mmol). The resulting mixture was stirred at 110° C. for 1 h, then cooled to room temperature, diluted with EtOAc (50 mL) and washed with brine (20 mL). The organic layer was separated, dried over anhydrous sodium sulfate, filtered, the filtrate was concentrated and purified by silica gel column chromatography (petroleum ether/EtOAc=1:1) to give a crude solid product tert-butyl (4-(4-(benzyloxy)-8-fluoro-2-(((2R,7aS)-2-fluorotetrahydro-1H-pyrrolizin-7a(5H)-yl) methoxy)-6-(trifluoromethyl)quinazolin-7-yl)-3-cyano-7-fluorobenzo[b]thiophen-2-yl)carbamate (3-13, 600 mg, 90% purity) as an atropoisomeric mixture. This mixture was further purified by chiral-HPLC to give enantiopure tert-butyl ((S)-4-(4-(benzyloxy)-8-fluoro-2-(((2R,7aS)-2-fluoro tetrahydro-1H-pyrrolizin-7a(5H)-yl)methoxy)-6-(trifluoromethyl)quinazolin-7-yl)-3-cyano-7-fluorobenzo[b]thiophen-2-yl)carbamate (3-13B, 228 mg) as a light yellow solid. MS (ESI) m/z=770.2 [M+H]$^+$.

Step 12: To a solution of 3-13B (228 mg, 0.3 mmol) in MeOH (6 mL) was added 10% Pd/C (50 mg) and the resulting mixture was stirred for 16 hours under $H_2$. The catalyst was removed by filtration and the filtrate was concentrated and purified by prep-TLC to provide tert-butyl ((S)-3-cyano-7-fluoro-4-(8-fluoro-2-(((2R,7aS)-2-fluorotetrahydro-1H-pyrrolizin-7a(5H)-yl)methoxy)-4-hydroxy-6-(trifluoromethyl)quinazolin-7-yl)benzo[b]thiophen-2-yl) carbamate (3-14, 100 mg) as a light yellow solid. MS (ESI) m/z=680.0 [M+H]$^+$.

Step 13: To a solution of 3-14 (200 mg, 0.29 mmol) in MeCN (6 mL) were added HCCP (102.4 mg, 0.29 mmol) and $K_3PO_4$ (93.8 mg, 0.44 mmol). The mixture was stirred for 1 hour, then a solution of tert-butyl (2R,3R)-3-(ethylamino)-2-methyl pyrrolidine-1-carboxylate (134.3 mg, 0.59 mmol) in MeCN (1 mL) was added and the resulting mixture stirred for 16 hours. $NH_3 \cdot H_2O$ (0.5 mL) was added and the mixture was stirred for 30 minutes, then saturated $K_2CO_3$ aqueous solution (4 mL) was added and the mixture stirred an additional 30 minutes. The mixture was diluted with DCM (50 mL), washed with brine (20 mL), and the organic layer was separated and dried over anhydrous sodium sulfate. After filtering off the drying agent, the filtrate was concentrated under vacuum. The residue was purified by prep-TLC to give tert-butyl (2R,3R)-3-(((S)-7-(2-((tert-butoxycarbonyl)amino)-3-cyano-7-fluorobenzo[b]thiophen-4-yl)-8-fluoro-2-(((2R,7aS)-2-fluorotetrahydro-1H-pyrrolizin-7a(5H)-yl)methoxy)-6-(trifluoromethyl)quinazolin-4-yl)(ethyl)amino)-2-methylpyrrolidine-1-carboxylate (3-15, 160 mg) as a light yellow solid. MS (ESI) m/z=890.3 [M+H]$^+$.

Step 14: To a solution of 3-15 (160 mg, 0.18 mmol) in DCM (5 mL) was added TFA (2 mL). The resulting mixture was stirred for 1 hour, then concentrated and the crude residue diluted with DCM (15 mL) and washed with saturated $NaHCO_3$ aqueous solution (10 mL). The organic layer was separated, dried over anhydrous sodium sulfate, concentrated and purified by prep-TLC to provide 2-amino-4-((S)-4-(ethyl((2R,3R)-2-methylpyrrolidin-3-yl) amino)-8-fluoro-2-(((2R,7aS)-2-fluorotetrahydro-1H-pyrrolizin-7a (5H)-yl)methoxy)-6-(trifluoromethyl)quinazolin-7-yl)-7-fluorobenzo[b]thiophene-3-carbonitrile (3-16, 60 mg) as a light yellow solid. MS (ESI) m/z=690.3 [M+H]$^+$.

Step 15: To a solution of 3-fluoro-1H-1,2,4-triazole (268 mg, 3.2 mmol) in ACN (10 mL) in an ice bath were added BTC (204 mg, 0.69 mmol) and N-methylimidazole (107 mg, 1.3 mmol). After stirring at 0° C. for 1 h, a portion (0.6 mL) of the mixture was added to a solution of 3-16 (45 mg, 0.06 mmol) and DIEA (50 mg, 0.39 mmol) in THF (1 mL) at 40° C. The mixture was stirred at 40° C. for 5 minutes, then diluted with EtOAc (20 mL) and washed with brine (10 mL). The organic layer was separated, dried over anhydrous sodium sulfate and filtered. The filtrate was concentrated under reduced pressure and the residue was purified by prep-HPLC to provide 2-amino-4-((S)-4-(ethyl((2R,3R)-1-(3-fluoro-1H-1,2,4-triazole-1-carbonyl)-2-methylpyrrolidin-3-yl)amino)-8-fluoro-2-(((2R,7aS)-2-fluorotetrahydro-1H-pyrrolizin-7a(5H)-yl)methoxy)-6-(trifluoromethyl) quinazolin-7-yl)-7-fluorobenzo[b]thiophene-3-carbonitrile (125) (14.03 mg) as a white solid. MS (ESI) m/z=803.2 [M+H]$^+$. $^1H$ NMR (400 MHz, DMSO-$d_6$) δ 9.14 (s, 1H), 8.25 (s, 1H), 8.09 (s, 2H), 7.28 (s, 1H), 7.15 (t, J=9.6 Hz, 1H), 5.27 (dd, J=146.4, 91.6 Hz, 2H), 4.69 (s, 1H), 4.01 (ddd, J=76.0, 36.8, 26.4 Hz, 6H), 3.02 (d, J=26.0 Hz, 3H), 2.81 (s, 1H), 2.43 (s, 1H), 1.91 (d, J=102.0 Hz, 7H), 1.27 (s, 3H), 1.05 (d, J=6.4 Hz, 3H).

Example 1d: Synthesis of (S)-2-amino-4-(4-(((2R,3R)-1-(2,4-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile (114)

3-16

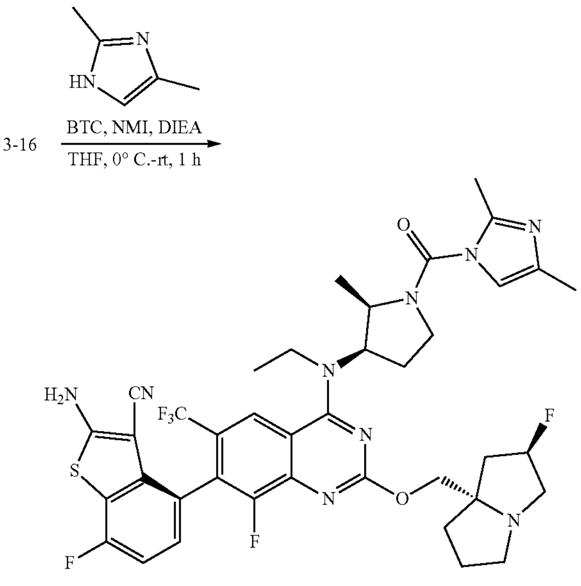

114

To a solution of 2,4-dimethyl-1H-imidazole (233 mg, 2.175 mmol) and N-methylimidazole (71.5 mg, 0.720 mmol) in THF (10 mL) at 0° C. was added BTC (128 mg, 0.435 mmol). The resulting mixture was stirred at 0° C. for 30 min, then transferred to a solution of 3-16 (60 mg, 0.087 mmol) and DIEA (67 mg, 0.522 mmol) in THF (2 mL). The mixture was stirred at room temperature for 10 min, then diluted with EtOAc (200 mL) and washed with brine (50 mL). The organic phase was collected, dried over anhydrous sodium sulfate, filtered and the filtrated was concentrated under reduced pressure. The residue was purified by prep-HPLC to give (S)-2-amino-4-(4-(((2R,3R)-1-(2,4-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile (114, 15.00 mg) as a white solid. MS (ESI) m/z=812.5 $[M+H]^+$. $^1H$ NMR (400 MHz, DMSO-d6) δ 8.24 (s, 1H), 8.18 (s, 1H), 8.09 (s, 2H), 7.30-7.26 (m, 1H), 7.18-7.10 (m, 2H), 5.30 (d, J=53.8 Hz, 1H), 4.80-4.72 (m, 2H), 4.20-4.12 (m, 2H), 3.98-3.90 (m, 1H), 3.82-3.74 (m, 1H), 3.72-3.60 (m, 1H), 3.58-3.46 (m, 1H), 3.18-3.06 (m, 2H), 3.04-2.96 (m, 1H), 2.84-2.80 (m, 1H), 2.50-2.42 (m, 1H), 2.42-2.30 (m, 4H), 2.24-2.12 (m, 1H), 2.10-2.06 (m, 1H), 2.06-2.02 (m, 3H), 2.00-1.96 (m, 1H), 1.90-1.74 (m, 3H), 1.28-1.20 (m, 3H), 0.97 (m, 3H).

Example 1e: Synthesis of (S)-2-amino-4-(4-(((2R,3R)-1-(3-chloro-1H-pyrazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile (193)

3-16

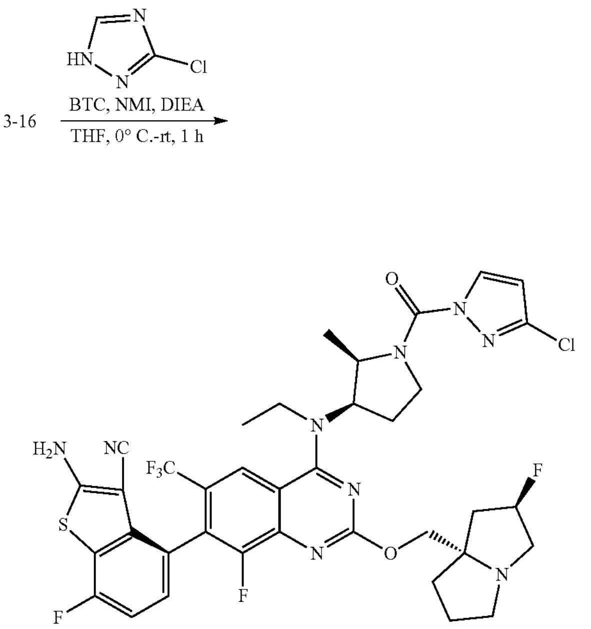

193

To a solution of 3-chloro-1H-pyrazole (185 mg, 1.81 mmol) and N-methylimidazole (60 mg, 0.73 mmol) in THF (5 mL) was added BTC (107 mg, 0.36 mmol) at 0° C. The reaction mixture was stirred at 0° C. for 2 h, then a portion of the mixture (2 mL) was transferred to a solution of 3-16 (50 mg, 0.073 mmol) and DIEA (0.3 mL) in THF (1 mL) at room temperature. Once the reaction was complete, the mixture was poured into water (30 mL) and extracted with ethyl acetate (30 mL×3). The organic layer was washed with brine (30 mL), dried over anhydrous sodium sulfate, filtered and the filtrate was concentrated to dryness under reduced pressure. The crude residue was purified by prep-HPLC (formic acid as modifier) to give (S)-2-amino-4-(4-(((2R,3R)-1-(3-chloro-1H-pyrazole-1-carbonyl)-2-methylpyrrolidin-3-yl)(ethyl)amino)-8-fluoro-2-(((2R,7aS)-2-fluorotetrahydro-1H-pyrrolizin-7-yl)methoxy)-6-(trifluoromethyl)quinazolin-7-yl)-7-fluorobenzo[b]thiophene-3-carbonitrile (193, 20.47 mg) as a white solid. MS m/z (ESI): 818.5 $[M+H]^+$. $^1H$ NMR (400 MHz, DMSO-$d_6$) δ 8.41 (d, J=2.8 Hz, 11), 8.26 (s, 11), 8.09 (s, 2H), 7.27 (d, J=5.0 Hz, 1H), 7.20-7.10 (m, 1H), 6.66 (d, J=2.8 Hz, 1H), 5.30 (d, J=55.6 Hz, 2H), 4.80-4.55 (m, 1H), 4.39-3.63 (m, 6H), 3.22-2.98 (m, 3H), 2.94- 2.78 (m, 1H), 2.45-2.37 (m, 1H), 2.26-1.52 (m, 7H), 1.30 (s, 3H), 1.11-1.00 (m, 3H).

Example 1f: Synthesis of N-((1-(7-(2-amino-3-cyano-7-fluorobenzo[b]thiophen-4-yl)-6-chloro-8-fluoro-2-(((2R,7aS)-2-carboxamide (109)

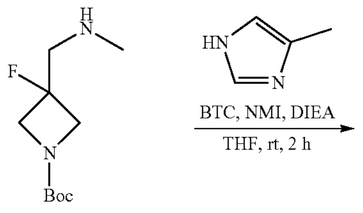

6-1

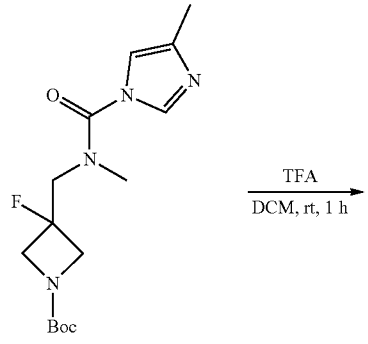

6-2

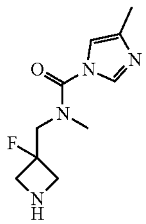

6-3

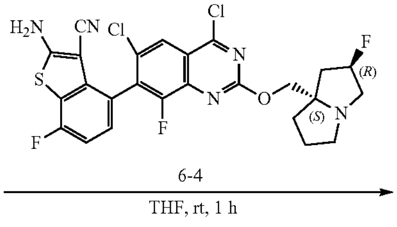

6-4

THF, rt, 1 h

-continued

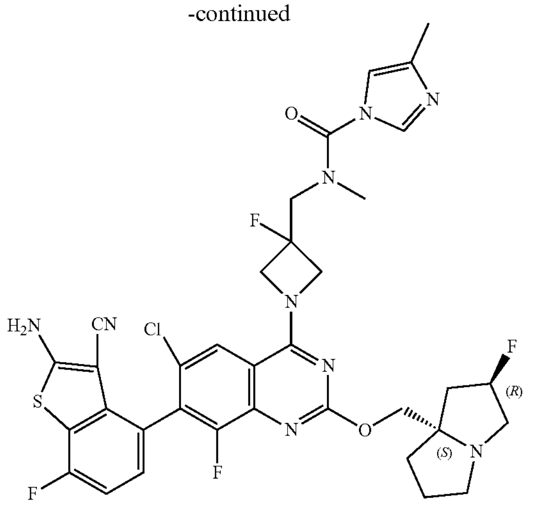

109 yl)-3-fluoroazetidin-3-yl)methyl)-N,4-dimethyl-1H-imidazole-1-carboxamide (109, 30.28 mg) as a white solid. MS m/z (ESI): 754.3 $[M+H]^+$. $^1H$ NMR (400 MHz, DMSO-$d_6$) δ 8.25-8.07 (m, 2H), 8.01 (s, 1H), 7.80 (s, 1H), 7.30-7.10 (m, 3H), 5.45-5.24 (m, 1H), 5.18-4.53 (m, 4H), 4.41-4.02 (m, 5H), 3.83-3.65 (m, 2H), 3.15 (s, 1H), 3.01-2.88 (m, 1H), 2.28-2.03 (m, 6H), 2.00-1.75 (m, 3H).

Example 1g: Synthesis of N-(1-((R)-7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-4-fluoropyrrolidin-3-yl)-N,4-dimethyl-1H-imidazole-1-carboxamide (151)

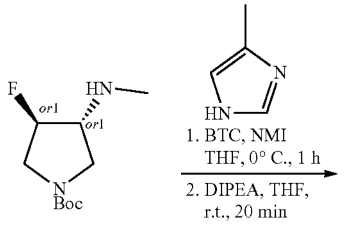

7-1

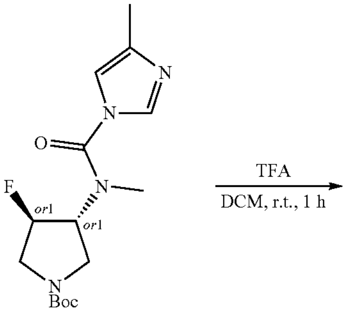

7-2

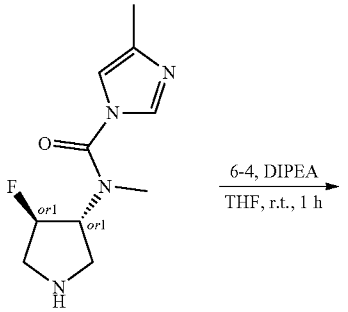

7-3

Step 1: To a solution of 2-methyl imidazole (1.88 g, 22.91 mmol) and N-methylimidazole (752 mg, 9.163 mmol) in THF (20 mL) was added BTC (1.36 g, 4.58 mmol) at 0° C. The reaction mixture was stirred at 0° C. for 1 h, then a portion (15 mL) of the mixture was added to a solution of tert-butyl 3-fluoro-3-((methylamino)methyl)azetidine-1-carboxylate (6-1, 672 mg, 2.89 mmol) and DIEA (4.54 mL, 27.49 mmol) in THF (7 mL) at 30° C. The mixture was stirred at 30° C. for 2 h, then poured into water (30 mL) and extracted with ethyl acetate (50 mL×3). The organic layer was washed with brine (30 mL), dried over anhydrous sodium sulfate, filtered and the filtrate was concentrated to dryness under reduced pressure. The residue was purified by silica gel column chromatography (petroleum ether: EtOAc=3/1) to give tert-butyl 3-((N,4-dimethyl-1H-imidazole-1-carboxamido)methyl)-3-fluoroazetidine-1-carboxylate (6-2, 500 mg) as a colorless oily liquid. MS m/z (ESI): 327.2 $[M+H]^+$.

Step 2: To a solution of 6-2 (190 mg, 0.58 mmol) in DCM (2 mL) was added TFA (2 mL). The reaction mixture was stirred at 20° C. for 30 min, then solvent was removed under reduced pressure. The residue was diluted with saturated aqueous $NaHCO_3$ solution (80 mL) and DCM/MeOH=10/1 (100 mL). The combined organic layer was washed with brine, dried over sodium sulfate, filtered, and the filtrate was concentrated to give crude N-((3-fluoroazetidin-3-yl)methyl)-N,4-dimethyl-1H-imidazole-1-carboxamide (6-3, 130 mg) as a yellow solid. MS m/z (ESI): 227.0 $[M+H]^+$.

Step 3: A mixture of 6-3 (130 mg, 0.57 mmol) and 2-amino-4-(4,6-dichloro-8-fluoro-2-(((2R,7aS)-2-fluorotetrahydro-1H-pyrrolizin-7a (5H)-yl)methoxy) quinazolin-7-yl)-7-fluorobenzo[b]thiophene-3-carbonitrile (6-4, 99 mg, 0.18 mmol) in THF (3 mL) was stirred for 1 h. The solution was treated with water (50 mL) and extracted with ethyl acetate (50 mL×3). The organic layer was washed with brine (50 mL), dried over anhydrous sodium sulfate, filtered and the filtrate was concentrated to dryness under reduced pressure. The residue was purified by prep-HPLC (formic acid as modifier) to give N-((1-(7-(2-amino-3-cyano-7-fluorobenzo[b]thiophen-4-yl)-6-chloro-8-fluoro-2-(((2R,7aS)-2-fluoro-tetrahydro-1H-pyrrolizin-7a(5H)-yl)methoxy)quinazolin-4-

-continued

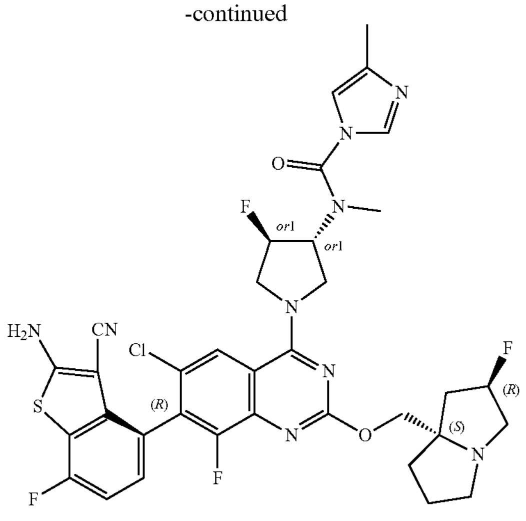

151

Step 1: To a stirred solution of 4-methyl-1H-imidazole (300 mg, 3.6 mmol) in THF (8 mL) were added N-methylimidazole (120 mg, 1.4 mmol) and BTC (217 mg, 0.73 mmol) at 0° C. After stirring at 0° C. for 1 h, the reaction mixture was added to a stirred solution of tert-butyl 3-fluoro-4-(methylamino)pyrrolidine-1-carboxylate (7-1, 160 mg, 0.73 mmol) and DIPEA (566 mg, 4.4 mmol) in THF (3 mL) at 40° C. After stirring at 40° C. for 15 min, the reaction mixture was diluted with water (10 mL) and extracted with EtOAc (10 ml×2). The organic layer was washed with brine (20 mL×3), dried over anhydrous sodium sulfate, filtered and the filtrate was concentrated to dryness under reduced pressure. The crude product tert-butyl 3-(N,4-dimethyl-1H-imidazole-1-carboxamido)-4-fluoropyrrolidine-1-carboxylate was used for the next step directly without purification (7-2, 200 mg, 83%). MS (ESI) m/z=327.1 $[M+H]^+$.

Step 2: To a stirred solution of 7-2 (200 mg, 0.61 mmol) in DCM (1 mL) was added TFA (1 mL). The reaction mixture was stirred for 1 h, then concentrated under reduced pressure. Crude N-(4-fluoropyrrolidin-3-yl)-N,4-dimethyl-1H-imidazole-1-carboxamide (7-3, 200 mg, 144.7 mmol) was used directly in next step. MS (ESI) m/z=227.1 $[M+H]^+$.

Step 3: A solution of 7-3 (100 mg, 0.44 mmol) in THF (3 mL) was adjusted to pH=8 with DIPEA (0.2 mL). Then, 6-4 (40 mg, 0.071 mmol) was added and the resulting mixture stirred for 1 h. The mixture was then diluted with EtOAc (20 mL) and washed with saturated $NaHCO_3$ solution (10 mL×2). The organic layer was dried over anhydrous sodium sulfate, filtered and the filtrate was concentrated in vacuo. The crude residue was purified by prep-HPLC to give N-(1-((R)-7-(2-amino-3-cyano-7-fluorobenzo[b]thiophen-4-yl)-6-chloro-8-fluoro-2-(((2R,7aS)-2-fluorotetrahydro-1H-pyrrolizin-7a(5H)-yl)methoxy)quinazolin-4-yl)-4-fluoropyrrolidin-3-yl)-N,4-dimethyl-1H-imidazole-1-carboxamide (151, 13.87 mg) as a white solid. MS (ESI) m/z=672.1 $[M+H]^+$. $^1$HNMR (400 MHz, DMSO-$d_6$) δ 8.18 (s, 1H), 8.13 (d, J=6.4 Hz, 2H), 8.00 (s, 1H), 7.30-7.20 (m, 2H), 7.18-7.13 (m, 1H), 5.62 (d, J=49.2 Hz, 1H), 5.32 (d, J=54.8 Hz, 1H), 4.91-4.83 (m, 1H), 4.52-4.40 (m, 2H), 4.34-3.98 (m, 4H), 3.24-2.83 (m, 7H), 2.27-1.99 (m, 6H), 1.99-1.74 (m, 3H).

Example 1h: Synthesis of 2-amino-4-(4-(((2R,3R)-1-(2,4-dimethyl-1H-imidazole-1-carbonyl)-2-methyl pyrrolidin-3-yl)(ethyl)amino)-8-fluoro-2-(((2R,7aS)-2-fluorotetrahydro-1H-pyrrolizin-7a(5H)-yl) methoxy)-6-iodoquinazolin-7-yl)-7-fluorobenzo[b] thiophene-3-carbonitrile (184)

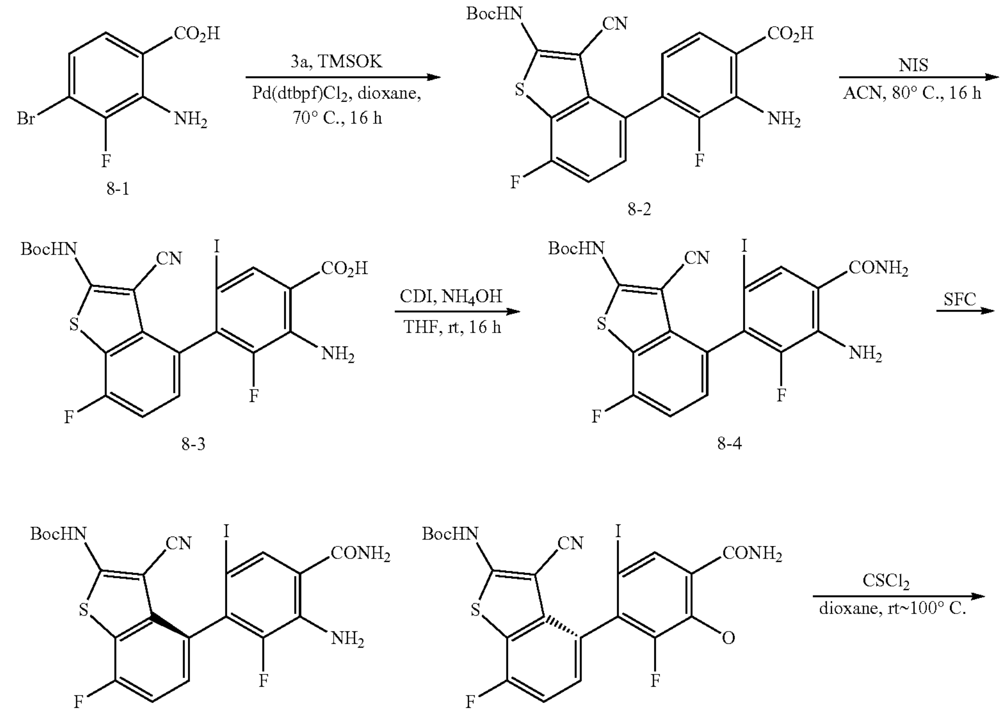

8-1 8-2 8-3 8-4 8-4-P1 8-4-P2

-continued
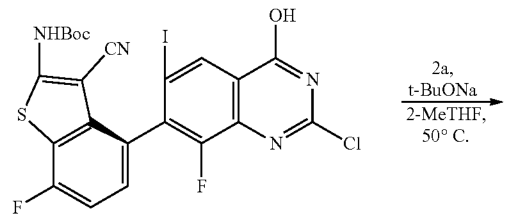
8-5
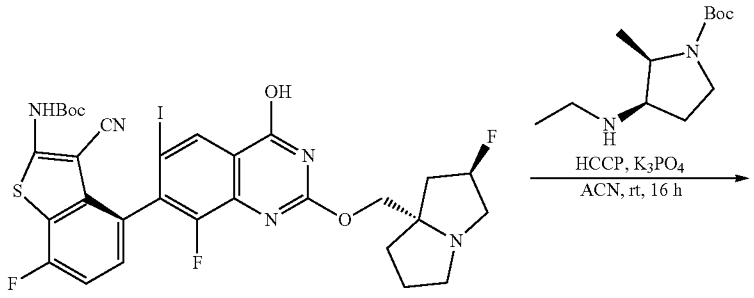
8-6
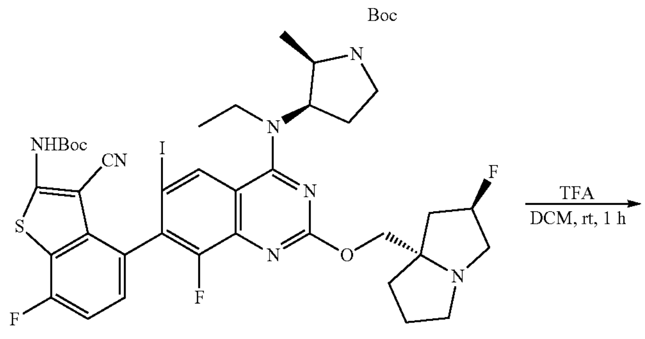
8-7
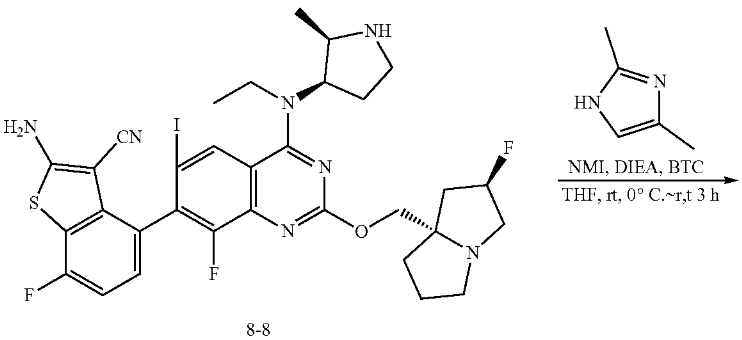
8-8

-continued

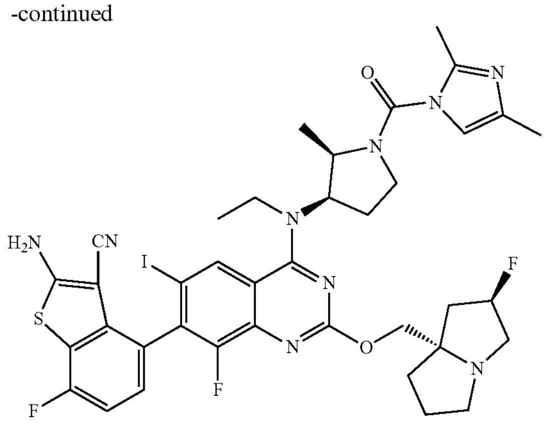

184

Step 1: To a solution of 2-amino-4-bromo-3-fluorobenzoic acid (8-1, 15 g, 64.10 mmol) and 3a (31.05 g, 76.81 mmol) in dioxane (225 mL) were added TMSOK (24.6 g, 191.75 mmol) and Pd(dtbpf)$Cl_2$ (2.25 g, 3.45 mmol). The resulting mixture was stirred at 70° C. for 16 h, then concentrated in vacuo. The residue was treated with $H_2O$ (200 mL) and extracted with EtOAc (120 mL×3). To the aqueous layer was added saturated $KHSO_4$ solution to adjust the pH to 4, then the mixture was extracted with EtOAc again (150 mL×3). The combined organic layer was washed with brine (300 mL), dried over anhydrous sodium sulfate, filtered and the filtrate was concentrated to dryness under reduced pressure to give crude 2-amino-4-(2-((tert-butoxycarbonyl)amino)-3-cyano-7-fluorobenzo[b]thiophen-4-yl)-3-fluoro benzoic acid (8-2, 22 g) as a light purple solid. MS m/z (ESI): 446.0 $[M+H]^+$.

Step 2: To a solution of 8-2 (10 g, 22.45 mmol) in MeCN (150 mL) was added NIS (7.58 g, 33.69 mmol). The reaction mixture was stirred at room temperature for 3 h, then concentrated in vacuo. The residue was purified by flash column chromatography (EtOAc/petroleum ether=0~40%) to give 2-amino-4-(2-((tert-butoxycarbonyl)amino)-3-cyano-7-fluorobenzo[b]thiophen-4-yl)-3-fluoro-5-iodobenzoic acid (8-3, 7.3 g) as an orange solid. MS m/z (ESI): 571.7 $[M+H]^+$.

Step 3: To a solution of 8-3 (8.8 g, 15.40 mmol) in THF (88 mL) was added CDI (2.99 g, 18.44 mmol). The resulting mixture was stirred for 3 h, then $NH_{40}H$ (44 mL) was added and the mixture was stirred and additional 16 h. The mixture was then poured into ice water (100 mL) and extracted with ethyl acetate (200 mL×3). The organic layer was washed with brine (200 mL), dried over anhydrous sodium sulfate, filtered and the filtrate was concentrated to dryness under reduced pressure. The residue was purified by silica gel column chromatography (EtOAc/petroleum ether=45%) to give tert-butyl (4-(3-amino-4-carbamoyl-2-fluoro-6-iodophenyl)-3-cyano-7-fluorobenzo[b]thiophen-2-yl) carbamate (8-4, 6.25 g) as an atropoisomeric mixtures. MS m/z (ESI): 571.1 $[M+H]^+$. This mixture was further purified by chiral-HPLC to give enantiopure tert-butyl (R)-(4-(3-amino-4-carbamoyl-2-fluoro-6-iodophenyl)-3-cyano-7-fluorobenzo [b]thiophen-2-yl)carbamate (8-4-P1) and tert-butyl (S)-(4-(3-amino-4-carbamoyl-2-fluoro-6-iodophenyl)-3-cyano-7-fluorobenzo [b]thiophen-2-yl)carbamate (8-4-P2).

Step 4: To a solution of 8-4-P1 (5 g, 8.77 mmol) in dioxane (50 mL) was added $CsCl_2$ (3 g, 26.09 mmol). The mixture was stirred at 100° C. for 1 h, then cooled to room temperature. The mixture was poured into water (50 mL) and extracted with ethyl acetate (100 mL×3). The organic layer was washed with brine (100 mL), dried over anhydrous sodium sulfate, filtered and the filtrate was concentrated to dryness under reduced pressure. The residue was purified by C18 flash column chromatography (MeCN/$H_2O$=0~50%, $NH_4HCO_3$) to give tert-butyl (R)-(4-(2-chloro-8-fluoro-4-hydroxy-6-iodoquinazolin-7-yl)-3-cyano-7-fluorobenzo[b] thiophen-2-yl)carbamate (8-5, 3.7 g) as a light yellow solid. MS m/z (ESI): 614.9 $[M+H]^+$.

Step 5: To a solution of 8-5 (1.7 g, 2.77 mmol) and 2a (660.32 mg, 4.15 mmol) in 2-MeTHF (40 mL), was added NaOtBu (1.33 g, 13.84 mmol). The mixture was stirred at 50° C. for 1.5 h. The mixture was then adjusted to pH=5 with 10% citric acid, and the solution was extracted with ethyl acetate (100 mL×3). The organic layer was washed with brine (100 mL), dried over anhydrous sodium sulfate, filtered and the filtrate was concentrated to dryness under reduced pressure. The residue was purified by silica gel C18 column flash column chromatography (MeCN/$H_2O$=0~70%, formic acid as modifier) to give tert-butyl ((R)-3-cyano-7-fluoro-4-(8-fluoro-2-(((2R,7aS)-2-fluorotetrahydro-1H-pyrrolizin-7a(5H)-yl)methoxy)-4-hydroxy-6-iodoquinazolin-7-yl)benzo[b]thiophen-2-yl)carbamate (8-6, 1.09 g) as a yellow solid. MS m/z (ESI): 738.0 $[M+H]^+$.

Step 6: To a solution of 8-6 (0.5 g, 0.678 mmol) and $K_3PO_4$ (0.42 g, 1.98 mmol) in MeCN (15 mL) was added HCCP (270 mg, 0.778 mmol). The reaction was stirred for 3 h, then tert-butyl (2R,3R)-3-(ethylamino)-2-methylpyrrolidine-1-carboxylate (460 mg, 2.01 mmol) in ACN (5 mL) was added. The reaction was stirred for 16 h, then ammonium hydroxide (4 mL) was added and the mixture stirred an additional 30 min. Next, the mixture was poured into ice water (20 mL) and extracted with ethyl acetate (100 mL×3). The organic layer was washed with brine (100 mL), dried over anhydrous sodium sulfate, filtered and the filtrate was concentrated to dryness under reduced pressure. The residue was purified by silica gel column chromatography (DCM/MeOH=15/1) to give tert-butyl (2R,3R)-3-((7-(2-((tert-butoxycarbonyl)amino)-3-cyano-7-fluorobenzo[b]thiophen-4-yl)-8-fluoro-2-(((2R,7aS)-2-fluorotetrahydro-1H-pyrrolizin-7a(5H)-yl)methoxy)-6-iodoquinazolin-4-yl) (ethyl)amino)-2-methylpyrrolidine-1-carboxylate (8-7, 0.3 g) as a yellow solid. MS m/z (ESI): 947.9 $[M+H]^+$.

Step 7: To a solution of 8-7 (0.3 g, 0.316 mmol) in DCM (10 mL) was added TFA (5 mL). The reaction mixture was stirred for 1 h, then concentrated under reduced pressure.

The crude material was diluted with saturated aqueous $NaHCO_3$ solution (200 mL) and DCM/MeOH=10/1 (200 mL×3). The organic layer was collected and washed with brine (50 mL), dried over anhydrous sodium sulfate, filtered and the filtrate was concentrated to dryness under reduced pressure. The residue was purified by prep-TLC (DCM/7 M $NH_3$ in MeOH=9/1) to give 2-amino-4-(4-(ethyl((2R,3R)-2-methylpyrrolidin-3-yl)amino)-8-fluoro-2-(((2R,7aS)-2-fluorotetrahydro-1H-pyrrolizin-7a(5H)-yl)methoxy)-6-iodoquinazolin-7-yl)-7-fluorobenzo[b]thiophene-3-carbonitrile (8-8, 200 mg) as a yellow solid. MS m/z (ESI): 748.0 $[M+H]^+$.

Step 8: To a solution of 2,4-dimethyl-1H-imidazole (225 mg, 2.34 mmol) and N-methylimidazole (77 mg, 0.94 mmol) in THF (10 mL) at 0° C. was added BTC (139 mg, 0.47 mmol). After the mixture was stirred at 0° C. for 30 min it was transferred into a solution of 8-8 (50 mg, 0.067 mmol) and DIEA (67 mg, 0.522 mmol) in THF (1 mL). The mixture was stirred at room temperature for 10 min, then diluted with EtOAc (200 mL) and washed with brine (50 mL). The organic layer was dried over anhydrous sodium sulfate, filtered and the filtrate was concentrated under reduced pressure. The residue was purified by prep-HPLC to give 2-amino-4-(4-(((2R,3R)-1-(2,4-dimethyl-1H-imidazole-1-carbonyl)-2-methylpyrrolidin-3-yl)(ethyl) amino)-8-fluoro-2-(((2R,7aS)-2-fluorotetrahydro-1H-pyrrolizin-7a(5H)-yl) methoxy)-6-iodoquinazolin-7-yl)-7-fluorobenzo[b] thiophene-3-carbonitrile (184, 30.09 mg) as a white solid. MS m/z (ESI): 856.2 $[M+H]^+$. $^1H$ NMR (400 MHz, DMSO-$d_6$) δ 8.36 (s, 1H), 8.09 (s, 2H), 7.29-7.13 (m, 2H), 7.09 (s, 1H), 5.28 (d, J=54.0 Hz, 1H), 4.85-4.47 (m, 2H), 4.21-4.00 (m, 2H), 3.96-3.81 (m, 1H), 3.80-3.60 (m, 2H), 3.57-3.50 (m, 1H), 3.10-2.98 (m, 3H), 2.87-2.71 (m, 1H), 2.47-2.27 (m, 5H), 2.18-2.10 (m, 1H), 2.12-1.96 (m, 5H), 1.93-1.71 (m, 3H), 1.19-1.06 (m, 3H), 0.91 (s, 3H).

Example 1i: Synthesis of ((2R,3R)-3-((7-(5-amino-4-fluoro-3-methyl-2-(trifluoromethyl)phenyl)-8-fluoro-2-(((2R,7aS)-2-fluorotetrahydro-1H-pyrrolizin-7a(5H)-yl)methoxy)pyrido[4,3-d]pyrimidin-4-yl)(ethyl)amino)-2-methylpyrrolidin-1-yl)(3-chloro-1H-1,2,4-triazol-1-yl)methanone (208)

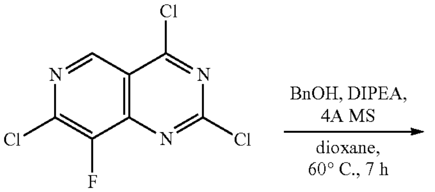

9-1

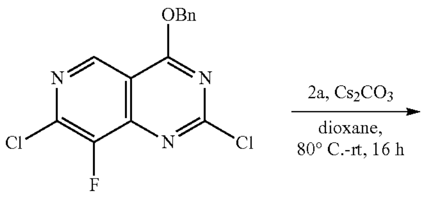

9-2

-continued

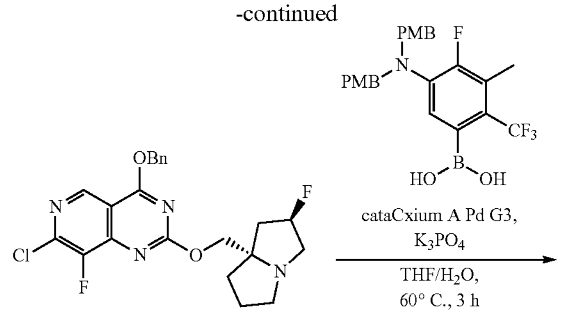

9-3

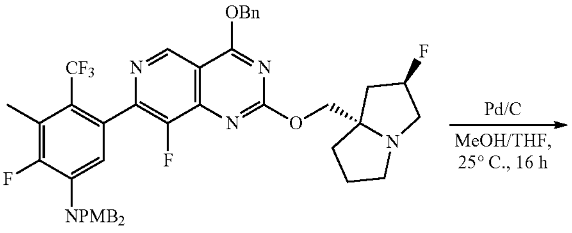

9-4

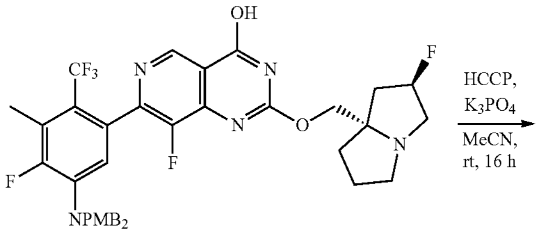

9-5

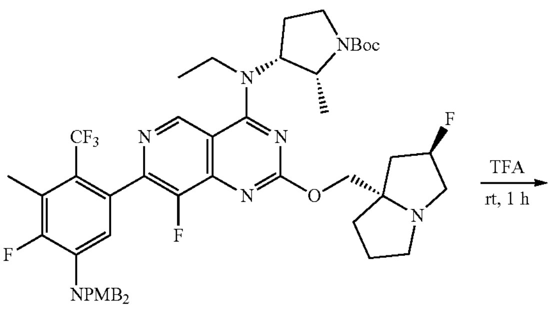

9-6

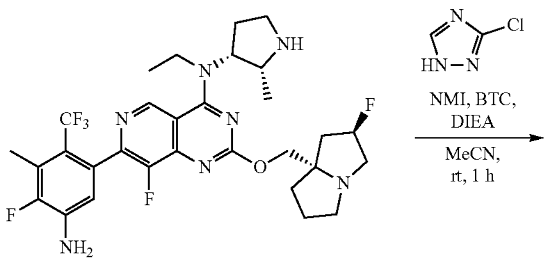

9-7

-continued

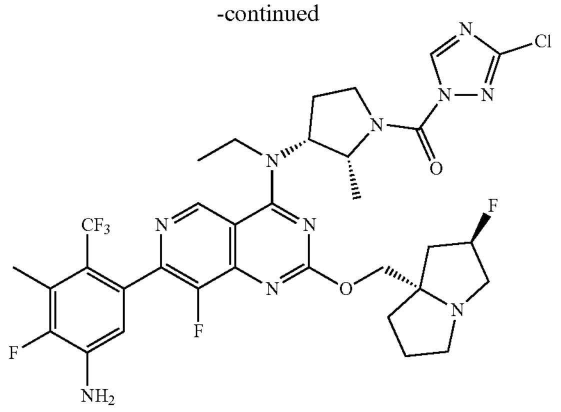

208

Step 1: To a stirred solution of 2,4,7-trichloro-8-fluoro-pyrido[4,3-d]pyrimidine (9-1, 6.2 g, 24.56 mmol) in dioxane (62 mL) were added 4 Å molecular sieve (1.55 g), benzyl alcohol (2.92 g, 27.02 mmol) and DIPEA (9.52 g, 73.68 mmol). The reaction mixture was stirred at 60° C. for 7 h, then filtered to remove solid. The filtrate was treated with EtOAc (100 mL) and washed with water (50 mL×3). The organic layer was dried over anhydrous sodium sulfate, filtered and the filtrate was concentrated in vacuo. The crude product was purified by silica gel column chromatography (petroleum ether/EtOAc=5:1) to give 4-(benzyloxy)-2,7-dichloro-8-fluoropyrido [4,3-d]pyrimidine (9-2, 4 g) as a white solid. $^1$H NMR (400 MHz, DMSO-d6) δ 9.20 (s, 2H), 9.20 (s, 2H), 7.65-7.58 (m, 4H), 7.65-7.58 (m, 4H), 7.48-7.40 (m, 6H), 7.50-7.31 (m, 7H), 5.73 (s, 4H), 5.73 (s, 4H).

Step 2: To a stirred solution of 9-2 (10 g, 30.85 mmol) in dioxane (100 mL) were added 2a (6.88 g, 43.19 mmol) and $Cs_2CO_3$ (25.13 g, 77.13 mmol). The mixture was stirred at 80° C. for 3 h, cooled to room temperature and stirred an additional 16 h, then diluted with EtOAc (500 mL) and washed with water (100 mL×3). The organic layer was dried over anhydrous sodium sulfate, filtered and the filtrate was concentrated in vacuo. The crude product was purified by silica gel column chromatography (DCM:MeOH=20:1) to give 4-(benzyloxy)-7-chloro-8-fluoro-2-(((2R,7aS)-2-fluorotetrahydro-1H-pyrrolizin-7a(5H)-yl)methoxy)pyrido[4,3-d]pyrimidine (9-3, 11.3 g) as a yellow oil. MS (ESI) m/z=447.2 [M+H]$^+$.

Step 3: To a stirred solution of 9-3 (2.3 g, 5.15 mmol) in THF/$H_2O$ (50 mL/5 mL) were added (5-(bis(4-methoxybenzyl) amino)-4-fluoro-3-methyl-2-(trifluoromethyl)phenyl) boronic acid (3.69 g, 7.73 mmol), $K_3PO_4$ (4.37 g, 20.60 mmol) and cataCxium A Pd G3 (1.13 g, 1.55 mmol). The reaction mixture was stirred at 60° C. for 3 h, then diluted with EtOAc (200 mL) and washed with water (100 mL×3). The organic layer was dried over anhydrous sodium sulfate, filtered and the filtrate was concentrated in vacuo. The crude product was purified by silica gel column chromatography (DCM:MeOH=15:1) to give 5-(4-(benzyloxy)-8-fluoro-2-(((2R,7aS)-2-fluorotetrahydro-1H-pyrrolizin-7a(5H)-yl) methoxy)pyrido[4,3-d]pyrimidin-7-yl)-2-fluoro-N,N-bis(4-methoxybenzyl)-3-methyl-4-(trifluoromethyl)aniline (9-4, 2.1 g) as a yellow oil. MS (ESI) m/z=844.4 [M+H]$^+$.

Step 4: To a stirred solution of 9-4 (6 g, 7.11 mmol) in THF/MeOH (40 mL/30 mL) was added 10% Pd/C (500 mg). The reaction mixture was stirred at 25° C. under $H_2$ for 16 h, then filtered to remove catalyst. The filtrate was concentrated and purified by silica gel column chromatography (DCM:MeOH=10:1) to give 7-(5-(bis(4-methoxybenzyl) amino)-4-fluoro-3-methyl-2-(trifluoromethyl)phenyl)-8-fluoro-2-(((2R,7aS)-2-fluorotetrahydro-1H-pyrrolizin-7a (5H)-yl)methoxy)pyrido[4,3-d]pyrimidin-4-ol (9-5, 2.7 g) as a white solid. MS (ESI) m/z=754.0 [M+H]$^+$.

Step 5: To a solution of 9-5 (300 mg, 0.398 mmol) and $K_3PO_4$ (0.21 g, 50.99 mmol) in MeCN (5 mL) was added HCCP (221 mg, 0.636 mmol). The reaction was stirred for 3 h, then tert-butyl(3R)-3-(ethylamino)-2-methylpyrrolidine-1-carboxylate (181 mg, 0.793 mmol) in ACN (5 mL) was added. The mixture was stirred for 16 h, then ammonium hydroxide (4 mL) was added and the resulting mixture stirred for 30 min. The mixture was poured into ice water (20 mL), then extracted with ethyl acetate (100 mL×3). The organic layer was washed with brine (100 mL), dried over anhydrous sodium sulfate, filtered and the filtrate was concentrated to dryness under reduced pressure. The residue was purified by silica gel column chromatography (DCM/MeOH=15/1) to give tert-butyl(2R,3R)-3-((7-(5-(bis (4-methoxybenzyl)amino)-4-fluoro-3-methyl-2-(trifluoromethyl)phenyl)-8-fluoro-2-(((2R,7aS)-2-fluorotetrahydro-1H-pyrrolizin-7a(5H)-yl)methoxy)pyrido[4,3-d]pyrimidin-4-yl)(ethyl)amino)-2-methylpyrrolidine-1-carboxylate (9-6, 280 mg) as a yellow solid. MS (ESI) m/z=964.5 [M+H]$^+$.

Step 6: To a solution of 9-6 (280 mg, 0.29 mmol) in DCM (2 mL) was added TFA (2 mL). The resulting mixture was stirred for 1 h, then concentrated under reduced pressure. The residue was treated with $NH_3$·MeOH (50 mL) and concentrated again in vacuo. The residue was purified by preparative TLC to give 7-(5-amino-4-fluoro-3-methyl-2-(trifluoromethyl)phenyl)-N-ethyl-8-fluoro-2-(((2R,7aS)-2-fluorotetrahydro-1H-pyrrolizin-7a(5H)-yl)methoxy)-N-((2R,3R)-2-methylpyrrolidin-3-yl)pyrido[4,3-d]pyrimidin-4-amine (9-7, 150 mg) as a yellow solid. MS (ESI) m/z=624.1 [M+H]$^+$.

Step 7: To a solution of 3-chloro-1H-1,2,4-triazole (249 mg, 2.4 mmol) and N-methylimidazole (78 mg, 0.95 mmol) in THF (9 mL) was added BTC (144 mg, 0.48 mmol) at 0° C. The resulting mixture was stirred at 0° C. for 2 h, then a portion of the mixture (3 mL) was transferred to a solution of 9-7 (100 mg, 0.16 mmol) and DIEA (1 mL) in THF (2 mL) at room temperature. Once the reaction was complete, the mixture was poured into water (30 mL) and extracted with ethyl acetate (30 mL×3). The organic layer was washed with brine (30 mL), dried over anhydrous sodium sulfate, filtered and the filtrate was concentrated to dryness under reduced pressure. The crude residue was purified by prep-HPLC (formic acid as modifier) to give ((2R,3R)-3-((7-(5-amino-4-fluoro-3-methyl-2-(trifluoromethyl) phenyl)-8-fluoro-2-(((2R,7aS)-2-fluorotetrahydro-1H-pyrrolizin-7a (5H)-yl)methoxy)pyrido[4,3-d]pyrimidin-4-yl)(ethyl) amino)-2-methylpyrrolidin-1-yl)(3-chloro-1H-1,2,4-triazol-1-yl)methanone (208, 33.44 mg) as a white solid. MS m/z (ESI): 753.4 [M+H]$^+$. $^1$H NMR (400 MHz, DMSO-$d_6$) δ 9.26 (s, 1H), 9.11 (s, 1H), 6.58 (d, J=8.4 Hz, 1H), 6.03 (s, 2H), 5.51-4.79 (m, 3H), 4.25-4.00 (m, 3H), 3.96-3.70 (m, 3H), 3.15-2.95 (m, 3H), 2.85-2.75 (m, 1H), 2.38-2.30 (m, 4H), 2.20-1.70 (m, 7H), 1.39 (s, 3H), 1.08 (s, 3H).

Example 1j: Synthesis of ((2R,3R)-3-((7-(5-amino-4-fluoro-3-methyl-2-(trifluoromethyl)phenyl)-8-fluoro-2-(((2R,7aS)-2-fluorotetrahydro-1H-pyrrolizin-7a(5H)-yl)methoxy)pyrido[4,3-d]pyrimidin-4-yl)(ethyl)amino)-2-methylpyrrolidin-1-yl)(2,4-dimethyl-1H-imidazol-1-yl)methanone (196)

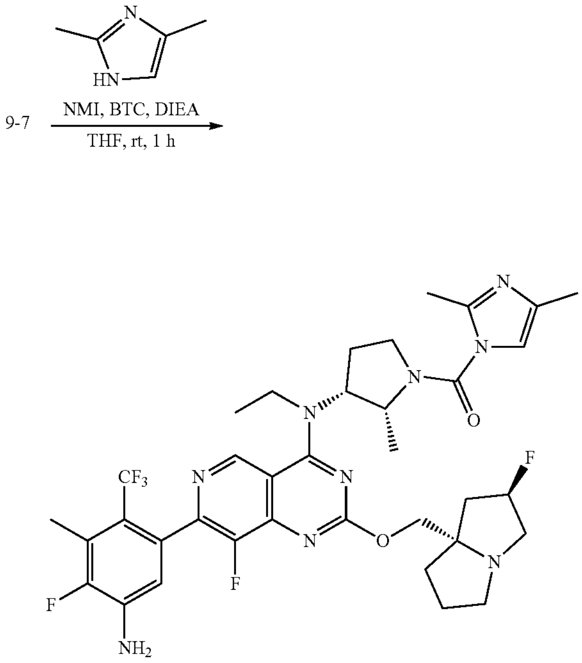

196

To a solution of 2,4-dimethyl-1H-imidazole (116 mg, 1.204 mmol) and N-methylimidazole (79 mg, 0.963 mmol) in 5 mL THF was added BTC (72 mg, 0.240 mmol) at 0° C. The reaction mixture was stirred at 0° C. for 1 h before a portion of the mixture (0.5 mL) was transferred to a solution of 9-7 (55 mg, 0.088 mmol) and DIEA (40 mg, 0.31 mmol) in THF (0.5 mL) at 30° C. After completion of the reaction, the mixture was poured into water (10 mL) and extracted with ethyl acetate (15 mL×3). The organic layer was washed with brine (10 mL), dried over anhydrous sodium sulfate, filtered and the filtrate was concentrated to dryness under reduced pressure. The crude residue was purified by prep-HPLC (formic acid as modifier) to give ((2R,3R)-3-((7-(5-amino-4-fluoro-3-methyl-2-(trifluoromethyl)phenyl)-8-fluoro-2-(((2R,7aS)-2-fluorotetrahydro-1H-pyrrolizin-7a(5H)-yl)methoxy)pyrido[4,3-d]pyrimidin-4-yl)(ethyl)amino)-2-methylpyrrolidin-1-yl)(2,4-dimethyl-1H-imidazol-1-yl)methanone (196, 23.00 mg). MS m/z (ESI): 746.4 $[M+H]^+$. $^1H$ NMR (400 MHz, DMSO-d6) δ 9.11 (s, 1H), 8.13 (s, 1H), 7.09 (s, 1H), 6.65-6.50 (m, 1H), 6.04 (s, 2H), 5.60-5.20 (m, 1H), 4.96-4.72 (m, 2H), 4.40-3.95 (m, 3H), 3.95-3.80 (m, 1H), 3.80-3.60 (m, 1H), 3.60-3.35 (m, 2H), 3.33-2.70 (m, 4H), 2.40-2.30 (m, 7H), 2.20-2.05 (m, 5H), 2.00-1.70 (m, 3H), 1.45-1.30 (m, 3H), 1.10-0.80 (m, 3H).

Example 1k: Synthesis of 2-amino-4-(6-cyclopropyl-4-(((2R,3R)-1-(2,4-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile (190)

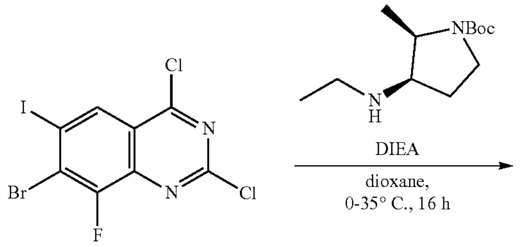

11-1

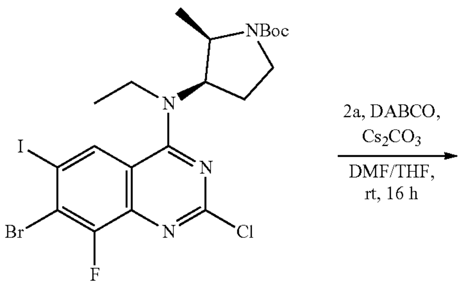

11-2

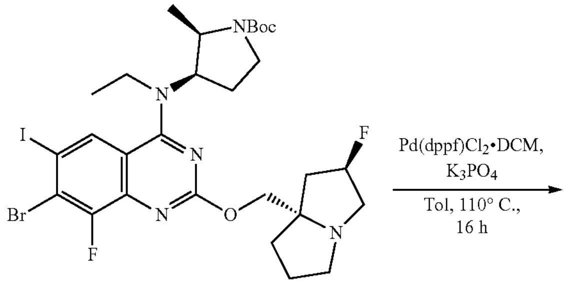

11-3

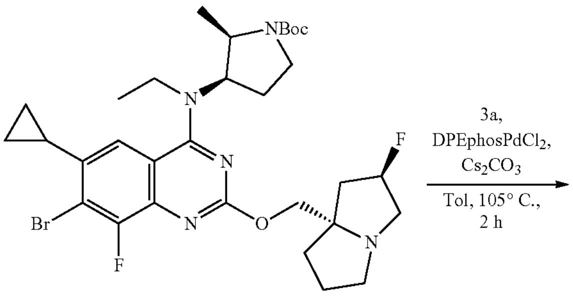

11-4

-continued

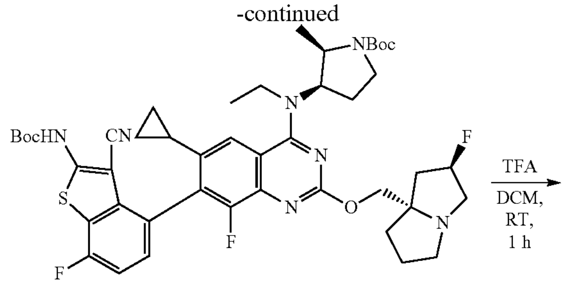

11-5

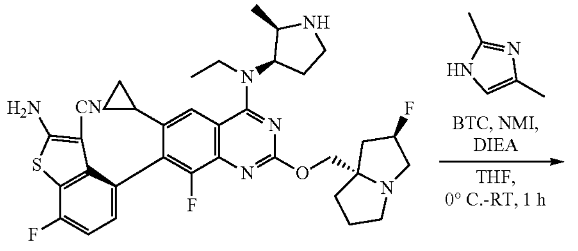

11-6

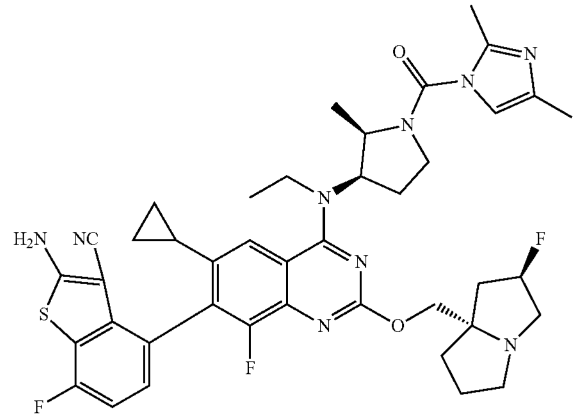

190

Step 1: To a solution of 7-bromo-2,4-dichloro-8-fluoro-6-iodoquinazoline (11-1, 10 g, 23.81 mmol) in dioxane (100 mL) were added DIEA (9.24 g, 71.43 mmol) and tert-butyl (2R,3R)-3-(ethylamino)-2-methylpyrrolidine-1-carboxylate (5.98 g, 236.2 mmol) at 0° C. The mixture was stirred at room temperature for 16 hours, then concentrated to dryness under reduced pressure. The residue was diluted with water (200 mL) and extracted with EtOAc (200 mL×3). The organic layer was washed with brine, dried over anhydrous sodium sulfate, filtered and the filtrate was concentrated to dryness under reduced pressure. The residue was purified by silica gel column chromatography (petroleum ether/EtOAc=4/1) to give tert-butyl (2R,3R)-3-((7-bromo-2-chloro-8-fluoro-6-iodoquinazolin-4-yl)(ethyl) amino)-2-methylpyrrolidine-1-carboxylate as a yellow solid. (11-2, 8.5 g). MS m/z (ESI): 615.1 $[M+H]^+$.

Step 2: To a solution of 11-2 (8.5 g, 13.9 mmol) in DMF/THF (90 mL+90 mL) were added 2a (4.42 g, 27.79 mmol), cesium carbonate (13.6 g, 41.7 mmol) and triethylenediamine (779 mg, 6.95 mmol). The mixture was stirred at room temperature for 16 h, then diluted with water (200 mL) and extracted with EtOAc (200 mL×3). The organic layer was washed with brine (200 mL) and dried over anhydrous sodium sulfate, filtered and the filtrate was concentrated to dryness under reduced pressure. The residue was purified by silica gel column chromatography (petroleum ether/EtOAc=0~100%) to give tert-butyl (2R,3R)-3-((7-bromo-8-fluoro-2-(((2R,7aS)-2-fluoro tetrahydro-1H-pyrrolizin-7a(5H)-yl)methoxy)-6-iodoquinazolin-4-yl)(ethyl)amino)-2-methylpyrrolidine-1-carboxylate as a yellow solid. (11-3, 4.05 g). MS m/z (ESI): 736.1 $[M+H]^+$.

Step 3: To a solution of 11-3 (4.05 g, 5.51 mmol) in toluene (50 mL) were added cyclopropyl boronic acid (2.37 g, 27.51 mmol), $K_3PO_4$ (2.37 g, 11.02 mmol) and Pd(dppf)$Cl_2$·DCM (450 mg, 0.551 mmol). The resulting mixture was stirred at 110° C. for 2 h, then cooled to room temperature and diluted with water (200 mL) and extracted with EtOAc (200 mL×3). The organic layer was washed with brine (100 mL), dried over anhydrous sodium sulfate, filtered and the filtrate was concentrated to dryness under reduced pressure. The residue was purified by silica gel column chromatography (petroleum ether/EtOAc=0~100%) to give tert-butyl (2R,3R)-3-((7-bromo-6-cyclopropyl-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carboxylate (11-4, 4.05 g) as a yellow solid. MS m/z (ESI): 650.1 $[M+H]^+$.

Step 4: To a solution of 11-4 (4.05 g, 4.7 mmol) in toluene (50 mL) were added 3a (2.85 g, 7.05 mmol), cesium carbonate (4.6 g, 14.1 mmol) and DPEPhosPd$Cl_2$ (675 mg, 0.94 mmol). The resulting mixture was stirred at 105° C. for 2 h, then diluted with water (200 mL) and extracted with EtOAc (200 mL×3). The organic layer was washed with brine (100 mL), dried over anhydrous sodium sulfate, filtered and the filtrate was concentrated to dryness under reduced pressure. The residue was purified by silica gel column chromatography (DCM:EtOAc=80%) to give tert-butyl (2R,3R)-3-((7-(2-((tert-butoxycarbonyl)amino)-3-cyano-7-fluorobenzo[b]thiophen-4-yl)-6-cyclopropyl-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carboxylate (11-5, 1.44 g) as an atropoisomeric mixture. MS m/z (ESI): 862.1 $[M+H]^+$. This mixture was purified by chiral HPLC to provide enantiopure tert-butyl (2R,3R)-3-((7-((R)-2-((tert-butoxycarbonyl)amino)-3-cyano-7-fluorobenzo[b]thiophen-4-yl)-6-cyclopropyl-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carboxylate (11-5P1) and tert-butyl (2R,3R)-3-((7-((S)-2-((tert-butoxycarbonyl)amino)-3-cyano-7-fluorobenzo[b]thiophen-4-yl)-6-cyclopropyl-8-fluoro-2-(((2R,7aS)-2-fluorotetrahydro-1H-pyrrolizin-7a(5H)-yl)methoxy)quinazolin-4-yl)(ethyl)amino)-2-methylpyrrolidine-1-carboxylate (11-5P2).

Step 5: To a solution of 11-5P2 (560 mg, 0.650 mmol) in DCM (5 mL) was added TFA (1 mL). The resulting mixture was stirred for 2 h, then concentrated under reduced pressure. The residue was treated with $NH_3$-MeOH (20 mL) and concentrated again under reduced pressure. The crude material was purified by preparative TLC (DCM: $NH_3$·MeOH=90%) to give (S)-2-amino-4-(6-cyclopropyl-4-(ethyl((2R,3R)-2-methylpyrrolidin-3-yl) amino)-8-fluoro-2-(((2R,7aS)-2-fluorotetrahydro-1H-pyrrolizin-7a(5H)-yl) methoxy)quinazolin-7-yl)-7-fluorobenzo[b]thiophene-3-carbonitrile (11-6, 300 mg) as a yellow solid. MS m/z (ESI): 662.1 $[M+H]^+$.

Step 6: To a solution of 2,4-dimethylimidazole (182 mg, 1.890 mmol) and N-methylimidazole (62 mg, 0.756 mmol) in THF (15 mL) at 0° C. was added BTC (112 mg, 0.378 mmol). The resulting mixture was stirred at 0° C. for 30 min, then a portion of the mixture (5 mL) was transferred to a solution of 11-6 (50 mg, 0.076 mmol) and DIEA (88 mg, 0.680 mmol) in THF (1 mL). The mixture was stirred at room temperature for 10 min, then diluted with EtOAc (200 mL) and washed with brine (50 mL). The organic phase was dried over anhydrous sodium sulfate, filtered and the filtrate was concentrated under reduced pressure. The residue was purified by prep-HPLC to give (S)-2-amino-4-(6-cyclopropyl-4-(((2R,3R)-1-(2,4-dimethyl-1H-imidazole-1-carbonyl)-2-methylpyrrolidin-3-yl)(ethyl)amino)-8-fluoro-2-(((2R,7aS)-2-fluorotetrahydro-1H-pyrrolizin-7a(5H)-yl)methoxy)quinazolin-7-yl)-7-fluorobenzo[b]thiophene-3-carbonitrile (190, 25.76 mg) as a white solid. MS m/z (ESI): 784.3 $[M+H]^+$. $^1H$ NMR (400 MHz, DMSO-d6) δ 8.16 (s, 1H), 8.01 (s, 2H), 7.35 (s, 1H), 7.20-7.12 (m, 1H), 7.10-7.02 (m, 1H), 5.29 (d, J=53.6 Hz, 1H), 4.84-4.58 (m, 2H), 4.22-4.10 (m, 1H), 4.10-3.98 (m, 1H), 3.90-3.76 (m, 1H), 3.72-3.60 (m, 2H), 3.58-3.42 (m, 1H), 3.12-3.06 (m, 2H), 3.04-2.96 (m, 1H), 2.90-2.70 (m, 1H), 2.44-2.28 (m, 5H), 2.22-2.14 (m, 1H), 2.12-2.00 (m, 5H), 1.92-1.72 (m, 3H), 1.56-1.48 (m, 1H), 1.22-1.10 (m, 3H), 0.92 (s, 3H), 0.78-0.68 (m, 3H), 0.66-0.58 (m, 1H).

Example 11: Synthesis of (4S)-4-(2-((1-((8-oxa-3-azabicyclo[3.2.1]octan-3-yl)methyl)cyclopropyl)methoxy)-4-(((2R,3R)-1-(3-chloro-1H-1,2,4-triazole-1-carbonyl)-2-methylpyrrolidin-3-yl)(ethyl)amino)-8-fluoro-6-(trifluoromethyl)quinazolin-7-yl)-2-amino-7-fluorobenzo[b]thiophene-3-carbonitrile (204)

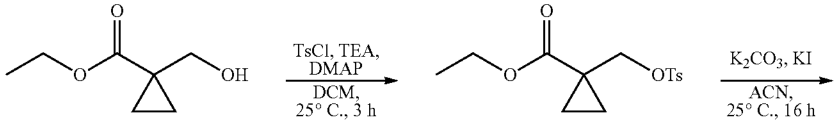

12-1 12-2

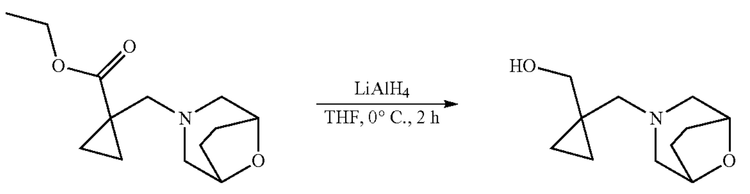

12-3 12A

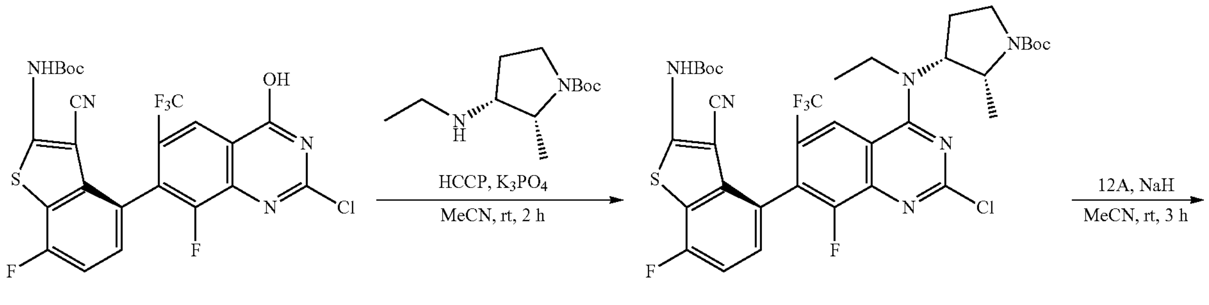

12-4 12-5

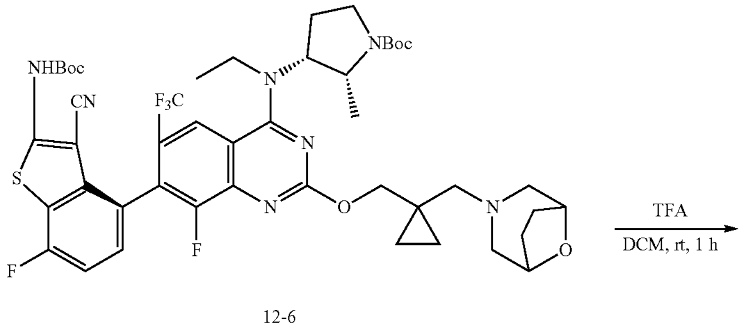

12-6

-continued

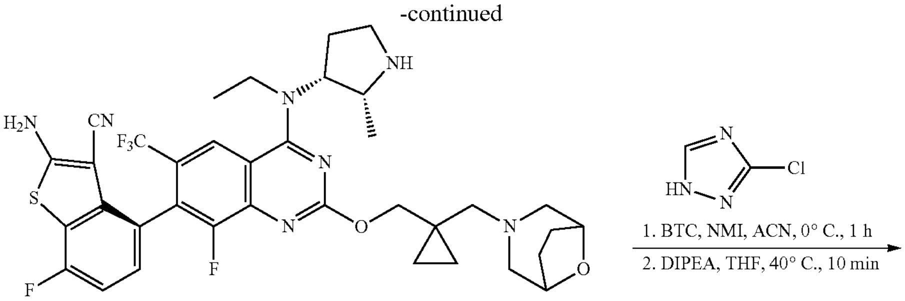

12-7

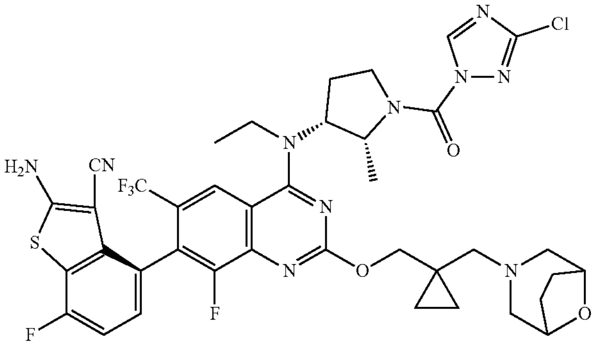

204

Step 1: To a stirred solution of ethyl 1-(hydroxymethyl) cyclopropane-1-carboxylate (12-1, 7 g, 48.61 mmol) in DCM (100 mL) were added TEA (14.72 g, 145 mmol), TsCl (12.0 g, 63.19 mmol) and DMAP (177 mg, 1.45 mmol) at 0° C. The reaction mixture was stirred at room temperature for 2 h, then diluted with EtOAc (100 mL) and washed with brine (50 mL×3). The organic layer was dried over anhydrous sodium sulfate, filtered and the filtrated was concentrated in vacuo. The crude product was purified by silica gel column chromatography (petroleum ether/EtOAc=10:1) to give ethyl 1-((tosyloxy)methyl)cyclopropane-1-carboxylate as a yellow oil (12-2, 8 g). MS (ESI) m/z=316.1 $[M+Na]^+$.

Step 2: To a stirred solution of 12-2 (8 g, 16.7 mmol) in MeCN (100 mL) were added 8-oxa-3-azabicyclo [3.2.1] octane hydrochloride (5.58 g, 37.4 mmol), $K_2CO_3$ (11.07 g, 80.3 mmol) and KI (4.44 g, 16.7 mmol). The reaction mixture was stirred for 16 hours, then diluted with EtOAc (100 mL) and washed with brine (50 mL×3). The organic layer was dried over anhydrous sodium sulfate, filtered and the filtrate was concentrated in vacuo. The crude product was purified by silica gel column chromatography (petroleum ether/EtOAc=3:1) to give ethyl 1-((8-oxa-3-azabicyclo [3.2.1]octan-3-yl)methyl) cyclopropane-1-carboxylate (12-3, 5 g) as a yellow oil. MS (ESI) m/z=240.2 $[M+H]^+$.

Step 3: To a solution of 12-3 (4 g, 16.7 mmol) in THF (60 mL) was added $LiAlH_4$ (1.3 g, 33.4 mmol) at 0° C. After stirring at room temperature for 2 h, the reaction mixture was quenched with water (30 mL). The mixture was filtered, the filter cake was rinsed with DCM:MeOH=10:1 (200 mL) and the filtrate was concentrated in vacuo. The crude product was purified by silica gel column chromatography (DCM: MeOH=10:1) to give (1-((8-oxa-3-azabicyclo[3.2.1]octan-3-yl)methyl)cyclopropyl) methanol (12A, 3 g) as a yellow oil. MS (ESI) m/z=198.2 $[M+H]^+$.

Step 4: To a stirred solution of tert-butyl (S)-(4-(2-chloro-8-fluoro-4-hydroxy-6-(trifluoromethyl) quinazolin-7-yl)-3-cyano-7-fluorobenzo[b]thiophen-2-yl)carbamate (12-4, 1.22 g, 2.19 mmol) in MeCN (30 mL) was added HCCP (837 mg, 2.41 mmol) and $K_3PO_4$ (698 mg, 3.3 mmol). The mixture was stirred for 1 h, then tert-butyl (2R,3R)-3-(ethylamino)-2-methyl pyrrolidine-1-carboxylate (650 mg, 2.85 mmol) was added. The mixture was stirred for an additional 1 h, then diluted with water (50 mL) and extracted with EtOAc (50 mL×3). The organic layer was washed with brine (50 mL), dried over anhydrous sodium sulfate, filtered and the filtrate was concentrated in vacuo. The crude product was purified by silica gel column chromatography (DCM: MeOH=10:1) to give tert-butyl (2R,3R)-3-((7-((S)-2-((tert-butoxycarbonyl)amino)-3-cyano-7-fluorobenzo[b]thiophen-4-yl)-2-chloro-8-fluoro-6-(trifluoromethyl)quinazolin-4-yl)(ethyl)amino)-2-methylpyrrolidine-1-carboxylate (12-5, 1.2 g) as a yellow solid. MS (ESI) m/z=767.0 $[M+H]^+$.

Step 5: To a solution of 12A (625 mg, 3.175 mmol) in MeCN (20 mL) was added NaH (522 mg, 13.06 mmol, 60%) at 0° C. The mixture was stirred at 0° C. for 20 min, then 12-5 (500 mg, 0.653 mmol) was added at room temperature. The resulting mixture was stirred at room temperature for 3 h, then diluted with water (50 mL) and extracted with EtOAc (50 mL×3). The organic layer was washed with brine (50 mL), dried over anhydrous sodium sulfate, filtered and the filtrate was concentrated in vacuo. The residue was purified by silica gel column chromatography (DCM:MeOH=10:1) to give tert-butyl (2R,3R)-3-((2-((1-((8-oxa-3-azabicyclo [3.2.1]octan-3-yl)methyl)cyclopropyl)methoxy)-7-((S)-2-((tert-butoxycarbonyl)amino)-3-cyano-7-fluorobenzo [b]thiophen-4-yl)-8-fluoro-6-(trifluoromethyl)quinazolin-4-yl)(ethyl)amino)-2-methylpyrrolidine-1-carboxylate (12-6, 600 mg) as an off-white oil. MS (ESI) m/z=928.1 $[M+H]^+$.

Step 6: To a solution of 12-6 (350 mg, 0.38 mmol) in DCM (3 mL) was added TFA (3 mL) and the resulting mixture was stirred for 1 h. The reaction mixture was concentrated under reduced pressure and the residue was diluted with DCM (80 mL) and washed with saturated $NaHCO_3$ aqueous solution (50 mL). The organic layer was concentrated and purified by silica gel column chromatography (DCM:$NH_3$MeOH=10:1) to give (4S)-4-(2-((1-((8-oxa-3-azabicyclo[3.2.1]octan-3-yl)methyl)cyclopropyl) methoxy)-4-(ethyl((2R,3R)-2-methylpyrrolidin-3-yl) amino)-8-fluoro-6-(trifluoromethyl)quinazolin-7-yl)-2-amino-7-fluorobenzo[b]thiophene-3-carbonitrile (12-7, 200 mg) as a yellow solid. MS (ESI) m/z=728.2 $[M+H]^+$.

Step 7: To a solution of 3-chloro-1H-1,2,4-triazole (60 mg, 0.58 mmol) in MeCN (2 mL) were added N-methylimidazole (19 mg, 0.23 mmol) and BTC (34 mg, 0.11 mmol) at 0° C. The reaction mixture was stirred at 0° C. for 1 h before a portion of the mixture (0.8 mL, 0.28 mmol) was transferred into a solution of 12-7 (100 mg, 0.14 mmol) and DIEA (106 mg, 0.83 mmol) in THF (6 mL) at 40° C. The reaction mixture was stirred at 40° C. for 5 min, then diluted with EtOAc (30 mL) and washed with brine (20 mL). The organic layer was dried over anhydrous sodium sulfate, filtered and the filtrated was concentrated in vacuo. The crude product was purified by prep-HPLC to give (4S)-4-(2-((1-((8-oxa-3-azabicyclo[3.2.1]octan-3-yl)methyl)cyclopropyl) methoxy)-4-(((2R,3R)-1-(3-chloro-1H-1,2,4-triazole-1-carbonyl)-2-methylpyrrolidin-3-yl)(ethyl)amino)-8-fluoro-6-(trifluoromethyl)quinazolin-7-yl)-2-amino-7-fluorobenzo[b]thiophene-3-carbonitrile (204) as a white solid (45.68 mg). MS (ESI) m/z=843.3 $[M+H]^+$. $^1H$ NMR (400 MHz, DMSO-$d_6$) δ 9.25 (s, 11), 8.25 (s, 11), 8.09 (s, 2H), 7.27 (s, 11), 7.16 (d, J=8.8 Hz, 11), 4.61 (d, J=53.0 Hz, 2H), 4.24- 3.89 (m, 7H), 2.65 (d, J=18.8 Hz, 4H), 2.43-2.33 (m, 3H), 2.14-2.11 (m, 3H), 1.70 (s, 1H), 1.49 (s, 3H), 1.25 (s, 3H), 1.03 (d, J=6.4 Hz, 3H), 0.61 (s, 2H), 0.37 (s, 2H).

Example 1m: Synthesis of (4R)-2-amino-4-(6-chloro-4-(((2R,3R)-1-(2,4-dimethyl-1H-imidazole-1-carbonyl)-2-methylpyrrolidin-3-yl)(ethyl)amino)-8-fluoro-2-((3-(((6-(trifluoromethyl)pyrimidin-4-yl) oxy)methyl)tetrahydro-1H-pyrrolizin-7a(5H)-yl) methoxy)quinazolin-7-yl)-7-fluorobenzo[b] thiophene-3-carbonitrile (197)

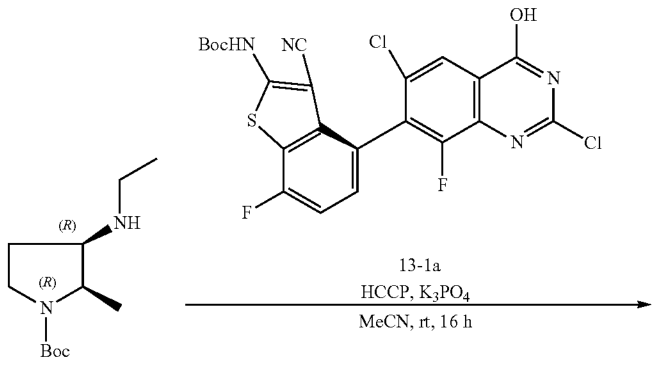

13-1

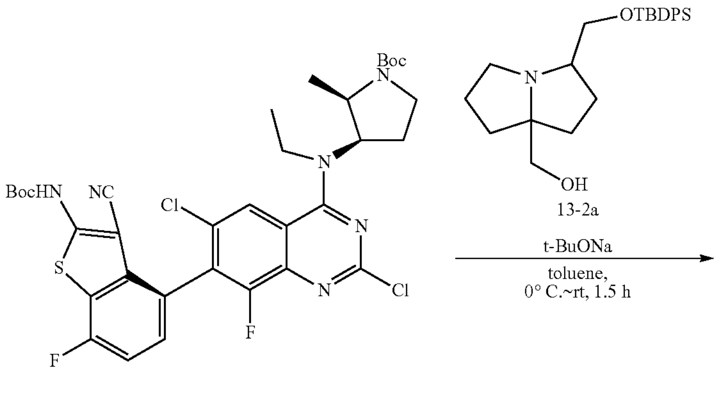

13-2

-continued
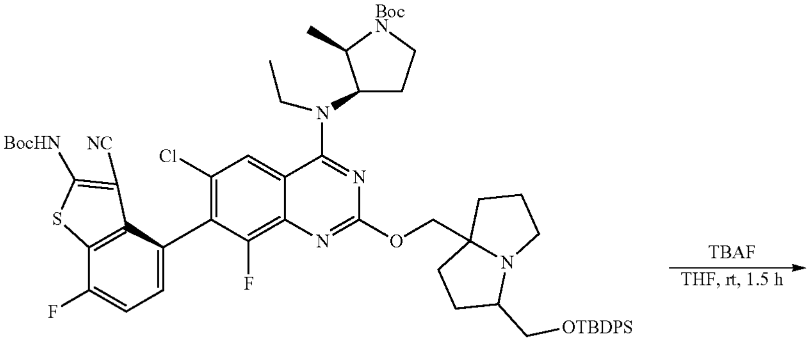
13-3
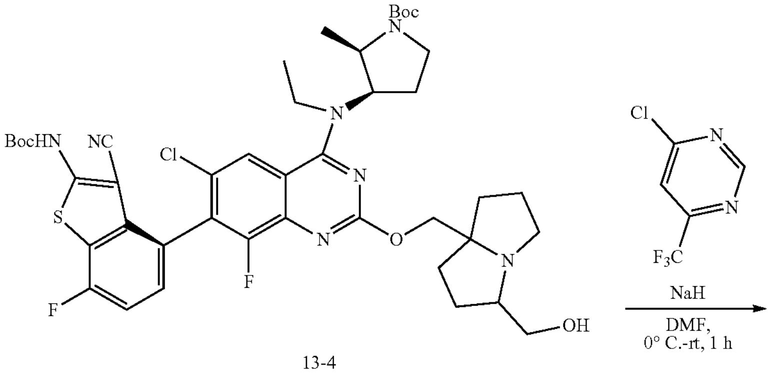
13-4
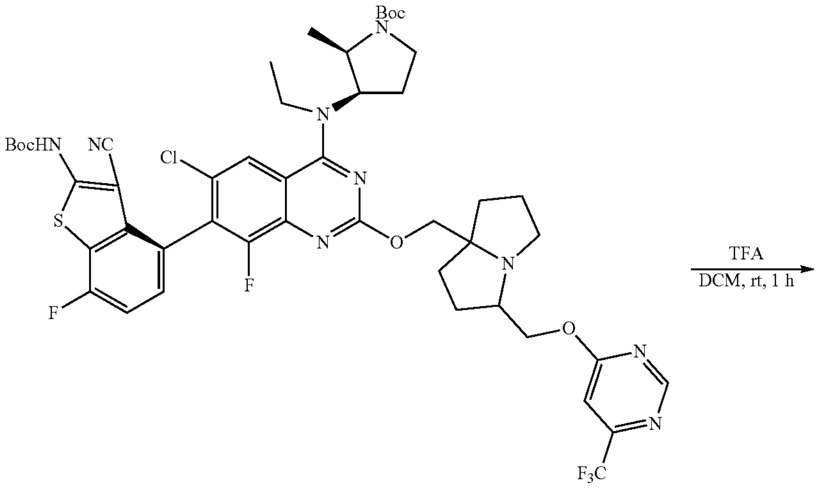
13-5

-continued

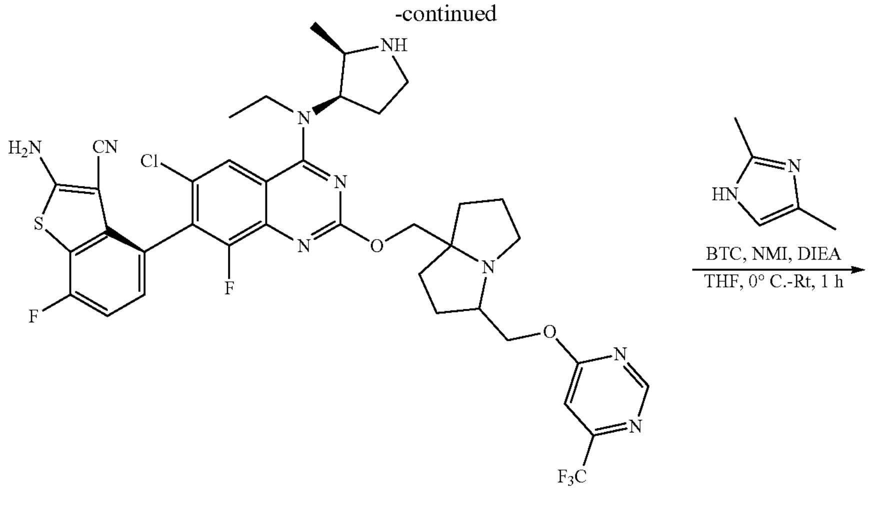

13-6

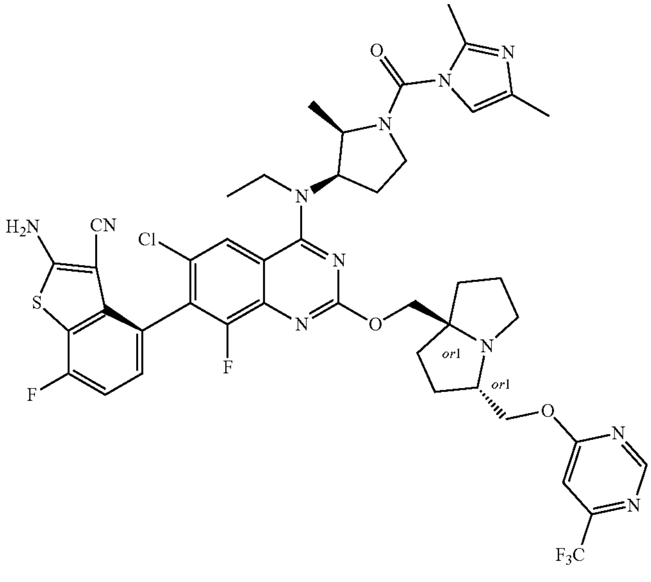

197

Step 1: To a solution of tert-butyl (R)-(3-cyano-4-(2,6-dichloro-8-fluoro-4-hydroxyquinazolin-7-yl)-7-fluorobenzo[b]thiophen-2-yl)carbamate (13-1a, 1.5 g, 2.32 mmol) and $K_3PO_4$ (1.23 g, 5.80 mmol) in MeCN (15 mL) was added HCCP (807 mg, 2.32 mmol). The reaction was stirred for 3 h, then tert-butyl (2R,3R)-3-(ethylamino)-2-methylpyrrolidine-1-carboxylate (13-1, 596 mg, 2.78 mmol) in ACN (5 mL) was added. The resulting mixture was stirred for 16 h, then ammonium hydroxide (4 mL) was added and the mixture stirred an additional 30 min. The mixture was then poured into ice water (20 mL) followed by extraction with ethyl acetate (100 mL×3). The organic layer was washed with brine (100 mL), dried over anhydrous sodium sulfate, filtered and the filtrate was concentrated to dryness under reduced pressure. The residue was purified by silica gel column chromatography (DCM/MeOH=15/1) to give tert-butyl (2R,3R)-3-((7-((R)-2-((tert-butoxycarbonyl)amino)-3-cyano-7-fluorobenzo[b]thiophen-4-yl)-2,6-dichloro-8-fluoroquinazolin-4-yl)(ethyl)amino)-2-methylpyrrolidine-1-carboxylate (13-2, 1.0 g) as a yellow solid. MS (ESI) m/z=733.3 $[M+H]^+$.

Step 2: To a solution of (3-(((tert-butyldiphenylsilyl)oxy)methyl)tetrahydro-1H-pyrrolizin-7a(5H)-yl)methanol (13-2a, trans isomer, 377 mg, 0.922 mmol) and 4 Å MS (500 mg) in toluene (4.5 mL) at 0° C. was added NaOtBu (295 mg, 3.073 mmol). After the mixture was stirred at 0° C. for 30 min, 13-2 (450 mg, 0.615 mmol) was added and the resulting mixture was stirred at room temperature for 1 h. The reaction mixture was then diluted with EtOAc (200 mL) and washed with saturated $NH_4Cl$ aqueous solution (50 mL) and brine (50 mL). The organic phase was dried over anhydrous sodium sulfate, filtered and the filtrate was concentrated in vacuo. The residue was purified by silica gel flash column chromatography to give tert-butyl (2R,3R)-3-((7-((R)-2-((tert-butoxycarbonyl)amino)-3-cyano-7-fluorobenzo[b]thiophen-4-yl)-2-((3-(((tert-butyldiphenylsilyl)oxy) methyl)tetrahydro-1H-pyrrolizin-7a(5H)-yl)methoxy)-6-chloro-8-fluoroquinazolin-4-yl)(ethyl)amino)-2-methylpyrrolidine-1-carboxylate (13-3, 472 mg) as a white solid. MS (ESI) m/z=1106.5 $[M+H]^+$.

Step 3: To a solution of 13-3 (422 mg, 0.382 mmol) in THF (8 mL) was added TBAF (0.76 mL, 0.763 mmol). The mixture was stirred for 15 h, then diluted with EtOAc (200 mL) and washed with water (50 mL). The organic phase was dried over anhydrous sodium sulfate, filtered and the filtrate was concentrated in vacuo. The residue was purified by preparative TLC to give tert-butyl (2R,3R)-3-((7-((R)-2-((tert-butoxycarbonyl)amino)-3-cyano-7-fluorobenzo[b]thiophen-4-yl)-6-chloro-8-fluoro-2-((3-(hydroxymethyl)tetrahydro-1H-pyrrolizin-7a(5H)-yl)methoxy)quinazolin-4-yl)(ethyl)amino)-2-methylpyrrolidine-1-carboxylate (13-4, 255 mg) as a white solid. MS (ESI) m/z=868.3 $[M+H]^+$.

Step 4: To a solution of 13-4 (100 mg, 0.115 mmol) in DMF (5 mL) was added NaH (7 mg, 0.173 mmol) at 0° C. After the mixture was stirred at 0° C. for 10 min, 4-chloro-6-(trifluoromethyl)pyrimidine (31.6 mg, 0.173 mmol) was added. The reaction was stirred at room temperature for 1 h, then quenched with saturated $NH_4Cl$ solution (30 mL) and extracted with EtOAc (3×50 mL). The organic phase was washed with brine, dried over saturated sodium sulfate, filtered and the filtrated was concentrated in vacuo. The residue was purified by preparative TLC to give tert-butyl (2R,3R)-3-((7-((R)-2-((tert-butoxycarbonyl)amino)-3-cyano-7-fluorobenzo[b]thiophen-4-yl)-6-chloro-8-fluoro-2-((3-(((6-(trifluoromethyl)pyrimidin-4-yl)oxy)methyl)tetrahydro-1H-pyrrolizin-7a(5H)-yl)methoxy)quinazolin-4-yl)(ethyl)amino)-2-methylpyrrolidine-1-carboxylate (13-5, 143 mg) as a white solid. MS (ESI) m/z=1013.7 $[M+H]^+$.

Step 5: To a solution of 13-5 (130 mg, 0.128 mmol) in DCM (2 mL) was added TFA (2 mL). The mixture was stirred for 60 min, then concentrated under reduced pressure. Then residue was treated with $NH_3$·MeOH (50 mL) and concentrated again under reduced pressure. The residue was purified by preparative TLC to give (4R)-2-amino-4-(6-chloro-4-(ethyl((2R,3R)-2-methylpyrrolidin-3-yl)amino)-8-fluoro-2-((3-(((6-(trifluoromethyl)pyrimidin-4-yl)oxy)methyl)tetrahydro-1H-pyrrolizin-7a(5H)-yl)methoxy)quinazolin-7-yl)-7-fluorobenzo[b]thiophene-3-carbonitrile (13-6, 93 mg). MS (ESI) m/z=813.6 $[M+H]^+$.

Step 6: To a solution of 2,4-dimethylimidazole (106 mg, 1.107 mmol) and N-methylimidazole (36 mg, 0.443 mmol) in THF (10 mL) was added BTC (65.7 mg, 0.221 mmol) at 0° C. and the resulting mixture was stirred at 0° C. for 30 min. Next, a portion of the mixture (5 mL) was transferred to a solution of 13-6 (36 mg, 0.044 mmol) and DIEA (51 mg, 0.399 mmol) in THF (2 mL). The resulting mixture was stirred at room temperature for 10 min, then diluted with EtOAc (200 mL) and washed with brine (50 mL). The organic phase was dried over anhydrous sodium sulfate, filtered and the filtrate was concentrated under reduced pressure. The residue was purified by prep-HPLC to give (4R)-2-amino-4-(6-chloro-4-(((2R,3R)-1-(2,4-dimethyl-1H-imidazole-1-carbonyl)-2-methylpyrrolidin-3-yl)(ethyl)amino)-8-fluoro-2-((3-(((6-(trifluoromethyl)pyrimidin-4-yl)oxy)methyl)tetrahydro-1H-pyrrolizin-7a(5H)-yl)methoxy)quinazolin-7-yl)-7-fluorobenzo[b]thiophene-3-carbonitrile (197, 15.88 mg). MS (ESI) m/z=936.2 $[M+H]^+$. $^1$H NMR (400 MHz, DMSO-d6) δ 8.99 (s, 1H), 8.11 (s, 2H), 7.99 (s, 1H), 7.54 (s, 1H), 7.20-7.16 (m, 11), 7.18-7.14 (m, 1H), 7.12-7.04 (m, 1H), 4.76-4.52 (m, 4H), 4.20-4.12 (m, 2H), 3.98-3.86 (m, 1H), 3.76-3.64 (m, 2H), 3.56-3.48 (m, 2H), 2.80-2.72 (m, 2H), 2.42-2.26 (m, 5H), 2.10-2.02 (m, 4H), 1.86-1.70 (m, 6H), 1.64-1.52 (m, 1H), 1.16-1.04 (m, 3H), 0.91 (s, 3H).

Example 2: Ras Sequences

```
Human K-Ras Wildtype sequence (SEQ ID NO. 1)
  1    MTEYKLVVVG AGGVGKSALT IQLIQNHFVD EYDPTIEDSY RKQVVIDGET

 51    CLLDILDTAG QEEYSAMRDQ YMRTGEGFLC VFAINNTKSF EDIHHYREQI

101    KRVKDSEDVP MVLVGNKCDL PSRTVDTKQA QDLARSYGIP FIETSAKTRQ

151    GVDDAFYTLV REIRKHKEKM SKDGKKKKKK SKTKCVIM

Human K-Ras G12D (SEQ ID NO. 2)
  1    MTEYKLVVVG ADGVGKSALT IQLIQNHFVD EYDPTIEDSY RKQVVIDGET

 51    CLLDILDTAG QEEYSAMRDQ YMRTGEGFLC VFAINNTKSF EDIHHYREQI

101    KRVKDSEDVP MVLVGNKCDL PSRTVDTKQA QDLARSYGIP FIETSAKTRQ

151    GVDDAFYTLV REIRKHKEKM SKDGKKKKKK SKTKCVIM

Human K-Ras G12V (SEQ ID NO. 3)
  1    MTEYKLVVVG AVGVGKSALT IQLIQNHFVD EYDPTIEDSY RKQVVIDGET

 51    CLLDILDTAG QEEYSAMRDQ YMRTGEGFLC VFAINNTKSF EDIHHYREQI

101    KRVKDSEDVP MVLVGNKCDL PSRTVDTKQA QDLARSYGIP FIETSAKTRQ

151    GVDDAFYTLV REIRKHKEKM SKDGKKKKKK SKTKCVIM

Human K-Ras G12S (SEQ ID NO. 4):
  1    MTEYKLVVVG ASGVGKSALT IQLIQNHFVD EYDPTIEDSY RKQVVIDGET

 51    CLLDILDTAG QEEYSAMRDQ YMRTGEGFLC VFAINNTKSF EDIHHYREQI

101    KRVKDSEDVP MVLVGNKCDL PSRTVDTKQA QDLARSYGIP FIETSAKTRQ

151    GVDDAFYTLV REIRKHKEKM SKDGKKKKKK SKTKCVIM
```

-continued

```
Human N-Ras wildtype (SEQ ID NO. 5)
  1    MTEYKLVVVG AGGVGKSALT IQLIQNHFVD EYDPTIEDSY RKQVVIDGET

 51    CLLDILDTAG QEEYSAMRDQ YMRTGEGFLC VFAINNSKSF ADINLYREQI

101    KRVKDSDDVP MVLVGNKCDL PTRTVDTKQA HELAKSYGIP FIETSAKTRQ

151    GVEDAFYTLV REIRQYRMKK LNSSDDGTQG CMGLPCVVM

Human H-Ras G12D (SEQ ID NO. 6)
  1    MTEYKLVVVG ADGVGKSALT IQLIQNHFVD EYDPTIEDSY RKQVVIDGET

 51    CLLDILDTAG QEEYSAMRDQ YMRTGEGFLC VFAINNTKSF EDIHQYREQI

101    KRVKDSDDVP MVLVGNKCDL AARTVESRQA QDLARSYGIP YIETSAKTRQ

151    GVEDAFYTLV REIRQHKLRK LNPPDESGPG CMSCKCVLS

Human H-Ras wildtype (SEQ ID NO. 7)
  1    MTEYKLVVVG AGGVGKSALT IQLIQNHFVD EYDPTIEDSY RKQVVIDGET

 51    CLLDILDTAG QEEYSAMRDQ YMRTGEGFLC VFAINNTKSF EDIHQYREQI

101    KRVKDSDDVP MVLVGNKCDL AARTVESRQA QDLARSYGIP YIETSAKTRQ

151    GVEDAFYTLV REIRQHKLRK LNPPDESGPG CMSCKCVLS

Human N-Ras G12D (SEQ ID NO. 8)
  1    MTEYKLVVVG ADGVGKSALT IQLIQNHFVD EYDPTIEDSY RKQVVIDGET

 51    CLLDILDTAG QEEYSAMRDQ YMRTGEGFLC VFAINNSKSF ADINLYREQI

101    KRVKDSDDVP MVLVGNKCDL PTRTVDTKQA HELAKSYGIP FIETSAKTRQ

151    GVEDAFYTLV REIRQYRMKK LNSSDDGTQG CMGLPCVVM

Human K-Ras G12C (SEQ ID NO. 9):
  1    MTEYKLVVVG ACGVGKSALT IQLIQNHFVD EYDPTIEDSY RKQVVIDGET

 51    CLLDILDTAG QEEYSAMRDQ YMRTGEGFLC VFAINNTKSF EDIHHYREQI

101    KRVKDSEDVP MVLVGNKCDL PSRTVDTKQA QDLARSYGIP FIETSAKTRQ

151    GVDDAFYTLV REIRKHKEKM SKDGKKKKKK SKTKCVIM
```

Example 3: Protein Expression

DNA expression constructs encoding one or more protein sequences of interest (e.g., KRAS fragments thereof, mutant variants thereof, etc.) and its corresponding DNA sequences are optimized for expression in *E. coli* and synthesized by, for example, the GeneArt Technology at Life Technologies. In some cases, the protein sequences of interest are fused with a tag (e.g., glutathione S-transferase (GST), histidine (His), or any other affinity tags) to facilitate recombinant expression and purification of the protein of interest. Such tag can be cleaved subsequent to purification. Alternatively, such tag may remain intact to the protein of interest and may not interfere with activities (e.g., target binding and/or phosphorylation) of the protein of interest.

A resulting expression construct is additionally encoded with (i) att-site sequences at the 5' and 3' ends for subcloning into various destination vectors using, for example, the Gateway Technology, as well as (ii) a Tobacco Etch Virus (TEV) protease site for proteolytic cleavage of one or more tag sequences. The applied destination vectors can be a pET vector series from Novagen (e.g., with ampicillin resistance gene), which provides an N-terminal fusion of a GST-tag to the integrated gene of interest and/or a pET vector series (e.g., with ampicillin resistance gene), which provides an N-terminal fusion of a HIS-tag to the integrated gene. To generate the final expression vectors, the expression construct of the protein of interest is cloned into any of the applied destination vectors. The expression vectors are transformed into an *E. coli* strain, e.g., BL21 (DE3). Cultivation of the transformed strains for expression is performed in a 10 L or 1 L fermenter. The cultures are grown, for example, in Terrific Broth media (MP Biomedicals, Kat. #1 13045032) with 200 μg/mL ampicillin at a temperature of 37° C. to a density of 0.6 (OD600), shifted to a temperature of ~27° C. (for K-Ras expression vectors) induced for expression with 100 mM IPTG, and further cultivated for 24 hours. After cultivation, the transformed *E. coli* cells are harvested by centrifugation and the resulting pellet is suspended in a lysis buffer, as provided below, and lysed by passing three-times through a high-pressure device. The lysate is centrifuged (49000 g, 45 min, 4° C.) and the supernatant is used for further purification.

Example 4: Ras Protein Purification

A Ras (e.g., K-Ras wildtype or a mutant such as K-Ras G12S, K-Ras G12D, K-Ras G12V or K-Ras G12C) construct or a variant thereof is tagged with GST. *E. coli* culture from a 10 L fermenter is lysed in lysis buffer (50 mM Tris HCl 7.5, 500 mM NaCl, 1 mM DTT, 0.5% CHAPS, Complete Protease Inhibitor Cocktail-(Roche)). As a first chromatography step, the centrifuged lysate is incubated with 50 mL Glutathione Agarose 4B (Macherey-Nagel; 745500.100) in a spinner flask (16 h, 10° C.). The Glutathione Agarose 4B loaded with protein is transferred to a chromatography column connected to a chromatography system, e.g., an Akta chromatography system. The column is washed with wash buffer (50 mM Tris HCl 7.5, 500 mM NaCl, 1 mM DTT) and the bound protein is eluted with elution buffer (50 mM Tris HCl 7.5, 500 mM NaCl, 1 mM DTT, 15 mM glutathione). The main fractions of the elution peak (monitored by OD280) are pooled. For further purification by size-exclusion chromatography, the above eluate volume is applied to a column Superdex 200 HR prep grade (GE Healthcare) and the resulting peak fractions of the eluted fusion protein is collected. Native mass spectrometry analyses of the final purified protein construct can be performed to assess its homogeneous load with GDP.

Example 5: HTRF (Homogenous Time-Resolved Fluorescence) Resonance Energy Transfer Assay The ability of a compound of the present disclosure to reduce Ras signaling output can be demonstrated by an HTRF assay. This assay can be also used to assess a selective inhibition or reduction of signaling output of a mutant Ras protein relative to a wildtype, or relative to a different mutant Ras protein. For example, the equilibrium interaction of wildtype KRAS or K-Ras mutant (e.g., wildtype or a mutant thereof) with SOS1 (e.g., hSOS1) can be assessed as a proxy or an indication for the ability of a subject compound to bind and inhibit Ras protein. The HTRF assay detects from (i) a fluorescence resonance energy transfer (FRET) donor (e.g., antiGST-Europium) that is bound to GST-tagged K-Ras mutant to (ii) a FRET acceptor (e.g., anti-6His-XL665) bound to a His-tagged hSOSL1.

The assay buffer can contain ~5 mM HEPES pH 7.4, ~150 mM NaCl, ~1 mM DTT, 0.05% BSA and 0.0025% (v/v) Igepal. A Ras working solution is prepared in an assay buffer containing typically a suitable amount of the protein construct (e.g., GST-tagged K-Ras mutant) and the FRET donor (e.g., antiGST-Eu(K) from Cisbio, France). A SOS1 working solution is prepared in an assay buffer containing suitable amount of the protein construct (e.g., His-hSOS1) and the FRET acceptor (e.g., anti-6His-XL665 from Cisbio, France). A suitable amount of the protein construct will depend on the range of activity or range of IC50 values being detected or under investigation. For detecting an IC50 within a range of 500 nM, the protein constructs of the same range of molarity can be utilized. An inhibitor control solution is prepared in an assay buffer containing a comparable amount of the FRET acceptor without the SOS1 protein.

A fixed volume of DMSO with or without test compound is transferred into a 384-well plate. Ras working solution is added to all wells of the test plate. SOS1 working solution is added to all wells except for those that are subsequently filled with inhibitor control solution. Upon incubation for about 10 minutes or longer, the fluorescence is measured with a M1000Pro plate reader (Tecan) using HTRF detection (excitation 337 nm, emission 1: 620 nm, emission 2: 665 nm). Compounds are tested in duplicate at different concentrations (for example, 10 μM, 2.5 μM, 0.63 μM, 0.16 μM, 0.04 μM, 0.01 μM test compound). The ratiometric data (i.e., emission 2 divided by emission 1) is used to calculate IC50 values against Ras using GraphPad Prism (GraphPad software). Signaling output measured in terms of IC50 values can be obtained and a ratio of IC50 against one mutant relative to another mutant can be calculated. For instance, a selective reduction of K-Ras G12S signaling output can be evidenced by a ratio greater than one. In particular, a selective reduction of K-Ras G12S signaling relative to K-Ras WT signaling is evidenced if the ratio of IC50 (against K-Ras WT) to IC50 (against K-Ras G12S) is greater than 1. In some embodiments, one or more subject compounds disclosed herein are expected to exhibit selective inhibition of a Ras mutant (e.g., G12C, G12S, or G13C) over WT by at least 1-fold, and in some instances greater than 2-, 3-, 4- or 5-fold. In some embodiments, subject compounds are expected to exhibit an IC50 against KRas mutants (e.g., G12C or G12S) less than 500 nM, such as less than 100 nM, 50 nM, or even less. For example, Compound 197 was found to exhibit an IC50 of <5 nM against each of KRAS G121, KRAS G12V, and KRAS G12S.

The ability of one or more compounds exemplified in Table 1 to inhibit wildtype KRAS or a KRAS mutant is demonstrated utilizing the procedures described above. Table 2 shows the resulting IC50 values of exemplary compounds against KRAS G121D, KRAS G12V, KRAS G12S, and wildtype KRAS using the HTRF assay described herein. Compound numbers correspond to the numbers and structures provided in Table 1.

TABLE 2

| | <500 nM | 500 nM to 1000 nM |
|---|---|---|
| Inhibition of KRAS G12D ($IC_{50}$) | 101, 102, 104, 105, 106, 107, 108, 109, 110, 111, 112, 113, 114, 115, 116, 117, 118, 119, 120, 121, 123, 124, 125, 126, 127, 128, 129, 130, 131, 132, 134, 135, 136, 137, 138, 139, 140, 141, 144, 145, 146, 147, 148, 149, 150, 151, 152, 153, 154, 156, 157, 158, 159, 160, 161, 162, 163, 164, 165, 168, 169, 170, 171, 172, 173, 174, 175, 176, 177, 178, 179, 180, 181, 182, 183, 184, 185, 186, 187, 188, 189, 190, 191, 192, 193, 194, 195, 197, 198, 199, 200, 201, 202, 203, 204, 205, 206, 207, 208, 209, 210, 211, 212, 213, 214, 215, 217, 218, 219, 220 | 196, 216 |
| Inhibition of KRAS WT ($IC_{50}$) | 101, 102, 104, 105, 106, 107, 108, 109, 110, 111, 112, 113, 114, 115, 116, 117, 118, 119, 120, 121, 123, 124, 125, 126, 127, 128, 129, 130, 131, 132, 134, 135, 136, 137, 138, 139, 140, 141, 144, 145, 146, 147, 148, 149, 150, 151, 152, 153, 154, 156, 157, 158, 159, 160, 161, 162, 163, 164, 165, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 209, 210, 211, 212, 213, 214, 215, 216, 217, 218, 219, 220 | 208 |

TABLE 2-continued

| | <500 nM | 500 nM to 1000 nM |
|---|---|---|
| Inhibition of KRAS G12V ($IC_{50}$) | 101, 102, 104, 105, 106, 107, 108, 109, 110, 111, 112, 113, 114, 115, 116, 117, 118, 119, 120, 121, 123, 124, 125, 126, 127, 128, 129, 130, 131, 132, 134, 135, 136, 137, 138, 139, 140, 141, 144, 145, 146, 147, 148, 149, 150, 151, 152, 153, 154, 156, 157, 158, 159, 160, 161, 162, 163, 164, 165, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 | n/a |
| Inhibition of KRAS G12S ($IC_{50}$) | 101, 102, 104, 105, 106, 107, 108, 109, 110, 111, 112, 113, 114, 115, 116, 117, 118, 119, 120, 121, 123, 124, 125, 126, 127, 128, 129, 130, 131, 132, 134, 135, 136, 137, 138, 139, 140, 141, 144, 145, 146, 147, 148, 149, 150, 151, 152, 153, 154, 156, 157, 158, 159, 160, 161, 162, 163, 164, 165, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 | n/a |

Example 6: GTPase Activity Assay

The ability of a compound of the present disclosure to inhibit Ras protein signaling can be demonstrated by a reduced GTPase activity. This assay can also be used to assess selective inhibition of a mutant Ras protein relative to a wildtype or different mutant Ras protein. For instance, the assay can be used to establish a subject compound's ability to selectively inhibit KRAS G12S relative to wildtype, KRAS G12S relative to KRAS G12V, KRAS G12S relative to KRAS G12D, KRAS G12C relative to KRAS G12D, or KRAS G12C relative to KRAS G12V or wildtype. In particular, intrinsic and GTPase-activating protein (GAP)-stimulated GTPase activity for a K-Ras construct or a mutant thereof can be measured using EnzCheck phosphate assay system (Life Technologies). For example, K-Ras WT, K-Ras D154Q mutant, K-Ras G12D mutant, K-Ras G12S mutant, and K-Ras G12D/D154Q mutant proteins (2.5 mg/mL) in buffer (20 mmol/L Tris, pH 8.0, 50 mM NaCl) are loaded with GTP at room temperature for 2 hours by exposing to exchange buffer containing EDTA. Proteins are buffer exchanged to assay buffer (30 mM Tris, pH 7.5, 1 mM DTT) and the concentration is adjusted to 2 mg/mL. GTP loading is verified by back extraction of nucleotide using 6M urea and evaluation of nucleotide peaks by HPLC using an ion-exchange column. The assay is performed in a clear 384-well plate (Costar) by combining GTP-loaded K-Ras proteins (50 mM final) with 2-amino-6-mercapto-7-methyl-purine ribonucleoside (MESG) (200 mM final), and purine nucleotide phosphorylase (5 U/mL final). GTP hydrolysis is initiated by the addition of $MgCl_2$ at a working concentration of 40 mM. For GAP stimulation, Ras p21 protein activator 1 (P120GAP) can be included at 50 mM. Absorbance at 360 nm can be measured every 8 to 15 s for 1,000 s at 20° C. Samples are tested with or without a subject compound disclosed herein to assess the ability of each compound to inhibit signaling of a given Ras protein (e.g., a given mutant KRAS) of interest.

Example 7: Nucleotide Exchange Assay

The ability of a compound of the present disclosure to inhibit Ras protein signaling can be demonstrated by reduced nucleotide exchange activity. This assay can be also used to assess selective inhibition of a mutant Ras protein relative to a wildtype or different mutant Ras protein. For example, 250 nM or 500 nM GDP-loaded K-Ras protein (e.g., wildtype or a mutant thereof, including those mentioned in Example 4) is incubated with different concentrations of compounds (for example ~60 μM, ~20 μM, ~6.7 μM, ~2.2 μM, ~0.7 μM, or ~0.2 μM subject compound). A control reaction without subject compound is also included. SOS1 (catalytic domain) protein is added to the K-Ras protein solution. The nucleotide exchange reaction is initiated by adding fluorescent labelled GDP (guanosine 5'-diphosphate, BODIPY™ FL 2'-(or -3')-O—(N-(2-aminoethyl) urethane) to a final concentration of 0.36 μM. Fluorescence is measured every 30 s for 70 minutes at 490 nm/515 nm (excitation/emission) in a M1000Pro plate reader (Tecan). Data is exported and analyzed to calculate an IC50 using GraphPad Prism (GraphPad Software). Sample(s) can be tested with or without a subject compound disclosed herein to assess the ability of the compound to inhibit K-Ras signaling or its IC50 against a given Ras protein (e.g., a given mutant K-Ras) of interest.

Example 8: Testing for Modification of Ras Protein Via Covalent Binding

Test compounds are prepared as 10 mM stock solutions in DMSO (Fisher cat #BP231-100). KRAS protein (His-tagged GDP-loaded wildtype 1-169, His-tagged GDP-loaded G12S 1-169 or His-tagged GDP-loaded G12D 1-169) is diluted to ~2 μM in appropriate buffer (e.g., a Hepes buffer at physiological conditions). For testing KRAS modification, compounds are diluted to 50× final test concentration in DMSO in 96-well storage plates. 2 μL of the diluted 50× compounds are added to appropriate wells in the PCR plate (Fisher cat #AB-0800). ~49 μL of the stock protein solution is added to each well of the 96-well PCR plate. Reactions are mixed carefully. The plate is sealed well with aluminum plate seal and stored in a drawer at room temperature for 24 hrs. 5 μL of 2% formic acid (Fisher cat #A117-50) in MilliQ $H_2O$ is then added to each well followed by mixing with a pipette. The plate is then resealed with aluminum seal and stored until mass spectrometry analysis.

The extent of covalent modification of KRAS proteins can be determined by liquid chromatography electrospray mass spectrometry analysis of the intact proteins on a Thermo Q-Exactive Plus mass spectrometer. 20 μL of sample is injected onto a bioZen 3.6 μm Intact $C_4$ column (Phenomenex cat #OOB-4767-AN) placed in a column oven set to 40° C. and separated using a suitable LC gradient from ~20% to ~60% solvent B. Solvent A is 0.1% formic acid and solvent B is 0.1% formic acid in acetonitrile. HESI source settings are set to 40, 5 and 1 for the sheath, auxiliary and sweep gas flow, respectively. The spray voltage is 4 kV, and the capillary temperature is 320° C. S-lens RF level is 50 and auxiliary gas heater temperature is set to 200° C. The mass spectrometry is acquired using a scan range from 650 to 1750 m/z using positive polarity at a mass resolution of 70,000, AGC target of 1e6 ions and maximum injection time of 250 ms. The recorded protein mass spectrum is deconvoluted from the raw data file using Protein Deconvolution v4.0 (Thermo). The protein mass and adduct masses are exported with their peak intensities. The peak intensities for the unmodified and modified protein are used to calculate the percent covalent modification of the KRAS protein based on the following equation: % KRAS protein modification=((KRAS−compound)/(KRAS)+(KRAS−Compound))*100.

Example 9: Ras Cellular Assay

The ability of a compound of the present disclosure to inhibit Ras protein signaling can be demonstrated by inhibiting growth of a given KRAS mutant cell line. For example, this assay can be also used to assess selective growth inhibition of a mutant Ras protein relative to a wildtype or different mutant Ras protein.

a. Growth of Cells with K-Ras G12C Mutation

MIA PaCa-2 (ATCC CRL-1420) and NCI-H1792 (ATCC CRL-5895) cell lines comprise a G12C mutation and can be used to assess Ras cellular signaling in vitro, e.g., in response to an inhibitor compound of the present disclosure. This cellular assay can also be used to discern selective inhibition of a subject compound against certain types of KRAS mutants, e.g., more potent inhibition against KRAS G12C relative to KRAS G12D mutant, by comparing inhibition of MIA PaCa-2 (G12C driven tumor cell line) to inhibition of GP2d (G12D driven tumor cell line). MIA PaCa-2 culture medium is prepared with DMEM/Ham's F12 (e.g., with stable glutamine, 10% FCS, and 2.5% horse serum. NCI-H1792 culture medium is prepared with RPMI 1640 (e.g., with stable glutamine) and 10% FCS.

On a first day (e.g., Day 1), Softagar (Select Agar, Invitrogen, 3% in dd$H_2O$ autoclaved) is boiled and tempered at 48° C. Appropriate culture medium (i.e., medium) is tempered to 37° C. Agar (3%) is diluted 1:5 in medium (=0.6%) and plated into 96 well plates (Corning, #3904), then incubated at room temperature for agar solidification. A 3% agar is diluted to 0.25% in medium (1:12 dilution) and tempered at 42° C. Cells are trypsinized, counted, and tempered at 37° C. The cells (e.g., MIA PaCa-2 at about 125-150 cells, NCI-H1792 at about 1000 cells) are resuspended in 100 mL 0.25% Agar and plated, followed by incubation at room temperature for agar solidification. The wells are overlaid with 50 mL of the medium. Sister wells in a separate plate are plated for time zero determination. All plates are incubated overnight at 37° C. and 5% $CO_2$.

On a second day (e.g., Day 2), time zero values are measured. A 40 mL volume of Cell Titer 96 Aqueous Solution (Promega) is added to each well and incubated in the dark at 37° C. and 5% $CO_2$. Absorption can be measured at 490 nm and reference wavelength 660 nm. DMSO-prediluted test compounds are added to wells of interest, e.g., with HP Dispenser, to one or more desired concentrations (e.g., a final DMSO concentration of 0.3%).

On a tenth day (e.g., Day 10), absorption by wells treated with the test compounds and control wells are measured with, for example, Cell Titer 96 AQueous and analyzed in comparison to the time zero measurements. The IC50 values are determined using the four parameter fit. The resulting IC50 value is a measurement of the ability of the test compound to reduce cell growth of Ras-driven cells (e.g., tumor cell lines) in vitro and/or in vivo. One or more compounds disclosed herein is expected to exhibit an IC50 value less than 5 μM, 1 μM, 100 nM, or even less, against one or more KRAS G12C cell line (including MIA PaCa-2 and NCI-H1792). For example, Compound 197 was found to exhibit an IC50 against MiaPaca2 cells of 0.42 nM.

b. Growth of Cells with K-Ras G12S Mutation

A549 (ATCC CRL-185) and LS123 (ATCC CRL-255) cell lines comprise a G12S mutation and can be used to assess Ras cellular signaling in vitro, e.g., in response to treatment with a compound described herein. A549 culture medium is prepared with RPMI-1640 and 10% heat-inactivated FBS. LS123 culture medium is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384WZ). The day after plating, cells are treated with a dilution series (e.g., a 10 point, 3-fold dilution series) of the compounds herein (e.g., approximately 40 μL final volume per well). Cell viability can be monitored (e.g., approximately 6 days later) according to the manufacturer's recommended instructions, where CellTiter-Glo reagent is added (e.g., approximately 10 μL), vigorously mixed, covered, and placed on a plate shaker (e.g., approximately for 20 min) to ensure sufficient cell lysis prior to assessment of luminescent signal. The IC50 values are determined using the four parameter fit. The resulting IC50 value is a measurement of the ability of the test compound to reduce cell growth of Ras-driven cells (e.g., tumor cell lines) in vitro and/or in vivo. One or more compounds disclosed herein is expected to exhibit an IC50 value less than 5 μM, 1 μM, 100 nM, or even less, against one or more KRAS G12S cell line (including A549 and LS123). For example, Compound 197 was found to exhibit an IC50 against LS123 cells of 4.6 nM.

Table 3 shows the resulting IC50 values of exemplary compounds against MiaPaca2 cells using the cell proliferation assays described herein. Compound numbers correspond to the numbers and structures provided in Table 1.

TABLE 3

| | ≤500 nM | >500 nM |
|---|---|---|
| Inhibition of MiaPaca2 Cells ($IC_{50}$) | 101, 102, 104, 106, 107, 108, 109, 110, 111, 112, 114, 115, 116, 117, 118, 119, 120, 121, 123, 124, 125, 126, 127, 128, 130, 131, 134, 135, | 216 |

TABLE 3-continued

| ≤500 nM | >500 nM |
|---|---|
| 136, 137, 138, 139, 140, 141, 144, 145, 146, 147, 148, 149, 150, 151, 152, 153, 154, 156, 157, 158, 159, 160, 161, 162, 163, 164, 165, 168, 169, 170, 171, 172, 173, 174, 175, 176, 177, 178, 179, 180, 181, 182, 183, 184, 185, 186, 187, 188, 189, 191, 192, 193, 194, 195, 196, 197, 198, 199, 200, 201, 202, 204, 205, 208, 209, 210, 211, 212, 213, 214, 215, 217, 218, 220 | |

Example 10: In Vivo Ras Inhibition

The in vivo reduction in Ras signaling output by a compound of the present disclosure is determined in a mouse tumor xenograft model, particularly by using a mutant K-Ras model including without limitation a K-Ras G12S model, a K-Ras G12C model, a K-Ras G12D model, a K-Ras G13D model, and a K-Ras G13C model. These models can be generated by the methods and procedures described below. In particular, the methods disclosed below involving the use of a K-Ras G12S mutant cell line for generating a K-Ras G12S xenograft model can be applied to other K-Ras mutant animal models using the respective K-Ras mutant cell lines described above.

Xenograft with K-Ras G12D, G12C, or G12S Mutation

Tumor xenografts are established by administration of tumor cells with a K-Ras G12D mutation (e.g., ASPC-1 cells), a K-Ras G12C mutation (e.g., MIA PaCa-2 cells), or a K-Ras G12S mutation (e.g., A549 or LS123 cells) into mice. Female 6- to 8-week-old athymic BALB/c nude (NCr) nu/nu mice are used for xenografts. The tumor cells (e.g., approximately $5\times10^6$) are harvested on the day of use and injected in growth-factor-reduced Matrigel/PBS (e.g., 50% final concentration in 100 μL). One flank is inoculated subcutaneously per mouse. Mice are monitored daily, weighed twice weekly, and caliper measurements begin when tumors become visible. For efficacy studies, animals are randomly assigned to treatment groups by an algorithm that assigns animals to groups to achieve best case distributions of mean tumor size with lowest possible standard deviation. Tumor volume can be calculated by measuring two perpendicular diameters using the following formula: $(L\times w^2)/2$, in which L and w refer to the length and width of the tumor, respectively. Percent tumor volume change can be calculated using the following formula: $(V_{final}-V_{initial})/V_{initial}\times100$. Percent of tumor growth inhibition (% TGI) can be calculated using the following formula: % TGI=100×(1−(average $V_{final}-V_{initial}$ of treatment group)/(average $V_{final}-V_{initial}$ of control group). When tumors reach a threshold average size (e.g., approximately 200-400 $mm^3$), mice are randomized into 3-10 mice per group and are treated with vehicle (e.g., 100% Labrasol®) or a compound disclosed herein, using, for example, a daily schedule by oral gavage. Results can be expressed as mean and standard deviation of the mean.

What is claimed is:

1. A compound of Formula (II):

(II)

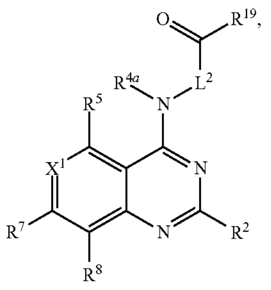

or a pharmaceutically acceptable salt or solvate thereof, wherein:

$X^1$ is selected from $CR^6$ and N;

$R^{4a}$ is selected from $C_{1-6}$ alkyl and $C_{2-6}$ alkenyl;

$L^2$ is saturated, monocyclic 4- to 7-membered heterocycle, wherein the heterocycle is optionally substituted with $C_{1-6}$ alkyl, and wherein —C(O)$R^{19}$ is bound to a nitrogen atom of $L^2$ thereby forming a urea;

$R^{19}$ is selected from pyrrol-1-yl, pyrazol-1-yl, imidazol-1-yl, 1,2,3-triazol-1-yl, 1,2,3-triazol-2-yl, 1,2,4-triazol-1-yl, and 1,2,4-triazol-4-yl, each of which is optionally substituted with one or two substituents independently selected from halogen, —CN, $C_{1-6}$ alkyl, —O($C_{1-6}$ alkyl), and $C_{3-6}$ cycloalkyl, wherein each of $C_{1-6}$ alkyl, —O($C_{1-6}$ alkyl), and $C_{3-6}$ cycloalkyl is optionally substituted with one, two, or three substituents independently selected from halogen, —CN, $C_{1-6}$ alkyl, —O($C_{1-6}$ alkyl), and —O($C_{1-6}$ haloalkyl);

$R^2$ is —O($C_{1-3}$ alkyl)(4- to 10-membered heterocycle) optionally substituted with one, two, or three substituents independently selected from halogen, $C_{1-3}$ alkyl, $C_{1-3}$ haloalkyl, and =C($R^{21}$)$_2$, wherein $R^{21}$ is independently selected at each occurrence from hydrogen, halogen, and $C_{1-3}$ alkyl;

$R^5$ is hydrogen;

$R^6$ is selected from hydrogen, halogen, and $C_{1-3}$ haloalkyl;

$R^7$ is selected from $C_{6-12}$ aryl and 5- to 12-membered heteroaryl, each of which is substituted with one, two, three, or four substituents independently selected from halogen, —CN, —$CH_3$, —$CH_2CH_3$, —CH=$CH_2$, —$CF_3$, —C≡CH, —OH, —$NH_2$, and -cyclopropyl; and $R^8$ is fluorine.

2. The compound, salt, or solvate of claim 1, wherein $L^2$ is selected from pyrrolidin-1,3-diyl, 2-methylpyrrolidin-1,3-diyl, 2-ethylpyrrolidin-1,3-diyl, 2-isopropylpyrrolidin-1,3-diyl, 5-methylpyrrolidin-1,3-diyl, and 5-isopropylpyrrolidin-1,3-diyl.

3. The compound, salt, or solvate of claim 1, wherein $R^{4a}$ is selected from —$CH_3$, —$CH_2CH_3$, and —CH($CH_3$)$_2$.

4. The compound, salt, or solvate of claim 1, wherein $R^{19}$ is selected from imidazol-1-yl and 1,2,4-triazol-1-yl, each of which is optionally substituted with one or two substituents independently selected from halogen, —CN, $C_{1-6}$ alkyl, —O($C_{1-6}$ alkyl), and $C_{3-6}$ cycloalkyl, wherein each of $C_{1-6}$ alkyl, —O($C_{1-6}$ alkyl), and $C_{3-6}$ cycloalkyl is optionally substituted with one, two, or three substituents independently selected from halogen, —CN, $C_{1-6}$ alkyl, —O($C_{1-6}$ alkyl), and —O($C_{1-6}$ haloalkyl).

5. The compound, salt, or solvate of claim 1, wherein $R^2$ is

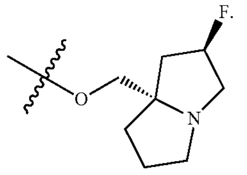 [SMILES: *OC[C@@]12CCCN1C[C@H](F)C2]

6. The compound, salt, or solvate of claim 1, wherein $X^1$ is N.

7. The compound, salt, or solvate of claim 1, wherein $R^7$ is selected from naphthyl, isoquinolinyl, indazolyl, benzothiazolyl, benzothiophenyl, phenyl, and pyridinyl, each of which is substituted with one, two, three, or four substituents independently selected from halogen, —CN, —$CH_3$, —$CH_2CH_3$, —CH=$CH_2$, —$CF_3$, —C≡CH, —OH, —$NH_2$, and -cyclopropyl.

8. The compound, salt, or solvate of claim 1, wherein $R^7$ is

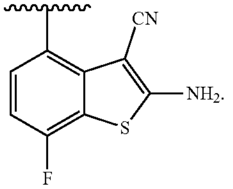 [SMILES: *c1ccc(F)c2sc(N)c(C#N)c12]

9. The compound, salt, or solvate of claim 1, wherein the compound is

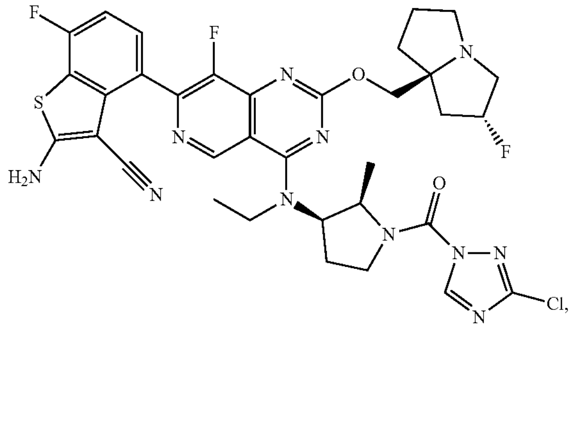 [SMILES: CCN(c1nc(OC[C@@]23CCCN2C[C@H](F)C3)nc2c(F)c(-c3ccc(F)c4sc(N)c(C#N)c34)ncc12)[C@@H]1CCN(C(=O)n2cnc(Cl)n2)[C@@H]1C]

or a pharmaceutically acceptable salt or solvate thereof.

10. The compound, salt, or solvate of claim 1, wherein the compound is

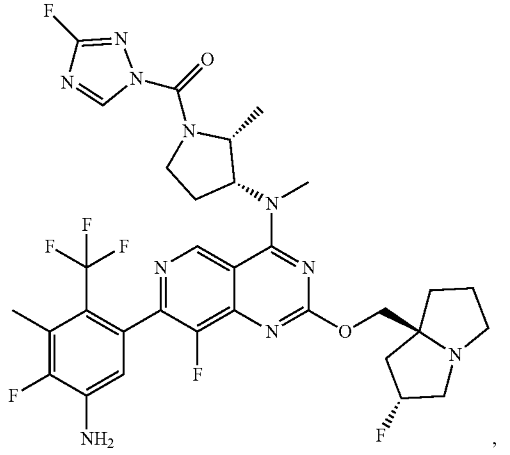 [SMILES: Cc1c(F)c(N)cc(-c2ncc3c(N(C)[C@@H]4CCN(C(=O)n5cnc(F)n5)[C@@H]4C)nc(OC[C@@]45CCCN4C[C@H](F)C5)nc3c2F)c1C(F)(F)F]

or a pharmaceutically acceptable salt or solvate thereof.

11. The compound, salt, or solvate of claim 1, wherein the compound is

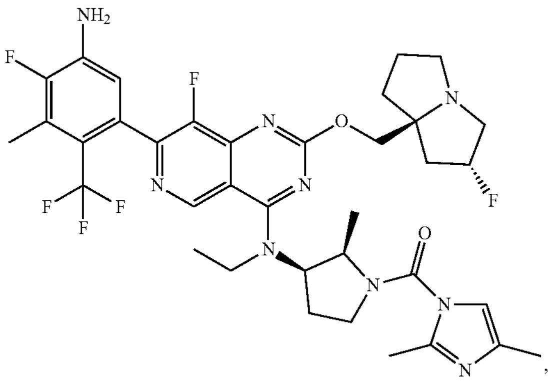 [SMILES: CCN(c1nc(OC[C@@]23CCCN2C[C@H](F)C3)nc2c(F)c(-c3cc(N)c(F)c(C)c3C(F)(F)F)ncc12)[C@@H]1CCN(C(=O)n2cc(C)nc2C)[C@@H]1C]

or a pharmaceutically acceptable salt or solvate thereof.

12. The compound, salt, or solvate of claim 1, wherein the compound is

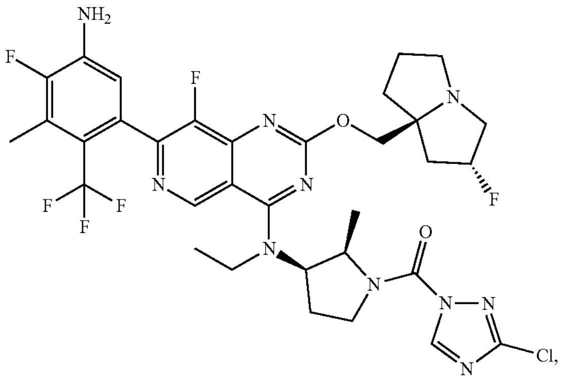 [SMILES: CCN(c1nc(OC[C@@]23CCCN2C[C@H](F)C3)nc2c(F)c(-c3cc(N)c(F)c(C)c3C(F)(F)F)ncc12)[C@@H]1CCN(C(=O)n2cnc(Cl)n2)[C@@H]1C]

or a pharmaceutically acceptable salt or solvate thereof.

13. A compound selected from:
-continued
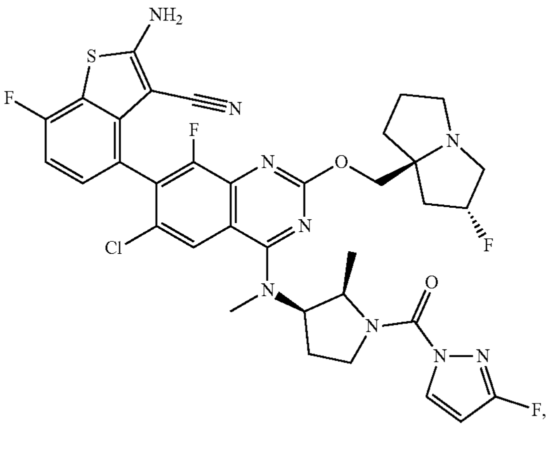
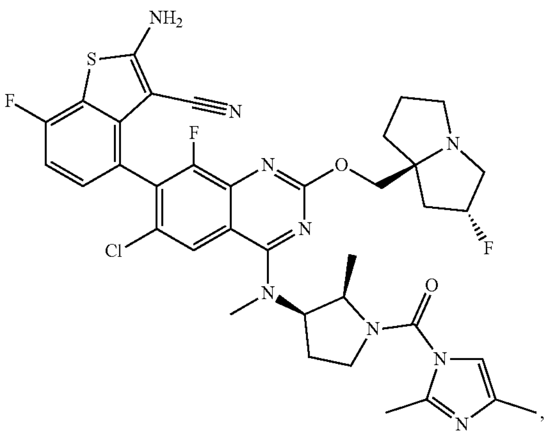
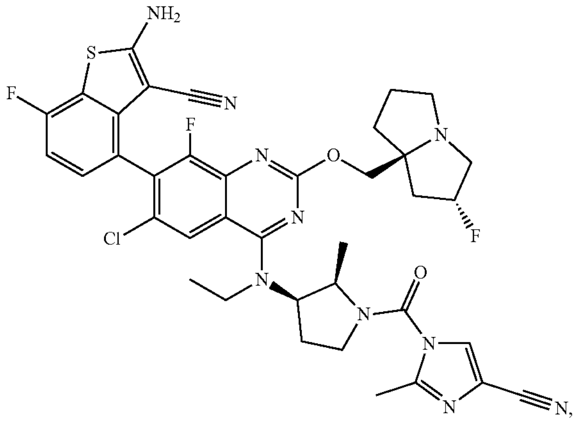
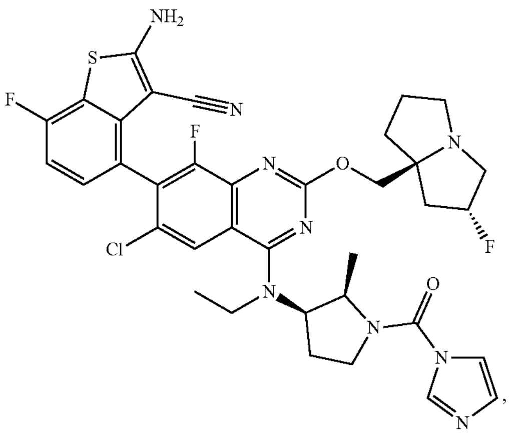
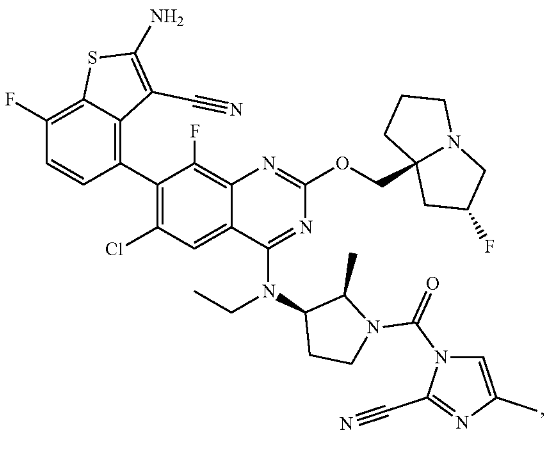
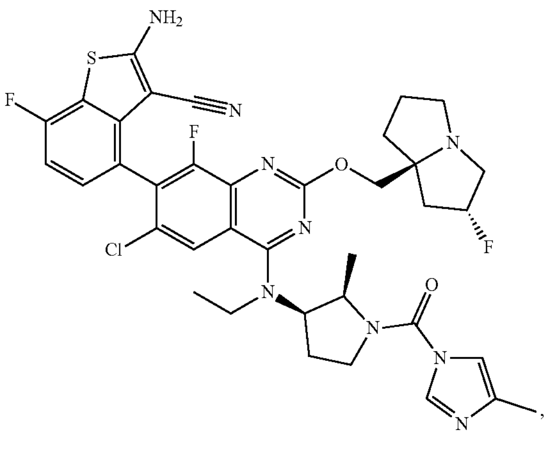

-continued
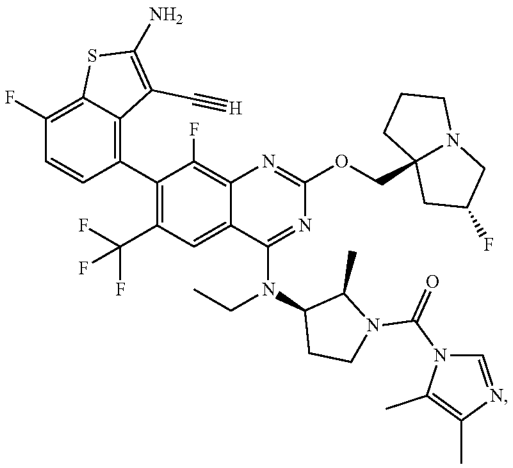
,
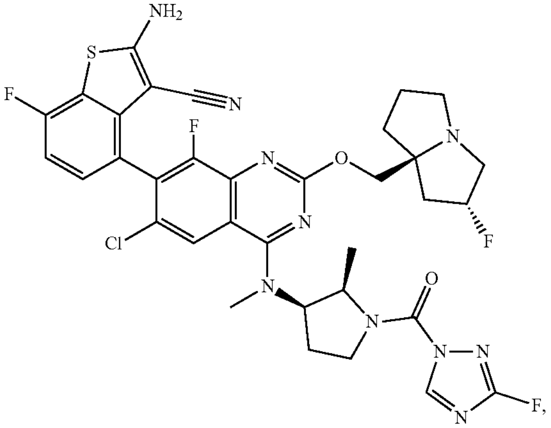
,
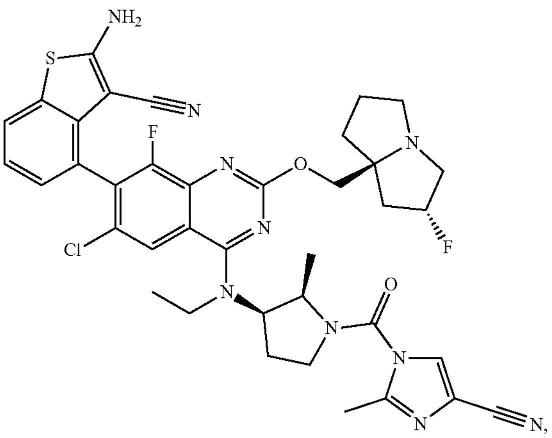
,
-continued
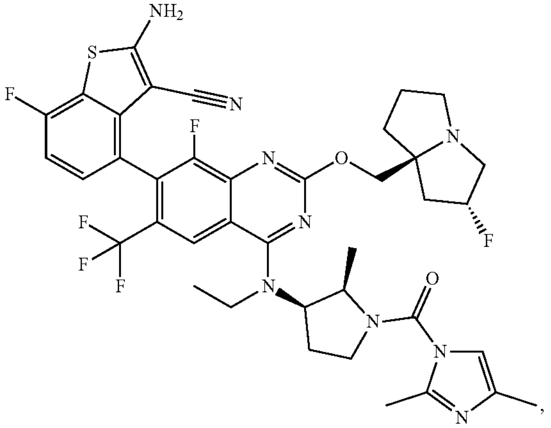
,
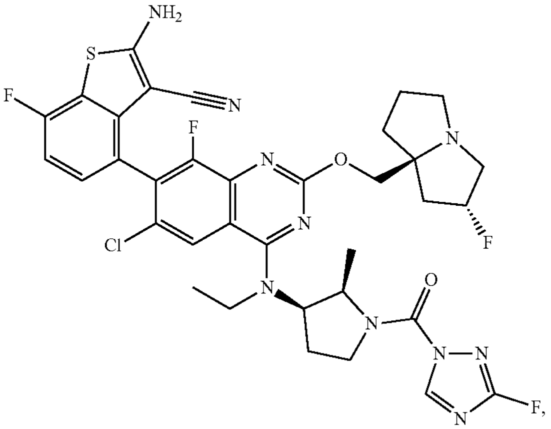
,
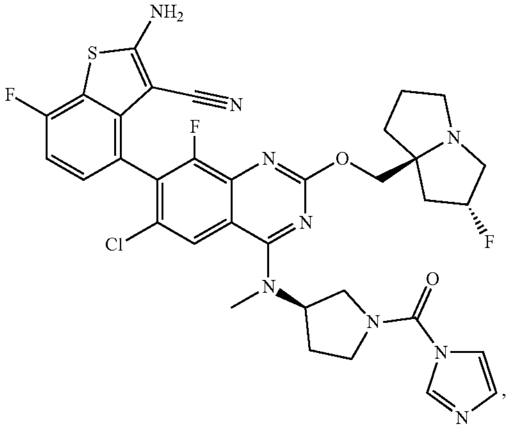
,
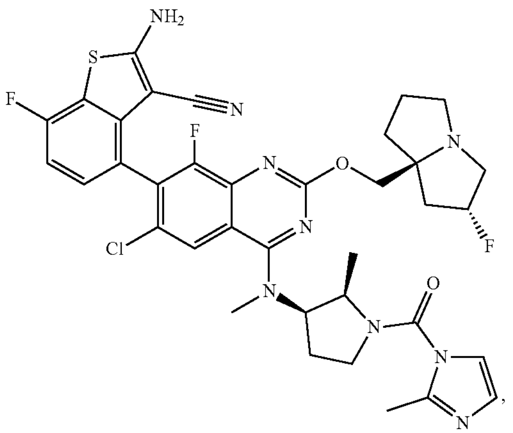
, -continued
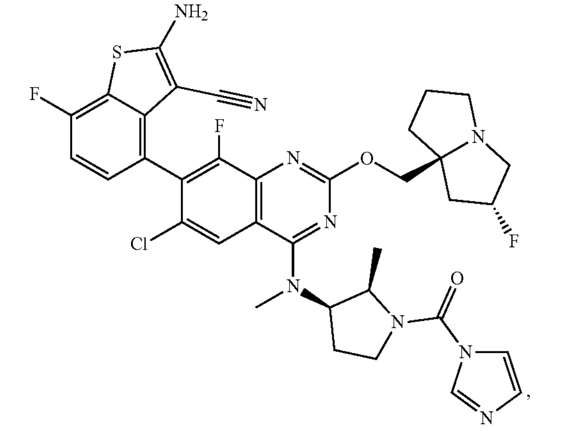
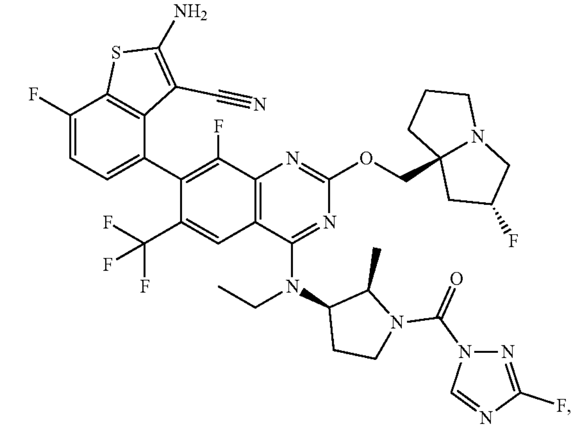
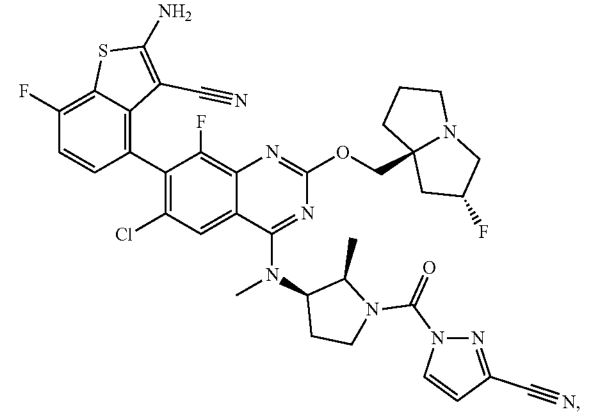
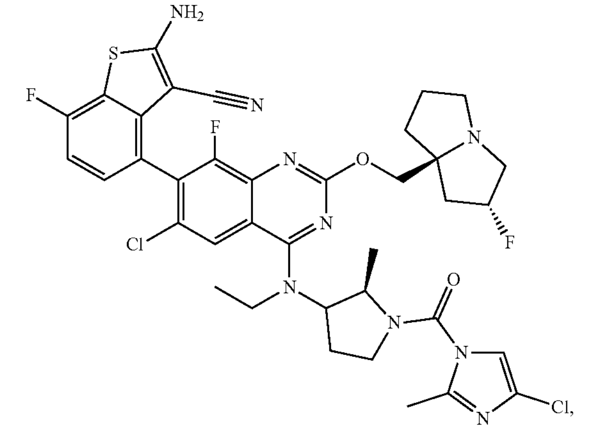
-continued
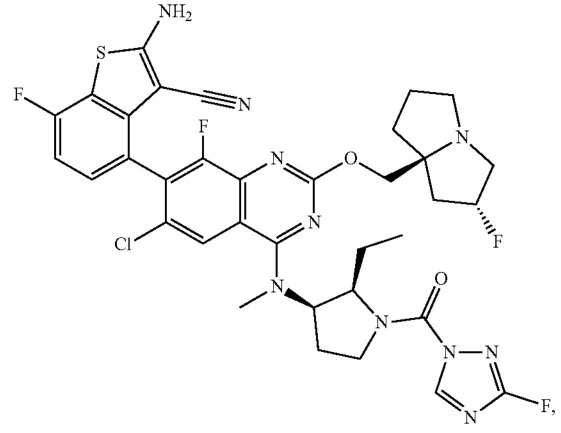
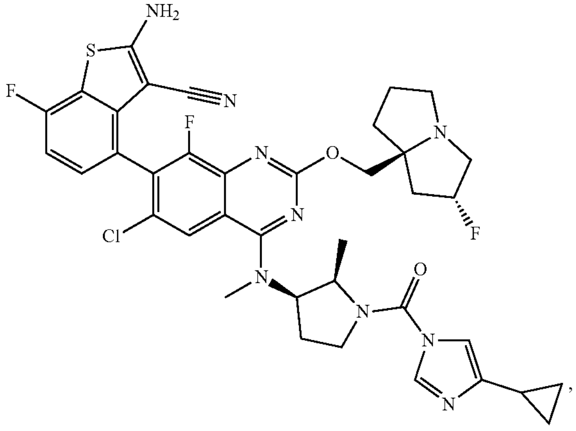
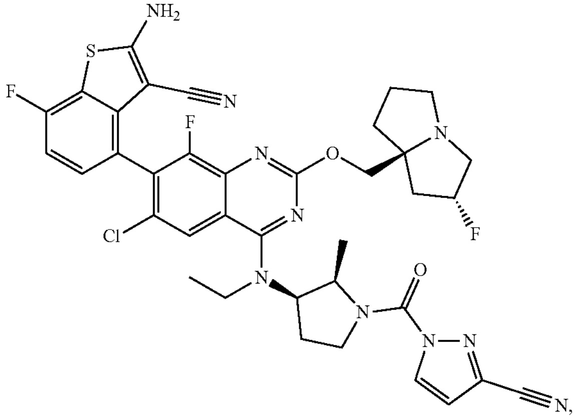
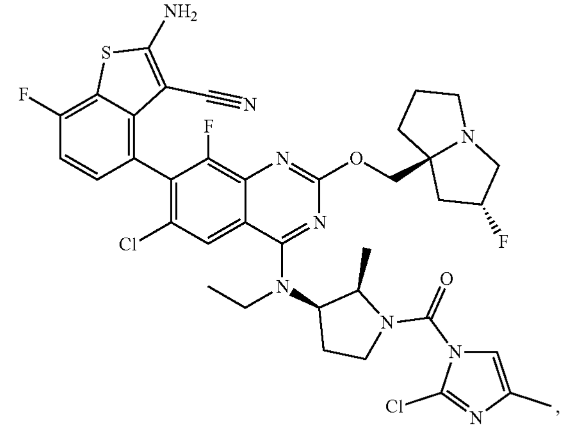

-continued
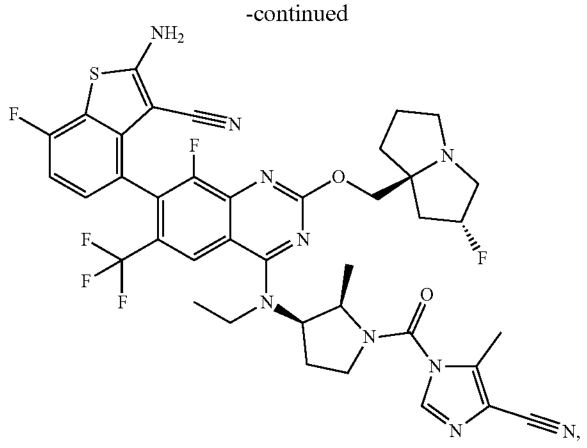
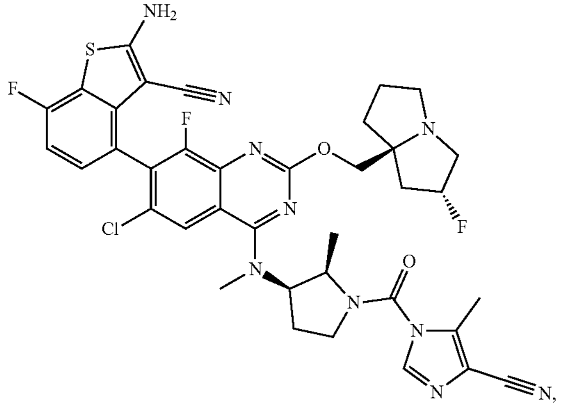
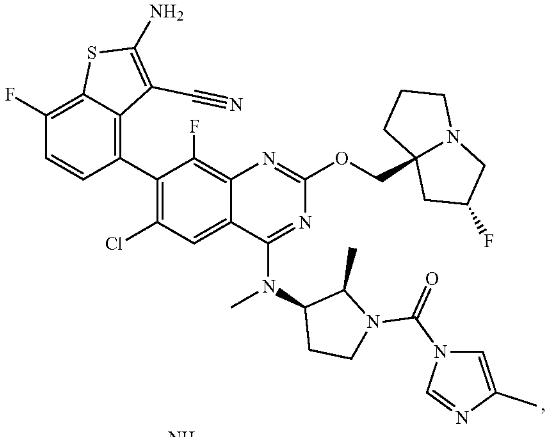
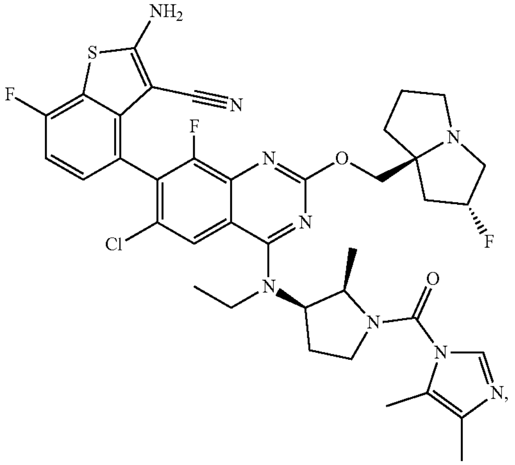
-continued
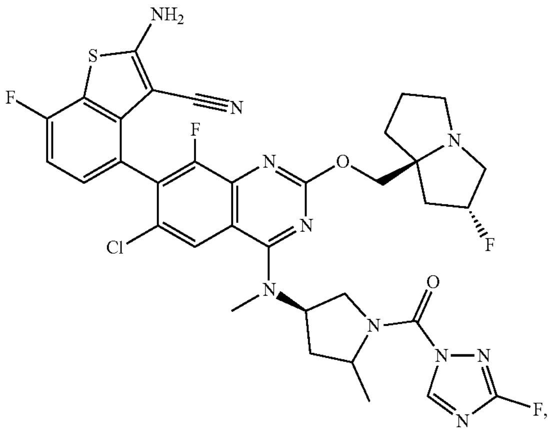
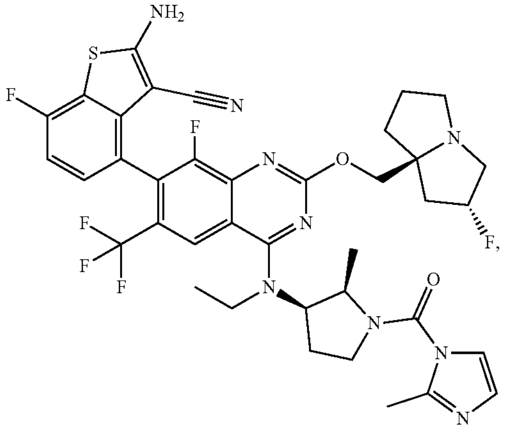
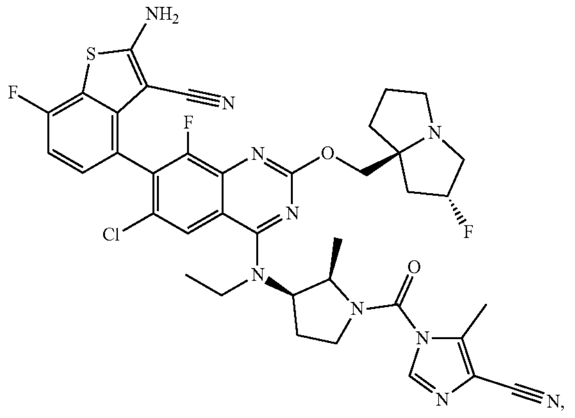
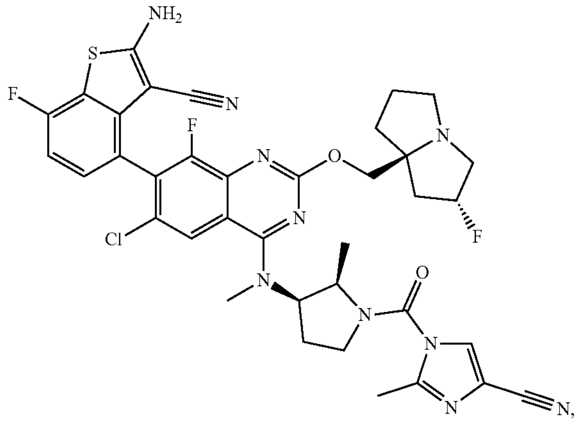

-continued
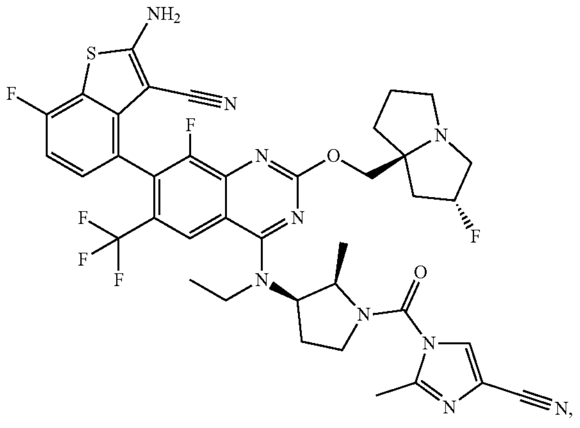
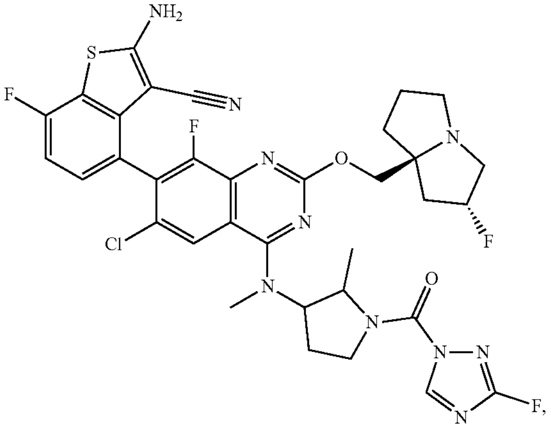
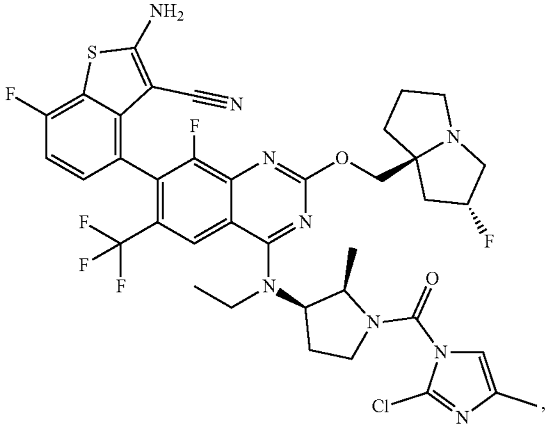
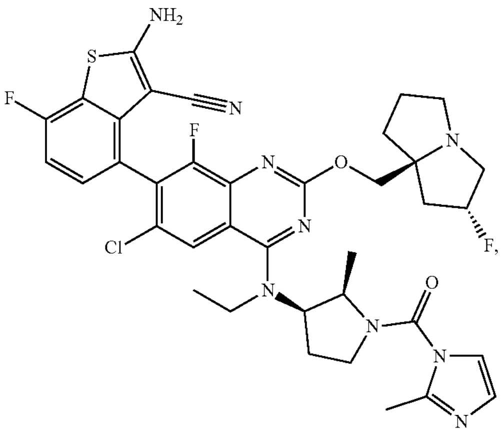
-continued
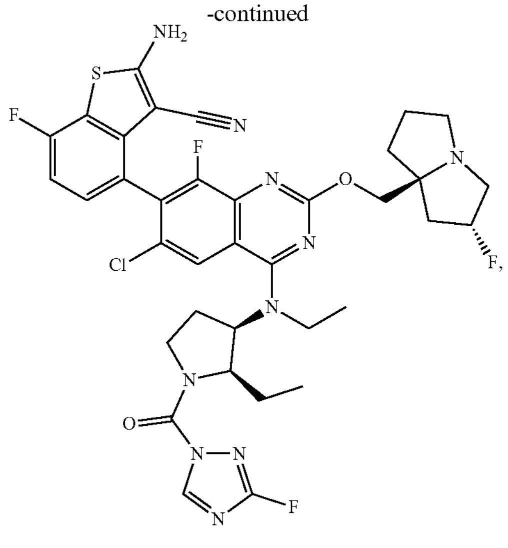
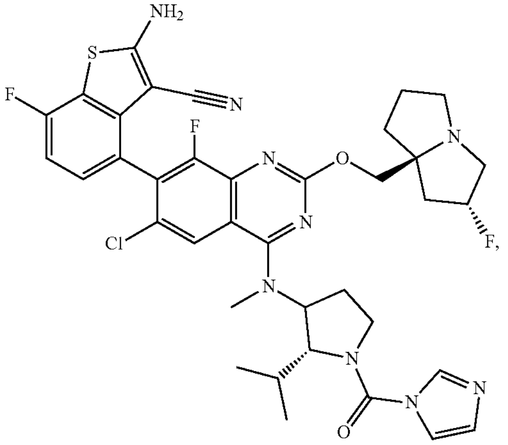
and
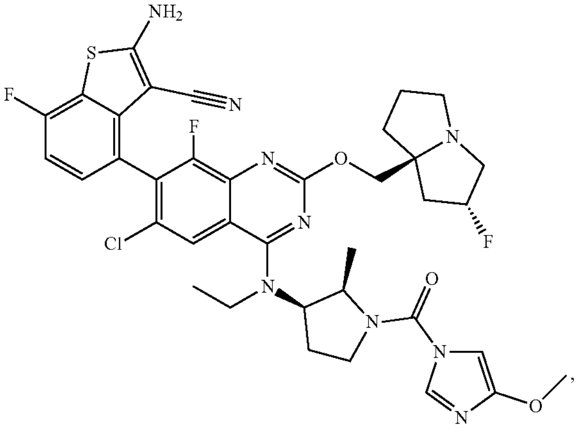
or a pharmaceutically acceptable salt or solvate thereof.

14. A compound of the formula

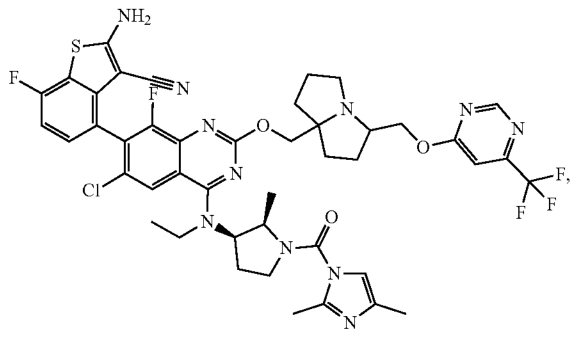 [SMILES: CCN(c1nc(OCC23CCCN2C(COc2cc(C(F)(F)F)ncn2)CC3)nc2c(F)c(-c3ccc(F)c4sc(N)c(C#N)c34)c(Cl)cc12)[C@@H]1CCN(C(=O)n2cc(C)nc2C)[C@@H]1C]

or a pharmaceutically acceptable salt or solvate thereof.

15. A pharmaceutical composition comprising a compound of claim 1, or a pharmaceutically acceptable salt or solvate thereof, and a pharmaceutically acceptable excipient.

16. A pharmaceutical composition comprising a compound of claim 13, or a pharmaceutically acceptable salt or solvate thereof, and a pharmaceutically acceptable excipient.

17. A pharmaceutical composition comprising a compound of claim 14, or a pharmaceutically acceptable salt or solvate thereof, and a pharmaceutically acceptable excipient.

18. A method of treating cancer comprising a K-Ras mutant protein in a subject in need thereof, comprising administering to the subject a therapeutically effective amount of a compound of claim 1, or a pharmaceutically acceptable salt or solvate thereof.

19. A method of treating cancer comprising a K-Ras mutant protein in a subject in need thereof, comprising administering to the subject a therapeutically effective amount of a compound of claim 13, or a pharmaceutically acceptable salt or solvate thereof.

20. A method of treating cancer comprising a K-Ras mutant protein in a subject in need thereof, comprising administering to the subject a therapeutically effective amount of a compound of claim 14, or a pharmaceutically acceptable salt or solvate thereof.

* * * * *

SEQUENCE LISTING

```
Sequence total quantity: 14
SEQ ID NO: 1            moltype = AA  length = 188
FEATURE                 Location/Qualifiers
source                  1..188
                        mol_type = protein
                        organism = Homo sapiens
SEQUENCE: 1
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 2            moltype = AA  length = 188
FEATURE                 Location/Qualifiers
source                  1..188
                        mol_type = protein
                        organism = Homo sapiens
SEQUENCE: 2
MTEYKLVVVG ADGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 3            moltype = AA  length = 188
FEATURE                 Location/Qualifiers
source                  1..188
                        mol_type = protein
                        organism = Homo sapiens
SEQUENCE: 3
MTEYKLVVVG AVGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188
```

```
SEQ ID NO: 4            moltype = AA  length = 188
FEATURE                 Location/Qualifiers
source                  1..188
                        mol_type = protein
                        organism = Homo sapiens
SEQUENCE: 4
MTEYKLVVVG ASGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                         188

SEQ ID NO: 5            moltype = AA  length = 189
FEATURE                 Location/Qualifiers
source                  1..189
                        mol_type = protein
                        organism = Homo sapiens
SEQUENCE: 5
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                        189

SEQ ID NO: 6            moltype = AA  length = 189
FEATURE                 Location/Qualifiers
source                  1..189
                        mol_type = protein
                        organism = Homo sapiens
SEQUENCE: 6
MTEYKLVVVG ADGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL  120
AARTVESRQA QDLARSYGIP YIETSAKTRQ GVEDAFYTLV REIRQHKLRK LNPPDESGPG  180
CMSCKCVLS                                                        189

SEQ ID NO: 7            moltype = AA  length = 189
FEATURE                 Location/Qualifiers
source                  1..189
                        mol_type = protein
                        organism = Homo sapiens
SEQUENCE: 7
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL  120
AARTVESRQA QDLARSYGIP YIETSAKTRQ GVEDAFYTLV REIRQHKLRK LNPPDESGPG  180
CMSCKCVLS                                                        189

SEQ ID NO: 8            moltype = AA  length = 189
FEATURE                 Location/Qualifiers
source                  1..189
                        mol_type = protein
                        organism = Homo sapiens
SEQUENCE: 8
MTEYKLVVVG ADGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                        189

SEQ ID NO: 9            moltype = AA  length = 188
FEATURE                 Location/Qualifiers
source                  1..188
                        mol_type = protein
                        organism = Homo sapiens
SEQUENCE: 9
MTEYKLVVVG ACGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                         188

SEQ ID NO: 10           moltype = AA  length = 108
FEATURE                 Location/Qualifiers
source                  1..108
                        mol_type = protein
                        organism = Homo sapiens
SEQUENCE: 10
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSED             108
```

-continued

```
SEQ ID NO: 11          moltype = AA  length = 108
FEATURE                Location/Qualifiers
source                 1..108
                       mol_type = protein
                       organism = Homo sapiens
SEQUENCE: 11
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDD             108

SEQ ID NO: 12          moltype = AA  length = 108
FEATURE                Location/Qualifiers
source                 1..108
                       mol_type = protein
                       organism = Homo sapiens
SEQUENCE: 12
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDD             108

SEQ ID NO: 13          moltype = AA  length = 119
FEATURE                Location/Qualifiers
source                 1..119
                       mol_type = protein
                       organism = Homo sapiens
SEQUENCE: 13
MAANKPKGQN SLALHKVIMV GSGGVGKSAL TLQFMYDEFV EDYEPTKADS YRKKVVLDGE  60
EVQIDILDTA GQEDYAAIRD NYFRSGEGFL CVFSITEMES FAATADFREQ ILRVKEDEN  119

SEQ ID NO: 14          moltype = AA  length = 120
FEATURE                Location/Qualifiers
source                 1..120
                       mol_type = protein
                       organism = Homo sapiens
SEQUENCE: 14
MAANKSKGQS SLALHKVIMV GSGGVGKSAL TLQFMYDEFV EDYEPTKADS YRKKVVLDGE  60
EVQIDILDTA GQEDYAAIRD NYFRSGEGFL LVFSITEHES FTATAEFREQ ILRVKAEEDK 120
```